US009029638B2

(12) United States Patent
Deng et al.

(10) Patent No.: US 9,029,638 B2
(45) Date of Patent: May 12, 2015

(54) PLANTS HAVING ALTERED GROWTH AND/OR DEVELOPMENT RESULTED FROM MODULATED EXPRESSION OF UBIQUITIN-SPECIFIC PROTEASES AND A METHOD FOR MAKING THE SAME

(75) Inventors: Xing Wang Deng, New Haven, CT (US); Yanfen Liu, Beijing (CN)

(73) Assignee: National Institute for Biological Sciences, Beijing (CN)

( * ) Notice: Subject to any disclaimer, the term of this patent is extended or adjusted under 35 U.S.C. 154(b) by 358 days.

(21) Appl. No.: 12/864,528

(22) PCT Filed: Jan. 30, 2009

(86) PCT No.: PCT/IB2009/050372
§ 371 (c)(1),
(2), (4) Date: Jul. 26, 2010

(87) PCT Pub. No.: WO2009/095881
PCT Pub. Date: Aug. 6, 2009

(65) Prior Publication Data
US 2010/0313308 A1 Dec. 9, 2010

Related U.S. Application Data

(63) Continuation-in-part of application No. PCT/CN2008/000245, filed on Jan. 31, 2008.

(51) Int. Cl.
| | | |
|---|---|---|
| *C12N 15/82* | (2006.01) | |
| *C12N 15/87* | (2006.01) | |
| *C12N 5/04* | (2006.01) | |
| *C12N 5/10* | (2006.01) | |
| *C12N 15/00* | (2006.01) | |
| *A01H 1/00* | (2006.01) | |
| *C12N 9/50* | (2006.01) | |

(52) U.S. Cl.
CPC .............. *C12N 15/8261* (2013.01); *C12N 9/50* (2013.01)

(58) Field of Classification Search
USPC ....................................................... 800/290
See application file for complete search history.

(56) References Cited

U.S. PATENT DOCUMENTS

| 8,324,454 B2 * | 12/2012 | Zhou et al. ................... 800/278 |
| 2003/0233670 A1 * | 12/2003 | Edgerton et al. .............. 800/278 |
| 2005/0210544 A1 | 9/2005 | Feher et al. |

FOREIGN PATENT DOCUMENTS

| CN | 1366057 A | 8/2002 |
| WO | WO-2004/061080 A2 | 7/2004 |
| WO | WO-2006/067232 A2 | 6/2006 |
| WO | WO-2007/054522 A1 | 5/2007 |
| WO | WO-2007/113237 A2 | 10/2007 |
| WO | WO 2009/095881 A2 | 8/2009 |

OTHER PUBLICATIONS

Yan et al (2000, Plant Physiology 124:1828-1843).*
Yan et al., The Ubiquitin-specific protease family of *Arabidopsis*. AtUBP1 and 2 are required for the resistance to the amino acid analog canavanine, 124 Plant Physiology, 1828-1843 (2000).*
Liu et al., Functional characterization of the *Arabidopsis* ubiquitin-specific protease gene family reveals specific role and redundancy of individual members in development, 55 The Plant Journal 844-856 (2008).*
Moon et al., Structure and Expression of OsUBP6, an Ubiquitin-specific protease 6 homolog in Rice (*Oryza sativa* L.), Molecules and Cells, 463-472 (2009).*
Terence A. Brown, Genomes Chapter 7 § 7.1.1; 7.2.1 (Oxford: Wiley-Liss) (2nd ed. 2002) available at http://www.ncbi.nlm.nih.gov/books/NBK21136/).*
Yan et al. (The Ubiquitin-specific protease family of *Arabidopsis*: AtUBP1 and 2 are required for the resistance to the amino acid analog canavanine, 124 Plant Physiology, 1828-1843 (2000)).*
Perez et al., Biodegradation and biological treatments of cellulose, hemicellulose and lignin: an overview, 5 Int Microbiol, 53-63 (2002).*
NCBI BLAST alignment of SEQ ID No: 2 obtained Dec. 9, 2013; available at http://blast.ncbi.nlm.nih.gov/Blast.cgi.*
Vasanthaiah et al., Cloning and characterization of differentially expressed genes of internal breakdown in mango fruit (*Mangifera indica*), 163 J Plant Phys., 671-679 at 673-674 (2006)).*
Jorgensen, R.A., et al., Functional genomics by sense-RNAi: A forward genetic approach for cell-type-targeted mutagenesis, Plant Genomics in China VI, (2005), pp. 1-251.
Amerik, A.Y., et al., "Mechanism and function of deubiquitinating enzymes," Biochim. Biophys. Acta (2004), vol. 1695, pp. 189-207.
Ma, L., et al., "Organ-Specific Expression of *Arabidopsis* Genome during Development," Plant Physiol (2005), vol. 138, pp. 80-91.
Liu, Y., et al., "Functional characterization of the *Arabidopsis* ubiquitin-specific protease gene family reveals specific role and redundancy of individual members in development," The Plant Journal (2008), vol. 55, pp. 844-856.
Ang, L.-H., et al., "Molecular Interaction between COP1 and HY5 Defines a Regulatory Switch for Light Control of *Arabidopsis* Development," Molecular Cell (1998), vol. 1, pp. 213-222.

(Continued)

*Primary Examiner* — Cynthia Collins
*Assistant Examiner* — Rebecca Coobs
(74) *Attorney, Agent, or Firm* — Drinker Biddle & Reath LLP

(57) ABSTRACT

The present invention relates generally to the field of molecular biology and concerns a method for altering various aspects of plant growth and/or development by modulating expression in a plant of a nucleic acid encoding an UBiquitin-Specific Protease (UBP) of the UBP15 subfamily or a homologue thereof. The present invention also concerns plants having modulated expression of a nucleic acid encoding a UBP15 or a homologue thereof, which plants have altered growth and/or development relative to corresponding wild type plants or other control plants. The invention also provides constructs useful in the methods of the invention.

20 Claims, 41 Drawing Sheets

(56) References Cited

OTHER PUBLICATIONS

Baek, K.-H., et al., "DUB-2A, a new member of the DUB subfamily of hematopoietic deubiquitinating enzymes," Blood (2001), vol. 98, No. 3, pp. 636-642.

Balakirev, M.Y., et al., "Otubains: a new family of cysteine proteases in the ubiquitin pathway," EMBO reports (2003), vol. 4, No. 5, pp. 517-522.

Burnett, B., et al., "The polyglutamine neurodegenerative protein ataxin-3 binds polyubiquitylated proteins and has ubiquitin protease activity," Human Molecular Genetics (2003), vol. 12, No. 23, pp. 3195-3205.

Byrne, M.E., et al., "Phyllotactic pattern and stem cell fate are determined by the *Arabidopsis* homeobox gene Bellringer," Development (2003), vol. 130, pp. 3941-3950.

Chandler, J.S., et al., "AtUBP3 and AtUBP4 are two closely related *Arabidopsis thaliana* ubiquitin-specific proteases present in the nucleus," Mol Gen Genet (1997), vol. 255, pp. 302-310.

Crosas, B., et al., "Ubiquitin Chains Are Remodeled at the Proteasome by Opposing Ubiquitin Ligase and Deubiquitinating Activities," Cell (2006), vol. 127, pp. 1401-1413.

Fleury, D., et al., "The *Arabidopsis thaliana* Homolog of Yeast BRE1 Has a Function in Cell Cycle Regulation during Early Leaf and Root Growth," The Plant Cell (2007), vol. 19, pp. 417-432.

Gross, C.T., et al., "Deaf-1, a novel protein that binds an essential region in a Deformed response element," The EMBO Journal (1996), vol. 15, No. 8, pp. 1961-1970.

Hanna, J., et al., "Deubiquitinating Enzyme Ubp6 Functions Noncatalytically to Delay Proteasomal Degradation," Cell (2006), vol. 127, pp. 99-111.

Hershko, A., et al., "The Ubiquitin System," Annu. Rev. Biochem. (1998), vol. 67, pp. 425-479.

Hochstrasser, M. "Ubiquitin-Dependent Protein Degradation," Annu. Rev, Genet. (1996), vol. 30, pp. 405-439.

Hofmann, K., et al., "The UBA domain: a sequence motif present in multiple enzyme classes of the ubiquitination pathway," TIBS (1996), vol. 21, pp. 172-173.

Horiguchi, G., et al., "The transcription factor AtGRF5 and the transcription coactivator AN3 regulate cell proliferation in leaf primordia of *Arabidopsis thaliana*," The Plant Journal (2005), vol. 43, pp. 68-78.

Hu, M., et al., "Crystal Structure of a UBP-Family Deubiquitinating Enzyme in Isolation and in Complex with Ubiquitin Aldehyde," Cell (2002), vol. 111, pp. 1041-1054.

Johnston, S.C., et al., "Structural basis for the specificity of ubiquitin C-terminal hydrolases," The EMBO Journal (1999), vol. 18, No. 14, pp. 3877-3887.

Johnston, J.C., et al., "Crystal structure of a deubiquitinating enzyme (human UCH-L3) at 1.8 Å resolution," The EMBO Journal (1997), vol. 16, No. 13, pp. 3787-3796.

Kim, J.-H., et al., "A transcriptional coactivator, AtGIF1, is involved in regulating leaf growth and morphology in *Arabidopsis*," PNAS (2004), vol. 101, No. 36, pp. 13374-13379.

Kumar, S., et al., "MEGA3: Integrated software for Molecular Evolutionary Genetics Analysis and sequence alignment," Briefings in Bioinformatics (2004), vol. 5, No. 2, pp. 150-163.

Lutterbach, B., et al., "The MYND Motif is Required for Repression of Basal Transcription from the Multidrug Resistance 1 Promoter by the t(8;21) Fusion Protein," Molecular and Cellular Biology (1998), vol. 18, No. 6, pp. 3604-3611.

Lutterbach, B., et al., "ETO, a Target of t(8;21) in Acute Leukemia, Interacts with the N-CoR and mSin3 Corepressors," Molecular and Cellular Biology (1998), vol. 18, No. 12, pp. 7176-7184.

Ma, L., et al., "Genomic Evidence for COP1 as a Repressor of Light-Regulated Gene Expression and Development in *Arabidopsis*," The Plant Cell (2002), vol. 14, pp. 2383-2398.

Maere, S., et al., "BiNGO: a Cytoscape plugin to assess over-representation of Gene Ontology categories in Biological Networks," Bioinformatics (2005), vol. 21, No. 16, pp. 3448-3449.

Masselink, H., et al., "The adenovirus E1A binding protein BS69 is a corepressor of transcription through recruitment of N-CoR," Oncogene (2000), vol. 19, pp. 1538-1546.

Mueller, T.D., et al., "Solution Structures of UBA Domains Reveal a Conserved Hydrophobic Surface for Protein-Protein Interactions," J. Mol. Biol. (2002), vol. 319, pp. 1243-1255.

Nanao, M.H., et al., "Crystal structure of human otubain 2," EMBO Reports (2004), vol. 5, No. 8, pp. 783-788.

Papa, F.R., et al., "The yeast DOA4 gene encodes a deubiquitinating enzyme related to a product of the human tre-2 oncogene," Nature (1993), vol. 366, pp. 313-319.

Park, Y.C., et al., "Structural basis for self-association and receptor recognition of human TRAF2," Nature (1999), vol. 398, pp. 533-538.

Pickart, C.M., "Back to the Future with Ubiquitin," Cell (2004), vol. 116, pp. 181-190.

Qin, G., et al., "An Indole-3-Acetic Acid Carboxyl Methyltransferase Regulates *Arabidopsis* Leaf Development," The Plant Cell (2005), vol. 17, pp. 2693-2704.

Rao-Naik, C., et al., "Ubiquitin-Specific Proteases from *Arabidopsis thaliana*: Cloning of AtUBP5 and Analysis of Substrate Specificity of AtUBP3, AtUBP4, and AtUBP5 Using *Escherichia coli* in Vivo and in Vitro Assays," Archives of Biochemistry and Biophysics (2000), vol. 379, No. 2, pp. 198-208.

Scheel, H., et al., "Elucidation of ataxin-3 and ataxin-7 function by integrative bioinformatics," Human Molecular Genetics (2003), vol. 12, No. 21, pp. 2845-2852.

Sunnerhagen, M., et al., "The new MATH: homology suggests shared binding surfaces in meprin etramers and TRAF trimers," FEBS Letters (2002), vol. 530, pp. 1-3.

Thompson, J.D., et al., "Clustal W: improving the sensitivity of progressive multiple sequence alignment through sequence weighting, position-specific gap penalties and weight matrix choice," Nucleic Acids Research (1994), vol. 22, No. 22, pp. 4673-4680.

Tsukaya, H., "Mechanism of Leaf-Shape Determination," Annu. Rev. Plant Biol. (2006), vol. 57, pp. 477-496.

Varshavsky, A., "The ubiquitin system," TIBS (1997), vol. 22, pp. 383-387.

Verma, R., et al., "Role of Rpn11 Metalloprotease in Deubiquitination and Degradation by the 26S Proteasome," Science (2002), vol. 298, pp. 611-615.

Weissman, A.M., "Themes and Variations on Ubiquitylation," Nature Reviews Molecular Cell Biology (2001), vol. 2, pp. 169-177.

Wilkinson, K.D., "Regulation of ubiquitin-dependent processes by deubiquitinating enzymes," The FASEB Journal (1997), vol. 11, pp. 1245-1256.

Wilkinson, K.D., "Ubiquitin-Dependent Signaling: The Role of Ubiquitination in the Response of Cells to Their Environment," The Journal of Nutrition (1999), vol. 129, pp. 1933-1936.

Yang, J., et al., "Light Regulates COP1-Mediated Degradation of HFR1, a Transcription Factor Essential for Light Signaling in *Arabidopsis*," The Plant Cell (2005), vol. 17, pp. 804-821.

Ye, H., et al., "The Structural Basis for the Recognition of Diverse Receptor Sequences by TRAF2," Molecular Cell (1999), vol. 4, pp. 321-330.

Yang, P., et al., "Ubiquitin C-terminal Hydrolases 1 and 2 Affect Shoot Architecture in *Arabidopsis*", The Plant Journal, vol. 51, (2007), pp. 441-457.

"Ubiquitin Carboxyl-Terminal Hydrolase"; UniProt; Accession No. Q9FPS9; Jan. 15, 2008.

Yan, N., et al., "The Ubiquitin-Specific Protease Family from *Arabidopsis*. AtUBP1 and 2 are Required for the Resistance to the Amino Acid Analog Canavanine", Plant Physiology, vol. 124, (2000), pp. 1828-1843.

Nijman, S.M.B., et al., "A Genomic and Functional Inventory of Deubiquitinating Enzymes", Cell, vol. 123, (2005), pp. 773-786.

Liu, Y., et al., "Functional Characterization of the *Arabidopsis* Ubiquitin-Specific Protease Gene Family Reveals Specific Role and Redundancy of Individual Members in Development", The Plant Journal, vol. 55, (2008), pp. 844-856.

Doelling, J.H., et al., "The Ubiquitin-Specific Protease Subfamily UBP3/UBP4 is Essential for Pollen Development and Transmission in *Arabidopsis*", Plant Physiology, vol. 145, (2007), pp. 801-813.

(56) References Cited

OTHER PUBLICATIONS

Doelling, J.H., et al., "The Ubiquitin-Specific Protease UBP14 is Essential for Early Embryo Development in *Arabidopsis thaliana*", The Plant Journal, vol. 27, No. 5, (2001), pp. 393-405.

"Ubiquitin-Specific Protease 15 [*Arabidopsis thaliana*]", NCBI GenBank Database Accession No. AAG42756, Dec. 28, 2000.

Office Action Issued on Mar. 3, 2013 in Russian Application No. 2010135783.

Wu, F. K., et al., "Purification of the Human Immunodeficiency Virus Type-1 Enhancer and TAR Binding Proteins EBP-1 and UBP-1", The EMBO J., 1988, vol. 7, No. 7, pp. 2117-2130.

"pCambia Vectors", Downloaded from Cambia Website (cambia.org/daisy/cambia/585.html) on Feb. 22, 2013.

* cited by examiner

```
              1                                                50
UBP9    (1)   NLKQGNLYFVISKRWYTSWQEYVEN---------------SANECSTGESSEAP
UBP10   (1)   NLKEGNLYFVISKRWYTSWEKYVEQ---------------STKEYISGESSEAS
UBP11   (1)   -LKEGNLYFVISNRWYTRWQRFVGL---------------LTEEFRSGEPSEVT
UBP5    (1)   NSKEGDTFYLITQRWWQEWIEYVNQDQPCNTNDGSSLSEHCDSPGSSTLK
UBP8    (1)   --------------------------------------------------
UBP24   (1)   --------------------------------------------------
UBP3    (1)   --------------------------------------------------
UBP4    (1)   --------------------------------------------------
UBP12   (1)   --------------------------------------------------
UBP13   (1)   --------------------------------------------------
UBP26   (1)   --------------------------------------------------
UBP14   (1)   --------------------------------------------------
UBP6    (1)   --------------------------------------------------
UBP7    (1)   --------------------------------------------------
UBP1    (1)   --------------------------------------------------
UBP2    (1)   --------------------------------------------------
UBP27   (1)   --------------------------------------------------
UBP22   (1)   --------------------------------------------------
UBP20   (1)   --------------------------------------------------
UBP21   (1)   --------------------------------------------------
UBP23   (1)   --------------------------------------------------
UBP25   (1)   --------------------------------------------------
UBP15   (1)   --------------------------------------------------
UBP16   (1)   --------------------------------------------------
UBP17   (1)   --------------------------------------------------
UBP18   (1)   --------------------------------------------------
UBP19   (1)   --------------------------------------------------
```

FIGURE 12

```
            51                                                  100
UBP9   (40) RPGPIDNHDIIES---DSDINDPQLRRLLVEGEDYVLVPKQVWKRLVEWY
UBP10  (40) RPGPIDNHDIIES---ESDVNDPQLRRLLMERVDYVLVPQEVWKRLVEWY
UBP11  (39) RPGPIDNHDIIDS---ESDASDPQLRMLEEGVDYTLVQQEVWRKLVKWY
UBP5   (51) KPSRIDNSDLIYDSSLEDPSNTSEIETLQEGRDYVLLPQEVWNQLRSWY
UBP8    (1) --------------------------------------------------
UBP24   (1) --------------------------------------------------
UBP3    (1) --------------------------------------------------
UBP4    (1) --------------------------------------------------
UBP12   (1) ---------------------------------LKFTWTIPNFSRQ
UBP13   (1) ---------------------------------LKFTWTIPMFTRL
UBP26   (1) --------------------------------------------------
UBP14   (1) --------------------------------------------------
UBP6    (1) --------------------------------------------------
UBP7    (1) --------------------------------------------------
UBP1    (1) --------------------------------------------------
UBP2    (1) --------------------------------------------------
UBP27   (1) --------------------------------------------------
UBP22   (1) --------------------------------------------------
UBP20   (1) --------------------------------------------------
UBP21   (1) --------------------------------------------------
UBP23   (1) --------------------------------------------------
UBP25   (1) --------------------------------------------------
UBP15   (1) --------------------------------------------------
UBP16   (1) --------------------------------------------------
UBP17   (1) --------------------------------------------------
UBP18   (1) --------------------------------------------------
UBP19   (1) --------------------------------------------------
```

FIGURE 12 (continued)

```
                 101                                                 150
UBP9     ( 87)   SGGPPIERKLICQGFYTRSYSVEVYPLCLMLTDGRDESRTVIRLGKQASI
UBP10    ( 87)   SGGPPIERKLICQGFYTRSYSVEVYPLCLMLTDGRDESRTVIRLGKQASI
UBP11    ( 86)   KGGPPVPRKLISQGFYTKSFSVEVYLLCLTLTDSRDESTTIIRLSKQASI
UBP5     (101)   GGGPTLARRVISSGLSQTELAVEVYPLRLQLLLMPKSDHSAIRISKKETI
UBP8     (  1)   --------------------------------------------------
UBP24    (  1)   --------------------------------------------------
UBP3     (  1)   --------------------------------------------------
UBP4     (  1)   --------------------------------------------------
UBP12    ( 14)   NTRKHYSDVFVVGGYKWRILIFPKGNNVDHLSMYLDVSDAAASLPYGWSRY
UBP13    ( 14)   NTRKHYSDVFVVGGYKWRILIFPKGNNVDHLSMYLDVADAANLPYGWSRY
UBP26    (  1)   --------------------------------------------------
UBP14    (  1)   ----------------------------------CSKCDKTENLWLN---
UBP6     (  1)   ---------------------------------------TVSVKWQKK--
UBP7     (  1)   ---------------------------------------LTVSVKWQKK-
UBP1     (  1)   -------------------------------------RNAIWLCLECGYY
UBP2     (  1)   --------------------------------------AIWLCLECGCY-
UBP27    (  1)   --------------------------------------------------
UBP22    (  1)   --------------------------------------------------
UBP20    (  1)   --------------------------------------------------
UBP21    (  1)   --------------------------------------------------
UBP23    (  1)   --------------------------------------------------
UBP25    (  1)   --------------------------------------------------
UBP15    (  1)   --------------------------------------------------
UBP16    (  1)   --------------------------------------------------
UBP17    (  1)   --------------------------------------------------
UBP18    (  1)   --------------------------------------------------
UBP19    (  1)   --------------------------------------------------
```

FIGURE 12 (continued)

```
                151                                                              200
UBP9   (137)    RELYEKVCAMTGVPQEKAHIWDYFDKRKNGLLDPLSYKSLEESSLHMDQD
UBP10  (137)    RELYEKVCALTGVPQEKAHIWDYFDKRKNGLLDSLSYKSLEESSLHMDQD
UBP11  (136)    GQLYEMVCAGKGVAKEKARIWDYFEKKKSVLLDPSSEQSVEEAGLQFNQD
UBP5   (151)    RELHRRACEIFDLDSEHVRIWDYYGHQKYSLMNDLD-KTLDDANLQMDQD
UBP8     (1)    --------------------------------------------------
UBP24    (1)    --------------------------------------------------
UBP3     (1)    --------------------------------------------------
UBP4     (1)    --------------------------------------------------
UBP12   (64)    AQFSLAVVNQIHTRYTVRKETQHQFNARESDWGFTSFMPLSELYDPSRGY
UBP13   (64)    SQFSLAVVNQVNNRYSIRKETQHQFNARESDWGFTSFMPLSELYEPTRGY
UBP26    (1)    --------------------------------------------------
UBP14   (14)    LTDGMILCGRKNWDGTGGNNHAVEHYKETAYPLAVKLGTITADLEAADVY
UBP6    (10)    VLDGIEIDVSLPPYVFKAQLYDLTGVPPERQKIMVKGGLLKDD---GDWA
UBP7    (11)    VFESIEIDTSQPPFVFKAQLYDLSGVPPERQKIMVKGGLLKDD----ADWS
UBP1    (14)    VCGDVGLPTEAQSHVMGHNRLTRHRLVIQCKNPQLRWCFSCQSLLPFDNE
UBP2    (12)    VCGGVGLPNGPQSHVLRHSRVTRHRLVIQWENPQLRWCFPCQLLLPVEKE
UBP27    (1)    --------------------------------------------------
UBP22    (1)    --------------------------------------------------
UBP20    (1)    --------------------------------------------------
UBP21    (1)    --------------------------------------------------
UBP23    (1)    --------------------------------------------------
UBP25    (1)    --------------------------------------------------
UBP15    (1)    ---------------------------------CARCFGPAKTRCSRCKSVRYCSGKCQIIHWRVA
UBP16    (1)    ---------------------------------CPVCYCLATTRCSRCKAVRYCSGKCQIIHWRQG
UBP17    (1)    ---------------------------------CAVCLYPTTRCSQCKSVRYCSSKCQILHWRRG
UBP18    (1)    ---------------------------------CSVCGNFSTKKCSRCKSVRYCSAECQRSDWSSG
UBP19    (1)    ---------------------------------CSVCGKATTKKCSRCKSVRYCSAACQTSDWKSG
```

FIGURE 12 (continued)

```
                 201                                                      250
UBP9    (187) ILVEVD------GLSNLGNTCFMNSALQCLAHTPPIVEY--FLQ-DY
UBP10   (187) ILLEVD------GLSNLGNTCFMNSALQCLAHTPPIVEY--FLQ-DY
UBP11   (186) ILLEVDGSA---SSQGLQNLGNTCFMNSTLQCLAHTPPIVEY--FLQ-DY
UBP5    (200) ILVEVLDINGTLSSAGLLNLGNTCFMNSAIQCLVHTPEFASY--FQE-DY
UBP8      (1) ------------GLQNLGNTCFMNSSLQCLAHTPKLVDF--FLG-EY
UBP24     (1) --PR--------GLINAGNLCFLNATLQALLSCSPFVQL--LQK-IQ
UBP3      (1) ------------GFENFGNTCYCNSVLQALYFCVPFREQ--LLEYYT
UBP4      (1) ------------GFENFGNTCYCNSVLQALYFCAPFREQ--LLEHYA
UBP12   (114) LVNDTVLVEAEVGFVGLKNQGATCYMNSLLQTLYHIPYFRKAVYHMPTTE
UBP13   (114) LVNDTVLIEAEVGFVGLKNQGATCYMNSLLQTLYHIPYFRKAVYHMPTTE
UBP26     (1) ------------GLTNLGATCYANSILQCLYMNTAFREG--VFSVEV
UBP14    (64) SYPEDDSVLDPLLAEGLVNLGNSCYLAATMQIVFSTHSFISR--YFSHQS
UBP6     (57) AIGVKDGQKLMMGTGLVNLGNTCYMNSTVQCLKSVPELKSA--LSNYS-
UBP7     (58) TLGLKNGQKLMMGTGLVNLGNTCYMNSTMQCLISVPELKSE--LSNY--
UBP1     (64) ENG---------GLVNLGNTCFFNSVMQNLLSLDQLREH--FLKEDL
UBP2     (62) DNGEKKD-----GLVNLGNTCFFNSIMQNLLSLDRLRDH--FLKENG
UBP27     (1) ------------GLQNLGNNCFLNVILQALASCKDFRSFLQWVLEDA
UBP22     (1) --R---------GLNNLGSTCFMNAVLQALVHAPPLRNF--WLSGQH
UBP20     (1) GA----------GLWNLGNSCFLNSVFQCFTHTVPLIES--LLSFRY
UBP21     (1) GA----------GLYNSGNTCFIASVLQCFTHTVPLIDS--LRSFMY
UBP23     (1) GA----------GLQNLGNTCFLNSVLQCLTYTEPLAAT--LQTAAH
UBP25     (1) PL----------GLRNLGNTCYLNSVLQCLTFTPPLANF--CLTHKH
UBP15    (34) HK---PR-----GLVNCGNSCYANAVLQSLTCTKPLVAY--LLRRSH
UBP16    (34) HKDECPC-----GLINVGNSCFANVVFQCLMFTPPLTTY--FLQQFH
UBP17    (34) HKEECPF-----GLVNLGNSCYANAVLQCLAFTRPLISY--LIRGLH
UBP18    (34) HQRNCPC-----GLMNCGNSCFANVILQCLSWTRPLVAY--LLEKGH
UBP19    (34) HKLKCPC-----GLTNCGNSCFANVVLQCLSWTRPLVAY--LLERGH
```

FIGURE 12 (continued)

```
       251                                                                  300
UBP9   (225) SDDINR------DNPLGMCGELAIAFGDL---------------LKKL--WSS-
UBP10  (225) SDDINR------DNPLGMCGELAIAFGDL---------------LKKL--WSS-
UBP11  (230) RSDINA------KNPLGMRGELAIAFGEL---------------LRKL--WSS-
UBP5   (247) HQEINW------QNPLGMVGELALAFGDL---------------LRKL--WAP-
UBP8   (33)  SKEINL------DNPLGMKGEIALAFGDL---------------LRSL--WAP-
UBP24  (35)  LQDI-------------------------------------------------
UBP3   (34)  SNKSVAD-----AEEN-------LMTCLADL-------------FSQIS--SQK
UBP4   (34)  NNK---AD----AEEN-------LLTCLADL-------------FSQIS--SQK
UBP12  (164) NDAPT-------AS---------IPLALQSL-------------FYK----LQY
UBP13  (164) NDAPT-------AS---------IPLALQSL-------------FYK----LQY
UBP26  (34)  HVLK--------QNP--------VLDQIARL-------------FAQLH--ASQ
UBP14  (112) LKMAFE------MAPADPTLDLNMQLTKLGHGLLSGKYSMPATQKDATTGD
UBP6   (104) ------------LAARSNDVDQTSHMLTV---------------ATRELFGELD
UBP7   (104) ------------QSARTKDVDQTSHMLTV---------------ATRELFSELD
UBP1   (100) S---VSG-----PLVSSLKEL-----------------------FAESNSEASV
UBP2   (102) SG--VGG-----PLASSLRKL-----------------------FTETKPEAG-
UBP27  (36)  RGSLAGE-----QEE-QL-----PLTFALSAL------------LQELGTVGS-
UBP22  (35)  NRDLCPR-----RTMGLL-----CLPCDLDVI------------FSAM--FSG-
UBP20  (36)  EVPCHCG-----NEFF-------CVIRAIRYH------------IEAA--LRP-
UBP21  (36)  GNPCNCG-----NEKF-------CVMQALRDH------------IELA--LRS-
UBP23  (36)  QKYCH-------VAGF-------CALCAIQKH------------VRTA---RQA
UBP25  (36)  SSHCDTYVDGERKRD--------CPFCIVEKR------------IARS---LSV
UBP15  (71)  SRSCS-------GKDW-------CLMCELEQH------------VMM----LRE
UBP16  (74)  SRACT-------KKEQ-------CFTCGFEKL------------VVK----AKE
UBP17  (74)  SKTCR-------KKSW-------CFVCEFEHL------------ILK----ARG
UBP18  (74)  KRECM-------RNDW-------CFLCEFQTH------------VER----ASQ
UBP19  (74)  KRECR-------RNDW-------CFLCEFENH------------LDR----ANY
```

FIGURE 12 (continued)

```
              301                                                        350
UBP9   (255)  GR-NAVAPRAFKTKLARFAPQFSGYN-----QHDSQELLAFLLDGLHEDL
UBP10  (255)  GR-NSVAPRAFKTKLARFAPQFSGYN-----QHDSQELLAFLLDGLHEDL
UBP11  (260)  GQ-NTVAPRAFKTKLARFAPQFSGYN-----QHDSQEMLAFLLDGLHEDL
UBP5   (277)  GR-TPIAPRPFKAKLARFAPQFSGYN-----QHDSQELLAFLLDGLHEDL
UBP8    (63)  GA-STVAPRTFKAKLARFAPQFSGFN-----QHDSQELLAFLLDGLHEDL
UBP24   (39)  -------PKADSPTLAAFSEFISELD-----VPSS--------------
UBP3    (61)  KKTGVIAPKRFVQRLKKQNELFRSYM-----HQDAHEFLNYLLNEVVD--
UBP4    (59)  KKTGVIAPKRFVQRLKKQNELFRSYM-----HQDAHEFLNYLLNELVE--
UBP12  (185)  ND-TSVATKELTKSFGWDT--YDSFM-----QHDVQELNRVLCEKLED--
UBP13  (185)  ND-TSVATKELTKSFGWDT--YDSFM-----QHDVQELNRVLCEKLED--
UBP26   (57)  K--SFVDSDAFVKTLELDN-----GV-----QQDTHEFLTLLSLLER---
UBP14  (157)  PRQEGIPPRMFKNVIAASHAEFSSMR-----QQDALDFFLHLVGKVER--
UBP6   (131)  RSVNAVSPSQFWMVLRKKYPQFSQLQNGMHMQQDAEECWTQLLYTLSQ--
UBP7   (131)  KSVKAVAPMPFWMVLQKKYPQFAQLHNGNHMQQDAEECWTQMLYTLSQ--
UBP1   (123)  FR-NEINPRDLFFSVCSQAPQFRGYQ-----QHDSHELLRCLLDGLSIEE
UBP2   (125)  LK-SVINPRAFFGSFCSKAPQFRGYD-----QHDSHELIRCLLDSLSTEE
UBP27   (66)  RR-SVSNPRKVMVTLTDYAKNFNLTS-----QQDAAEALLHLISSLQEEI
UBP22   (64)  DR-TPYSPAHLLYSWWQHSTNLATYE-----QQDSHEFFISLLDRIHE--
UBP20   (63)  ER-CPIAPYFFFDNLNYFSPDFQRYQ-----QEDAHEFLQAFLEKLEI--
UBP21   (63)  SG-YGINIDRFRDNLTYFSSDFMINH-----QEDAHEFLQSFLDKLER--
UBP23   (61)  NG-RILAPKDLVSNLRCISRNFRNCR-----QEDAHEYMINLLECMHK--
UBP25   (67)  DL-TTDAPNKISSCLKIFAEHFKLGR-----QEDAHEFLRYVIDACHN--
UBP15   (95)  SG-GPLSASRILSHMRSINCQIGDGS-----QEDAHEFLRLLVASMQS--
UBP16   (98)  EK-SPLSPNGLLSQLQNIGIFLGNGK-----EEDAHEFLRFVVDTMQS--
UBP17   (98)  GE-SPLSPIKILSKLQKIGKHLGPGK-----EEDAHEFLRCAVDTMQS--
UBP18   (98)  SR-FPFSPMNIISRLTNIGGTLGYGR-----QEDAHEFMRYAIDMMQS--
UBP19   (98)  SR-FPFSPMNIISRLPNIGGNLGYGR-----QEDAHELMRFAIDMMQS--
```

FIGURE 12 (continued)

```
           351                                                           400
UBP9   (299) NKVKRRKPYIELKDSDSR------------------PDDEVAEELWNYHKARNDS-----
UBP10  (299) NKVKRRKPYIELKDSDSR------------------PDDEVAEELWNYHKARNDS-----
UBP11  (304) NKVKRRKPYIEAKDSDGR------------------PDDEVAEEKWKYHKARNDS-----
UBP5   (321) NRVKHKPYINSRDADGR-------------------PDEEVADEFWKNHIARNDS-----
UBP8   (107) NRVKNKPYVEAKDGDGR-------------------PDAEVADEYWRNHVARNDS-----
UBP24   (62) ------S-----------------------------------------SIRNNV-----
UBP3   (104) ------ILEKEAKATKTE---H-ETSSSSSPEKIANGLKVPQANGVVHK-----------
UBP4   (102) ------ILEKETQATKAD---N-ETSS--SPEKIANVLKAPLANG-VHK-----------
UBP12  (225) ------KMKG--------------------------------------TVVEG------
UBP13  (225) ------KMKG--------------------------------------TVVEG------
UBP26   (93) ------CLLHSGVKAK--------------------------------------------
UBP14  (200) ------ASNTTPDLD-----------------------------PSRSFKFGIEEK---
UBP6   (179) ------SLKAPTSSE-----------------------------GADAVKALFGVN---
UBP7   (179) ------SLKLPSPSE-----------------------------DPDAVKALFGLN---
UBP1   (167) SSLRKKLGVSDSNDSSTYQKPTLIDSVFGGEISSTVSCLECGHFSK--------------
UBP2   (169) SALRKKRGVSDNDEKST-------TLIESVFGGETSSIVSCMECGHSSK-----------
UBP27  (110) VVCYRP--SQSSNLSD--------------ILF------S--RNLRMLAPSE-------
UBP22  (106) ------NEGKSK------------------CLY------Q--DNEECQCIT--------
UBP20  (105) ------CGSDRTSF-----------------------------RGDITSQD--------
UBP21  (105) ------CCLDPKNQ-----------------------------LGSVSSQDLN------
UBP23  (103) ------CSLPSGVP-----------------------------SESSDAYRRS------
UBP25  (109) ------TSLRLKKLR----------------------------Y-NGNEPFNGNS----
UBP15  (137) ------ICLERLGGE----------------------------T-KVDPRLQETT----
UBP16  (140) ------VCIKASEYD----------------------------M-TKSSKLEDTT----
UBP17  (140) ------VFLKEAP------------------------------AAGPFAEETT------
UBP18  (140) ------VCLDEFGGE----------------------------K-IVPPRSQETT----
UBP19  (140) ------VCLDEFGGE----------------------------K-VVPPRAQETT----
```

FIGURE 12 (continued)

```
                                                                           450
UBP9   (335) ----VIVD------------------------------------------------------
UBP10  (335) ----VIVD------------------------------------------------------
UBP11  (340) ----VIVD------------------------------------------------------
UBP5   (357) ----IIVD------------------------------------------------------
UBP8   (143) ----IIVD------------------------------------------------------
UBP24  (69)  ----TVVE------------------------------------------------------
UBP3   (143) EPIVTWVHN-----------------------------------------------------
UBP4   (138) EPIVTWVHK-----------------------------------------------------
UBP12  (234) ----TIQQ------------------------------------------------------
UBP13  (234) ----TIQK------------------------------------------------------
UBP26  (103) ----TIVQD-----------------------------------------------------
UBP14  (221) ----ILCP------------------------------------------------------
UBP6   (200) ----LQS-------------------------------------------------------
UBP7   (200) ----LLN-------------------------------------------------------
UBP1   (213) -VYEPFMDLSLPVPSMKLPPKKQQILSQAKEVLKNGAVSKDSEVVSAKPA
UBP2   (211) -VYEPFLDLSLPVPFKKSPPKKPQPVSRAKKAKLP------PKRVP--KNV
UBP27  (138) -GLHGLMEL-----------K---RWHKHLRG------------------------------
UBP22  (125) ----------------K---RWHKHLRG----------------------------------
UBP20  (121) ---------------HK---------------------------------------------
UBP21  (123) ----IVDN------------------------------------------------------
UBP23  (121) ----LVHK------------------------------------------------------
UBP25  (129) ----VVKE------------------------------------------------------
UBP15  (157) ----LVQH------------------------------------------------------
UBP16  (160) ----LIGL------------------------------------------------------
UBP17  (157) ----LVGL------------------------------------------------------
UBP18  (160) ----LIQY------------------------------------------------------
UBP19  (160) ----LIQY------------------------------------------------------
```

FIGURE 12 (continued)

```
                451                                                             500
UBP9   (339) ------------VCQG-------------------QYKSTLVCPVCGK-----ISI-
UBP10  (339) ------------VCQG-------------------QYKSTLVCPACGK-----ISI-
UBP11  (344) ------------VFQG-------------------QYKSTLVCPDCGK-----ISI-
UBP5   (361) ------------VCQG-------------------QYKSTLVCPICNK----VSV-
UBP8   (147) ------------VCQG-------------------QYKSTLVCPICKK----VSV-
UBP24   (73) ------------AGR--------------------------------------
UBP3   (152) ------------IFQG-------------------ILTNETRCLRCET----VTA-
UBP4   (147) ------------IFQG-------------------ILTNETRCLRCET----VTA-
UBP12  (238) ------------LFEG-------------------HHMNYIECINVDF----KST-
UBP13  (238) ------------LFEG-------------------HHMNYIECINVDY----KST-
UBP26  (108) ------------LFSG-------------------SVSHVTTCSKCGRDS-EASS-
UBP14  (225) ------------S-GK-------------------VGYNKREDCILSLNIPLHEATN
UBP6   (203) ------------------------------------------RLHCQESG--EESS-
UBP7   (203) ------------------------------------------RLHCQESS--EESS-
UBP1   (262) SDHNSTVPLFPSDHKIQSRPETSDNETDLVLLSDVSDTAPSTE--AKG-
UBP2   (253) SKVSKVSKVLPG---MVLSELNSSGKS--MAVTADSDTSCSSL--APL-
UBP27  (155) ------------PFDG-------------------ILGSTLMCRTCSSQ---ISL-
UBP22  (127) ------------AFSG-------------------LLRSDVTCTTCGS----TST-
UBP20  (121) ------------VFSG-------------------RLISGLRCCNCDY----VSE-
UBP21  (127) ------------VFGG-------------------GLMSTLCCCNCNS----VSN-
UBP23  (125) ------------IFGG-------------------SLRSQVKCEQCSH----CSN-
UBP25  (133) ------------IFGG-------------------ALQSQVKCLSCGA----ESN-
UBP15  (161) ------------MFGG-------------------RLRSKVKCLRCDH----ESE-
UBP16  (164) ------------TFGG-------------------YLRSKIKCMKCQV----KSE-
UBP17  (161) ------------TFGG-------------------YLHSKIKCMACLH----KSE-
UBP18  (164) ------------IFGG-------------------LLQSQVQCTVCNH----VSD-
UBP19  (164) ------------IFGG-------------------LLQSQVQCTACSN----VSD-
```

FIGURE 12 (continued)

```
                501                                                           550
UBP9   (359)  --TFDPFMYLSVPLPSTLTRSMTITVFYCDGSRLPMPYTVIVPKQGSIRD
UBP10  (359)  --TFDPFMYLSVPLPSTLTRSMTVTVFYCDGSHLPMPYTVIVPKNGSIRD
UBP11  (364)  --TFDPFMYLSLPLPSSRTRSMTVTVFYGDGSHLPMPYTVTVPKDGSCRD
UBP5   (381)  --TFDPFMYLSLPLQFNTTRAITVTVFSCDKTALPSTITVNVSKQGRCRD
UBP8   (167)  --MFDPFMYLSLPLPCTSMRTMDLTVMSADGSSLPIPLTVNVPKFGKFED
UBP24   (76)  --PFRPAMFEGV-----LRNFTPDVLN-----------------------
UBP3   (172)  --RDETFLDLSLDIE-----------------------------------
UBP4   (167)  --RDETFLDLSLDIE-----------------------------------
UBP12  (258)  --RKESFYDLQLDVKG----------------------------------
UBP13  (258)  --RKESFYDLQLDVKG----------------------------------
UBP26  (131)  --KMEDFYALELNVK-----------------------------------
UBP14  (250)  KDELEAFHKQKAGKGLEEND------------------------------
UBP6   (215)  --ETESVYSLKCHISHEVNH------------------------------
UBP7   (215)  --ETESVFSLKCHISHEVNH------------------------------
UBP1   (308)  --VNQILVGSTETL----MHDNDRTGKTVPDKEDVRATQSNEETSASGIS
UBP2   (294)  --DNGPVLETPSVL----TLDNNQASES------ASQSDTGFDGS-WL
UBP27  (176)  --EFQFFHTLPLSP----LLHH--------------------GG------
UBP22  (147)  --TYDPFIDISLT-------------------------------------
UBP20  (141)  --TYEKSVGLSLEI----ED------------------------------
UBP21  (147)  --TFEPSLGWSLEI----ED------------------------------
UBP23  (145)  --KFDPFLDLSLDI----S-------------------------------
UBP25  (153)  --KADEIMDISLEI----L-------------------------------
UBP15  (181)  --RYENIMDLTLEI----YG------------------------------
UBP16  (184)  --LREKMMDLTVEI----DG------------------------------
UBP17  (181)  --RPELMMDLTVEI----DG------------------------------
UBP18  (184)  --QYENMMDLIVEM----HG------------------------------
UBP19  (184)  --QYENMMDLTVEI----HG------------------------------
```

FIGURE 12 (continued)

```
         551                                                            600
UBP9   (407) LITALGTAC---------------CLAEDE-------------------------------
UBP10  (407) LITALGTAC---------------LLAEDE-------------------------------
UBP11  (412) LSNALGTAC---------------CLDNDE-------------------------------
UBP5   (429) LIQALTNAC---------------SLKQSE-------------------------------
UBP8   (215) LHKALVTAC---------------SLPEEE-------------------------------
UBP24   (96) -------------------------------------------------------------
UBP3   (185) -------------------------------------------------------------
UBP4   (180) -------------------------------------------------------------
UBP12  (272) -------------------------------------------------------------
UBP13  (272) -------------------------------------------------------------
UBP26  (144) -------------------------------------------------------------
UBP14  (270) -------------------------------------------------------------
UBP6   (233) -------------------------------------------------------------
UBP7   (233) -------------------------------------------------------------
UBP1   (352) AVIDEAQVCGCPDLEQSSSSANQGADEELALMVADSQVLYMPYKDHLFYD
UBP2   (329) DFIGPETSGDETNLDMQEDGIDNVITAEVNQIVPSPNIV-----------
UBP27  (194) -------------------------------------------------------------
UBP22  (158) -------------------------------------------------------------
UBP20  (155) -------------------------------------------------------------
UBP21  (161) -------------------------------------------------------------
UBP23  (158) -------------------------------------------------------------
UBP25  (166) -------------------------------------------------------------
UBP15  (195) -------------------------------------------------------------
UBP16  (198) -------------------------------------------------------------
UBP17  (195) -------------------------------------------------------------
UBP18  (198) -------------------------------------------------------------
UBP19  (198) -------------------------------------------------------------
```

FIGURE 12 (continued)

```
                                                    601                                                    650
UBP9   (422) ------------------------------------------------S---LLL-AEVYD
UBP10  (422) ------------------------------------------------S---LLL-AEVYD
UBP11  (427) ------------------------------------------------S---LLL-AEVYD
UBP5   (444) ------------------------------------------------E---LKL-AEIRN
UBP8   (230) ------------------------------------------------T---LLV-TEVYN
UBP24   (96) ----------------------------------------------------NMSG
UBP3   (185) --------------------------------------------------------
UBP4   (180) --------------------------------------------------------
UBP12  (272) --------------------------------------------------------
UBP13  (272) --------------------------------------------------------
UBP26  (144) --------------------------------------------------------
UBP14  (270) --------------------------------------------------------
UBP6   (233) --------------------------------------------------------
UBP7   (233) --------------------------------------------------------
UBP1   (402) DYMVAEASSSFVSGDHEPKKDYFDFSSFLDEPEIREGPVFRPLSKSEVYE
UBP2   (368) --ANSSVSSGDQ--------------------TLEGNTERLMQD--YE
UBP27  (194) --------------------------------------------------------
UBP22  (158) --------------------------------------------------------
UBP20  (155) --------------------------------------------------------
UBP21  (161) --------------------------------------------------------
UBP23  (158) --------------------------------------------------------
UBP25  (166) --------------------------------------------------------
UBP15  (195) --------------------------------------------------------
UBP16  (198) --------------------------------------------------------
UBP17  (195) --------------------------------------------------------
UBP18  (198) --------------------------------------------------------
UBP19  (198) --------------------------------------------------------
```

FIGURE 12 (continued)

```
              651                                                          700
UBP9   (431)  HKIFRYFEIPLDSLSAIKDDEHIVAYRLNQIPKGSRKAKLEILHGGQERA
UBP10  (431)  HKIFKYFENPLDSLSSIKDDEHIVAYRLNQMPKGSGKAKLEILHGGQKRP
UBP11  (436)  HKVFKYYENPRELLNGIKDNEHIVAYRFKQMHKGPGKVKLEILHGEQEK-
UBP5   (453)  NFIHRLFEDPLIPLSSIKDDDHLAAYKLSKSSENTTLLRLVLRRRDQKAG
UBP8   (239)  NRIIRFLEEPTDSLTLIRDGDKLVVYRLKKDANNS--PLIVYMHQKLEEQ
UBP24  (100)  RPR---QEDAQEFLSFIMDQMHDELLKLKE--------------------
UBP3   (185)  --------------------------------------------------
UBP4   (180)  --------------------------------------------------
UBP12  (272)  --------------------------------------------------
UBP13  (272)  --------------------------------------------------
UBP26  (144)  --------------------------------------------------
UBP14  (270)  --------------------------------------------------
UBP6   (233)  --------------------------------------------------
UBP7   (233)  --------------------------------------------------
UBP1   (452)  AGFKADCS-DDKTVSAGKGEASSSFISSDHEQNIDYVDFSSFFDEPEISE
UBP2   (392)  EIAKAEANLDEKDVQAMQSDEC----------------------------P
UBP27  (194)  ------YNIMSG--C-----------------------------------
UBP22  (158)  ------LDSMNG--F-----------------------------------
UBP20  (155)  --------------------------------------------------
UBP21  (161)  --------------------------------------------------
UBP23  (158)  --------------------------------------------------
UBP25  (166)  --------------------------------------------------
UBP15  (195)  --------------------------------------------------
UBP16  (198)  --------------------------------------------------
UBP17  (195)  --------------------------------------------------
UBP18  (198)  --------------------------------------------------
UBP19  (198)  --------------------------------------------------
```

FIGURE 12 (continued)

```
         701                                                                750
UBP9   (481) VLDSVRGSDVKLFGTPFVTYVNT-EPLSGTDIDAVISGFLSPLHK-----
UBP10  (481) ILESVRGRDVKLFGTPFVTYVNT-EPLSGADIDAVLSRFLSPLHK-----
UBP11  (485) --SSDRGP--KCFGTPLVTYINK-EPLSGTDIATSIGLLSPLRR-----
UBP5   (503) --ERESTVQLKPCGTPLLSSASCGDALTKGKIHCLVQNMLSPFRREE---
UBP8   (287) FISGKSSPTWKAFGIPLVSRLC--DVENGSDVENLYLKLLSSFKMP----
UBP24  (127) --QS-------------------PKVTASK-------------------
UBP3   (185) -------------------------------------------------
UBP4   (180) -------------------------------------------------
UBP12  (272) -------------------------------------------------
UBP13  (272) -------------------------------------------------
UBP26  (144) -------------------------------------------------
UBP14  (270) -------------------------------------------------
UBP6   (233) -------------------------------------------------
UBP7   (233) -------------------------------------------------
UBP1   (501) RPFFRPLSKSEVSEAGFKADCSDDKTVSAGKGEASSFVSSDHEQNIDYV
UBP2   (415) ----ATSGISAEFSQASCIG----CDPGIGESSS----SVNP-------
UBP27  (201) ----TLEHCL---------------------------------------
UBP22  (165) ----SPADCR---------------------------------------
UBP20  (155) -------------------------------------------------
UBP21  (161) -------------------------------------------------
UBP23  (158) -------------------------------------------------
UBP25  (166) -------------------------------------------------
UBP15  (195) -------------------------------------------------
UBP16  (198) -------------------------------------------------
UBP17  (195) -------------------------------------------------
UBP18  (198) -------------------------------------------------
UBP19  (198) -------------------------------------------------
```

FIGURE 12 (continued)

```
                    751                                                          800
UBP9   (525)  -----VHAPSKIHNGSDNGHLADAT-VDQASGILSSPDTEIDNASD---R
UBP10  (525)  -----VHAPSKIHNGSENGHLPDAT-VDEASEILSSPDTEIDDASD---R
UBP11  (525)  -----VHMSCVVNSGNENGHVP---DESSRSILSRDTETEDN-D---R
UBP5   (548)  SVGKKGNSDSSIPERRSARFNTEEEDKVGGLKKAKKSNSSDLGAS
UBP8   (331)  TEFFTENLENPTEEEATDKTD-TDGTTSVEDTNSTDVKETTES-LP
UBP24  (136)  ---------SSVISSANDDG------DEWETVGPKNKSAVT-----
UBP3   (185)  ----------------------------------------------
UBP4   (180)  ----------------------------------------------
UBP12  (272)  ----------------------------------------------
UBP13  (272)  ----------------------------------------------
UBP26  (144)  ----------------------------------------------
UBP14  (270)  ----------------------------------------------
UBP6   (233)  ----------------------------------------------
UBP7   (233)  ----------------------------------------------
UBP1   (551)  DFSSEFDEPEISERPFFRPLSKSEVSEAGFMAVSGNDKTVRAGKGET---
UBP2   (445)  ----WDEEELP------LVVADSQILYMPYKEISCNDKSVEG-ECEA
UBP27  (207)  ---------------------------------------K--KF-
UBP22  (171)  ---------------------------------------K--NR-
UBP20  (155)  ----------------------------------------------
UBP21  (161)  ----------------------------------------------
UBP23  (158)  ----------------------------------K-----------
UBP25  (166)  ----------------------------------Q-----------
UBP15  (195)  ----------------------------------W-----------
UBP16  (198)  ----------------------------------D-----------
UBP17  (195)  ----------------------------------D-----------
UBP18  (198)  ----------------------------------D-----------
UBP19  (198)  ----------------------------------D-----------
```

FIGURE 12 (continued)

```
                  801                                                   850
UBP9    (566) ELSFRIFLTDERGLNIKP-LQSESSISPGTVTRVLVEWNEGEHERYDSSY
UBP10   (566) ELSFRIFLTDERGLNFKP-LQSESSISLGIATRVLVEWNEGEHERYDSSY
UBP11   (561) ELSLSLLR-DYYSFNLQP-LESDSVVNPGSVTKVLVKWNEKEHEKYDSSY
UBP5    (594) KLSLQLIDEDNKTINLPDNEAEAMKLPSSATVTIYLDWTPELSGMYDITC
UBP8    (375) DPVLRLYLTDDRGNSIEAEMLKEKPVNKSKRLNVIARWPVKELDVYDTCL
UBP24   (162) ------------------RTQSFVP---SELSEIFGGQLKSVVKAKGTKASATVQPYL
UBP3    (185) --------------------------------------------------
UBP4    (180) --------------------------------------------------
UBP12   (272) --------------------------------------------------
UBP13   (272) --------------------------------------------------
UBP26   (144) --------------------------------------------------
UBP14   (270) --------------------------------------------------
UBP6    (233) --------------------------------------------------
UBP7    (233) --------------------------------------------------
UBP1    (598) ------FSSFMSGDNE-RNIDYVEFTNRIFDDRGTSERPVFGPPSKAKV
UBP2    (481) -------SSSFVTGDHEPQNSDFVDFGG-LFDEPETTEGPVFGPPSKAEA
UBP27   (210) -----LNTEKV----ENYFCYRC---------------------W----
UBP22   (174) -----YSGGPS----VN---------------------------------
UBP20   (155) --------------------------------------------------
UBP21   (161) --------------------------------------------------
UBP23   (159) --------------------------------------------------
UBP25   (167) --------------------------------------------------
UBP15   (196) --------------------------------------------------
UBP16   (199) --------------------------------------------------
UBP17   (196) --------------------------------------------------
UBP18   (199) --------------------------------------------------
UBP19   (199) --------------------------------------------------
```

FIGURE 12 (continued)

```
           851                                                              900
UBP9   (615) LSDLPEVHKTS--FSAKKTRQESISLFSCLEAFLAEEPLG-PDDMWFCPS
UBP10  (615) LSDLPEVHKTS--FSAKKTRQESISLFSCLEAFLAEEPLG-PDDMWFCPS
UBP11  (609) LNDLPKVHKN---VLAKKTMQEGISLFSCIEAFLAEEPLG-PDDMYCPG
UBP5   (644) LESLPEVLKYG--PTTKKARSEPLSLYACLEAFLREEPLV-PDEMWFCPQ
UBP8   (425) LSSLPEVSKS----GTKRPQESVSLFKCLEAFLTEEPLG-PDDMYCPG
UBP24  (199) LLHL-DIHPD------GVQGIEDALHLFSAQEDLEGYRASV-TGKTGVVS-
UBP3   (185) --Q---NSS------------------ITSCLKNFSSTETLH-AEDKFFCDK
UBP4   (180) --Q---NSS------------------ITSCLKNFSSTETLH-AEDKFFCDK
UBP12  (272) ------CKD------------------VYASFDKYVEVERLE-GDNKYHAEG
UBP13  (272) ------CKD------------------VYASFDKYVEVERLE-GDNKYHAEG
UBP26  (144) --G---LKS------------------LDASLNDYLSLEQLN-GDNQYFCGS
UBP14  (270) ------MRSSD-------EI--VRPRVPLEACLANFASSEPIE----DYYSSA
UBP6   (233) ------LHEG--------------------LKHGLKGELEKT-------SPA
UBP7   (233) ------LHEG--------------------LKHGLKGELEKT-------SPS
UBP1   (640) SEAGFVAVSSDSDPAVLDESDSPVSVDRCLAQFTKHEILS-EDNAWHCEN
UBP2   (523) SGVGFMAFSSESDPEEIDDSDLPVSVERCLGHFTKHEILS-DDNAWNCEN
UBP27  (225) HGAALKYLS-----------------VIGAAETEIEKLR-SCGGEDQCD
UBP22  (182) --AIMPTLS------------------GCLDFFTRSEKL-----GPDQKLN
UBP20  (155) ------VDT------------------LGSALESFTRVEKLD---EQLTCDN
UBP21  (161) ------VNT------------------LWKALESFTCVEKLE---DQLTCDN
UBP23  (159) ------ADS------------------LQRALSRFTAVELLDNGAKVYQCER
UBP25  (167) ------SSS------------------VKESLQKFFQSEILD-GNNKYRCES
UBP15  (196) ------VES------------------LQDALTQFTRPEDLD-GENMYRCSR
UBP16  (199) ------IST------------------LDDALRRFTRTEILD-GENKYRCGS
UBP17  (196) ------IGS------------------LEEALAQFTAYEVLD-GENRYFCGR
UBP18  (199) ------AGS------------------LEECLDQFTAEEWLH-GDNMYKCDR
UBP19  (199) ------AVS------------------LEECLDQFTAKEWLQ-GDNLYKCDR
```

FIGURE 12 (continued)

```
         901                                                     950
UBP9   (662) CKE----------------------------------------------
UBP10  (662) CKE----------------------------------------------
UBP11  (655) CKE----------------------------------------------
UBP5   (691) CNE----------------------------------------------
UBP8   (469) CKE----------------------------------------------
UBP24  (241) -------------------------------------------------
UBP3   (213) CCS----------------------------------------------
UBP4   (208) CCS----------------------------------------------
UBP12  (299) -HG----------------------------------------------
UBP13  (299) -HD----------------------------------------------
UBP26  (172) CNA----------------------------------------------
UBP14  (304) LKG----------------------------------------------
UBP6   (252) LGR----------------------------------------------
UBP7   (252) LGR----------------------------------------------
UBP1   (689) CSKNLKLQRLREKRRTKEGLSNRWVNENGASSAFDECRDSSLNQSCIDLE
UBP2   (572) CSKNLKLQRLREKRKSNE-------------DESR-SS------NTS
UBP27  (256) CKTSLHLQRMP--WSNS--------------------------------
UBP22  (208) CQS---------CGE----------------------------------
UBP20  (180) CNE----------------------------------------------
UBP21  (186) CKE----------------------------------------------
UBP23  (187) CKQ----------------------------------------------
UBP25  (194) CEK----------------------------------------------
UBP15  (223) CAG----------------------------------------------
UBP16  (226) CKS----------------------------------------------
UBP17  (223) CKS----------------------------------------------
UBP18  (226) CSD----------------------------------------------
UBP19  (226) CDD----------------------------------------------
```

FIGURE 12 (continued)

```
                                951                                                1000
UBP9   (665) ------------------------------------------HRQANKKLLDLWKLPDI--LV
UBP10  (665) ------------------------------------------HRQANKKLLDLWKLPDI--LV
UBP11  (658) ------------------------------------------HRQANKKLLDLWKLPDI--LV
UBP5   (694) ------------------------------------------RRQASKKLDLWRLPEV--LV
UBP8   (472) ------------------------------------------HRQAIKKLDLWRLPEI--LV
UBP24  (241) ------------------------------------------ASKSIKIQKLSKI--MI
UBP3   (216) ------------------------------------------LQEAQKRMKIKKPPHI--LV
UBP4   (211) ------------------------------------------LQEAQKRMKIKKPPHI--LV
UBP12  (301) ------------------------------------------LQDAKKGVLFIDFPPV--LQ
UBP13  (301) ------------------------------------------LQDAKKGVLFIDFPPV--LQ
UBP26  (175) ------------------------------------------RVDATRCIKLRTLPPV--LT
UBP14  (307) ------------------------------------------MTTAIKTTGLTSFPDY--LV
UBP6   (255) ------------------------------------------TALYVKESLIDSLPRY--LT
UBP7   (255) ------------------------------------------TAVYVKESLIDSLPRY--LT
UBP1   (739) NGYKAAPPITKLPNCKEEESAIDDGFVGEENTKQAPITSVTETPLLGGET
UBP2   (599) NGWVKE------NEDEGFGETEILAVKQDPNDTSCVKDHSSDGRKA
UBP27  (271) ------------------------------------------YSHILKQLIIARFPKL--LC
UBP22  (214) ------------------------------------------KRESSKQMSIRRLPLL--LC
UBP20  (183) ------------------------------------------KVSKEKQLLLDKLPLV--AT
UBP21  (189) ------------------------------------------KVTKEKQLRFDKLPPV--AT
UBP23  (190) ------------------------------------------KVKAKKQLTVSKAPYV--LT
UBP25  (197) ------------------------------------------LVTARKQMSILQAPNI--LV
UBP15  (226) ------------------------------------------YVRARKELSIHEAPNI--LT
UBP16  (229) ------------------------------------------YERAKKKLKITEPPNV--LT
UBP17  (226) ------------------------------------------YQKAKKKLMILEGPNI--LT
UBP18  (229) ------------------------------------------YVKACKRLTIRRAPNI--LT
UBP19  (229) ------------------------------------------YVKACKRLSIRCAPNI--LT
```

FIGURE 12 (continued)

```
UBP9   (683)  FHLKRFTYSRYLK---NKIDTFVNFPVH-------DLDLSK--------
UBP10  (683)  FHLKRFTYSRYLK---NKIDTFVNFPVH-------DLDLSK--------
UBP11  (676)  FHLKRFTYSRYFK---NKIDTLVNFHIH-------DLDLSK--------
UBP5   (712)  IHLKRFSYSRSMK---HKLETFVNFPIH-------DLDLTK--------
UBP8   (490)  IHLKRFSYSREMK---NKLEAYVDFPLD-------NLDLSS--------
UBP24  (256)  LHLMRFSYGSQGS---TKLRKGVKFPLEL------NLNRSH--------
UBP3   (234)  IHLKRFKYIEQLG-RYKKLSYRVVFP---------LELKLSN-------
UBP4   (229)  IHLKRFKYMEQLG-RYKKLSYRVVFP---------LELKLSN-------
UBP12  (319)  LQLKRFEYDFMRDT-MVKINDRYEFP---------LELDLDR-------
UBP13  (319)  LQLKRFEYDFMRDT-MVKINDRYEFP---------LQLDLDR-------
UBP26  (193)  FQLKRCIFLPKTT-AKKKITSSESFP---------QVLDMGS-------
UBP14  (325)  LHMRKFVME-EGW-VPKKLDVYIDVP---------DVIDISHMRSKGLQPG
UBP6   (273)  VQFVRFFWKRESN-QKAKILRKVDYP---------LVLDIFDLCSEDLR-
UBP7   (273)  VQFVRFFWKRESN-QKAKILRKVDYP---------LELDIYDLCSEDLR-
UBP1   (789)  ISSQPASDNECENWEDLAVDSEEVI-VKRDARKKVLINKAPPVLTIHL-
UBP2   (639)  ARIHSADESESKGTQDEDEDSEKVITVKRDATKKVLINKAPPVLTIHL-
UBP27  (289)  IQVQRASFNMFEEF---KLSGHIAF------P-LVLNLS----LFTP--
UBP22  (232)  LHVKRFEHSLTRKTS-RKIDSYLQY------P-FRLNMSP---YLSS--
UBP20  (201)  FHLKRFKNNGLY---MEKIYKHVKIP--------LEIDLQP--------
UBP21  (207)  FHLKRFTNDGVT---MEKIFDHIEFP--------LELDLSP--------
UBP23  (208)  VHLKRFEAHRSE---KIDRKVDFT----------SAIDMKP--------
UBP25  (215)  IQLKRFGGIFGG---KIDKAISFG----------EILVLSN--------
UBP15  (244)  IVLKRFQEGRYG---KINKCISFP----------EMLDMIP--------
UBP16  (247)  IALKRFQAGKFG---KLNKLIRFP----------ETLDLAP--------
UBP17  (244)  VVLKRFQSDNFG---KLSKPIHFP----------ELLDISP--------
UBP18  (247)  IALKRYQGGRYG---KLNKRISFP----------ETLDLNP--------
UBP19  (247)  IALKRFQGGRFG---KLNKRISFP----------ETFDLGP--------
```

FIGURE 12 (continued)

```
UBP9   (714)  ---------------------------------------------------
UBP10  (714)  ---------------------------------------------------
UBP11  (707)  ---------------------------------------------------
UBP5   (743)  ---------------------------------------------------
UBP8   (521)  ---------------------------------------------------
UBP24  (288)  ---------------------------------------------------
UBP3   (266)  ---------------------------------------------------
UBP4   (261)  ---------------------------------------------------
UBP12  (351)  ---------------------------------------------------
UBP13  (351)  ---------------------------------------------------
UBP26  (225)  ---------------------------------------------------
UBP14  (365)  EELLPDGVPEEVMESAQPVANEEIVAQLVSMGFSQLHCQKAAINTSNAGV
UBP6   (312)  ---------------------------------------------------
UBP7   (312)  ---------------------------------------------------
UBP1   (836)  ---------------------------------------------------
UBP2   (687)  ---------------------------------------------------
UBP27  (322)  ---------------------------------------------------
UBP22  (268)  ---------------------------------------------------
UBP20  (231)  ---------------------------------------------------
UBP21  (237)  ---------------------------------------------------
UBP23  (236)  ---------------------------------------------------
UBP25  (243)  ---------------------------------------------------
UBP15  (272)  ---------------------------------------------------
UBP16  (275)  ---------------------------------------------------
UBP17  (272)  ---------------------------------------------------
UBP18  (275)  ---------------------------------------------------
UBP19  (275)  ---------------------------------------------------
```

FIGURE 12 (continued)

```
UBP9   (714)
UBP10  (714)
UBP11  (707)
UBP5   (743)
UBP8   (521)
UBP24  (288)
UBP3   (266)
UBP4   (261)
UBP12  (351)
UBP13  (351)
UBP26  (225)
UBP14  (415) EEAMNWLLSHMDDPDIDAPISHQTSDIDQSSVDTLLSFGFAEDVARKALK
UBP6   (312) ----------------------------KKLEAPR-QKLREEEGK------KLGLQ
UBP7   (312) ----------------------------KKLEAPR-QKLRDIEGQ------KLGLQ
UBP1   (836) --------------------------------------------------K--RFS
UBP2   (687) --------------------------------------------------K--RFS
UBP27  (322) --------------------------------------------------S--SIG
UBP22  (268) --------------------------------------------------S--IIG
UBP20  (231)
UBP21  (237)
UBP23  (236)
UBP25  (243)
UBP15  (272)
UBP16  (275)
UBP17  (272)
UBP18  (275)
UBP19  (275)
```

FIGURE 12 (continued)

```
                 1151                                                       1200
UBP9   (714)     ------------------------------------YVKNKNG-QS-Y---------LYEL
UBP10  (714)     ------------------------------------YVKNKND-QS-Y---------LYEL
UBP11  (707)     ------------------------------------YVKNEDG-QS-Y---------LYEL
UBP5   (743)     ------------------------------------YVANKNL-SQPQ---------LYEL
UBP8   (521)     ------------------------------------YISYKNG-QTTY---------RYML
UBP24  (288)     ------------------------------------LVSLSN--ES-L---------RYEL
UBP3   (266)     ------------------------------------TVEPYA--D--V---------EYSL
UBP4   (261)     ------------------------------------TVDEYV--D--I---------EYSL
UBP12  (351)     --ED--------------------------------GKYLSPDADRSVRN---------LYTL
UBP13  (351)     --ED--------------------------------GRYLSPDADKSVRN---------LYTL
UBP26  (225)     ------------------------------------RLAESS--QNKL---------TYDL
UBP14  (465)     ASGGDIEKATDWVFNNPNASVSDMDVSSSNSAQTPAQSG-LPDGGKYKL
UBP6   (333)     TSAKSGSKDSDVKMTDAEASANGSGESSTVNPQEGTSSEKETHMTGIYDL
UBP7   (333)     ASAKSSSKGDDVKMTDAEGSSNQSGESSTGDQQEGASP---HMTGIYDL
UBP1   (840)     QDARGRVSKLSGHVDFQEFIDLSKYMDTRCSEEDEP---------VYRL
UBP2   (691)     QDLRGRLSKLNGHVAFKEVIDLRQYMDSRCSGEDPP---------VYRL
UBP27  (326)     VNIEERIEMSS-------------------------EYQKPEAS-KNHG---------MYRL
UBP22  (272)     KRFGNRIFAFDG----------E-----GEYDSSSSS-SPSA---------EFEI
UBP20  (231)     ------------------------------------YMRNIQENEVST---------KYHL
UBP21  (237)     ------------------------------------FMSSNHDPEVST---------RYHL
UBP23  (236)     ------------------------------------FVSGPHE-GNL---------KYTL
UBP25  (243)     ------------------------------------FMSKASK-DPQP---------EYKL
UBP15  (272)     ------------------------------------FMTRTGD-VPP---------LYML
UBP16  (275)     ------------------------------------YVSGGSE-KSH---------DYKL
UBP17  (272)     ------------------------------------YMSDPNH-GDHP---------VYSL
UBP18  (275)     ------------------------------------YMSEGGD-GSD---------VYKL
UBP19  (275)     ------------------------------------YMSGGGE-GSD---------VYKL
```

FIGURE 12 (continued)

```
              1201                                                    1250
UBP9   (728)  YAVSNHYGG-LGG----GHYTAYAKLIDDN--------------------KWYHFDD--
UBP10  (728)  YAVSNHYGG-LGG----GHYTAYAKLIDDN--------------------EWYHFDD--
UBP11  (721)  YAISNHYGG-LGG----GHYTAYAKLMDET--------------------KWYNFDD--
UBP5   (758)  YALTNHYGG-MGS----GHYTAHIKLLDDS--------------------RWYNFDD--
UBP8   (536)  YAISNHYGS-MGG----GHYTAYVHHGGD---------------------RWYDFDD--
UBP24  (301)  VATITHHGWDPSK----GHYTTDARRKNG---------------------QWLRFDD--
UBP3   (278)  FAVVVHVGSGPNH----GHYVSLVKSHNH---------------------WLFFDD--
UBP4   (273)  FAVVVHVGSGPNH----GHYVSLVKSHNH---------------------WLFFDD--
UBP12  (371)  HSVLVHSGG-VHG----GHYYAFIRPTLS---------------------DQWYKFDD--
UBP13  (371)  HSVLVHSGG-VHG----GHYYAFIRPTLS---------------------DQWYKFDD--
UBP26  (239)  SAVLIHKGSAVNS----GHYVAHIKDEKTG--------------------LWWEFDD--
UBP14  (514)  FGIVSHMGT-SVHC---GHYVAHILKE-G---------------------RWVIFND--
UBP6   (383)  VAVLTHKGR-SADS---GHYVAWKQESG----------------------KWIQYDDDN
UBP7   (379)  VSVLTHKGR-SADS---GHYVAWKQESG----------------------KWVQYDDAN
UBP1   (880)  AGLVEHLGA-MSR----GHYVSYIRGGHKERRDSDTKEPNSSIWYHASD--
UBP2   (731)  AGLVEHSGT-MRG----GHYVAYVRGGQR-VKETDS---SSTAWYNVSD--
UBP27  (353)  VTVVEHFGR-TGS----GHYTVYRSVRVFSQEEEEEDCDEDLSWFSISD--
UBP22  (302)  FAVVTHKGM-LES----GHYVTYLRLKGL---------------------WYRCDD--
UBP20  (247)  YALVEHFGY-SVA----YGHYSSYVRSAPK--------------------IWHHFDD--
UBP21  (253)  YAFVEHIGI-RAT----FGHYSSYVRSAPE--------------------TWHNFDD--
UBP23  (250)  YGVLVHYGR-SSH----SGHYACFVRTSSG--------------------MWYSLDD--
UBP25  (258)  FGIIVHSGF-SPE----SGHYYAYVKDSLG--------------------RWYCCND--
UBP15  (286)  YAVIVHLDT-LNASFSGHYISYVKDLRG----------------------NWYRIDD--
UBP16  (289)  YGVIVHLDV-MNAAFSGHYVCYIRNQN-----------------------KWYKADD--
UBP17  (287)  YAVVVHLDA-MSTLFSGHYVCYIKTLDG----------------------DWFKIDD--
UBP18  (289)  YAVIVHLDM-LNASFFGHYICYIKDFCG----------------------NWYRIDD--
UBP19  (289)  YAVIVHLDM-LNASFFGHYICYVKDFRG----------------------NWYRIDD--
```

FIGURE 12 (continued)

```
UBP9   (760) -----SHVSSVNESEIRNSAA-------------------------------
UBP10  (760) -----SHVSSVNESEIKNSAA-------------------------------
UBP11  (753) -----SRVSAVNESEIKTSAA-------------------------------
UBP5   (790) -----SHISHINEDDVKSGAA-------------------------------
UBP8   (567) -----SHVHQISQEKIKTSAA-------------------------------
UBP24  (333) -----ASVTPIGTKLVLHDQA-------------------------------
UBP3   (309) -----ENVEMIEESAVQTFFGSSQEYSSN-----------------------
UBP4   (304) -----ESVEIIEESAVQTFFGSSQEYSSN-----------------------
UBP12  (403) -----ERVTKEDLKRALEEQYGGEEELPQTNPGFNNN---------------
UBP13  (403) -----ERVTKEDVKRALEEQYGGEEELPQNNPGFNN----------------
UBP26  (272) -----EHVSELGKRPCNEASSTPQSESNGTASSGNITDGIQSGSSDCR
UBP14  (545) -----DKVGISTDPPKDMG---------------------------------
UBP6   (417) PSMQREEDITKLSGGGDWHMA-------------------------------
UBP7   (413) TSLQRGEDIIKLSGGGDWHMA-------------------------------
UBP1   (924) -----SQVRPASLEEVLRSEA-------------------------------
UBP2   (771) -----AYVRQVSLEKVLHSEA-------------------------------
UBP27  (397) -----SEVCRVSESDVLGAEA-------------------------------
UBP22  (332) -----AWINEVEEEVVRGCEC-------------------------------
UBP20  (279) -----SKVTRIDEDMVLSQDS-------------------------------
UBP21  (285) -----SKVTRISEERVLSRPA-------------------------------
UBP23  (282) -----NRVVQVSEKTVFNQKA-------------------------------
UBP25  (290) -----SFVSLSTLQEVLSEKA-------------------------------
UBP15  (320) -----SEIHPVPMTQVMSEGA-------------------------------
UBP16  (322) -----STVVTSDVERILTKGA-------------------------------
UBP17  (321) -----SNVFPVQLETVLLEGA-------------------------------
UBP18  (323) -----SEIESVELEDVLSQRA-------------------------------
UBP19  (323) -----SEVEKVELEDVLSQRA-------------------------------
```

FIGURE 12 (continued)

```
                    1301                                                      1350
UBP9    (776)  ------------------YVLFYR---------------------------------------
UBP10   (776)  ------------------YVLFYR---------------------------------------
UBP11   (769)  ------------------YVLFYQ---------------------------------------
UBP5    (806)  ------------------YVLFYR---------------------------------------
UBP8    (583)  ------------------YVLFYK---------------------------------------
UBP24   (349)  ------------------YVLFY----------------------------------------
UBP3    (333)  ----------------TDHGYILFYE-------------------------------------
UBP4    (328)  ----------------TDHGYILLYE-------------------------------------
UBP12   (435)  --PPFKFTKYSNAYMLVYIRESD----------------------------------------
UBP13   (434)  --PPFKFTKYSNAYMLVYIRESD----------------------------------------
UBP26   (316)  SAIKSEVFSSSDAYMLMYSQSLEEQYFWISTDWLRLWADTLPPALDNTP
UBP14   (559)  ------------------YVYFFQ---------------------------------------
UBP6    (438)  ------------------YITMYK---------------------------------------
UBP7    (434)  ------------------YIVMYK---------------------------------------
UBP1    (940)  ------------------YILFYE---------------------------------------
UBP2    (787)  ------------------YILFYE---------------------------------------
UBP27   (413)  ------------------SLLFYE---------------------------------------
UBP22   (348)  ------------------YMLFY----------------------------------------
UBP20   (295)  ------------------YILFYA---------------------------------------
UBP21   (301)  ------------------YILFYA---------------------------------------
UBP23   (298)  ------------------YMLFYV---------------------------------------
UBP25   (306)  ------------------YILFFS---------------------------------------
UBP15   (336)  ------------------YMLFYM---------------------------------------
UBP16   (338)  ------------------YMLFYA---------------------------------------
UBP17   (337)  ------------------YMLLYA---------------------------------------
UBP18   (339)  ------------------YMLLYS---------------------------------------
UBP19   (339)  ------------YMLLYSSEESQDEKKTDTLNTESNQDGSVESSGVGTN
```

FIGURE 12 (continued)

| | | 1351 | 1400 |
|---|---|---|---|
| UBP9 | (782) | ------------------------------------------------- | |
| UBP10 | (782) | ------------------------------------------------- | |
| UBP11 | (775) | ------------------------------------------------- | |
| UBP5 | (812) | ------------------------------------------------- | |
| UBP8 | (589) | ------------------------------------------------- | |
| UBP24 | (354) | ------------------------------------------------- | |
| UBP3 | (343) | ------------------------------------------------- | |
| UBP4 | (338) | ------------------------------------------------- | |
| UBP12 | (456) | ------------------------------------------------- | |
| UBP13 | (455) | ------------------------------------------------- | |
| UBP26 | (366) | LLCSHGKVHASKVNCMKRISELAWIKLESKFNGGPKLGKGDYCRDRTNYG | |
| UBP14 | (565) | ------------------------------------------------- | |
| UBP6 | (444) | ------------------------------------------------- | |
| UBP7 | (440) | ------------------------------------------------- | |
| UBP1 | (946) | ------------------------------------------------- | |
| UBP2 | (793) | ------------------------------------------------- | |
| UBP27 | (419) | ------------------------------------------------- | |
| UBP22 | (353) | ------------------------------------------------- | |
| UBP20 | (301) | ------------------------------------------------- | |
| UBP21 | (307) | ------------------------------------------------- | |
| UBP23 | (304) | ------------------------------------------------- | |
| UBP25 | (312) | ------------------------------------------------- | |
| UBP15 | (342) | ------------------------------------------------- | |
| UBP16 | (344) | ------------------------------------------------- | |
| UBP17 | (343) | ------------------------------------------------- | |
| UBP18 | (345) | ------------------------------------------------- | |
| UBP19 | (376) | DTSVSSLCNGIISHSEDPEYEKESSLSASVPVSEEGKEVDVKVDTVDSES | |

FIGURE 12 (continued)

```
                                                                1401                                              1450
UBP9    (782)  --------------------------------------------------
UBP10   (782)  --------------------------------------------------
UBP11   (775)  --------------------------------------------------
UBP5    (812)  --------------------------------------------------
UBP8    (589)  --------------------------------------------------
UBP24   (354)  --------------------------------------------------
UBP3    (343)  --------------------------------------------------
UBP4    (338)  --------------------------------------------------
UBP12   (456)  --------------------------------------------------
UBP13   (455)  --------------------------------------------------
UBP26   (416)  NLTSLKVSATTTVYQLKMMIWELLGVMKENQELHKGSKVIDQESATLADM
UBP14   (565)  --------------------------------------------------
UBP6    (444)  --------------------------------------------------
UBP7    (440)  --------------------------------------------------
UBP1    (946)  --------------------------------------------------
UBP2    (793)  --------------------------------------------------
UBP27   (419)  --------------------------------------------------
UBP22   (353)  --------------------------------------------------
UBP20   (301)  --------------------------------------------------
UBP21   (307)  --------------------------------------------------
UBP23   (304)  --------------------------------------------------
UBP25   (312)  --------------------------------------------------
UBP15   (342)  --------------------------------------------------
UBP16   (344)  --------------------------------------------------
UBP17   (343)  --------------------------------------------------
UBP18   (345)  --------------------------------------------------
UBP19   (426)  NRSIDMEHDSGTDHQEEEANGKEDPTVENLAVDSSCLDITTPSPSAATEF
```

FIGURE 12 (continued)

```
                1451                                                  1500
UBP9   (782)  ------------------------------------------------------
UBP10  (782)  ------------------------------------------------------
UBP11  (775)  ------------------------------------------------------
UBP5   (812)  ------------------------------------------------------
UBP8   (589)  ------------------------------------------------------
UBP24  (354)  ------------------------------------------------------
UBP3   (343)  ------------------------------------------------------
UBP4   (338)  ------------------------------------------------------
UBP12  (456)  ------------------------------------------------------
UBP13  (455)  ------------------------------------------------------
UBP26  (466)  NIFPGDRLWVRDT-----------------------------------------
UBP14  (565)  ------------------------------------------------------
UBP6   (444)  ------------------------------------------------------
UBP7   (440)  ------------------------------------------------------
UBP1   (946)  ------------------------------------------------------
UBP2   (793)  ------------------------------------------------------
UBP27  (419)  ------------------------------------------------------
UBP22  (353)  ------------------------------------------------------
UBP20  (301)  ------------------------------------------------------
UBP21  (307)  ------------------------------------------------------
UBP23  (304)  ------------------------------------------------------
UBP25  (312)  ------------------------------------------------------
UBP15  (342)  ------------------------------------------------------
UBP16  (344)  ------------------------------------------------------
UBP17  (343)  ------------------------------------------------------
UBP18  (345)  ------------------------------------------------------
UBP19  (476)  IPQENERSDTESKPLEKEHSDTESNKPLEKEHLDSESKPLEKEHSDTEMID
```

FIGURE 12 (continued)

SEQUENCE LISTING

```
<160> NUMBER OF SEQ ID NOS: 52

<210> SEQ ID NO 1
<211> LENGTH: 3320
<212> TYPE: DNA
<213> ORGANISM: Arabidopsis thaliana

<400> SEQUENCE: 1
ggagagagac agagtatgcg aggagtgtga aaacgaagag cataaacaac acgggacgag      60
```

```
gagagagaaa ctagtgtgtt ttagaaagaa gaaagagaga gatagacaaa gagactgttt    120
gtgtcttctt acccattcga ggaatcaaag catctatttc cgagctctca agacgacgag    180
aagctaaaag ataaggctga agaaatttag ggttttttct tccttttgta ttcagctcgt    240
taattaaggg ctatccatct tccgagttct tcagtagctt cacaagctgg acctgaaaat    300
agatcttggc gcatatcagg agtgtgatta tggttatctg aattcatgta atttgaaggg    360
attttcacga gctgtgatcg ggtcatgaat gcgtgtctga ggacatgctt gaaccaaggg    420
gagcggacat accaatattg ttcctggttt tggttgtact tcctgtggta gcttacattt    480
tattaggaaa atggagtaac atttctgaaa aaagagtaag ggctaacttg ctggctcaga    540
tggcagctga agaagcttta agagctgaga ccgtggttaa tgcggataga ggtgtaagat    600
ttgagagtgt ggctactgag aatagggctc aaagaaccag gaccaagact gtttctgctg    660
gtggtggtgc tgtaagagca gagtttgacg ctggtgcgag agaaactgta gccgagcaga    720
gatctgattc cgtgactgct acatgtgggg ttacagttgt ggctcctgtc aataataatg    780
agttacatgt atgtgcaagg tgttttggtc ctgctaagac acgttgctcg agatgtaaat    840
ctgttagata ctgctccggg aagtgtcaaa taattcactg gagggtagct cacaaagatg    900
aatgtgtccc agtggagtct tgctcttcgt catctgagag ggtttccttc gagaaagatt    960
ctgttttgta tgaccatggc atggattcta caatgtatag taacaatact acgcaggcag   1020
caaagggaaa gacttcaaaa agctctgtgg attttgctag cttgggtatc tctcagaatg   1080
atattacgcc acaaatcaac acgcaaggga ggaaaagcgt aggaaaacaa cattcttcca   1140
aggccaaccg agaatcatgt agaagagaca gtgctactgt gtttgattct tctgatgaag   1200
ctgcttctgc tggtggcgat aacaagacga gtcacataaa acataagtcg agaggcaaca   1260
gttatgctgc agaaacaaat cctagaaggc attctgttga cagctctgct gtgcaaatga   1320
atggacaatc ttttgtaagt ggtatgcagg aaagtcacaa acacgaaaac aatttgggag   1380
tcagaagctc ttttggttgt ccaaacacac aatatccttc aaacgggacc agaactgcaa   1440
cactgcccag aacaggtatt aacaaatctg gagaacagtc atgcacagag acaagtaaga   1500
aggggcaagt cgctgcagta tcaaagactg ttcggtctaa ggatactggc atcagtgaag   1560
aaagcaatgg catctcctca acgatgggaa taatgaagat gatgggttta agaaattcta   1620
caaagcatga tgatcgatat aagaacctga aaatgctttt tccatacgag gaatttctta   1680
aattctttca gtgtgaagtg tttgatttat cacctagggg gcttgtaaat tgtggaaaca   1740
gttgctatgc gaacgctgtt ttgcaatcct taacatgtac aaaaccactc gttgcttatt   1800
tgcttcgacg atcacattca agatcatgtt ctgggaaaga ttggtgcctt atgtgtgaac   1860
ttgagcaaca tgtaatgatg ctaagagaat ccggaggtcc acttctctct agcagaattc   1920
tctcacacat gcgaagtata aattgtcaga ttggtgatgg gagtcaggaa gatgctcatg   1980
agttcttaag gcttttggtt gcctctatgc aatccatatg tttggagaga cttggaggtg   2040
agactaaagt ggatccgaga ctgcaagaaa caaccttagt tcaacatatg tttggtggac   2100
gtctccgctc aaaggttaaa tgcctgaggt gtgatcatga atcagaaaga tacgagaata   2160
taatggatct cacattagag atatacggtt gggtagaatc tcttcaagat gccttgactc   2220
agtttactag accggaagat ctcgacggag aaaacatgta tagatgcagc aggtgcgctg   2280
gatatgttag agcgaggaaa gaattgagca ttcatgaagc accaaacatt ctcacaattg   2340
ttcttaagcg attccaggaa ggaagatacg ggaaaataaa caaatgtata agttttcctg   2400
```

```
aaatgctaga catgattcct ttcatgacaa gaaccggaga cgttcctccg ctttatatgc    2460
tttacgccgt catagttcac ttggatactc tcaacgcatc tttctcgggt cactacattt    2520
cgtatgtcaa agatttgaga gggaattggt acagaatcga tgattcagag attcatccag    2580
tgccaatgac tcaagttatg tcagaaggag cttacatgtt gttctacatg agatcgtatc    2640
cacgtcctca agaggagag cacaatggaa aagctccggt tcaccattcg caaccaagaa     2700
acgagatgaa ggaacagagg aaacctgtta accgcttcaa accgagagcg atcacaaga    2760 acacagagtc atcatcaagc gaatggtctc tcttcacaag ctcagacgag gcttctttca   2820
ccacagaatc aaccagagac tctttcagca ccatagacta cacagatgtt tgccacgtcg   2880
tagactcttc ttctcctttc gccatcttca acaacgtata ccacaacgta gagccatcgc   2940
cacacaacac tgtcgcttgc agaatgttct caggtaccaa acccgaaacc cggtatttcg   3000
tggagcaaga acaaatcac aacaacacgg tcgtgctgga cgcaacacca tcactatatc    3060
ctattccagc accgtatccg ccccatgatt attacgatca gagtatgtat gtaaattacg   3120
agactaaccc agaatttaac aatggtcagg atcaggatag aacttacagt tactggtagt   3180
aagtagaaga gactagagag gattctgttt ttgaacctcc ctgattttta ttaaatatgt    3240
ttagagatct ctttagggat acttaactcg agtgccctga gattttttt ttgtctttag     3300 tcatctgttt ctttggtatc                                                3320

<210> SEQ ID NO 2
<211> LENGTH: 924
<212> TYPE: PRT
<213> ORGANISM: Arabidopsis thaliana

<400> SEQUENCE: 2

Met Leu Glu Pro Arg Gly Ala Asp Ile Pro Ile Leu Phe Leu Val Leu
1               5                   10                  15

Val Val Leu Pro Val Val Ala Tyr Ile Leu Leu Gly Lys Trp Ser Asn
                20                  25                  30

Ile Ser Glu Lys Arg Val Arg Ala Asn Leu Leu Ala Gln Met Ala Ala
            35                  40                  45

Glu Glu Ala Leu Arg Ala Glu Thr Val Val Asn Ala Asp Arg Gly Val
        50                  55                  60

Arg Phe Glu Ser Val Ala Thr Glu Asn Arg Ala Gln Arg Thr Arg Thr
65                  70                  75                  80

Lys Thr Val Ser Ala Gly Gly Ala Val Arg Ala Glu Phe Asp Ala
                85                  90                  95

Gly Ala Arg Glu Thr Val Ala Glu Gln Arg Ser Asp Ser Val Thr Ala
            100                 105                 110

Thr Cys Gly Val Thr Val Ala Pro Val Asn Asn Asn Glu Leu His
            115                 120                 125

Val Cys Ala Arg Cys Phe Gly Pro Ala Lys Thr Arg Cys Ser Arg Cys
        130                 135                 140

Lys Ser Val Arg Tyr Cys Ser Gly Lys Cys Gln Ile Ile His Trp Arg
145                 150                 155                 160

Val Ala His Lys Asp Glu Cys Val Pro Val Glu Ser Cys Ser Ser Ser
                165                 170                 175

Ser Glu Arg Val Ser Phe Glu Lys Asp Ser Val Leu Tyr Asp His Gly
            180                 185                 190

Met Asp Ser Thr Met Tyr Ser Asn Asn Thr Thr Gln Ala Ala Lys Gly
        195                 200                 205
```

```
Lys Thr Ser Lys Ser Ser Val Asp Phe Ala Ser Leu Gly Ile Ser Gln
    210                 215                 220
Asn Asp Ile Thr Pro Gln Ile Asn Thr Gln Gly Arg Lys Ser Val Gly
225                 230                 235                 240
Lys Gln His Ser Lys Ala Asn Arg Glu Ser Cys Arg Arg Asp Ser
                245                 250                 255
Ala Thr Val Phe Asp Ser Ser Asp Glu Ala Ser Ala Gly Gly Asp
                260                 265                 270
Asn Lys Thr Ser His Ile Lys His Lys Ser Arg Gly Asn Ser Tyr Ala
                275                 280                 285
Ala Glu Thr Asn Pro Arg Arg His Ser Val Asp Ser Ser Ala Val Gln
                290                 295                 300
Met Asn Gly Gln Ser Phe Val Ser Gly Met Gln Glu Ser His Lys His
305                 310                 315                 320
Glu Asn Asn Leu Gly Val Arg Ser Ser Phe Gly Cys Pro Asn Thr Gln
                325                 330                 335
Tyr Pro Ser Asn Gly Thr Arg Thr Ala Thr Leu Pro Arg Thr Gly Ile
                340                 345                 350
Asn Lys Ser Gly Glu Gln Ser Cys Thr Glu Thr Ser Lys Lys Gly Gln
                355                 360                 365
Val Ala Ala Val Ser Lys Thr Val Arg Ser Lys Asp Thr Gly Ile Ser
                370                 375                 380
Glu Glu Ser Asn Gly Ile Ser Ser Thr Met Gly Ile Met Lys Met Met
385                 390                 395                 400
Gly Leu Arg Asn Ser Thr Lys His Asp Asp Arg Tyr Lys Asn Leu Lys
                405                 410                 415
Met Leu Phe Pro Tyr Glu Glu Phe Leu Lys Phe Phe Gln Cys Glu Val
                420                 425                 430
Phe Asp Leu Ser Pro Arg Gly Leu Val Asn Cys Gly Asn Ser Cys Tyr
                435                 440                 445
Ala Asn Ala Val Leu Gln Ser Leu Thr Cys Thr Lys Pro Leu Val Ala
                450                 455                 460
Tyr Leu Leu Arg Arg Ser His Ser Arg Ser Cys Ser Gly Lys Asp Trp
465                 470                 475                 480
Cys Leu Met Cys Glu Leu Glu Gln His Val Met Met Leu Arg Glu Ser
                485                 490                 495
Gly Gly Pro Leu Ser Ala Ser Arg Ile Leu Ser His Met Arg Ser Ile
                500                 505                 510
Asn Cys Gln Ile Gly Asp Gly Ser Gln Glu Asp Ala His Glu Phe Leu
                515                 520                 525
Arg Leu Leu Val Ala Ser Met Gln Ser Ile Cys Leu Glu Arg Leu Gly
                530                 535                 540
Gly Glu Thr Lys Val Asp Pro Arg Leu Gln Glu Thr Thr Leu Val Gln
545                 550                 555                 560
His Met Phe Gly Gly Arg Leu Arg Ser Lys Val Lys Cys Leu Arg Cys
                565                 570                 575
Asp His Glu Ser Glu Arg Tyr Glu Asn Ile Met Asp Leu Thr Leu Glu
                580                 585                 590
Ile Tyr Gly Trp Val Glu Ser Leu Gln Asp Ala Leu Thr Gln Phe Thr
                595                 600                 605
Arg Pro Glu Asp Leu Asp Gly Glu Asn Met Tyr Arg Cys Ser Arg Cys
610                 615                 620
Ala Gly Tyr Val Arg Ala Arg Lys Glu Leu Ser Ile His Glu Ala Pro
```

```
                    625                 630                 635                 640
Asn Ile Leu Thr Ile Val Leu Lys Arg Phe Gln Glu Gly Arg Tyr Gly
                645                 650                 655
Lys Ile Asn Lys Cys Ile Ser Phe Pro Glu Met Leu Asp Met Ile Pro
                660                 665                 670
Phe Met Thr Arg Thr Gly Asp Val Pro Pro Leu Tyr Met Leu Tyr Ala
                675                 680                 685
Val Ile Val His Leu Asp Thr Leu Asn Ala Ser Phe Ser Gly His Tyr
                690                 695                 700
Ile Ser Tyr Val Lys Asp Leu Arg Gly Asn Trp Tyr Arg Ile Asp Asp
705                 710                 715                 720
Ser Glu Ile His Pro Val Pro Met Thr Gln Val Met Ser Glu Gly Ala
                725                 730                 735
Tyr Met Leu Phe Tyr Met Arg Ser Tyr Pro Arg Pro Gln Arg Gly Glu
                740                 745                 750
His Asn Gly Lys Ala Pro Val His His Ser Gln Pro Arg Asn Glu Met
                755                 760                 765
Lys Glu Gln Arg Lys Pro Val Asn Arg Phe Lys Pro Arg Ala Asp His
                770                 775                 780
Lys Asn Thr Glu Ser Ser Ser Glu Trp Ser Leu Phe Thr Ser Ser
785                 790                 795                 800
Asp Glu Ala Ser Phe Thr Thr Glu Ser Thr Arg Asp Ser Phe Ser Thr
                805                 810                 815
Ile Asp Tyr Thr Asp Val Cys His Val Val Asp Ser Ser Pro Phe
                820                 825                 830
Ala Ile Phe Asn Asn Val Tyr His Asn Val Glu Pro Ser Pro His Asn
                835                 840                 845
Thr Val Ala Cys Arg Met Phe Ser Gly Thr Lys Pro Glu Thr Arg Tyr
                850                 855                 860
Phe Val Glu Gln Glu Thr Asn His Asn Asn Thr Val Val Leu Asp Ala
865                 870                 875                 880
Thr Pro Ser Leu Tyr Pro Ile Pro Ala Pro Tyr Pro Pro His Asp Tyr
                885                 890                 895
Tyr Asp Gln Ser Met Tyr Val Asn Tyr Glu Thr Asn Pro Glu Phe Asn
                900                 905                 910
Asn Gly Gln Asp Gln Asp Arg Thr Tyr Ser Tyr Trp
                915                 920

<210> SEQ ID NO 3
<211> LENGTH: 3721
<212> TYPE: DNA
<213> ORGANISM: Arabidopsis thaliana

<400> SEQUENCE: 3
aaaagcaaag cgtcttggta tagaaaagta atatactgcc tcctaatttc ttcgtccttc    60
taccgaagaa tctctccact cttgccctct ttcgaaaccc taaaccagaa gcaccagatt   120
ttttcaactt tttcccagag aacaatagaa aacccaactt gtgctctcta ggttttcttt   180
tattccttct catctttgga ttttcttggg tcatcatttt ggaagcttac ccaccagcga   240
aaaaattata acttccatcg attcctggct tctctctctc gctctctctg catgtgctaa   300
atcgccggac tgatcctcac tgtcacctct gttcccggct tattcgccgg tgaaatctat   360
ggttggtgct cagatttatt tccaattgtt tgtgcatctg gtggaggata aatgctcctt   420
gttttggatc tagggatttc tagtctagtc cttgtggtct ctcttgtttt acctttgatc   480
```

```
ggtctctttg ttcgtcacaa atggagggtc gctgcccaaa gaagggagga gattagaaga    540
cttcttattc atgcttctga agaggctgcc agggctgagc tagaggcctc tgttgagttc    600
tcttctgttg ccgtctctaa tgtcttccat tgtcctgttt gctattgtct tgccacgact    660
cgttgctctc gctgcaaagc cgttcgatat tgttccggga aatgtcaaat cattcactgg    720
cggcaaggtc acaaagatga atgtcatcct gcttccattg tatatgatag tgaagatgag    780
agtgattccg atttgagatt aggagaagaa aatggacaaa atactcctga ggaaacttta    840
ctggtgggtc cagaaccagt tactatacca atcggggaat cactattatc taatcgtgcc    900
agatctcctg aagatgggaa tggagatatt gcagataaca aagatgacct tatagataag    960
gaagaagctg tttctgttgc tgaaacatct ggatcctcgt tttctggctt ctcctcctcc   1020
ccccgtaatg actctggcga cgagatttct cgttgtgaga gcttcagttc atctgaatcc   1080
gagagatcag agtccctact tgatgctcat gtctctgtag agccagaaga cacctgtttc   1140
agcaccattg aagatgctcc atccaaactg ttgtctccaa aatttgtgca cttggttgaa   1200
tctgtagata atctcgctaa tctgcctaaa ttaagtgtac ataaacctga ggatgatgct   1260
gggcagaacc agagccaatc aaggagctta cactcattag ttacggatag gcatccagta   1320
tcagctgacc catctctgaa gtcatctgat ttttgggta cggctcttgg atcagccgaa   1380
cgtgtgagtg attcttgtgt taaatctaaa tctggtagac tggtaactc ctctctgcat   1440 ttctcctttg gctctggctc ctctagagac acctcagctg ctaaagtttc tgagcagagg   1500
agtagcattt taaagaagc tcctaggggg actggttata tatctgatgg agtaaactta   1560
agagaaagaa atgctaaaag atttgatgaa gctgaaattg cattaccaat ttcctcttct   1620
actgatgcgc tgagtccttt ggactcttct aatttgtccc atgtgaccct tccgaagtca   1680
aagagcgcta gtagtgaaaa tggctctatg ttggccccctt tgaaggttgg ggaagtccaa   1740
cttttggcat ccaaggcctc gaataccaag aagtgtgctg atcttatgaa gcattctcct   1800
ttaggtgcaa aatcggtaag agttcttgat catcagaaac agaatggtgc tgtcgttcag   1860
catataaatt ctctacatgg aagaagtggt ttaaaggcat cagtactgaa agttgtagac   1920
cagtggacca gaccgaagtc tgaaaatgag atggcaggaa gacatggtca taagggggctc   1980 tttccatatg aagtctttgc taaactgtat acatataaaa ttgagttcca gccttgtggc   2040
ctcatcaacg ttggcaatag ctgctttgct aatgttgtct ttcaatgcct tatgttcact   2100
cctcctctga cgacatactt cctccagcaa tttcattcca gagcatgtac aaaaaaagaa   2160
cagtgcttca cctgtgggtt tgagaagctg gtcgtaaagg caaaagaaga gaagtctcca   2220
ctgtccccta atggcttgct atctcagctg cagaatattg gaatctttct tgggaatggc   2280
aaggaagaag atgcacatga attccttagg tttgttgtcg atacaatgca gtctgtgtgc   2340
attaaggcat ctgaatatga tatgaccaag agtagcaaat tagaagatac aactcttatt   2400
ggtttgacat ttgggggata cctccggtca aagattaaat gcatgaaatg tcaagtaaaa   2460
tctgagctgc gtgagaaaat gatggatcta acggttgaga ttgatggaga tattagcacc   2520
ctggatgatg ctttgcgtcg atttacaagg actgagatat ggatggaga gaacaaatac   2580 agatgtggca gctgtaaatc ctatgagaga gccaaaaaga agctgaaaat aacagagcct   2640
ccgaatgtcc ttaccattgc actaaaacga ttccaggcag ggaaattcgg gaagctcaat   2700
aagttgatta ggtttccaga aactctagat ttggctccat atgtcagtgg gggaagtgaa   2760
aaatcacatg actacaaact ctatggagtt attgttcact ggatgtaat gaatgcagca   2820
```

-continued

```
tttttctggcc attatgtctg ctatattaga aaccaaaata agtggtacaa ggctgatgat    2880
agcacggtag taacttcgga tgtggaaagg atcttgacaa agggagcgta tatgttgttc    2940
tacgcaaggt gcactccaac gcctccaaga ttagcagtat gtaccaaaac tgaagcatcc    3000
aataaaaaaa gcagagtgcc actacctaag gctaatgaga aaagtaccat atcccggtct    3060
gtgtctactt caagtcctga gttgtcttcc aacacgcctg gtggtggtcg atccggcaat    3120
atacagtcat tttattctag tttccagagg ctgcagaaga ttttagaaga agactcggcg    3180
agtgacagtt catctctctt tgacagcaac tcagatgaat gctcttgtag cacagacagt    3240
acaagcatgg acgactttgc tgatttcatt tttggagatc atcagggacg ggctcacgga    3300
cagtctgaga ctccctcacc aacatcatcg tcttcctcat cttctccccc cttcacaagg    3360
cgttcgccgc tcagtcgttc ttctccagaa acttacggaa cctcaagaca tcagttgccc    3420
ttgggaggag aaaggtaagg gaaacaagat ggttttttgt ccacttggcc ccaactaagt    3480
caaaagtagt agaagaaagt agatttgatt acacgtagat tgagtggttt tattaacaac    3540
ccgtatttag gcttggtgaa agtggttaat gagagaagtg gtggtatata gtagtgtata    3600
gtggggaaga gagttttttgc ccatgaaatt gtatcacgta atggaacgga atttacctttt    3660
gttaataagt tgttttgact tttattataa tcaatcaata aagctaatct aatattgtct    3720
c                                                                    3721
```

<210> SEQ ID NO 4
<211> LENGTH: 1008
<212> TYPE: PRT
<213> ORGANISM: Arabidopsis thaliana

<400> SEQUENCE: 4

```
Met Leu Val Leu Asp Leu Gly Ile Ser Ser Leu Val Leu Val
1               5                   10                  15

Ser Leu Val Leu Pro Leu Ile Gly Leu Phe Val Arg His Lys Trp Arg
            20                  25                  30

Val Ala Ala Gln Arg Arg Glu Glu Ile Arg Arg Leu Leu Ile His Ala
        35                  40                  45

Ser Glu Glu Ala Ala Arg Ala Glu Leu Glu Ala Ser Val Glu Phe Ser
    50                  55                  60

Ser Val Ala Val Ser Asn Val Phe His Cys Pro Val Cys Tyr Cys Leu
65                  70                  75                  80

Ala Thr Thr Arg Cys Ser Arg Cys Lys Ala Val Arg Tyr Cys Ser Gly
                85                  90                  95

Lys Cys Gln Ile Ile His Trp Arg Gln Gly His Lys Asp Glu Cys His
            100                 105                 110

Pro Ala Ser Ile Val Tyr Asp Ser Glu Asp Glu Ser Asp Ser Asp Leu
        115                 120                 125

Arg Leu Gly Glu Glu Asn Gly Gln Asn Thr Pro Glu Glu Thr Leu Leu
    130                 135                 140

Val Gly Pro Glu Pro Val Thr Ile Pro Ile Gly Glu Ser Leu Leu Ser
145                 150                 155                 160

Asn Arg Ala Arg Ser Pro Glu Asp Gly Asn Gly Asp Ile Ala Asp Asn
                165                 170                 175

Lys Asp Asp Leu Ile Asp Lys Glu Glu Ala Val Ser Val Ala Glu Thr
            180                 185                 190

Ser Gly Ser Ser Phe Ser Gly Phe Ser Ser Ser Pro Arg Asn Asp Ser
        195                 200                 205
```

-continued

```
Gly Asp Glu Ile Ser Arg Cys Glu Ser Phe Ser Ser Glu Ser Glu
210                 215                 220

Arg Ser Glu Ser Leu Leu Asp Ala His Val Ser Val Glu Pro Glu Asp
225                 230                 235                 240

Thr Cys Phe Ser Thr Ile Glu Asp Ala Pro Ser Lys Leu Leu Ser Pro
                245                 250                 255

Lys Phe Val His Leu Val Glu Ser Val Asp Asn Leu Ala Asn Leu Pro
                260                 265                 270

Lys Leu Ser Val His Lys Pro Glu Asp Asp Ala Gly Gln Asn Gln Ser
                275                 280                 285

Gln Ser Arg Ser Leu His Ser Leu Val Thr Asp Arg His Pro Val Ser
290                 295                 300

Ala Asp Pro Ser Leu Lys Ser Ser Asp Phe Trp Gly Thr Ala Leu Gly
305                 310                 315                 320

Ser Ala Glu Arg Val Ser Asp Ser Cys Val Lys Ser Lys Ser Gly Arg
                325                 330                 335

Pro Gly Asn Ser Ser Leu His Phe Ser Phe Gly Ser Gly Ser Ser Arg
                340                 345                 350

Asp Thr Ser Ala Ala Lys Val Ser Glu Gln Arg Ser Ser Ile Leu Lys
                355                 360                 365

Glu Ala Pro Arg Gly Thr Gly Tyr Ile Ser Asp Gly Val Asn Leu Arg
370                 375                 380

Glu Arg Asn Ala Lys Arg Phe Asp Glu Ala Glu Ile Ala Leu Pro Ile
385                 390                 395                 400

Ser Ser Ser Thr Asp Ala Leu Ser Pro Leu Asp Ser Ser Asn Leu Ser
                405                 410                 415

His Val Thr Leu Pro Lys Ser Lys Ser Ala Ser Ser Glu Asn Gly Ser
                420                 425                 430

Met Leu Ala Pro Leu Lys Val Gly Glu Val Gln Leu Leu Ala Ser Lys
                435                 440                 445

Ala Ser Asn Thr Lys Lys Cys Ala Asp Leu Met Lys His Ser Pro Leu
450                 455                 460

Gly Ala Lys Ser Val Arg Val Leu Asp His Gln Lys Gln Asn Gly Ala
465                 470                 475                 480

Val Val Gln His Ile Asn Ser Leu His Gly Arg Ser Gly Leu Lys Ala
                485                 490                 495

Ser Val Leu Lys Val Val Asp Gln Trp Thr Arg Pro Lys Ser Glu Asn
                500                 505                 510

Glu Met Ala Gly Arg His Gly His Lys Gly Leu Phe Pro Tyr Glu Val
                515                 520                 525

Phe Ala Lys Leu Tyr Thr Tyr Lys Ile Glu Phe Gln Pro Cys Gly Leu
530                 535                 540

Ile Asn Val Gly Asn Ser Cys Phe Ala Asn Val Val Phe Gln Cys Leu
545                 550                 555                 560

Met Phe Thr Pro Pro Leu Thr Thr Tyr Phe Leu Gln Gln Phe His Ser
                565                 570                 575

Arg Ala Cys Thr Lys Lys Glu Gln Cys Phe Thr Cys Gly Phe Glu Lys
                580                 585                 590

Leu Val Val Lys Ala Lys Glu Glu Lys Ser Pro Leu Ser Pro Asn Gly
                595                 600                 605

Leu Leu Ser Gln Leu Gln Asn Ile Gly Ile Phe Leu Gly Asn Gly Lys
                610                 615                 620

Glu Glu Asp Ala His Glu Phe Leu Arg Phe Val Val Asp Thr Met Gln
```

Ser Val Cys Ile Lys Ala Ser Glu Tyr Asp Met Thr Lys Ser Ser Lys
625                 630                 635                 640
                645                 650                 655

Leu Glu Asp Thr Thr Leu Ile Gly Leu Thr Phe Gly Gly Tyr Leu Arg
                660                 665                 670

Ser Lys Ile Lys Cys Met Lys Cys Gln Val Lys Ser Glu Leu Arg Glu
                675                 680                 685

Lys Met Met Asp Leu Thr Val Glu Ile Asp Gly Asp Ile Ser Thr Leu
690                 695                 700

Asp Asp Ala Leu Arg Arg Phe Thr Arg Thr Glu Ile Leu Asp Gly Glu
705                 710                 715                 720

Asn Lys Tyr Arg Cys Gly Ser Cys Lys Ser Tyr Glu Arg Ala Lys Lys
                725                 730                 735

Lys Leu Lys Ile Thr Glu Pro Pro Asn Val Leu Thr Ile Ala Leu Lys
                740                 745                 750

Arg Phe Gln Ala Gly Lys Phe Gly Lys Leu Asn Lys Leu Ile Arg Phe
                755                 760                 765

Pro Glu Thr Leu Asp Leu Ala Pro Tyr Val Ser Gly Gly Ser Glu Lys
                770                 775                 780

Ser His Asp Tyr Lys Leu Tyr Gly Val Ile Val His Leu Asp Val Met
785                 790                 795                 800

Asn Ala Ala Phe Ser Gly His Tyr Val Cys Tyr Ile Arg Asn Gln Asn
                805                 810                 815

Lys Trp Tyr Lys Ala Asp Asp Ser Thr Val Val Thr Ser Asp Val Glu
                820                 825                 830

Arg Ile Leu Thr Lys Gly Ala Tyr Met Leu Phe Tyr Ala Arg Cys Thr
                835                 840                 845

Pro Thr Pro Pro Arg Leu Ala Val Cys Thr Lys Thr Glu Ala Ser Asn
                850                 855                 860

Lys Lys Ser Arg Val Pro Leu Pro Lys Ala Asn Glu Lys Ser Thr Ile
865                 870                 875                 880

Ser Arg Ser Val Ser Thr Ser Pro Glu Leu Ser Ser Asn Thr Pro
                885                 890                 895

Gly Gly Gly Arg Ser Gly Asn Ile Gln Ser Phe Ser Ser Phe Gln
                900                 905                 910

Arg Leu Gln Lys Ile Leu Glu Glu Asp Ser Ala Ser Asp Ser Ser Ser
                915                 920                 925

Leu Phe Asp Ser Asn Ser Asp Glu Cys Ser Cys Ser Thr Asp Ser Thr
930                 935                 940

Ser Met Asp Asp Phe Ala Asp Phe Ile Phe Gly Asp His Gln Gly Arg
945                 950                 955                 960

Ala His Gly Gln Ser Glu Thr Pro Ser Pro Thr Ser Ser Ser Ser Ser
                965                 970                 975

Ser Ser Pro Pro Phe Thr Arg Arg Ser Pro Leu Ser Arg Ser Ser Pro
                980                 985                 990

Glu Thr Tyr Gly Thr Ser Arg His Gln Leu Pro Leu Gly Gly Glu Arg
                995                 1000                1005

<210> SEQ ID NO 5
<211> LENGTH: 2196
<212> TYPE: DNA
<213> ORGANISM: Arabidopsis thaliana

<400> SEQUENCE: 5

| | |
|---|---|
| atgatgttgg tttttcttct gattcgccgg caatggagat ctgcttctgt gagaagagaa | 60 |
| gaggtgattc gtctcattgc tttagccacc gaggaatctt atttggcgga ggaagttcgt | 120 |
| cccgccactg ttgattacgg cggagactcg gtttctgatg tttaccgttg tgccgtttgt | 180 |
| ctataccta ccactactcg ttgctctcag tgcaaatctg ttcgttactg ttcaagcaag | 240 |
| tgtcaaattc ttcactggcg acgaggtcat aaggaagaat gtcgatcgcc tgattatgat | 300 |
| gaagaaaagg aggagtatgt tcaatctgat tatgatgcta agagtctaa tgtggatttt | 360 |
| ccatctcgtg ggactgcgta tgaatcatca tctaatgtgt ctgttgatgt tgcctgtgat | 420 |
| atgtctacaa gtaggcctag tattcataaa gtgcaaccta gatctgaagc tgtggatttc | 480 |
| actacttctt taaacataaa ggataatctc tatgagacca ggccactaag taggaagaaa | 540 |
| tcacgtaatc gtacagacaa ggttgagtca gccagtaatt attccaaagg aaagactgat | 600 |
| gcaaagctgc ggaaacttgg caatcaaaat tcacgtaggt caggtgattc ggctaatatg | 660 |
| tcaatttcag atcaattttt gtcagttggg tttgaagaag aaatgaatgc acttaaacat | 720 |
| gaaagaatta catctgaacc atctagtgct tctgctgcaa tgtcttcgtc ttcaactctt | 780 |
| ctcctacctt caaaagctaa cagtaagcca aaagtgtcac aagcttcaag tagtggattg | 840 |
| aaaacatcgg tgcagaaagt tgttcagcat tttagacctc cacagtcgtc caaaaagtct | 900 |
| caaccttcca gttctattga tgagatgagc ttctcgtatg agttgtttgt gaaactttat | 960 |
| tgtgatagag tagaattaca gccatttggc cttgtgaact tagggaacag ttgttatgca | 1020 |
| aatgctgtcc ttcagtgctt ggcattcact cggccactga tatcatacct tattagggga | 1080 |
| ttacactcta aacatgtag aaagaagagt tggtgttttg tttgtgagtt tgaacactta | 1140 |
| atttttaaagg caaggggagg agaatctcct cttcaccta tcaagatctt atcaaaatta | 1200 |
| caaaagattg ggaagcatct tggccctgga aagaagaag acgcgcacga gttttttaagg | 1260 |
| tgtgctgttg atacaatgca atctgttttt ctcaaagagg ctcctgcagc tggtccgttt | 1320 |
| gctgaagaaa ctactttagt aggccttacg tttggtggat atcttcactc caagattaaa | 1380 |
| tgcatggcat gcctccacaa atctgagcga ccggagctga tgatggatct aactgttgag | 1440 |
| attgatgggg atataggaag cctcgaagaa gcacttgctc aattcacagc atacgaagtc | 1500 |
| ctagatggag agaaccggta tttctgtggc agatgtaaat cttaccagaa agccaaaaag | 1560 |
| aaattgatga tattggaagg acccaatatt cttactgtcg tgctgaaacg ttttcagtct | 1620 |
| gataactttg ggaagctgag caaacccatc cattttcccg agcttctcga tattagcccg | 1680 |
| tatatgagtc acccaaatca tggggatcat ccggtttata gtctctacgc agtggtggtc | 1740 |
| catttggatg ctatgagcac tttatttca ggtcattatg tttgctacat aaaaaccctt | 1800 |
| gatggagatt ggttcaaaat tgatgacagc aatgttttcc cggttcagtt agagactgtg | 1860 |
| ttactagaag gagcatacat gcttctttat gcaagggatt ctccgagacc ggtgagcaag | 1920 |
| aacggtggtc ggaaatcaaa gcaaagaaga aatttggccg caattccgtc aagaaagggc | 1980 |
| aacaagaaac agagagacgg tgataataac agtttgttgc cgcgtgtgga ctggtcgagt | 2040 |
| ggaagcctgt cgtcaatgtt tagctcatcg gacacaacaa gctcatgtag cacaaaagac | 2100 |
| tcatcaggta ttgagaattt atcagattac ctgtttggtg gagttgaacc ggtttggaaa | 2160 |
| tgggatcgtc ataataaatc tcaaacgttt gattga | 2196 |

<210> SEQ ID NO 6
<211> LENGTH: 731
<212> TYPE: PRT
<213> ORGANISM: Arabidopsis thaliana

<400> SEQUENCE: 6

```
Met Met Leu Val Phe Leu Leu Ile Arg Arg Gln Trp Arg Ser Ala Ser
1               5                   10                  15

Val Arg Arg Glu Glu Val Ile Arg Leu Ile Ala Leu Ala Thr Glu Glu
            20                  25                  30

Ser Tyr Leu Ala Glu Glu Val Arg Pro Ala Thr Val Asp Tyr Gly Gly
        35                  40                  45

Asp Ser Val Ser Asp Val Tyr Arg Cys Ala Val Cys Leu Tyr Pro Thr
    50                  55                  60

Thr Thr Arg Cys Ser Gln Cys Lys Ser Val Arg Tyr Cys Ser Ser Lys
65                  70                  75                  80

Cys Gln Ile Leu His Trp Arg Arg Gly His Lys Glu Glu Cys Arg Ser
                85                  90                  95

Pro Asp Tyr Asp Glu Glu Lys Glu Glu Tyr Val Gln Ser Asp Tyr Asp
            100                 105                 110

Ala Lys Glu Ser Asn Val Asp Phe Pro Ser Arg Gly Thr Ala Tyr Glu
        115                 120                 125

Ser Ser Ser Asn Val Ser Val Asp Val Ala Cys Asp Met Ser Thr Ser
    130                 135                 140

Arg Pro Ser Ile His Lys Val Gln Pro Arg Ser Glu Ala Val Asp Phe
145                 150                 155                 160

Thr Thr Ser Leu Asn Ile Lys Asp Asn Leu Tyr Glu Thr Arg Pro Leu
                165                 170                 175

Ser Arg Lys Lys Ser Arg Asn Arg Thr Asp Lys Val Glu Ser Ala Ser
            180                 185                 190

Asn Tyr Ser Lys Gly Lys Thr Asp Ala Lys Leu Arg Lys Leu Gly Asn
        195                 200                 205

Gln Asn Ser Arg Arg Ser Gly Asp Ser Ala Asn Met Ser Ile Ser Asp
    210                 215                 220

Gln Phe Leu Ser Val Gly Phe Glu Glu Met Asn Ala Leu Lys His
225                 230                 235                 240

Glu Arg Ile Thr Ser Glu Pro Ser Ser Ala Ser Ala Ala Met Ser Ser
                245                 250                 255

Ser Ser Thr Leu Leu Pro Ser Lys Ala Asn Ser Lys Pro Lys Val
            260                 265                 270

Ser Gln Ala Ser Ser Ser Gly Leu Lys Thr Ser Val Gln Lys Val Val
        275                 280                 285

Gln His Phe Arg Pro Pro Gln Ser Ser Lys Ser Gln Pro Ser Ser
    290                 295                 300

Ser Ile Asp Glu Met Ser Phe Ser Tyr Glu Leu Phe Val Lys Leu Tyr
305                 310                 315                 320

Cys Asp Arg Val Glu Leu Gln Pro Phe Gly Leu Val Asn Leu Gly Asn
                325                 330                 335

Ser Cys Tyr Ala Asn Ala Val Leu Gln Cys Leu Ala Phe Thr Arg Pro
            340                 345                 350

Leu Ile Ser Tyr Leu Ile Arg Gly Leu His Ser Lys Thr Cys Arg Lys
        355                 360                 365

Lys Ser Trp Cys Phe Val Cys Glu Phe Glu His Leu Ile Leu Lys Ala
    370                 375                 380

Arg Gly Gly Glu Ser Pro Leu Ser Pro Ile Lys Ile Leu Ser Lys Leu
385                 390                 395                 400

Gln Lys Ile Gly Lys His Leu Gly Pro Gly Lys Glu Glu Asp Ala His
```

```
            405                 410                 415
Glu Phe Leu Arg Cys Ala Val Asp Thr Met Gln Ser Val Phe Leu Lys
        420                 425                 430

Glu Ala Pro Ala Ala Gly Pro Phe Ala Glu Glu Thr Thr Leu Val Gly
    435                 440                 445

Leu Thr Phe Gly Gly Tyr Leu His Ser Lys Ile Lys Cys Met Ala Cys
450                 455                 460

Leu His Lys Ser Glu Arg Pro Glu Leu Met Met Asp Leu Thr Val Glu
465                 470                 475                 480

Ile Asp Gly Asp Ile Gly Ser Leu Glu Glu Ala Leu Ala Gln Phe Thr
                485                 490                 495

Ala Tyr Glu Val Leu Asp Gly Glu Asn Arg Tyr Phe Cys Gly Arg Cys
            500                 505                 510

Lys Ser Tyr Gln Lys Ala Lys Lys Leu Met Ile Leu Glu Gly Pro
        515                 520                 525

Asn Ile Leu Thr Val Val Leu Lys Arg Phe Gln Ser Asp Asn Phe Gly
    530                 535                 540

Lys Leu Ser Lys Pro Ile His Phe Pro Glu Leu Leu Asp Ile Ser Pro
545                 550                 555                 560

Tyr Met Ser Asp Pro Asn His Gly Asp His Pro Val Tyr Ser Leu Tyr
                565                 570                 575

Ala Val Val Val His Leu Asp Ala Met Ser Thr Leu Phe Ser Gly His
            580                 585                 590

Tyr Val Cys Tyr Ile Lys Thr Leu Asp Gly Asp Trp Phe Lys Ile Asp
        595                 600                 605

Asp Ser Asn Val Phe Pro Val Gln Leu Glu Thr Val Leu Leu Glu Gly
    610                 615                 620

Ala Tyr Met Leu Leu Tyr Ala Arg Asp Ser Pro Arg Pro Val Ser Lys
625                 630                 635                 640

Asn Gly Gly Arg Lys Ser Lys Gln Arg Asn Leu Ala Ala Ile Pro
                645                 650                 655

Ser Arg Lys Gly Asn Lys Lys Gln Arg Asp Gly Asp Asn Asn Ser Leu
            660                 665                 670

Leu Pro Arg Val Asp Trp Ser Gly Ser Leu Ser Ser Met Phe Ser
        675                 680                 685

Ser Ser Asp Thr Thr Ser Ser Cys Ser Thr Lys Asp Ser Ser Gly Ile
    690                 695                 700

Glu Asn Leu Ser Asp Tyr Leu Phe Gly Gly Val Glu Pro Val Trp Lys
705                 710                 715                 720

Trp Asp Arg His Asn Lys Ser Gln Thr Phe Asp
                725                 730
```

<210> SEQ ID NO 7
<211> LENGTH: 2121
<212> TYPE: DNA
<213> ORGANISM: Arabidopsis thaliana

<400> SEQUENCE: 7

```
aaaaaaggtg aatacttgaa atatataaaa gatacagaag acacgagaag ggagaagaga    60
tcgatgattt tgagaagcga attagatgca tgaggttggt tttccgttgg atctctctgt    120
cttcactcgc cttatagcga ctctattttt cctcgccgtt ggtgtttttt actttctcaa    180
aaacaccgcc gctaagtact tcgacatcgg agccgccgcc gccggaggtt tcgacaggga    240
cttcatggcg gttgatgctg aggattgctc tgtctgtggg aattttttcca ccaagaaatg    300
```

```
ctcccgctgc aaatccgttc gatactgctc agcagagtgc caaaggtcag attggagttc    360
gggtcatcaa agaaactgca gggattatgg gattactaca ttaacaccat ctgcaaagaa    420
tggcttaagg ttcagagctt ctccattcgg ggatagttct gcgtctagta ttgcactgat    480
ttccgaacgg ggccaaaaca agagtagtct caagccaaga gaagttcttt ttccatatga    540
agaatttgtt gaatatttta actgggacaa tccagaattg ctccctgtg ggctcatgaa     600
ttgtggaaat agttgtttcg ccaatgtgat tctacaatgc ctttcctgga cacgtcctct    660
tgttgcatat ctgctggaga aaggccacaa gagagaatgt atgcgcaacg attggtgctt    720
cctctgtgaa tttcaaaccc atgttgagag agcgagtcaa agtcggttcc cttttcacc    780
aatgaacatt atttcacggt taactaatat tggtggaact cttggatatg aagacagga    840
ggatgctcat gagttcatga ggtatgcgat tgatatgatg cagtctgttt gccttgatga    900
attcggtgga gaaaaaatag tgcctcctcg ttcacaagaa acaacactta ttcagtatat    960
atttggaggt ctccttcaat cacaggttca atgtactgtt tgcaatcatg tttctgacca   1020
atatgaaaat atgatggatc taatcgttga gatgcatggg gatgcggggt ctttggagga   1080
atgtcttgat caatttacag ccgaagagtg gcttcatgga gataatatgt acaaatgtga   1140
taggtgtagt gactatgtaa aagcatgtaa gcgtcttacg attcgacgcg ctccaaatat   1200
tcttactatt gccttaaaaa gatatcaggg aggaagatac ggaaaattga acaaaagaat   1260
aagttttccc gagacattgg atcttaatcc ttacatgagt gaaggcggag atggatcaga   1320
tgtatataaa ctctatgcag tgattgtcca tttagatatg ctgaatgcat cattcttcgg   1380
ccattacata tgctacatta aggattttttg cggaaactgg tatagaatag atgattccga   1440
gatagaaagt gttgaattag aagatgtcct ttctcaaaga gcttatatgc tcctctacag   1500
caggattcaa gctcggtcgt catcttcatg tcttagatca gaagttaaag acgagaagaa   1560
aacagacaca ttggacacag aatcttgcgt aaaagagtta gttgagagtt caatggtagg   1620
agctattgaa agcagaagca gcacccatgc gaccattgaa gaccctgtat gcgagcaatc   1680
accatcacca tcgccatcac catcaccatc accatcgcca tcaccatcac catcagtatt   1740
ggcctctgaa tgttgtagtg aggttgaaag gattgataca ttggattccg agtccaactc   1800
ttcgattgat gactctgcaa cagatcatca agaggatgta gcaaatggga caaagatcc    1860
agaggtaaaa tatcaggctg ccgattcttg gtcagaccct acaacttcaa ctccattggt   1920
ctgtacaaaa tccaaacctc cggtgagaga tatggacacc aagatgatcg acgctcagtg   1980
atgtggtatg ttcaaacatt tgaaaatcag cagagctttt tagcttacaa agttacaata   2040
gtgatgtaga tactattaca caatgacttc tatggtaata aagggtgatt atacgtagaa   2100
tttaaatgtt cgtgaattgc c                                             2121
```

<210> SEQ ID NO 8
<211> LENGTH: 631
<212> TYPE: PRT
<213> ORGANISM: Arabidopsis thaliana

<400> SEQUENCE: 8

```
Met His Glu Val Gly Phe Pro Leu Asp Leu Ser Val Phe Thr Arg Leu
1               5                   10                  15

Ile Ala Thr Leu Phe Phe Leu Ala Val Gly Val Phe Tyr Phe Leu Lys
            20                  25                  30

Asn Thr Ala Ala Lys Tyr Phe Asp Ile Gly Ala Ala Ala Ala Gly Gly
        35                  40                  45
```

```
Phe Asp Arg Asp Phe Met Ala Val Asp Ala Glu Asp Cys Ser Val Cys
 50                  55                  60
Gly Asn Phe Ser Thr Lys Lys Cys Ser Arg Cys Lys Ser Val Arg Tyr
 65                  70                  75                  80
Cys Ser Ala Glu Cys Gln Arg Ser Asp Trp Ser Ser Gly His Gln Arg
                 85                  90                  95
Asn Cys Arg Asp Tyr Gly Ile Thr Thr Leu Thr Pro Ser Ala Lys Asn
            100                 105                 110
Gly Leu Arg Phe Arg Ala Ser Pro Phe Gly Asp Ser Ser Ala Ser Ser
        115                 120                 125
Ile Ala Leu Ile Ser Glu Arg Gly Gln Asn Lys Ser Ser Leu Lys Pro
    130                 135                 140
Arg Glu Val Leu Phe Pro Tyr Glu Glu Phe Val Glu Tyr Phe Asn Trp
145                 150                 155                 160
Asp Asn Pro Glu Leu Ala Pro Cys Gly Leu Met Asn Cys Gly Asn Ser
                165                 170                 175
Cys Phe Ala Asn Val Ile Leu Gln Cys Leu Ser Trp Thr Arg Pro Leu
            180                 185                 190
Val Ala Tyr Leu Leu Glu Lys Gly His Lys Arg Glu Cys Met Arg Asn
        195                 200                 205
Asp Trp Cys Phe Leu Cys Glu Phe Gln Thr His Val Glu Arg Ala Ser
    210                 215                 220
Gln Ser Arg Phe Pro Phe Ser Pro Met Asn Ile Ile Ser Arg Leu Thr
225                 230                 235                 240
Asn Ile Gly Gly Thr Leu Gly Tyr Gly Arg Gln Glu Asp Ala His Glu
                245                 250                 255
Phe Met Arg Tyr Ala Ile Asp Met Met Gln Ser Val Cys Leu Asp Glu
            260                 265                 270
Phe Gly Gly Glu Lys Ile Val Pro Pro Arg Ser Gln Glu Thr Thr Leu
        275                 280                 285
Ile Gln Tyr Ile Phe Gly Gly Leu Leu Gln Ser Gln Val Gln Cys Thr
    290                 295                 300
Val Cys Asn His Val Ser Asp Gln Tyr Glu Asn Met Met Asp Leu Ile
305                 310                 315                 320
Val Glu Met His Gly Asp Ala Gly Ser Leu Glu Glu Cys Leu Asp Gln
                325                 330                 335
Phe Thr Ala Glu Glu Trp Leu His Gly Asp Asn Met Tyr Lys Cys Asp
            340                 345                 350
Arg Cys Ser Asp Tyr Val Lys Ala Cys Lys Arg Leu Thr Ile Arg Arg
        355                 360                 365
Ala Pro Asn Ile Leu Thr Ile Ala Leu Lys Arg Tyr Gln Gly Gly Arg
    370                 375                 380
Tyr Gly Lys Leu Asn Lys Arg Ile Ser Phe Pro Glu Thr Leu Asp Leu
385                 390                 395                 400
Asn Pro Tyr Met Ser Glu Gly Gly Asp Gly Ser Asp Val Tyr Lys Leu
                405                 410                 415
Tyr Ala Val Ile Val His Leu Asp Met Leu Asn Ala Ser Phe Phe Gly
            420                 425                 430
His Tyr Ile Cys Tyr Ile Lys Asp Phe Cys Gly Asn Trp Tyr Arg Ile
        435                 440                 445
Asp Asp Ser Glu Ile Glu Ser Val Glu Leu Glu Asp Val Leu Ser Gln
    450                 455                 460
```

```
Arg Ala Tyr Met Leu Leu Tyr Ser Arg Ile Gln Ala Arg Ser Ser Ser
465                 470                 475                 480

Ser Cys Leu Arg Ser Glu Val Lys Asp Glu Lys Thr Asp Thr Leu
            485                 490                 495

Asp Thr Glu Ser Cys Val Lys Glu Leu Val Glu Ser Ser Met Val Gly
                500                 505                 510

Ala Ile Glu Ser Arg Ser Ser Thr His Ala Thr Ile Glu Asp Pro Val
            515                 520                 525

Cys Glu Gln Ser Pro Ser Pro Ser Pro Ser Pro Ser Pro Ser
            530                 535                 540

Pro Ser Pro Ser Pro Ser Val Leu Ala Ser Glu Cys Cys Ser Glu Val
545                 550                 555                 560

Glu Arg Ile Asp Thr Leu Asp Ser Glu Ser Asn Ser Ser Ile Asp Asp
                565                 570                 575

Ser Ala Thr Asp His Gln Glu Asp Val Ala Asn Gly Asn Lys Asp Pro
            580                 585                 590

Glu Val Lys Tyr Gln Ala Ala Asp Ser Trp Ser Asp Pro Thr Thr Ser
            595                 600                 605

Thr Pro Leu Val Cys Thr Lys Ser Lys Pro Pro Val Arg Asp Met Asp
    610                 615                 620

Thr Lys Met Ile Asp Ala Gln
625                 630

<210> SEQ ID NO 9
<211> LENGTH: 2317
<212> TYPE: DNA
<213> ORGANISM: Arabidopsis thaliana

<400> SEQUENCE: 9
aaaacacaga gcaaagaaaa acagaggag gttgattctc tttggcatct ccgaatcgaa     60
tctgagaaga gaagaggaag aaaaacgaag atcgatgttc gagagggaat tagatgcatg    120
aagttggatt atttgtggat ctgaattcct tcacgcagct tatattgacg ctcttctttg    180
tctctatcgg tcttctctac tttgttaaaa gaacggcagc caagtacttc gaggtcggtg    240
gtggctccgg tggtttcgat agagaccatc gccgagattt catggtttcc gacacggctg    300
aatgttctgt ctgtgggaag gctactacca aaaagtgctc tcgctgcaaa tctgtgagat    360
actgctctgc ggcatgccaa acgtcagatt ggaaatcagg acataaacta aaatgcaagg    420
ggtttcggag tactgactca tcaccagtga aagagatga tatcgatttc gaagcttctc    480
tgtttgggaa tagatctgct tctaagaaga ctaggattgc attggttcct caacagagcc    540
aaagcaaagc taccctcaag ccaacagatg ttctttttccc atacgaaagt tttgttagat    600
attataactg ggacagacca ataatggctc cttgtgggct caccaattgt ggaaacagtt    660
gtttcgctaa tgtggttcta caatgccttt cctggacacg ccctcttgtt gcttaccttc    720
tggagagagg ccacaaaaga gaatgtaggc gaaatgattg tgcttcctta tgcgaatttg    780
aaaatcatct tgacagagca aactatagcc ggtttccttt ttccaatg aacattatct    840 cgcggctgcc taatattggt ggaaatcttg gtatgggag acaggaggat gctcatgagt    900
tgatgaggtt tgcaattgat atgatgcaat ctgtttgcct cgacgaattt ggtggagaaa    960
aagtggtgcc tcctcgcgcc caagagacaa cacttattca atatatattt ggtggtctcc   1020
ttcagtcaca ggtccagtgt actgcttgca gtaatgtttc tgaccaatat gaaaatatga   1080
tggatttaac tgttgagatc catggggatg cggtatcatt ggaggaatgt ctcgatcagt   1140
```

-continued

```
ttacagctaa agaatggctt cagggagata acttatacaa atgtgataga gtgtgatgact    1200 atgtgaaagc atgcaagcgc ctttcaattc gttgtgctcc aaatattctt acaattgcct    1260
taaaaagatt ccagggtggg agattcggta aactgaacaa aagaattagt tttcctgaga    1320
catttgatct aggcccttac atgagcggtg gaggagaagg atcagatgta tacaaactct    1380
acgctgtgat tgttcatcta gatatgttga atgcttcatt tttcggccat acatatgct    1440 atgtcaagga cttccgtgga aactggtata gaatagacga ttctgaggtg gaaaaggttg    1500
aactagaaga tgtcctttct caacgagcat acatgctcct ctacagcagg gttcagccca    1560
gaccatcaaa tcttagatcc gaagaaagtc aagatgagaa gaaaacagat acattgaaca    1620
cagaatctaa ccaagatggc tctgttgaga gttccggggt gggaacaaat gacacaagtg    1680
tgtcctcgct gtgtaacggc atcatctcac attcagaaga ccctgaatac gaaaaagaat    1740
catcattgtc agcatccgta ccagtctctg aagaaggaaa ggaagttgac gtaaaggttg    1800
atacagtaga ttctgaatca aaccgttcta ttgacatgga acatgattct ggaacagatc    1860
atcaagaaga agaagcaaat gggaaagaag atccaacggt tgaaaatctg gctgttgatt    1920
cttcttgttt ggacattact actccatctc catctgctgc tacagagttc atacctcagg    1980
agaacgaacg ttcagacacc gagtccaaac tctggagaa agaacattca gacaccgagt    2040
ccaacaaacc gctggagaaa gaacatttag acagcgagtc caaaccctg gagaaagaac    2100 attcagacac cgagatgatc gatgctcaat gattctaaag gatggtggt ggaatcacaa    2160 acatttttca tggctcttga aaatcaacaa gggcgcttct aacttaacaa taatgctgca    2220
aaaaaattgc tttagacact gcaatttctg gtgtctgaag gatatataga atttgttgga    2280
tcctggagtt ttccatatct agaagaaatt tttaggg    2317
```

<210> SEQ ID NO 10
<211> LENGTH: 672
<212> TYPE: PRT
<213> ORGANISM: Arabidopsis thaliana

<400> SEQUENCE: 10

```
Met His Glu Val Gly Leu Phe Val Asp Leu Asn Ser Phe Thr Gln Leu
1               5                   10                  15

Ile Leu Thr Leu Phe Phe Val Ser Ile Gly Leu Leu Tyr Phe Val Lys
            20                  25                  30

Arg Thr Ala Ala Lys Tyr Phe Glu Val Gly Gly Ser Gly Gly Phe
        35                  40                  45

Asp Arg Asp His Arg Arg Asp Phe Met Val Ser Asp Thr Ala Glu Cys
    50                  55                  60

Ser Val Cys Gly Lys Ala Thr Thr Lys Cys Ser Arg Cys Lys Ser
65                  70                  75                  80

Val Arg Tyr Cys Ser Ala Ala Cys Gln Thr Ser Asp Trp Lys Ser Gly
                85                  90                  95

His Lys Leu Lys Cys Lys Gly Phe Arg Ser Thr Asp Ser Ser Pro Val
            100                 105                 110

Arg Arg Asp Asp Ile Asp Phe Glu Ala Ser Leu Phe Gly Asn Arg Ser
        115                 120                 125

Ala Ser Lys Lys Thr Arg Ile Ala Leu Val Pro Gln Gln Ser Gln Ser
    130                 135                 140

Lys Ala Thr Leu Lys Pro Thr Asp Val Leu Phe Pro Tyr Glu Ser Phe
145                 150                 155                 160

Val Arg Tyr Tyr Asn Trp Asp Arg Pro Ile Met Ala Pro Cys Gly Leu
```

```
                  165             170             175
Thr Asn Cys Gly Asn Ser Cys Phe Ala Asn Val Val Leu Gln Cys Leu
                180             185             190
Ser Trp Thr Arg Pro Leu Val Ala Tyr Leu Leu Glu Arg Gly His Lys
                195             200             205
Arg Glu Cys Arg Arg Asn Asp Trp Cys Phe Leu Cys Glu Phe Glu Asn
            210             215             220
His Leu Asp Arg Ala Asn Tyr Ser Arg Phe Pro Phe Ser Pro Met Asn
225             230             235             240
Ile Ile Ser Arg Leu Pro Asn Ile Gly Gly Asn Leu Gly Tyr Gly Arg
                245             250             255
Gln Glu Asp Ala His Glu Leu Met Arg Phe Ala Ile Asp Met Met Gln
                260             265             270
Ser Val Cys Leu Asp Glu Phe Gly Gly Glu Lys Val Val Pro Pro Arg
                275             280             285
Ala Gln Glu Thr Thr Leu Ile Gln Tyr Ile Phe Gly Gly Leu Leu Gln
                290             295             300
Ser Gln Val Gln Cys Thr Ala Cys Ser Asn Val Ser Asp Gln Tyr Glu
305             310             315             320
Asn Met Met Asp Leu Thr Val Glu Ile His Gly Asp Ala Val Ser Leu
                325             330             335
Glu Glu Cys Leu Asp Gln Phe Thr Ala Lys Glu Trp Leu Gln Gly Asp
                340             345             350
Asn Leu Tyr Lys Cys Asp Arg Cys Asp Asp Tyr Val Lys Ala Cys Lys
                355             360             365
Arg Leu Ser Ile Arg Cys Ala Pro Asn Ile Leu Thr Ile Ala Leu Lys
                370             375             380
Arg Phe Gln Gly Gly Arg Phe Gly Lys Leu Asn Lys Arg Ile Ser Phe
385             390             395             400
Pro Glu Thr Phe Asp Leu Gly Pro Tyr Met Ser Gly Gly Gly Glu Gly
                405             410             415
Ser Asp Val Tyr Lys Leu Tyr Ala Val Ile Val His Leu Asp Met Leu
                420             425             430
Asn Ala Ser Phe Phe Gly His Tyr Ile Cys Tyr Val Lys Asp Phe Arg
                435             440             445
Gly Asn Trp Tyr Arg Ile Asp Asp Ser Glu Val Glu Lys Val Glu Leu
                450             455             460
Glu Asp Val Leu Ser Gln Arg Ala Tyr Met Leu Leu Tyr Ser Arg Val
465             470             475             480
Gln Pro Arg Pro Ser Asn Leu Arg Ser Glu Glu Ser Gln Asp Glu Lys
                485             490             495
Lys Thr Asp Thr Leu Asn Thr Glu Ser Asn Gln Asp Gly Ser Val Glu
                500             505             510
Ser Ser Gly Val Gly Thr Asn Asp Thr Ser Val Ser Ser Leu Cys Asn
                515             520             525
Gly Ile Ile Ser His Ser Glu Asp Pro Glu Tyr Glu Lys Glu Ser Ser
                530             535             540
Leu Ser Ala Ser Val Pro Val Ser Glu Glu Gly Lys Glu Val Asp Val
545             550             555             560
Lys Val Asp Thr Val Asp Ser Glu Ser Asn Arg Ser Ile Asp Met Glu
                565             570             575
His Asp Ser Gly Thr Asp His Gln Glu Glu Glu Ala Asn Gly Lys Glu
                580             585             590
```

```
Asp Pro Thr Val Glu Asn Leu Ala Val Asp Ser Ser Cys Leu Asp Ile
        595                 600                 605

Thr Thr Pro Ser Pro Ser Ala Ala Thr Glu Phe Ile Pro Gln Glu Asn
    610                 615                 620

Glu Arg Ser Asp Thr Glu Ser Lys Pro Leu Glu Lys Glu His Ser Asp
625                 630                 635                 640

Thr Glu Ser Asn Lys Pro Leu Glu Lys Glu His Leu Asp Ser Glu Ser
                645                 650                 655

Lys Pro Leu Glu Lys Glu His Ser Asp Thr Glu Met Ile Asp Ala Gln
            660                 665                 670

<210> SEQ ID NO 11
<211> LENGTH: 2724
<212> TYPE: DNA
<213> ORGANISM: Oryza sativa

<400> SEQUENCE: 11
```

| | |
|---|---:|
| atgctccaac caagggaatc cgatgtgcct gtactatttg ttgtatttat tgtacttccg | 60 |
| gtgatagctt attttcttct tggaagatgg catgatgctg taagtaagaa ggcacgggta | 120 |
| agtgtgctgg cccagcgagc tgcagaagaa accttcaagg tggaaacaat ggcgactcca | 180 |
| gacgttatat tgccaggacc ttctttaaga cccatgcctt atatgagatc tgcaccttct | 240 |
| gcaagacccg aataccatga gtgtgctact tgccacgggc tgctaagac tcgctgctcc | 300 |
| agatgcaagt ctgttagata ctgctctgga aagtgtcaaa taattcactg gaggcaaggt | 360 |
| cataagcaaa catgtcagca atggaatggt tttggtacta gcagctctgg tggactacct | 420 |
| cctactgaga atactgaaca gatgccattc ttaagtaacc tgaactcacc tcttcgaggg | 480 |
| agcgatgttc atctgcatga catggatttc gataccatgt cagagccatc ctttgtgaca | 540 |
| acagatagct ataatcttga taccagccca tttctgtcag accgaagcaa catgaataaa | 600 |
| ccaaaccaat ttctcatata agtgaaaat ggtgctgcca ttggatctta tgagaagaac | 660 |
| gactatagta ttgatggaga agtcccttct tctgagattc tgtcaggaaa taagggttta | 720 |
| aataacagtt ctggttcagg tgaaaactgc ggaaaccgtg atgtaattta tcctctcaat | 780 |
| agtgtggtac atcaacccaa taattatgcc cctgaaataa gaaagcggcc caaagcaagc | 840 |
| atcacggttt atgaatctga taaggcgtg tatttaactt ctgatatgat cagttctggt | 900 |
| gaggggccat atgcttctgc tgcagagtca ctacaaagaa gtaactcgtc tggaaatgtt | 960 |
| accggaaaag gaaacatgat acataagaaa ccaccatacc catctggatc taccaaaaca | 1020 |
| gctgttttcaa caaacagcag tttgcaagga tgcaatggca tctcaaaagc aggagcatca | 1080 |
| aaggttgaag ccctgaagaa gccttcaaaa tttctcaaaa ccagtctggt gggtttgatc | 1140 |
| aatgataaca agaggagtaa ggtactgttc ccatatgaag atcttgttaa gttttttcag | 1200 |
| tatgaagtac ggggcatctc acctagaggt cttttcaatt gtggaaatag ttgctatgca | 1260 |
| aatgctgttc tacaatgtct catgtgcaca aaacccctga tgatctatct gcttctgaga | 1320 |
| ctgcattcca agactgttg ctcaaagaat tggtgcctca tgtgtgaact tgagcaatat | 1380 |
| gcttcaactt tgcgtgaaag tggtggccct gtttctccaa gtagaatcct ttctaatctg | 1440 |
| aggaatattg gatgtcgctt gggtggtgga agtcaagaag atgctcatga attttaagg | 1500 |
| catcttgtga tgtctatgca agggcatgc ctgatggac ttggtggtga gaagcaggta | 1560 |
| gaagcaagct tgcaggaaac tacactgata cagcagatgt ttggtggccg tcttaaatcg | 1620 |
| aaggttaagt gcctcagatg ctaccatgaa tctgaaagat acgagaatat aatggatctt | 1680 |

```
actttggaga ttcatggttg ggtcgagtcc ttgcaagatg ctttgacaca attcactgct    1740
cctgaagatt tggatggaga aaatatgtat aaatgtggaa ggtgttctgc ctatgtcaaa    1800
gctaggaaac aattaagcgt gcatgaggtg ccaaatatat taactgtagt tcttaaaaga    1860
ttccagacag ggaaatatgg gaagatcaac aaatgtgtta cttttcctga tatgttggac    1920
atggttccgt ttgtgactgg agctggtgat aatcctcctc tttacttctt gtatgccgtg    1980
gttgtacacg tggatacaga aaatgcatca ttctctggac attacatatc atatgtcaaa    2040
gatatgcagg gcacatggtt gagaattgat gattcagagg tccaggctgt ttcactgaat    2100
caagttatgt cagaaggtgc atatatgctg ttctacatga gatcttttcc tcgcccaccg    2160
aagatttaca ttgagaaggg cctatcatca gttcctacat gttcaaagcg ccattcatca    2220
aaatcctcca agggttctaa gcaagacctg aatcatactg agtcactctt tgcttccagt    2280
gatcaaacct atggaatata cgatttcaga ccagacaacg gctatataca agatcagcat    2340
gctgctttga gaaccagaaa tttctatcat accgatgatg cttttgcaga ttcaattagc    2400
acagacttct cagatgctac atcaagcgaa tggtcactgt ttaccagctc tgatgaatcc    2460
tcatttacga ctgaaagcac tagagattca ttcagtgttg tggactatgg tgacaatgct    2520
ggccttgatc caatttcctc tatatttggg ccttattatg ctcaagacca tcctcctggc    2580
agttttgcct cgtgtacaag gttgtcacct tccaatccac aaacaagatt tctaacccac    2640
ggaactctga aggagggat tccagcacta gaacttcagg ggaatatctg caattctcct    2700
aaaatttcag caaaagcaga atga                                          2724
```

<210> SEQ ID NO 12
<211> LENGTH: 907
<212> TYPE: PRT
<213> ORGANISM: Oryza sativa

<400> SEQUENCE: 12

```
Met Leu Gln Pro Arg Glu Ser Asp Val Pro Val Leu Phe Val Val Phe
1               5                   10                  15

Ile Val Leu Pro Val Ile Ala Tyr Phe Leu Gly Arg Trp His Asp
                20                  25                  30

Ala Val Ser Lys Lys Ala Arg Val Ser Val Leu Ala Gln Arg Ala Ala
            35                  40                  45

Glu Glu Thr Phe Lys Val Glu Thr Met Ala Thr Pro Asp Val Ile Leu
        50                  55                  60

Pro Gly Pro Ser Leu Arg Pro Met Pro Tyr Met Arg Ser Ala Pro Ser
65                  70                  75                  80

Ala Arg Pro Glu Tyr His Glu Cys Ala Thr Cys His Gly Pro Ala Lys
                85                  90                  95

Thr Arg Cys Ser Arg Cys Lys Ser Val Arg Tyr Cys Ser Gly Lys Cys
            100                 105                 110

Gln Ile Ile His Trp Arg Gln Gly His Lys Gln Thr Cys Gln Gln Trp
        115                 120                 125

Asn Gly Phe Gly Thr Ser Ser Gly Gly Leu Pro Pro Thr Glu Asn
    130                 135                 140

Thr Glu Gln Met Pro Phe Leu Ser Asn Leu Asn Ser Pro Leu Arg Gly
145                 150                 155                 160

Ser Asp Val His Leu His Asp Met Asp Phe Asp Thr Met Ser Glu Pro
                165                 170                 175

Ser Phe Val Thr Thr Asp Ser Tyr Asn Leu Asp Thr Ser Pro Phe Leu
```

-continued

```
                180                 185                 190
Ser Asp Arg Ser Asn Met Asn Lys Pro Asn Gln Phe Leu His Thr Ser
            195                 200                 205
Glu Asn Gly Ala Ala Ile Gly Ser Tyr Glu Lys Asn Asp Tyr Ser Ile
        210                 215                 220
Asp Gly Glu Val Pro Ser Ser Glu Ile Leu Ser Gly Asn Lys Gly Leu
225                 230                 235                 240
Asn Asn Ser Ser Gly Ser Gly Glu Asn Cys Gly Asn Arg Asp Val Ile
                245                 250                 255
Tyr Pro Leu Asn Ser Val Val His Gln Pro Asn Asn Tyr Ala Pro Glu
            260                 265                 270
Ile Arg Lys Arg Pro Lys Ala Ser Ile Thr Val Tyr Glu Ser Asp Lys
        275                 280                 285
Gly Val Tyr Leu Thr Ser Asp Met Ile Ser Ser Glu Gly Pro Tyr
    290                 295                 300
Ala Ser Ala Ala Glu Ser Leu Gln Arg Ser Asn Ser Ser Gly Asn Val
305                 310                 315                 320
Thr Gly Lys Gly Asn Met Ile His Lys Lys Pro Pro Tyr Pro Ser Gly
                325                 330                 335
Ser Thr Lys Thr Ala Val Ser Thr Asn Ser Ser Leu Gln Gly Cys Asn
            340                 345                 350
Gly Ile Ser Lys Ala Gly Ala Ser Lys Val Glu Ala Leu Lys Lys Pro
        355                 360                 365
Ser Lys Phe Leu Lys Thr Ser Leu Val Gly Leu Ile Asn Asp Asn Lys
    370                 375                 380
Arg Ser Lys Val Leu Phe Pro Tyr Glu Asp Leu Val Lys Phe Phe Gln
385                 390                 395                 400
Tyr Glu Val Arg Gly Ile Ser Pro Arg Gly Leu Phe Asn Cys Gly Asn
                405                 410                 415
Ser Cys Tyr Ala Asn Ala Val Leu Gln Cys Leu Met Cys Thr Lys Pro
            420                 425                 430
Leu Met Ile Tyr Leu Leu Arg Leu His Ser Lys Asp Cys Cys Ser
        435                 440                 445
Lys Asn Trp Cys Leu Met Cys Glu Leu Glu Gln Tyr Ala Ser Thr Leu
    450                 455                 460
Arg Glu Ser Gly Gly Pro Val Ser Pro Ser Arg Ile Leu Ser Asn Leu
465                 470                 475                 480
Arg Asn Ile Gly Cys Arg Leu Gly Gly Gly Ser Gln Glu Asp Ala His
                485                 490                 495
Glu Phe Leu Arg His Leu Val Met Ser Met Gln Gly Ala Cys Leu Asp
            500                 505                 510
Gly Leu Gly Gly Glu Lys Gln Val Glu Ala Ser Leu Gln Glu Thr Thr
        515                 520                 525
Leu Ile Gln Gln Met Phe Gly Gly Arg Leu Lys Ser Lys Val Lys Cys
    530                 535                 540
Leu Arg Cys Tyr His Glu Ser Glu Arg Tyr Glu Asn Ile Met Asp Leu
545                 550                 555                 560
Thr Leu Glu Ile His Gly Trp Val Glu Ser Leu Gln Asp Ala Leu Thr
                565                 570                 575
Gln Phe Thr Ala Pro Glu Asp Leu Asp Gly Glu Asn Met Tyr Lys Cys
            580                 585                 590
Gly Arg Cys Ser Ala Tyr Val Lys Ala Arg Lys Gln Leu Ser Val His
        595                 600                 605
```

Glu Val Pro Asn Ile Leu Thr Val Val Leu Lys Arg Phe Gln Thr Gly
610                 615                 620

Lys Tyr Gly Lys Ile Asn Lys Cys Val Thr Phe Pro Asp Met Leu Asp
625                 630                 635                 640

Met Val Pro Phe Val Thr Gly Ala Gly Asp Asn Pro Pro Leu Tyr Phe
            645                 650                 655

Leu Tyr Ala Val Val Val His Val Asp Thr Glu Asn Ala Ser Phe Ser
            660                 665                 670

Gly His Tyr Ile Ser Tyr Val Lys Asp Met Gln Gly Thr Trp Leu Arg
            675                 680                 685

Ile Asp Asp Ser Glu Val Gln Ala Val Ser Leu Asn Gln Val Met Ser
690                 695                 700

Glu Gly Ala Tyr Met Leu Phe Tyr Met Arg Ser Phe Pro Arg Pro Pro
705                 710                 715                 720

Lys Ile Tyr Ile Glu Lys Gly Leu Ser Ser Val Pro Thr Cys Ser Lys
                725                 730                 735

Arg His Ser Ser Lys Ser Ser Lys Gly Ser Lys Gln Asp Leu Asn His
                740                 745                 750

Thr Glu Ser Leu Phe Ala Ser Ser Asp Gln Thr Tyr Gly Ile Tyr Asp
            755                 760                 765

Phe Arg Pro Asp Asn Gly Tyr Ile Gln Asp Gln His Ala Ala Leu Arg
770                 775                 780

Thr Arg Asn Phe Tyr His Thr Asp Asp Ala Phe Ala Asp Ser Ile Ser
785                 790                 795                 800

Thr Asp Phe Ser Asp Ala Thr Ser Ser Glu Trp Ser Leu Phe Thr Ser
                805                 810                 815

Ser Asp Glu Ser Ser Phe Thr Thr Glu Ser Thr Arg Ser Ser Phe Ser
            820                 825                 830

Val Val Asp Tyr Gly Asp Asn Ala Gly Leu Asp Pro Ile Ser Ser Ile
835                 840                 845

Phe Gly Pro Tyr Tyr Ala Gln Asp His Pro Pro Gly Ser Phe Ala Ser
850                 855                 860

Cys Thr Arg Leu Ser Pro Ser Asn Pro Gln Thr Arg Phe Leu Thr His
865                 870                 875                 880

Gly Thr Leu Lys Gly Gly Ile Pro Ala Leu Glu Leu Gln Gly Asn Ile
                885                 890                 895

Cys Asn Ser Pro Lys Ile Ser Ala Lys Ala Glu
                900                 905

<210> SEQ ID NO 13
<211> LENGTH: 2937
<212> TYPE: DNA
<213> ORGANISM: Oryza sativa

<400> SEQUENCE: 13
atggcggagg cggcgggttc gtcgtcgtcg tcgtcggcgt cggcggtggt ggtggctgtg      60
gtgattgcgg tggtggtggt ggtgtgggtt gtggtgcggc ggaaggtgag gcgcgccgcg     120
gcgcggaggg aggaggtgct gcggctcacg cggctggcgc aggaggagtc ggagatggcg     180
gaggtggagt gcgcgcgcgc ctactactcg gagctgttcc cgagcgtcgt gcacgcgacg     240
gagatggtgg atgaggcggc gtgggggcg ccgccggccg tggttccggc tcaggcggag     300 gcagaggcg agatggaggc ccgggcccag ccgcagccgc agccgccggt gggtgccaag     360
ggggtctgcg cggtgtgctt ccggccgacg acgttcaggt gcaagcagtg caaggctgtc     420

```
aagtactgtt ccttcaaatg ccagatagcc cactggagac agggtcataa aaatgaatgc    480
cgcccaccaa gcactgatgc taatcatgat gatgtggctg aactttctgt tgcaaaggaa    540
aggaaaattg agcagacaag tgcttctgaa gaaaacatag ctgaaaccaa cacggcagcc    600
accgtgaaga atttaaatga taaaacaaaa gatatgccct cagaagtact tgcttcggtg    660
gaggttcctg atgatgacca ttctgtcagt gcggtcaaac tccctcaaag ttcttcacaa    720
gtagcttctc ttggcagtag aaagacagaa tcaaatatga aacctacaac tcctgttgaa    780
aatggttctt acacaaagga cttagatgag gcgttggtgt gtagatttca accttctcca    840
ccaaagatta gtggctctgg aagtcttatc aacaaagagt ccttaattga ttccaagaag    900
caccaggatt gctctcaaac tagtaacagc aaaaaatatg cagataacaa caatgctcaa    960
gctgctctac ctgttgcagt agaacctaaa acttccagga ctgctcttca tgtggaagtt   1020
ggacactcca agacaaaagc tgctggctca gacaacattg gtgtgtcaaa atggtgcca   1080 tctgttttga ctgttgataa agtttctcct gttcccggtg acgttctgt tacacctaat   1140 tcatcaaaaa gggctgataa tattgctgaa aggaattcta accatcaga gaaatcaatt    1200 tcaacagcaa atagcctggc aacatctctg aaaaaaattg tcaggcagca aacagcacca   1260
aaagttgtga ggcattatcc atcagagcca acacattttc catatgagct tttcattaag   1320
ctctatgaaa aggttgaatt gcaaccgttt ggtcttcata accttggcaa tagttgctat   1380
gcaaatgctg ttcttcagtg cttaatgttt acccgaccac ttacatcata tcttttggga   1440
gggcttcatt caaaaaattg ttccaaaaag gaatggtgct tcatgtgtga atttgaaaaa   1500
ctcgttgggg agggcagaca aggcaagatt gctttgtcac caactgggat actctctcat   1560
ttgcctgaca ttggaagtag ctttggtcct ggtaaacaag aagatgctca tgaattcctt   1620
aggtacgcca ttgatgctat gcaatctgta tgcatgaagg aagccaggaa aagcggcact   1680
catcggttac acgaagaaac aacacttatg caattaatat ttgggggcta tctgcgatct   1740
aagataagat gcacaagatg tgatgctact tccgagcaac atgagcgtat tttggatctt   1800
actgttgaaa tagatggcga catcagttca ctggaaggag cacttgagcg atttacatct   1860
acagaagtct tggatggaga taataaatat aaatgcagca gatgcaaatc gcatgagcgc   1920
gctaaaaaga agctgacaat atcggaagca ccaaatgtcc tgactattgc gctgaaaaga   1980
tatcagtctg gaaagtttgg aaagatcaac aaagccatca gatttccaga gaccttgaac   2040
ttgcagcgct atatgagccc aaaagctgat gacacttccc ctgtttacag cctgtatgca   2100
gtggttgtcc atcatgatat tatgaatgcc gccttttctg gtcattatgt atgctatgtg   2160
aaggacacgc atgggaagtg gtacaaaaca gatgacagtc aggtcaaacc tgtatctctg   2220
gaaaatgtca tgtcgaagtg cgcatacatg ctgctctatg caaggtgttc accaagagct   2280
ccaagctctg taaggccagc gctgatggct caagatccag cacgtgtaaa gaaggacaag   2340
gcaagggtaa attcaggacg gtggcatgga ggaggtccca tacaccaagg tggtcagatg   2400
tacgcagatc acatgacaga tgatttgccc catacatatg acgagtttgg acatggacca   2460
tattcgccag cagaatctcc tagtccaagt gagagttcat caattttcac cagttccgac   2520
acagggtcac atagcaccga cagcagtgaa agcactagaa actctaccag tgaggatatg   2580
gaacgcctca tatttggtga tcaagtttca tactttgatg gctctatgtt cggacatggg   2640
gaaaacggcc gtatgactta ttcccgatca aagtctagct gggtaccag ttcatcgggt    2700 caagaggtgg atcagtatag gcctgacgag cacaggcttc agggtgccag ggagggttgg   2760
```

-continued

```
aatcagggcg atgaaagttc ttccttgtat actaaccaaa gtaaacatca atttagtagt    2820
aagttaacag aacaatatag gaggaggtta gatgggactg agcatgatcc tggagaagcc    2880
aatagtgttt tattgaggag atcggctagg gaaaggacgg cccaaacatt ttattga       2937
```

```
<210> SEQ ID NO 14
<211> LENGTH: 978
<212> TYPE: PRT
<213> ORGANISM: Oryza sativa

<400> SEQUENCE: 14
```

```
Met Ala Glu Ala Ala Gly Ser Ser Ser Ser Ala Ser Ala Val
1               5                   10                  15

Val Val Ala Val Val Ile Ala Val Val Val Val Trp Val Val
                20                  25                  30

Arg Arg Lys Val Arg Arg Ala Ala Ala Arg Arg Glu Glu Val Leu Arg
            35                  40                  45

Leu Thr Arg Leu Ala Gln Glu Glu Ser Glu Met Ala Glu Val Glu Cys
        50                  55                  60

Ala Arg Ala Tyr Tyr Ser Glu Leu Phe Pro Ser Val Val His Ala Thr
65                  70                  75                  80

Glu Met Val Asp Glu Ala Ala Trp Gly Ala Pro Pro Ala Val Val Pro
                85                  90                  95

Ala Gln Ala Glu Ala Glu Ala Glu Met Glu Ala Arg Ala Gln Pro Gln
            100                 105                 110

Pro Gln Pro Pro Val Gly Ala Lys Gly Val Cys Ala Val Cys Phe Arg
        115                 120                 125

Pro Thr Thr Phe Arg Cys Lys Gln Cys Lys Ala Val Lys Tyr Cys Ser
    130                 135                 140

Phe Lys Cys Gln Ile Ala His Trp Arg Gln Gly His Lys Asn Glu Cys
145                 150                 155                 160

Arg Pro Pro Ser Thr Asp Ala Asn His Asp Asp Val Ala Glu Leu Ser
                165                 170                 175

Val Ala Lys Glu Arg Lys Ile Glu Gln Thr Ser Ala Ser Glu Glu Asn
            180                 185                 190

Ile Ala Glu Thr Asn Thr Ala Ala Thr Val Lys Asn Leu Asn Asp Lys
        195                 200                 205

Thr Lys Asp Met Pro Ser Glu Val Leu Ala Ser Val Glu Val Pro Asp
    210                 215                 220

Asp Asp His Ser Val Ser Ala Val Lys Leu Pro Gln Ser Ser Ser Gln
225                 230                 235                 240

Val Ala Ser Leu Gly Ser Arg Lys Thr Glu Ser Asn Met Lys Pro Thr
                245                 250                 255

Thr Pro Val Glu Asn Gly Ser Tyr Thr Lys Asp Leu Asp Glu Ala Leu
            260                 265                 270

Val Cys Arg Phe Gln Pro Ser Pro Lys Ile Ser Gly Ser Gly Ser
        275                 280                 285

Leu Ile Asn Lys Glu Ser Leu Ile Asp Ser Lys Lys His Gln Asp Cys
    290                 295                 300

Ser Gln Thr Ser Asn Ser Lys Lys Tyr Ala Asp Asn Asn Ala Gln
305                 310                 315                 320

Ala Ala Leu Pro Val Ala Val Glu Pro Lys Thr Ser Arg Thr Ala Leu
                325                 330                 335

His Val Glu Val Gly His Ser Lys Thr Lys Ala Ala Gly Ser Asp Asn
            340                 345                 350
```

```
Ile Gly Val Ser Lys Met Val Pro Ser Val Leu Thr Val Asp Lys Val
            355                 360                 365

Ser Pro Val Pro Gly Gly Arg Ser Val Thr Pro Asn Ser Ser Lys Arg
    370                 375                 380

Ala Asp Asn Ile Ala Glu Arg Asn Ser Lys Pro Ser Glu Lys Ser Ile
385                 390                 395                 400

Ser Thr Ala Asn Ser Leu Ala Thr Ser Leu Lys Lys Ile Val Arg Gln
                405                 410                 415

Gln Thr Ala Pro Lys Val Val Arg His Tyr Pro Ser Glu Pro Thr His
            420                 425                 430

Phe Pro Tyr Glu Leu Phe Ile Lys Leu Tyr Glu Lys Val Glu Leu Gln
            435                 440                 445

Pro Phe Gly Leu His Asn Leu Gly Asn Ser Cys Tyr Ala Asn Ala Val
        450                 455                 460

Leu Gln Cys Leu Met Phe Thr Arg Pro Leu Thr Ser Tyr Leu Leu Gly
465                 470                 475                 480

Gly Leu His Ser Lys Asn Cys Ser Lys Lys Glu Trp Cys Phe Met Cys
                485                 490                 495

Glu Phe Glu Lys Leu Val Gly Glu Gly Arg Gln Gly Lys Ile Ala Leu
            500                 505                 510

Ser Pro Thr Gly Ile Leu Ser His Leu Pro Asp Ile Gly Ser Ser Phe
        515                 520                 525

Gly Pro Gly Lys Gln Glu Asp Ala His Glu Phe Leu Arg Tyr Ala Ile
        530                 535                 540

Asp Ala Met Gln Ser Val Cys Met Lys Glu Ala Arg Lys Ser Gly Thr
545                 550                 555                 560

His Arg Leu His Glu Glu Thr Thr Leu Met Gln Leu Ile Phe Gly Gly
                565                 570                 575

Tyr Leu Arg Ser Lys Ile Arg Cys Thr Arg Cys Asp Ala Thr Ser Glu
            580                 585                 590

Gln His Glu Arg Ile Leu Asp Leu Thr Val Glu Ile Asp Gly Asp Ile
        595                 600                 605

Ser Ser Leu Glu Gly Ala Leu Glu Arg Phe Thr Ser Thr Glu Val Leu
        610                 615                 620

Asp Gly Asp Asn Lys Tyr Lys Cys Ser Arg Cys Lys Ser His Glu Arg
625                 630                 635                 640

Ala Lys Lys Lys Leu Thr Ile Ser Glu Ala Pro Asn Val Leu Thr Ile
                645                 650                 655

Ala Leu Lys Arg Tyr Gln Ser Gly Lys Phe Gly Lys Ile Asn Lys Ala
            660                 665                 670

Ile Arg Phe Pro Glu Thr Leu Asn Leu Gln Arg Tyr Met Ser Pro Lys
        675                 680                 685

Ala Asp Asp Thr Ser Pro Val Tyr Ser Leu Tyr Ala Val Val His
        690                 695                 700

His Asp Ile Met Asn Ala Ala Phe Ser Gly His Tyr Val Cys Tyr Val
705                 710                 715                 720

Lys Asp Thr His Gly Lys Trp Tyr Lys Thr Asp Asp Ser Gln Val Lys
                725                 730                 735

Pro Val Ser Leu Glu Asn Val Met Ser Lys Cys Ala Tyr Met Leu Leu
            740                 745                 750

Tyr Ala Arg Cys Ser Pro Arg Ala Pro Ser Ser Val Arg Pro Ala Leu
            755                 760                 765
```

```
Met Ala Gln Asp Pro Ala Arg Val Lys Lys Asp Lys Ala Arg Val Asn
        770                 775                 780
Ser Gly Arg Trp His Gly Gly Pro Ile His Gln Gly Gly Gln Met
785                 790                 795                 800
Tyr Ala Asp His Met Thr Asp Asp Leu Pro His Thr Tyr Asp Glu Phe
                    805                 810                 815
Gly His Gly Pro Tyr Ser Pro Ala Glu Ser Pro Ser Pro Ser Glu Ser
                820                 825                 830
Ser Ile Phe Thr Ser Ser Asp Thr Gly Ser His Ser Thr Asp Ser
        835                 840                 845
Ser Glu Ser Thr Arg Asn Ser Thr Ser Glu Asp Met Glu Arg Leu Ile
850                 855                 860
Phe Gly Asp Gln Val Ser Tyr Phe Asp Gly Ser Met Phe Gly His Gly
865                 870                 875                 880
Glu Asn Gly Arg Met Thr Tyr Ser Arg Ser Lys Ser Ser Leu Gly Thr
                    885                 890                 895
Ser Ser Ser Gly Gln Glu Val Asp Gln Tyr Arg Pro Asp Glu His Arg
                900                 905                 910
Leu Gln Gly Ala Arg Glu Gly Trp Asn Gln Gly Asp Glu Ser Ser Ser
            915                 920                 925
Leu Tyr Thr Asn Gln Ser Lys His Gln Phe Ser Ser Lys Leu Thr Glu
930                 935                 940
Gln Tyr Arg Arg Arg Leu Asp Gly Thr Glu His Asp Pro Gly Glu Ala
945                 950                 955                 960
Asn Ser Val Leu Leu Arg Arg Ser Ala Arg Glu Arg Thr Ala Gln Thr
                965                 970                 975
Phe Tyr

<210> SEQ ID NO 15
<211> LENGTH: 2814
<212> TYPE: DNA
<213> ORGANISM: Oryza sativa

<400> SEQUENCE: 15
atggcgtcgg cggcgttgtc gctcgcggtg gcggtggtgg ccgtggcggt cgccgcggtg      60
gtggcggtgg cgcgtggggc gctgcggcgc gccgcggcgc ggagggagga ggtgcggcgc     120
ctcgccaggc tcgcggcggt ggaggccgag gtcgcggagc gcgaggcgta ctgctacgcg     180
cgggggaggg gcggcgtggc gggtgcgccg ctgtggacgg tgcccgaggt ggcttcgccg     240
cgggaggacg aagaggagga ggaggaggag gaggccgcgg cggtggagtt ggaaatgccg     300
gcggcccgtc aggcggaggc agcggcggcg gcggcggcgg tgaaagggt gtgcgtgata      360 agctataatt tcctctgtat gaggatatta ttgtttgatt ctgataccttc aagtgccag     420 atatctcact ggagacaagg ccataaagat gaatgccatc accaagagt tgatgccagg      480 cctgacaata taacagtagt ttctagtgtt aaaaagggtg ttggaatgta caattcattt     540
gaacaaagtg tgaaatccag cgtagaacca gcggttgaag tcaacaagtc agttgctgct     600
gtgcctgaat tgtctgaggc aaaccttgtc tccgatggtg tagataatga agaaagaag      660 atgagaggtc agaaggcatc tattactgca aaggtttctg aggatgtcct tgacaacaat     720
aggattagat ctgttgatag ttctaggctc ccaacttctg gtaaagcttg caatattcag     780
gatgctactg ttaatgagaa tttctctaag acttcagcag cagctccag ttctcgagtt      840 gaacggtcta ccacgtcgga acctgaactg aaccattcta caaacaggc ttctggcaca      900
```

| gacaacctta aaagttcgag aggtttgcca tctgtgtcaa ctgttggcac aatttcttct | 960 |
| attcatggat cagagaaaga agctgctatg ccaaataatc ggtcattggt aaagaatatt | 1020 |
| cccaggcaac aagcagctgc aaaagttgtg aggcattatc catcggaaat gacactttt | 1080 |
| ccgtatgaac attttgtcaa gctctacaat tttgacaagg tggagctgcg ccctttggt | 1140 |
| cttgtgaacc ttgggaatag ttgttacgca aatgctgttc ttcagtgctt ggcatttacg | 1200 |
| cggccactta cagcatacct tacggaagga cttcattcaa gaaattgtaa cttaatacta | 1260 |
| agccagaatt gtgttacata ccatggttcc aaaaaggaat ggtgcttcat gtgtgagttt | 1320 |
| gaaaaactca ttctggaggg taggcgagga aaatctcact tgtcacctac tggaatacta | 1380 |
| tctcatttgc gtgacattgg aagtagcttt ggccccggta gagaagaaga tgctcatgaa | 1440 |
| tttctcaggt atgcaattga tactatgcaa tctgctagca tgaaggaagc caagaaaaac | 1500 |
| ggtgtttatg ggctgcctga agaaacaaca ctggtgcagt taatatttgg gggctatcta | 1560 |
| cgatcgaaga taaaatgcac aatgtgtcaa ggcagttcag aacaatgtga acgcatttg | 1620 |
| gatcttactg ttgaaataga tggggatatc aatacccttg aagaagcact tcatcggttt | 1680 |
| acatctacag aaattttaga tggtgataat agatacaatt gcagcagatg caagtcatat | 1740 |
| gaacgtgcca aaaagaagtt gacaatatca gaagcaccaa acatcctgac tattgcgctg | 1800 |
| aaaagatatc agtctggtaa ttttggcaag atcaacaagg ctgtcaggtt cacggagtac | 1860 |
| ttgaatttgt ctaactacat gagtacagca atgatatttt ccccgtgta ccagctctat | 1920 |
| gctgtggttg tccatcatga tgttatgaat gcagccttt ctggccatta tgtgtgttat | 1980 |
| gtcaaagaca cacaagggaa gtggcacaag atggatgaca gccaggtgaa acctgtttct | 2040 |
| ctggaaaaag tcttgtcaaa gtgtgcatac atgctatttt acgcaaggtg ttcaccacgg | 2100 |
| gcaccaaact ctgtaaggaa aatgattctt gctcaagact catcgtgcac aaagaaagcc | 2160 |
| aagcagatgg tggatccagg accaccatct ttggaaggag gaagttactt aagcagacac | 2220 |
| caaggtgggc agtcatgtag agatcatata gtctatgacc tcacctacac attcggtggc | 2280 |
| tcatcttata cagtagtgga gtccccgagt ccaagtgaca gctcctcgct gttcagcaac | 2340 |
| tctgatgcag ggtcaaccag cactttcagt agtgatagca ctgacagcac aaggaattcg | 2400 |
| accagcatgg aggagtatga ttacatattt ggaagctcgg atcaaatgta ccctgtaagc | 2460 |
| acggtggtta tacctgagga acatgaactt agctattcgc ggcagaggtc tagcttgaac | 2520 |
| cccagcactt caagtcaata tgtggatcaa gcagctgagg ttgagatgct gcaccagcac | 2580 |
| cagcatcagg ccggcagagg gggctgggat gagggtgatg tgatgccatt cttctattcc | 2640 |
| aaccaaggta acaccacga tagtagtaga agtagcaaca ttagtagtag taataggaag | 2700 |
| ttaacagaac agcgtaggac gattgggag gttgaccatg gccctggaga gggccatggc | 2760 |
| agcgttttac ttagaagggc ggctagggag aggattgccc aagcaattta ttga | 2814 |

<210> SEQ ID NO 16
<211> LENGTH: 937
<212> TYPE: PRT
<213> ORGANISM: Oryza sativa

<400> SEQUENCE: 16

Met Ala Ser Ala Ala Leu Ser Leu Ala Val Ala Val Ala Val Ala
1               5                   10                  15

Val Ala Ala Val Val Ala Val Ala Arg Gly Ala Leu Arg Arg Ala Ala
            20                  25                  30

Ala Arg Arg Glu Glu Val Arg Arg Leu Ala Arg Leu Ala Ala Val Glu

```
                35                  40                  45
Ala Glu Val Ala Glu Arg Glu Ala Tyr Cys Tyr Ala Arg Gly Arg Gly
             50                  55                  60

Gly Val Ala Gly Ala Pro Leu Trp Thr Val Pro Glu Val Ala Ser Pro
 65                  70                  75                  80

Arg Glu Asp Glu Glu Glu Glu Glu Glu Ala Ala Ala Val Glu
                 85                  90                  95

Leu Glu Met Pro Ala Ala Arg Gln Ala Glu Ala Ala Ala Ala
                100                 105                 110

Ala Val Lys Gly Val Cys Val Ile Ser Tyr Asn Phe Leu Cys Met Arg
            115                 120                 125

Ile Leu Leu Phe Asp Ser Asp Thr Phe Lys Cys Gln Ile Ser His Trp
        130                 135                 140

Arg Gln Gly His Lys Asp Glu Cys His Pro Pro Arg Val Asp Ala Arg
145                 150                 155                 160

Pro Asp Asn Ile Thr Val Val Ser Ser Val Lys Lys Gly Val Gly Met
                165                 170                 175

Tyr Asn Ser Phe Glu Gln Ser Val Lys Ser Val Glu Pro Ala Val
                180                 185                 190

Glu Val Asn Lys Ser Val Ala Ala Val Pro Glu Leu Ser Glu Ala Asn
            195                 200                 205

Leu Val Ser Asp Gly Val Asp Asn Glu Arg Lys Met Arg Gly Gln
    210                 215                 220

Lys Ala Ser Ile Thr Ala Lys Val Ser Glu Asp Val Leu Asp Asn Asn
225                 230                 235                 240

Arg Ile Arg Ser Val Asp Ser Ser Arg Leu Pro Thr Ser Gly Lys Ala
                245                 250                 255

Cys Asn Ile Gln Asp Ala Thr Val Asn Glu Asn Phe Ser Lys Thr Ser
                260                 265                 270

Ala Gly Ser Ser Ser Ser Arg Val Glu Arg Ser Thr Thr Ser Glu Pro
            275                 280                 285

Glu Leu Asn His Ser Asn Lys Gln Ala Ser Gly Thr Asp Asn Leu Lys
        290                 295                 300

Ser Ser Arg Gly Leu Pro Ser Val Ser Thr Val Gly Thr Ile Ser Ser
305                 310                 315                 320

Ile His Gly Ser Glu Lys Glu Ala Ala Met Pro Asn Asn Arg Ser Leu
                325                 330                 335

Val Lys Asn Ile Pro Arg Gln Gln Ala Ala Lys Val Val Arg His
            340                 345                 350

Tyr Pro Ser Glu Met Thr Leu Phe Pro Tyr Glu His Phe Val Lys Leu
        355                 360                 365

Tyr Asn Phe Asp Lys Val Glu Leu Arg Pro Phe Gly Leu Val Asn Leu
            370                 375                 380

Gly Asn Ser Cys Tyr Ala Asn Ala Val Leu Gln Cys Leu Ala Phe Thr
385                 390                 395                 400

Arg Pro Leu Thr Ala Tyr Leu Thr Glu Gly Leu His Ser Arg Asn Cys
                405                 410                 415

Asn Leu Ile Leu Ser Gln Asn Cys Val Thr Tyr His Gly Ser Lys Lys
            420                 425                 430

Glu Trp Cys Phe Met Cys Glu Phe Glu Lys Leu Ile Leu Glu Gly Arg
        435                 440                 445

Arg Gly Lys Ser His Leu Ser Pro Thr Gly Ile Leu Ser His Leu Arg
    450                 455                 460
```

```
Asp Ile Gly Ser Ser Phe Gly Pro Gly Arg Glu Asp Ala His Glu
465                 470                 475                 480

Phe Leu Arg Tyr Ala Ile Asp Thr Met Gln Ser Ala Ser Met Lys Glu
                485                 490                 495

Ala Lys Lys Asn Gly Val Tyr Gly Leu Pro Glu Glu Thr Thr Leu Val
                500                 505                 510

Gln Leu Ile Phe Gly Gly Tyr Leu Arg Ser Lys Ile Lys Cys Thr Met
                515                 520                 525

Cys Gln Gly Ser Ser Glu Gln Cys Glu Arg Ile Leu Asp Leu Thr Val
530                 535                 540

Glu Ile Asp Gly Asp Ile Asn Thr Leu Glu Glu Ala Leu His Arg Phe
545                 550                 555                 560

Thr Ser Thr Glu Ile Leu Asp Gly Asp Asn Arg Tyr Asn Cys Ser Arg
                565                 570                 575

Cys Lys Ser Tyr Glu Arg Ala Lys Lys Leu Thr Ile Ser Glu Ala
                580                 585                 590

Pro Asn Ile Leu Thr Ile Ala Leu Lys Arg Tyr Gln Ser Gly Asn Phe
                595                 600                 605

Gly Lys Ile Asn Lys Ala Val Arg Phe Thr Glu Tyr Leu Asn Leu Ser
                610                 615                 620

Asn Tyr Met Ser Thr Ala Asp Asp Ile Ser Pro Val Tyr Gln Leu Tyr
625                 630                 635                 640

Ala Val Val Val His His Asp Val Met Asn Ala Ala Phe Ser Gly His
                645                 650                 655

Tyr Val Cys Tyr Val Lys Asp Thr Gln Gly Lys Trp His Lys Met Asp
                660                 665                 670

Asp Ser Gln Val Lys Pro Val Ser Leu Glu Lys Val Leu Ser Lys Cys
                675                 680                 685

Ala Tyr Met Leu Phe Tyr Ala Arg Cys Ser Pro Arg Ala Pro Asn Ser
690                 695                 700

Val Arg Lys Met Ile Leu Ala Gln Asp Ser Ser Cys Thr Lys Lys Ala
705                 710                 715                 720

Lys Gln Met Val Asp Pro Gly Pro Pro Ser Leu Glu Gly Gly Ser Tyr
                725                 730                 735

Leu Ser Arg His Gln Gly Gly Gln Ser Cys Arg Asp His Ile Val Tyr
                740                 745                 750

Asp Leu Thr Tyr Thr Phe Gly Gly Ser Ser Tyr Thr Val Val Glu Ser
                755                 760                 765

Pro Ser Pro Ser Asp Ser Ser Ser Leu Phe Ser Asn Ser Asp Ala Gly
                770                 775                 780

Ser Thr Ser Thr Phe Ser Ser Asp Ser Thr Arg Asn Ser
785                 790                 795                 800

Thr Ser Met Glu Glu Tyr Asp Tyr Ile Phe Gly Ser Ser Asp Gln Met
                805                 810                 815

Tyr Pro Val Ser Thr Val Val Ile Pro Glu Glu His Glu Leu Ser Tyr
                820                 825                 830

Ser Arg Gln Arg Ser Ser Leu Asn Pro Ser Thr Ser Ser Gln Tyr Val
                835                 840                 845

Asp Gln Ala Ala Glu Val Glu Met Leu His Gln His Gln His Gln Ala
                850                 855                 860

Gly Arg Gly Gly Trp Asp Glu Gly Asp Val Met Pro Phe Phe Tyr Ser
865                 870                 875                 880
```

```
Asn Gln Gly Lys His His Asp Ser Ser Arg Ser Ser Asn Ile Ser Ser
                885                 890                 895

Ser Asn Arg Lys Leu Thr Glu Gln Arg Arg Thr Ile Gly Glu Val Asp
        900                 905                 910

His Gly Pro Gly Glu Gly His Gly Ser Val Leu Leu Arg Arg Ala Ala
            915                 920                 925

Arg Glu Arg Ile Ala Gln Ala Ile Tyr
        930                 935

<210> SEQ ID NO 17
<211> LENGTH: 3210
<212> TYPE: DNA
<213> ORGANISM: Oryza sativa

<400> SEQUENCE: 17
atgctggggg gaggcctcgg cggcggcggg ggcggcggcg gtgcgggtgg gctgggcctc      60
gacctctcgg cggtgatcca ggcggcggtg gtcggcctcg tgctgttctc ggcggccgtc     120
gtcgccgtgc gccgcgccgc gtcgaggtac ttcgtcgtcg acgccgcggg gttcgccgcc     180
tcctcgtacg acgatcacca ccaccccac caccacctcg tgatgacgcc tcgcggggag     240
gagcagcagc ggcagcaggg cggcggcgcg gcgcagggg cgcaagccgc cgccagtggg      300
ggcggggagc cctgtgccgc gtgcggctac atcgccacca aaaagtgctc cgggtgcaag     360
cgcgtgcggt attgttctca aggatgtcag tcaaagcatt ggcaatctgg tcacaagttc     420
aagtgcaaac aaatgaaaaa atcaagccct gctgacaagc tatcaggtgg aggcgaggaa     480
gacagaaata agttatctgg ttttggtccc atctcattag tacctgcccg tagaaaatta     540
aacaaggtca tctttccata tgatgaattt ctaaagctgt gcaactggag ggaccttgat     600
tatttacctt gtggcctttt gaattgtggc aacagttgct tgccaatgt tgttttacaa     660 tgtctttcat gtacgaggcc acttgcagcc tatctcttag gaatggacca tagcagggaa     720
tgttataaga gacatgaaga ttggtgtttc ttgtgcgaac tgcaatgcca atccaaagg     780 gcaagtgaaa gtatgcatcc atttgcgccg aagaacattc tttctcacct gccaaatata     840
ggtgggaacc ttggctttgg tagacaagag gatgctcatg aattcatgag gtttgcaata     900
gataagatgc aatctgcttg tcttgatgaa tttggaggcg agaaggctgt agaccctagc     960
acgcaagaaa cgactcttat tcaacacata tttggtggtc gtctgcaatc ccaggttcaa    1020
tgtactgcat gtggaatggt ctcaaatcgc tatgagaata tgatggactt aacagttgaa    1080
attcatggtg atgctgactc cttggaagaa tgcttagata agttcactgc agtagagtgg    1140
cttgatggtg ataataagta caatgtgat ggatgcagcg actatgtcaa agcacagaaa    1200
cgtcttacag tttatcaagc tccaaatatc ctcacaatta ctctgaaaag attccagagt    1260
ggtagatttg ggaaactaaa caagagagtt acattcccaa tgaagttaga cctaacgcca    1320
tacatgagta gcactgatgg aagtgaccaa tacgatctct atgctgttgt tgttcatctg    1380
gatatgctca atgcttcatt ttttgggcat tatatatgct atataaaaaa ttaccgagga    1440
cgctggtata aaattgatga ctgcaaggtt atggctgttg atgaggagga agtacatgct    1500
caaggtgctt atatgcttct atatagcagg agaacagctc gccctaggcc actaattgca    1560
gtagaagaac tcatgaaaca gcagcaacag ttgaaagtat gcccttttgaa tggacaaaat    1620 catttgatac aagaggatgt gccattagaa ggcgtgccat cttttgaaacc ctcagaagat    1680 ctggaagttg attttgaatc caacaacaaa tctttacata ctatggacag agagccagac    1740
ctggattttc atgtgagctt tgatagagat aagttcacta acaatgatat tatgcaccca    1800
```

| | |
|---|---|
| ccagtttcaa cggtatcgca tgcccttgat gaaaatacta gaggagattc aggttttcca | 1860 |
| ttggaagaat cgaacaccat gggatctgtg caatttggca actccacata tgaaacatct | 1920 |
| ttagtgcatt cccctgcaga gcagtgtgaa gaacctgcgt catgtattga ttcagttgac | 1980 |
| tacatggaaa ttgacactga agctggcgtt aaagttgaaa gatggagcag gcctgcctta | 2040 |
| ggtgattcag ttggagtgat ggggaatggt acattggtcc cggcattgga gaatggtttg | 2100 |
| gcgggtaaac caattcctgg ttttcccgac aaaccctcga gaataaattc attctttgca | 2160 |
| gaaggatgtc aaactggtga caatggtgct ggttcctcgc aagagttgaa tggtcattgc | 2220 |
| aatggagaac cagttgccc agagcaagga gttctgacca tggtggcaa cacgccctct | 2280 |
| ccaagcacac aatgctatga aaataagttt gcaacatcca ccaacggcaa ctattctatt | 2340 |
| gggaatggtg atacattatc tagcagcaac tcattacatg cgggcaaaca gaatgctggc | 2400 |
| tttacctata atggtttcaa tccaaaacct tacaaagaac catcaggaag caacacatat | 2460 |
| ctgaataata catgcaatgg taaaccatcg gaagataatc acaataaatg tgccccaaac | 2520 |
| ctgccggcaa aagattgcca agggggcatg ccattcttac atcgtggctt ccttctaagg | 2580 |
| ccttgttcta ggggaaatcc aggcaaatgt gatgatggct tgtcaattag taatggcaca | 2640 |
| tcatcatcct tgtgagtag taacagcaaa tcaagtaata tttcatcatc tcgaaatggt | 2700 |
| gaaggaggca caccattctt gtctcctagt tttcgcacaa atcattgcag agagtcagct | 2760 |
| gccatggaca cctctgcaag ctctgtccat gatttgaaaa ccagctataa catttccttg | 2820 |
| gagcaaaaat ctattggtgc tgcagtaccg tcagacctga taaaagaaag ttggggtgaa | 2880 |
| gatggcacga cttttggcac tgtttaccaa caaagagcaa cttctgttga taatgtaagc | 2940 |
| agccgccatg atgaaaatgg gcatgtgatt ttgggtgcca ataattccag ttatggagga | 3000 |
| gaaaacggca gtaataatgg aattcttgat atgaatagca gcagtagcca aagggacgca | 3060 |
| gcatctagta ccatgatggc ttctgagaaa ggcataggac ctaaaacagc tgaccaagtc | 3120 |
| aattacatat ctgatgcact tgaacatgat ggtttgcgac gaagattaac ctcaaatttt | 3180 |
| cctgatcaga atggtattga tgctcaataa | 3210 |

<210> SEQ ID NO 18
<211> LENGTH: 1069
<212> TYPE: PRT
<213> ORGANISM: Oryza sativa

<400> SEQUENCE: 18

Met Leu Gly Gly Gly Leu Gly Gly Gly Gly Gly Gly Gly Ala Gly
1               5                   10                  15

Gly Leu Gly Leu Asp Leu Ser Ala Val Ile Gln Ala Ala Val Val Gly
            20                  25                  30

Leu Val Leu Phe Ser Ala Ala Val Ala Val Arg Arg Ala Ala Ser
        35                  40                  45

Arg Tyr Phe Val Val Asp Ala Ala Gly Phe Ala Ala Ser Ser Tyr Asp
    50                  55                  60

Asp His His Pro His His His Leu Val Met Thr Pro Arg Gly Glu
65                  70                  75                  80

Glu Gln Gln Arg Gln Gln Gly Gly Gly Ala Ala Gln Gly Ala Gln Ala
                85                  90                  95

Ala Ala Ser Gly Gly Gly Glu Pro Cys Ala Ala Cys Gly Tyr Ile Ala
            100                 105                 110

Thr Lys Lys Cys Ser Gly Cys Lys Arg Val Arg Tyr Cys Ser Gln Gly

-continued

```
            115                 120                 125
Cys Gln Ser Lys His Trp Gln Ser Gly His Lys Phe Lys Cys Lys Gln
            130                 135                 140
Met Lys Lys Ser Ser Pro Ala Asp Lys Leu Ser Gly Gly Gly Glu Glu
145                 150                 155                 160
Asp Arg Asn Lys Leu Ser Gly Phe Gly Pro Ile Ser Leu Val Pro Ala
                165                 170                 175
Arg Arg Lys Leu Asn Lys Val Ile Phe Pro Tyr Asp Glu Phe Leu Lys
                180                 185                 190
Leu Cys Asn Trp Arg Asp Leu Asp Tyr Leu Pro Cys Gly Leu Leu Asn
                195                 200                 205
Cys Gly Asn Ser Cys Phe Ala Asn Val Val Leu Gln Cys Leu Ser Cys
            210                 215                 220
Thr Arg Pro Leu Ala Ala Tyr Leu Leu Gly Met Asp His Ser Arg Glu
225                 230                 235                 240
Cys Tyr Lys Arg His Glu Asp Trp Cys Phe Leu Cys Glu Leu Gln Cys
                245                 250                 255
His Ile Gln Arg Ala Ser Glu Ser Met His Pro Phe Ala Pro Lys Asn
                260                 265                 270
Ile Leu Ser His Leu Pro Asn Ile Gly Gly Asn Leu Gly Phe Gly Arg
                275                 280                 285
Gln Glu Asp Ala His Glu Phe Met Arg Phe Ala Ile Asp Lys Met Gln
            290                 295                 300
Ser Ala Cys Leu Asp Glu Phe Gly Gly Glu Lys Ala Val Asp Pro Ser
305                 310                 315                 320
Thr Gln Glu Thr Thr Leu Ile Gln His Ile Phe Gly Gly Arg Leu Gln
                325                 330                 335
Ser Gln Val Gln Cys Thr Ala Cys Gly Met Val Ser Asn Arg Tyr Glu
                340                 345                 350
Asn Met Met Asp Leu Thr Val Glu Ile His Gly Asp Ala Asp Ser Leu
                355                 360                 365
Glu Glu Cys Leu Asp Lys Phe Thr Ala Val Glu Trp Leu Asp Gly Asp
            370                 375                 380
Asn Lys Tyr Lys Cys Asp Gly Cys Ser Asp Tyr Val Lys Ala Gln Lys
385                 390                 395                 400
Arg Leu Thr Val Tyr Gln Ala Pro Asn Ile Leu Thr Ile Thr Leu Lys
                405                 410                 415
Arg Phe Gln Ser Gly Arg Phe Gly Lys Leu Asn Lys Arg Val Thr Phe
                420                 425                 430
Pro Met Lys Leu Asp Leu Thr Pro Tyr Met Ser Ser Thr Asp Gly Ser
                435                 440                 445
Asp Gln Tyr Asp Leu Tyr Ala Val Val His Leu Asp Met Leu Asn
            450                 455                 460
Ala Ser Phe Phe Gly His Tyr Ile Cys Tyr Ile Lys Asn Tyr Arg Gly
465                 470                 475                 480
Arg Trp Tyr Lys Ile Asp Asp Cys Lys Val Met Ala Val Asp Glu Glu
                485                 490                 495
Glu Val His Ala Gln Gly Ala Tyr Met Leu Leu Tyr Ser Arg Arg Thr
                500                 505                 510
Ala Arg Pro Arg Pro Leu Ile Ala Val Glu Glu Leu Met Lys Gln Gln
                515                 520                 525
Gln Gln Leu Lys Val Cys Pro Leu Asn Gly Gln Asn His Leu Ile Gln
            530                 535                 540
```

```
Glu Asp Val Pro Leu Glu Gly Val Pro Ser Leu Lys Pro Ser Glu Asp
545                 550                 555                 560

Leu Glu Val Asp Phe Glu Ser Asn Asn Lys Ser Leu His Thr Met Asp
                565                 570                 575

Arg Glu Pro Asp Leu Asp Phe His Val Ser Phe Asp Arg Asp Lys Phe
            580                 585                 590

Thr Asn Asn Asp Ile Met His Pro Pro Val Ser Thr Val Ser His Ala
        595                 600                 605

Leu Asp Glu Asn Thr Arg Gly Asp Ser Gly Phe Pro Leu Glu Glu Ser
610                 615                 620

Asn Thr Met Gly Ser Val Gln Phe Gly Asn Ser Thr Tyr Glu Thr Ser
625                 630                 635                 640

Leu Val His Ser Pro Ala Glu Gln Cys Glu Pro Ala Ser Cys Ile
                645                 650                 655

Asp Ser Val Asp Tyr Met Glu Ile Asp Thr Glu Ala Gly Val Lys Val
            660                 665                 670

Glu Arg Trp Ser Arg Pro Ala Leu Gly Asp Ser Val Gly Val Met Gly
        675                 680                 685

Asn Gly Thr Leu Val Pro Ala Leu Glu Asn Gly Leu Ala Gly Lys Pro
690                 695                 700

Ile Pro Gly Phe Pro Asp Lys Pro Ser Arg Ile Asn Ser Phe Phe Ala
705                 710                 715                 720

Glu Gly Cys Gln Thr Gly Asp Asn Gly Ala Gly Ser Ser Gln Glu Leu
                725                 730                 735

Asn Gly His Cys Asn Gly Glu Pro Ser Cys Pro Glu Gln Gly Val Leu
            740                 745                 750

Thr Asn Gly Gly Asn Thr Pro Ser Pro Ser Thr Gln Cys Tyr Glu Asn
        755                 760                 765

Lys Phe Ala Thr Ser Thr Asn Gly Asn Tyr Ser Ile Gly Asn Gly Asp
770                 775                 780

Thr Leu Ser Ser Ser Asn Ser Leu His Ala Gly Lys Gln Asn Ala Gly
785                 790                 795                 800

Phe Thr Tyr Asn Gly Phe Asn Pro Lys Pro Tyr Lys Glu Pro Ser Gly
                805                 810                 815

Ser Asn Thr Tyr Leu Asn Asn Thr Cys Asn Gly Lys Pro Ser Glu Asp
            820                 825                 830

Asn His Asn Lys Cys Ala Pro Asn Leu Pro Ala Lys Asp Cys Gln Gly
        835                 840                 845

Gly Met Pro Phe Leu His Arg Gly Phe Leu Leu Arg Pro Cys Ser Arg
850                 855                 860

Gly Asn Pro Gly Lys Cys Asp Asp Gly Leu Ser Ile Ser Asn Gly Thr
865                 870                 875                 880

Ser Ser Ser Phe Val Ser Ser Asn Ser Lys Ser Ser Asn Ile Ser Ser
                885                 890                 895

Ser Arg Asn Gly Glu Gly Gly Thr Pro Phe Leu Ser Pro Ser Phe Arg
            900                 905                 910

Thr Asn His Cys Arg Glu Ser Ala Ala Met Asp Thr Ser Ala Ser Ser
        915                 920                 925

Val His Asp Leu Lys Thr Ser Tyr Asn Ile Ser Leu Glu Gln Lys Ser
930                 935                 940

Ile Gly Ala Ala Val Pro Ser Asp Leu Ile Lys Glu Ser Trp Gly Glu
945                 950                 955                 960
```

```
Asp Gly Thr Thr Phe Gly Thr Val Tyr Gln Gln Arg Ala Thr Ser Val
            965                 970                 975

Asp Asn Val Ser Ser Arg His Asp Glu Asn Gly His Val Ile Leu Gly
        980                 985                 990

Ala Asn Asn Ser Ser Tyr Gly Gly Glu Asn Gly Ser Asn Asn Gly Ile
    995                1000                1005

Leu Asp Met Asn Ser Ser Ser Gln Arg Asp Ala Ala Ser Ser
    1010                1015                1020

Thr Met Met Ala Ser Glu Lys Gly Ile Gly Pro Lys Thr Ala Asp
    1025                1030                1035

Gln Val Asn Tyr Ile Ser Asp Ala Leu Glu His Asp Gly Leu Arg
    1040                1045                1050

Arg Arg Leu Thr Ser Asn Phe Pro Asp Gln Asn Gly Ile Asp Ala
    1055                1060                1065

Gln

<210> SEQ ID NO 19
<211> LENGTH: 2047
<212> TYPE: DNA
<213> ORGANISM: Zea mays

<400> SEQUENCE: 19
gattgttctt caaaaaaatg gtgccttatg tgtgaacttg agcaatatgc ttcaacttta    60
cgtgaaagtg gtgggccctt atctccaagt agaattcttt ctaatctgag gaatattgga   120
tgtcgcttgg gtggtggaac tcaggaagat gctcatgagt ttttaaggca tcttgtgatg   180
tctatgcaag cagcttgctt ggatgggctg ggtggtgaga agcatgttga gccaagtttg   240
caggaaacaa cactgataca acagatgttt ggtggccgtc ttaaatccaa ggttaagtgc   300
ctcagatgtt atcacgagtc tgaacgatat gagaatataa tggatcttac tttggagatt   360
cacggctggg tagagtcctt gcaggatgct ttgacacagt tcactgcccc tgaagattta   420
gatggtgata atatgtataa atgtggaagt tgtgctgcct atgttaaagc caggaagcaa   480
ctgagcgtgc atgaggtgcc aaacatatta acagttgttc ttaaaagatt tcagtcagga   540
aaatatggca agatcaacaa atgtgttact ttccctgata tgttggacat ggttcctttt   600
gtgactgggt ctggtgacaa tccccctctt tatttcttgt atgccgtggt tgtacatgtg   660
gatacagaaa atgcatcatt ctctgggcac tatatatcat atgtcaaaga tatgcagggt   720
acatggttga gaattgatga ttcagaggtc caggttgtat cagtgaatca agttatgtca   780
gaaggtgcat atatgctttt ctacatgagg tctttccccc gaccaccaag aatatacatc   840
gagaaggggc cgactgttcc atccgcgaag cgccacacat caaagtattc caagggctct   900
aaacacgagc gcgagcagac agagttactc ctctcggcga acgatccagc atacggtgtt   960
tatgacttta gacctgatgg cgagggctac acgcaagatc agcaagcaga gttgagatcc  1020
agggatttcc atcgcgccga cgatgccttc gcagactcgg tcagcgcgga cttctcggag  1080
gccacgtcaa gcgaatggtc gctgtttacc agctccgacg agtcctcatt caccaccgag  1140
agcacaaggg actcgttcag cgttgtggac tacggcgaca acgctggcct ggacccaatc  1200
tcctcgatat ttgggccaag ctatgctccg gagcatcatc ccgtccacc tggcagtttc  1260
gccgcgtgca cgaggctctc gccttccaac ccacagacaa ggtacttctc ggagagcaca  1320
gggttcgtct cggactactc ttccagcggc attgtacata gaggaaggga tccaggtagg  1380
gcatacacct gttcagcgga accgctcgct tcggctgcgg cggcgcacca gcaccagcgg  1440
```

| | |
|---|---|
| tacgcccttc gcggccgaga cggtttggtc cagacatctg ggttctgcca aatgtaaccg | 1500 |
| gctttacgat ttcgtagcta tagctgtagc tggtgctcgg gcagctgcgg gttagcactg | 1560 |
| ccactgatgc tgctgcctct atgttctttt tatttcaggt gaggcgtatt aaattttggc | 1620 |
| tgcatgtcat tcctaggcta gctcgattca atgtagcgag agagagagga acaaatttag | 1680 |
| attgtgtcta tatgcaggtg aaattttaga gcgcggtgga gctgctccgg ttgaagccat | 1740 |
| cccccgaggc ccgaaccagt aaattacgcc gaatccggca gtcgtatggc cctgcacacc | 1800 |
| agtgctttgt gaaaagcttg cagattcatc aattgacgtg cacttgcctt ttatatggac | 1860 |
| gctgacgtat ggaggtgcac actctccacc tccgtatatc tcgccaccta ctctgtttat | 1920 |
| attagaaggt tgattgctga cacacaacac ctgctcgtac ttttttgtcg aaatcatgac | 1980 |
| ggacaacaac gctaaacata tagtacaatc ttcttgtctt gctaaaaaaa aaaaaaaaa | 2040 |
| accgatt | 2047 |

<210> SEQ ID NO 20
<211> LENGTH: 493
<212> TYPE: DNA
<213> ORGANISM: Zea mays

<400> SEQUENCE: 20

| | |
|---|---|
| aatcggtttt tttttttttt ttttagcaag acaagaagat tgtactatat gtttagcgtt | 60 |
| gttgtccgtc atgatttcga caaaaaagta cgagcaggtg ttgtgtgtca gcaatcaacc | 120 |
| ttctaatata aacagagtag gtggcgagat atacggaggt ggagagtgtg cacctccata | 180 |
| cgtcagcgtc catataaaag gcaagtgcac gtcaattgat gaatctgcaa gcttttcaca | 240 |
| aagcactggt gtgcagggcc atacgactgc cggattcggc gtaatttact ggttcgggcc | 300 |
| tcggggatg gcttcaaccg gagcagctcc accgcgctct aaaatttcac ctgcatatag | 360 |
| acacaatcta aatttgttcc tctctctctc gctacattga atcgagctag cctaggaatg | 420 |
| acatgcagcc aaaatttaat acgccttacc tgaaataaaa agaacataga ggcagcagca | 480 |
| tcagtggcag tgc | 493 |

<210> SEQ ID NO 21
<211> LENGTH: 243
<212> TYPE: DNA
<213> ORGANISM: Zea mays

<400> SEQUENCE: 21

| | |
|---|---|
| taatgcgcct cacctgaaat aaaaagaaca tagaggcagc agcatcagtg gcagtgctaa | 60 |
| accgcagctg cccgagcacc agctacagct atagctacga aatcgtaaag ccggttacat | 120 |
| ttggcagaac ccagatgtct ggaccaaacc gtctcggccg ctaagggcgt accgctggtg | 180 |
| ctggtgcgcc gccgcagccg aagcgagtgg ttccgctgaa caggtgtatg ccctacctgg | 240 |
| atc | 243 |

<210> SEQ ID NO 22
<211> LENGTH: 243
<212> TYPE: DNA
<213> ORGANISM: Zea mays

<400> SEQUENCE: 22

| | |
|---|---|
| taatacgcct catctgaaat aaaaagaaca tagaggcagc agcatcagtg gcagtgctaa | 60 |
| accgcagctg cccgagcacc agctacagct atagctacga aatcgtaaag ccggttacat | 120 |
| ttggcagaac ccagatgtct ggaccaaacc gtctcggccg ctaagtgcgt accgctggtg | 180 |

```
ctggtgcgcc gcagccgccg aaccgagcgg ttccgctgaa caggtgtatg ccctacctgg    240
atc                                                                  243

<210> SEQ ID NO 23
<211> LENGTH: 243
<212> TYPE: DNA
<213> ORGANISM: Zea mays

<400> SEQUENCE: 23
taatacgcct cacctgaaat aaaaagaaca tagaggcagc agcatcagtg gcagtgctaa    60
accgcagctg cccgagcacc agctacagct atagctacga aatcgtaaag ccggttacat    120
ttggcagaac ccagatgtct ggaccaaacc gtctcggccg ctaagggcgt accgctggtg    180
ctggtgcgcc gccgcagccg aagcgagtgg ttccgctgaa caggtgtatg ccctaccggg    240
atc                                                                  243

<210> SEQ ID NO 24
<211> LENGTH: 243
<212> TYPE: DNA
<213> ORGANISM: Zea mays

<400> SEQUENCE: 24
gatccgggta gggcatacac ctgttcagcg gaaccgctcg gttcggcggc tgcggcgcac    60
cagcaccagc ggtacgcact agcggccga  gacggtttgg tccagacatc tgggttctgc    120
caaatgtaac cggctttacg atttcgtagc tatagctgta gctggtgctc gggcagctgc    180
ggtttagcac tgccactgat gctgctgcct ctatgttctt tttatttcag atgaggcgta    240
tta                                                                  243

<210> SEQ ID NO 25
<211> LENGTH: 243
<212> TYPE: DNA
<213> ORGANISM: Zea mays

<400> SEQUENCE: 25
gatccaggta gggcatacac ctgttcagcg gaaccgctcg gttcggcggc tgcggcgcac    60
cagcaccagc ggtacgcact agcggccga  gacggtttgg tccagacatc tgggttctgc    120
caaatgtaac cggctttacg atttcgtagc tatagctgta gctggtgctc gggcagctgc    180
ggtttagcac tgccactgat gctgctgcct ctatgttctt tttatttcag atgaggcgta    240
tta                                                                  243

<210> SEQ ID NO 26
<211> LENGTH: 243
<212> TYPE: DNA
<213> ORGANISM: Zea mays

<400> SEQUENCE: 26
taatacgcct catctgaaat aaaaagaaca tagaggcagc agcatcagtg gcagtgctaa    60
accgcagctg cccgagcacc agctacagct atagctacga aatcgtaaag ccggttacat    120
ttggcagaac ccagatgtct ggaccaaacc gtctcggccg ctaagtgcgt accgctggtg    180
ctggtgcgcc gcagccgccg aaccgagcgg ttccgctgaa caggtgtatg ccctaccggg    240
atc                                                                  243

<210> SEQ ID NO 27
```

```
<211> LENGTH: 130
<212> TYPE: DNA
<213> ORGANISM: Zea mays

<400> SEQUENCE: 27
gatctgccaa atgtaaccgg ctttacgatt tcgtagctat agctgtagct ggtgctcggg    60
cagctgcggt ttagcactgc cactgatgct gctgcctcta tgttcttttt atttcagatg   120
aggcgtatta                                                          130

<210> SEQ ID NO 28
<211> LENGTH: 243
<212> TYPE: DNA
<213> ORGANISM: Zea mays

<400> SEQUENCE: 28
gatccaggta gggcatacac ctgttcagcg gaaccgctcg gttcggcggc tgcggcgcac    60
cagcaccagc ggtacgcact tagcggccga gacggtttgg tccagacatc tgggttctgc   120
caaatgtaac cggctttacg atttcgtagc tatagctgta gctggtgctc gggcagctgc   180
ggtttagcac tgccactgat gctgctgcct ctatgttctt tttatttcag atgaggcgga   240
tta                                                                 243

<210> SEQ ID NO 29
<211> LENGTH: 243
<212> TYPE: DNA
<213> ORGANISM: Zea mays

<400> SEQUENCE: 29
gatccaggta gggcatacac ctgttcagcg gaaccgctcg gttcggcggc tgcggcgcac    60
cagcaccagc ggtacgcact tagcggccga gacggtttgg tccagacatc tgggttctgc   120
caaatgtaac cggctttacg atttcgtagc tatagctgta gctggtgctc gggcagctgc   180
ggtttagcac tgccactgat gctgctgcct ctatgttctt tttatttcag atgaggcgca   240
tta                                                                 243

<210> SEQ ID NO 30
<211> LENGTH: 243
<212> TYPE: DNA
<213> ORGANISM: Zea mays

<400> SEQUENCE: 30
gatccgggta gggcatacac ctgttcagcg gaaccgctcg gttcggcggc tgcggcgcac    60
cagcaccagc ggtacgcact tagcggccga gacggtttgg tccagacatc tgggttctgc   120
caaatgtaac cggctttacg atttcgtagc tatagctgta gctggtgctc gggcagctgc   180
ggtttagcac tgccactgat gctgctgcct ctatgttctt tttatttcag atgaggcgta   240
tta                                                                 243

<210> SEQ ID NO 31
<211> LENGTH: 243
<212> TYPE: DNA
<213> ORGANISM: Zea mays

<400> SEQUENCE: 31
gatccaggta gggcatacag gggttgagcg gaactgctcg gttcggcggc tgcggcgcac    60
cagcaccagc ggtacgcact tagcggccga gacggtttgg tccagacatc tgggttctgc   120
caaatgtaac cggctttacg atttcgtagc tatagctgta gctggtgctc gggcagctgc   180
```

```
ggtttagcac tgccactgag gcgggtgcct ctatgttctt tttatttcag atgaggcgta    240
tta                                                                  243

<210> SEQ ID NO 32
<211> LENGTH: 187
<212> TYPE: DNA
<213> ORGANISM: Zea mays

<400> SEQUENCE: 32
acgcacttag cggccgagac ggtttggtcc agacatctgg gttctgccaa atgtaaccgg     60
ctttacgatt tcgtagctat agctgtagct ggtgctcggg cagctgcggt ttagcactgc    120
cactgatgct gctgcctcta tgttcttttt atttcagatg aggcgtatta aattttggct    180
gcatgac                                                              187

<210> SEQ ID NO 33
<211> LENGTH: 368
<212> TYPE: DNA
<213> ORGANISM: Zea mays
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t

<400> SEQUENCE: 33
acgcacttag cggccgagac ggtttggtcc agacatctgg gttctgccaa atgtaaccgg     60
ctttacgatt tcgtagctat agtngttgcn ggtgctcggg cagctgcggt ttagcactgc    120
cactgatgct gctgcctcta tgttctttct atttcagatg aggcgtatta aattttggct    180
gcatgtcatt cctaggctag ctcgattcaa tgtagcgaga gagaaaaaat tagattgtgt    240
ctatatgcag gccaaatttt agagcgcggt ggagctgctc cggttgaagc catccctcga    300
accagtaaat tacgccgaat ccggcagtct aaggtagtgt ttggttgaag agtcaagtag    360
aacagagc                                                             368

<210> SEQ ID NO 34
<211> LENGTH: 847
<212> TYPE: DNA
<213> ORGANISM: Zea mays

<400> SEQUENCE: 34
tgagaattga tgattcagag gtccaggttg tatcagtgaa tcaagttatg tcagaaggtg     60
catatatgct tttctacatg aggtctttcc cccgaccacc aagaatatac atcgagaagg    120
ggccgactgt tccatccgcg aagcgccaca catcaaagta ttccaagggc tctaaacacg    180
agcgcgagca gacagagtta ctcctctcgg cgaacgatcc agcatacggt gtttatgact    240
ttagacctga tggcgagggc tacacgcaag atcagcaagc agagttgaga tccagggatt    300
tccatcgcgc cgacgatgcc ttcgcagact cggtcagcgc ggacttctcg gaggccacgt    360
caagcgaatg gtcgctgttt accagctccg acgagtcctc attcaccacc gagagcacaa    420
gggactcgtt cagcgttgtg gactacggcg acaacgctgg cctggaccca atctcctcga    480
tatttgggcc aagctatgct ccggagcatc atcccggtcc acctggcagt ttcgccgcgt    540
gcacgaggct ctcgccttcc aacccacaga caaggtactt ctcggagagc acagggttcg    600
```

```
tctcggacta ctcttccagc ggcattgtac atagaggaag ggatccaggt agggcataca      660
cctgttcagc ggaaccgctc gcttcggctg cggcggcgca ccagcaccag cggtacgccc      720
ttagcggccg agacggtttg gtccagacat ctgggttctg ccaaatgtaa ccggctttac      780
gatttcgtag ctatagctgt agctggtgct cgggcagctg cgggttagca ctgccactga      840
tgctgct                                                                847

<210> SEQ ID NO 35
<211> LENGTH: 793
<212> TYPE: DNA
<213> ORGANISM: Zea mays

<400> SEQUENCE: 35
actggttcgg gcctcggggg atggcttcaa ccggagcagc tccaccgcgc tctaaaattt       60
cacctgcata tagacacaat ctaaatttgt tcctctctct ctcgctacat tgaatcgagc      120
tagcctagga atgacatgca gccaaaattt aatacgcctc acctgaaata aaagaacat      180 agaggcagca gcatcagtgg cagtgctaaa ccgcagctgc ccgagcacca gctacagcta      240
tagctacgaa atcgtaaagc cggttacatt tggcagaacc cagatgtctg gaccaaaccg      300
tctcggccgc taagggcgta ccgctggtgc tggtgcgccg ccgcagccga agcgagcggt      360
tccgctgaac aggtgtatgc cctacctgga tcccttcctc tatgtacaat gccgctggaa      420
gagtagtccg agacgaaccc tgtgctctcc gagaagtacc ttgtctgtgg gttggaaggc      480
gagagcctcg tgcacgcggc gaaactgcca ggtggaccgg atgatgctc cggagcatag      540 cttgcccaa atatcgagga gattgggtcc aggccagcgt tgtcgccgta gtccacaacg      600
ctgaacgagt cccttgtgct ctcggtggtg aatgaggact cgtcggagct ggtaaacagc      660
gaccattcgc ttgacgtggc ctccgagaag tccgcgctga ccgagtctgc gaaggcatcg      720
tcggcgcgat ggaaatccct ggatctcaac tctgcttgct gatcttgcgt gtagccctcg      780
ccatcaggtc taa                                                         793

<210> SEQ ID NO 36
<211> LENGTH: 310
<212> TYPE: DNA
<213> ORGANISM: Zea mays

<400> SEQUENCE: 36
agggactcgt tcagcgttgt ggactacggc gacaacgctg gcctggaccc aatctcctcg       60
atatttgggc caagctatgc tccggagcat catcccggtc cacctggcag tttcgccgcg      120
tgcacgaggc tctcgccttc aacccacag acaaggtact tctcggagag cacagggttc      180
gtctcggact actcttccag cggcattgta catagaggaa gggatccagg tagggcatac      240
acctgttcag cggaaccgct cgcttcggct gcggcggcgc accagcacct gcggtacgcc      300
cttagcggcc                                                             310

<210> SEQ ID NO 37
<211> LENGTH: 805
<212> TYPE: DNA
<213> ORGANISM: Zea mays

<400> SEQUENCE: 37
gattgttctt caaaaaaatg gtgccttatg tgtgaacttg agcaatatgc ttcaacttta       60
cgtgaaagtg gtgggcccct atctccaagt agaattcttt ctaatctgag gaatattgga      120
tgtcgcttgg gtggtggaac tcaggaagat gctcatgagt ttttaaggca tcttgtgatg      180
```

```
tctatgcaag cagcttgctt ggatgggctg ggtggtgaga agcatgttga gccaagtttg    240
caggaaacaa cactgataca acagatgttt ggtggccgtc ttaaatccaa ggttaagtgc    300
ctcagatgtt atcacgagtc tgaacgatat gagaatataa tggatcttac tttggagatt    360
cacggctggg tagagtcctt gcaggatgct ttgacacagt tcactgcccc tgaagattta    420
gatggtgata atatgtataa atgtggaagt tgtgctgcct atgttaaagc caggaagcaa    480
ctgagcgtgc atgaggtgcc aaacatatta acagttgttc ttaaaagatt tcagtcagga    540
aaatatggca agatcaacaa atgtgttact ttccctgata tgttggacat ggttcctttt    600
gtgactgggt ctggtgacaa tcccctctt tatttcttgt atgccgtggt tgtacatgtg     660
gatacagaaa atgcatcatt ctctgggcac tatatatcat atgtcaaaga tatgcagggt    720
acatggttga gaattgatga ttcagaggtc caggttgtat cagtgaatca agttatgtca    780
gaaggtgcat atatgctttt ctaca                                          805
```

`<210>` SEQ ID NO 38
`<211>` LENGTH: 506
`<212>` TYPE: DNA
`<213>` ORGANISM: Zea mays

`<400>` SEQUENCE: 38

```
tgtgctgcct atgtcaagcc aggaagcaac tgagcgtgca tgaggtgcca aacatattaa     60
cagttgttct taaaagattt cagtcaggaa aatatggcaa gatcaacaaa tgtgttactt    120
tccctggata tgttggacat ggttcctttt gtgactgggt ctggtgacaa tcccctctt    180 tatttcttgt atgccgtggt tgtacatgtg gatacagaaa atgcatcatt ctctgggcac    240
tatatatcat atgtcaaaga tatgcagggt acatggttga gaattgatga ttcagaggtc    300
caggttgtat cagtgaatca agttatgtca gaaggtgcat atatgctttt ctacctgagg    360
tctttccccc gaccaccaag aatatacatc gagaaggggc cgactgttcc atccgcgaag    420
cgccacacat caaagtattc caagggctct aaacacgagc gcgagcaaac agagttaatc    480
ctctcggaga acgatccagc ataccg                                         506
```

`<210>` SEQ ID NO 39
`<211>` LENGTH: 805
`<212>` TYPE: DNA
`<213>` ORGANISM: Zea mays
`<220>` FEATURE:
`<221>` NAME/KEY: misc_feature
`<222>` LOCATION: (3)..(3)
`<223>` OTHER INFORMATION: n is a, c, g, or t
`<220>` FEATURE:
`<221>` NAME/KEY: misc_feature
`<222>` LOCATION: (17)..(17)
`<223>` OTHER INFORMATION: n is a, c, g, or t

`<400>` SEQUENCE: 39

```
acnccacgcc cgtccgnaaa cacttatcgc aagcagacag agttactctt tcctgcaaac     60
gatcaggcat atggcgtcta tgatttcaga cccgatggcg aaggctatgc ccaagatcag    120
catgcagagc tgtggtccag agctttccat caccgacgat gcctttgcag actcggttag    180
cgcggacttc tcggaagcga catcaagtga atggtcgctg tttaccagct ccgacgagtc    240
ctcgttcacc accgagagca caagggattc gttcagcgtc gtggactacg agacaacgc     300 cggcctggat ccgatttcct ccatattcgg gccaagctat gctccggagc acggtgctcc    360
cggcagtttc gtctcgcgca caaggttctc accttccagt ccacagacaa ggtacttctc    420
```

```
ggagagcaca ggctttgtct cggactcttc catgccggcc acccccacg gcattgtaca      480 tagaggaagg tatccggata gtagggcgtg cgcctcttgt gcggaaccgc ttgcgtcggc      540
ggcgcatcag cggagcgggt atggccggta cccccttagt cgagatggtt ttgttcaaac      600
atctggtttt tgccaaaatg taatcggctc acatttcatt agctagct ggtgcatcgg       660 cagttgcggt tcttagcact gccgttaatg ctgcctcatg ttcttttatt tcagatgagg     720
cttattgaat ttttagctac atgtcgtttc taggggtagc tcgattcgat gtagcgaaaa     780
aaagttagat tatgtctata tgcag                                            805

<210> SEQ ID NO 40
<211> LENGTH: 701
<212> TYPE: DNA
<213> ORGANISM: Zea mays
<220> FEATURE:
<221> NAME/KEY: misc_feature
<222> LOCATION: (18)..(134)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t

<400> SEQUENCE: 40
tttttttttt ttttttnnn nnnnnnnnn nnnnnnnnn nnnnnnnnn nnnnnnnnn            60 nnnnnnnnnn nnnnnnnnnn nnnnnnnnnn nnnnnnnnnn nnnnnnnnnn nnnnnnnnnn      120
nnnnnnnnnn nnnntttggc aaaaaccaga tgtttgaaca aaaccatctc gactaagggg      180
gtaccggcca tacccgctcc gctgatgcgc cgccgacgca agcggttccg cagaagaggc      240
gcacgcccta ctatccggat accttcctct atgtacaatg ccgtgggggt gggccggcat      300
ggaagagtcc gagacaaagc ctgtgctctc cgagaagtac cttgtctgtg gactggaagg      360
tgagaacctt gtgcgcgaga cgaaactgcc gggagcaccg tgctccggag catagcttgg      420
cccgaatatg gnaggaaatc ggatccaggc cggcgttgtc tccgtagtcc acgacgctga     480
acgaatccct tgtgctctcg gtggtgaacg aggactcgtc ggagctggta acagcgacc      540 attcacttga tgtcgcttcc gagaagtccg cgctaaccga gtctgcaaag gcatcgtcgg     600
cgtgatggaa agctctggac ctcagctctg catgctgatc ttgggcatag ccttcgccat     660
cgggtctgaa atcatagacg ccatatgcct gatcgtttgc a                         701

<210> SEQ ID NO 41
<211> LENGTH: 653
<212> TYPE: DNA
<213> ORGANISM: Zea mays

<400> SEQUENCE: 41
ctgcatatag acataatcta acttttttc gctacatcga atcgagctac ccctagaaac      60
gacatgtagc taaaaattca ataagcctca tctgaaataa agaacatga ggcagcatta     120 acggcagtgc taagaaccgc aactgccgat gcaccagcta cagctaatga atgtgagcc     180 gattacattt tggcaaaaac cagatgtttg aacaaaacca tctcgactaa ggggtaccg     240 gccatacccg ctccgctgat gcgccgccga cgcaagcggt tccgcacaag aggcgcacgc    300
cctactatcc ggataccttc ctctatgtac aatgccgtgg gggtgggccg gcatggaaga    360
gtccgagaca aagcctgtgc tctccgagaa gtaccttgtc tgtggactgg aagtgagaa     420 ccttgtgcgc gagacgaaac tgccgggagc accgtgctcc ggagcatagc ttggcccgaa    480
tatggaggaa atcggatcca ggccggcgtt gtctccgtag tccacgacgc tgaacgaatc    540
```

```
ccttgtgctc tcggtggtga acgaggactc gtcggagctg gtaaacagcg accattcact    600
tgatgtcgct tccgagaagt ccgcgctaac cgagtctgca aaggcatcgt cgg           653
```

<210> SEQ ID NO 42
<211> LENGTH: 777
<212> TYPE: DNA
<213> ORGANISM: Zea mays
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t

<400> SEQUENCE: 42

```
acnccacgcc cgtccgnaaa cacttatcgc aagcagacag agttactctt tcctgcaaac     60
gatcaggcat atggcgtcta tgatttcaga cccgatggcg aaggctatgc ccaagatcag    120
catgcagagc tgtggtccag agccgacgat gcctttgcag actcggttag cgcggacttc    180
tcggaagcga catcaagtga atggtcgctg tttaccagct ccgacgagtc ctcgttcacc    240
accgagagca caagggattc gttcagcgtc gtggactacg agacaacgc cggcctggat     300 ccgatttcct ccatattcgg gccaagctat gctccggagc acggcgctcc cggcagtttc    360
gtctcgcgca caaggttctc accttccagt ccacagacaa ggtacttctc ggagagcaca    420
ggctttgtct cggactcttc ttccatgccg gcccaccccc acggcattgt acatagagga    480
aggtatccgg atagtagggc gtgcgcctct tctgcgaaac cgcttgcgtc ggcggcgcat    540
cagcggagcg ggtatggccg gtacccccctt agtcgagatg gttttgttca aacatctggt    600
ttttgccaaa tgtaatcggc tcacatttca ttagctgtag ctggtgcagc ggcagttgcg    660
ggtcttagct ctgtcgttat gctgcctcat gttctttat ttcagatgag gcgtattgaa     720
tttttagcta catgtcgttt ctaggggtag ctcgattcga tgtngcgaaa aaaaagt       777
```

<210> SEQ ID NO 43
<211> LENGTH: 103
<212> TYPE: DNA
<213> ORGANISM: Zea mays

<400> SEQUENCE: 43

```
ggtcagttgc ggttcttagc actgccgtta atgctgcctc atgttctttt atttcagatg     60
aggcttattg aatttttagc tacatgtcgt ttctaggggt agc                      103
```

<210> SEQ ID NO 44
<211> LENGTH: 2242
<212> TYPE: DNA
<213> ORGANISM: Zea mays
<220> FEATURE:
<221> NAME/KEY: misc_feature
<222> LOCATION: (2227)..(2227)
<223> OTHER INFORMATION: n is a, c, g, or t

<400> SEQUENCE: 44

```
cggcagagag cacagtagcc aagcgagtgg aggagagttg gagactcatc actggagagc     60
atccgaagcc gcccagtgct cgcacaaccg ctcccgattc ccaacccctc cgtccgccca    120
```

```
aggggcgccg caccatctcc agcctccagg cctcgatccc taccggaccc cgtggccctg    180
ctgtgttatc tggctggaga tccggccgga gtggcattcc tgctctcggt caataagtat    240
tctggaatgt ttttccgagc tcaaatagag aacttctgga gctggatatc agtattctgt    300
tagggatatg ctccaaccaa gggaagctga tgtgcctgca ctctttcttg tcttcattgt    360
acttcccgtg gtagcttatt ttcttcttgg gagatggcat gactctgcaa gtaagaaggc    420
aagggcaagt gtgcttgcac agcgagctgc agaagaagcc tatagagagg aaacgatggc    480
gtgcccagac attattccgc caggcccttc cttgagaact atgccctatt caaacctgc     540
gccttcgtta agacaggaat accatgagtg tgcaacttgc catgcccctg caaagactcg    600
ttgctccaga tgcaagtctg ttagatactg ctctgggaag tgtcaaatag tacactggag    660
gcaaggacat aaggaaacat gccaaaaatg cttggtagt ggttctagca gctttggtgg     720
atctagcact gaggctactg aacagatgcc gttcttggct aacttgaatt cacctcttcc    780
aggtggtgac attcacttgc gtgacatgaa cttcgatact ttatcagaac catcctttcc    840
cacaactgat ggttacaatc tagatactga cccattcccg gcagatagaa gcaacatgaa    900
tagatcaaat caaggtattc atatgagcga aaatggtgct gttggtgtat cttttgaaaa    960
gaataattat aatgctgctg atgaaataca ctcttcggag attttatctg gaaacaaggt   1020
gtcaaagcaa ctattttggt tcagatgcaa tgagtggtaa tggggatgca acttatcctg   1080
ccaaaagtaa tgcacagcag cctagcagct gtgctcctga catgagaaaa cagccaaaag   1140
caagcatcac agtttatcag cctgacatag gtgtctattt aacttctgac atggtcagtt   1200
cttgtgaggg gtcatatgct tctgccagtg agccactgca aaggagcttg tcatctggaa   1260
gaactattgg gaaagcaaac gcggtgaata agaggcctcc atacccatca gtaaggtgg    1320
tttcagcaca aaagccacag gatagggtgt ctacatcata tcaaaatgat ggccatgaga   1380
agaatccttg caacaaaaat gaccaaagat ctaccccaa atgtgaatca agtcaatcaa    1440
caagcagcaa tctacaaaag tttggagcat ccaaggttga agttttaaag aagccttcaa   1500
aatttctcaa accagccttt gtgggattga tcaatgttta aaggaggaac aaggtattgt   1560
tcccatatga agatcttgtc aagttttttc agtatgaagc ccggggtatt tcccctagag   1620
gtcttttcaa ttgtggaaac aggtaataaa cgatgcttaa agtcatagtt cacacttacc   1680
taattgtttc tgttgctatt gtgtacttaa accgagaaaa atgccttctg gtatttataa   1740
gtggtgatgg tgccttctgg tatttgactt gagttgcaaa ataagaaaaa aatgcctaat   1800
ggatctttgc acactgcaga agggatgggg gaacttaaac aagtagagca actgaaaggc   1860
ctctgttaaa aacaagatag tacttaacag tggtttatca tgttgattga ctagttttgt   1920
ggtcatatta tcactccatt agtccttggtg catgagcaca ctacttatgg gacaatacgg   1980
gcctagaaca gatatgtctg acataagcat atacgctaca agaatggcat ccattcagca   2040
ttcatctcta catgtgtgta tgaatcccag tatatagtgt gggttaccaa gagtaggaca   2100
gtgcccaaag aatattaaca tatctgatga gatcaatttt gaaataagag atatgccaca   2160
gtttgtttct ttattgaaaa ggtttgctgt tttgaaaatt aaagctgaaa aattatattt   2220
gctgtancaa tgatcattat at                                            2242
```

<210> SEQ ID NO 45
<211> LENGTH: 175
<212> TYPE: DNA
<213> ORGANISM: Zea mays

<400> SEQUENCE: 45

| | | |
|---|---|---|
| taagacagga ataccatgaa tgtgcaactt gccatgcccc tgcaaagact cgttgctcca | 60 | |
| gatgcaaggc tgttagatat tgctctggga agtgtcaaat agtacactgg aggcaaggac | 120 | |
| ataaggaaac atgccaaaag tggcttggta gtggttctag cagctttggc ggatc | 175 | |

<210> SEQ ID NO 46
<211> LENGTH: 585
<212> TYPE: DNA
<213> ORGANISM: Zea mays

<400> SEQUENCE: 46

| | |
|---|---|
| tttggcagga taagttgcat ccccattacc actcattgca tctgaaccaa aatagttgct | 60 |
| ttgacacctt gtttccagat aaaatctccg aagagtgtat ttcatcagca gcattataat | 120 |
| tattcttttc aaaagataca ccaacagcac cattttcgct catatgaata ccttgatttg | 180 |
| atctattcat gttgcttcta tctgccggga atgggtcagt atctagattg taaccatcag | 240 |
| ttgtgggaaa ggatggttct gataaagtat cgaagttcat gtcacgcaag tgaatgtcac | 300 |
| cacctggaag aggtgaattc aagttagcca agaacggcat ctgttcagta gcctcagtgc | 360 |
| tagatccacc aaagctgctg gaaccactac caagccattt ttggcatgtt tccttatgtc | 420 |
| cttgcctcca gtgtactatt tgacacttcc cagagcagta tctaacagac ttgcatctgg | 480 |
| agcaacgagt ctttgcaggg gcatggcaag ttgcacactc atggtattcc tgtcttaacg | 540 |
| aaggcgcagg tttgaaatag ggcatagttc tcaaggaagg gcctg | 585 |

<210> SEQ ID NO 47
<211> LENGTH: 820
<212> TYPE: DNA
<213> ORGANISM: Zea mays
<220> FEATURE:
<221> NAME/KEY: misc_feature
<222> LOCATION: (805)..(805)
<223> OTHER INFORMATION: n is a, c, g, or t

<400> SEQUENCE: 47

| | |
|---|---|
| gtgaatcaag tcaatcaaca agcagcaatc tacaaaagtt tggagcatcc aaggttgaag | 60 |
| ttttaaagaa gccttcaaaa tttctcaaaa ccagccttgt gggattgatc aatgataata | 120 |
| agaggaacaa ggtattgttc ccatatgaag atcttgtcaa gttttttcag tatgaagccc | 180 |
| ggggtatttc ccctagaggt cttttcaatt gtggaaacag gtaataaacg atgcttaaag | 240 |
| tcatagttca cacttaccta attgtttctg ttgctattgt gtacttaaac cgagaaaaat | 300 |
| gccttctggt atttataagt ggtgatggtg ccttctggta tttgacttga gttgcaaaat | 360 |
| aagaaaaaaa tgcctaatgg atctttgcac actgcagaag ggatggggga acttaaacaa | 420 |
| gtagagcaac tgaaaggcct ctgttaaaaa caagatagta cttaacagtg gtttatcatg | 480 |
| ttgattgact agttttgtgg tcatattatc actccattag tcttggtgca tgagcacact | 540 |
| acttatggga caatacgggc ctagaacaga tatgtctgac ataagcatat acgctacaag | 600 |
| aatggcatcc attcagcatt catctctaca tgtgtgtatg aatcccagta tatagtgtgg | 660 |
| gttaccaaga gtaggacagt gcccaaagaa tattaacata tctgatgaga tcaattttga | 720 |
| aataagagat atgccacagt tgtttctttt attgaaaagg tttgctgttt tgaaaattaa | 780 |
| agctgaaaaa ttatatttgc tgtancaatg atcattatat | 820 |

<210> SEQ ID NO 48
<211> LENGTH: 824
<212> TYPE: DNA

<213> ORGANISM: Zea mays

<400> SEQUENCE: 48

```
cggcagagag cacagtagcc aagcgagtgg aggagagttg gagactcatc actggagagc    60
atccgaagcc gcccagtgct cgcacaaccg ctcccgattc caaccccctc cgtccgccca   120
aggggcgccg caccatctcc agcctccagg cctcgatccc taccggaccc cgtggccctg   180
ctgtgttatc tggctggaga tccgccggag tggcattcc tgctctcggt caataagtat    240
tctggaatgt ttttccgagc tcaaatagag aacttctgga gctggatatc agtattctgt   300
tagggatatg ctccaaccaa gggaagctga tgtgcctgca ctctttcttg tcttcattgt   360
acttcccgtg gtagcttatt ttcttcttgg gagatggcat gactctgcaa gtaagaaggc   420
aagggcaagt gtgcttgcac agcgagctgc agaagaagcc tatagagagg aaacgatggc   480
gtgcccagac attattccgc caggcccttc cttgagaact atgccctatt tcaaacctgc   540
gccttcgtta agacaggaat accatgagtg tgcaacttgc catgcccctg caaagactcg   600
ttgctccaga tgcaagtctg ttagatactg ctctgggaag tgtcaaatag tacactggag   660
gcaaggacat aaggaaacat gccaaaaatg gcttggtagt ggttctagca gctttggtgg   720
atctagcact gaggctactg aacagatgcc gttcttggca aacttgaatt cacctcttcc   780
aggtggtgac attcacttgc gtgacatgaa cttcgatact ttat            824
```

<210> SEQ ID NO 49
<211> LENGTH: 121
<212> TYPE: DNA
<213> ORGANISM: Zea mays

<400> SEQUENCE: 49

```
ttctttcaat tgtggaaaca ggtaataaac gatgcttaaa gtcatagttc acacttacct    60
aattgtttct gttgctatta gtgtacttaa accgagaaaa atgccttctg gtatttataa   120
g                                                                   121
```

<210> SEQ ID NO 50
<211> LENGTH: 754
<212> TYPE: DNA
<213> ORGANISM: Zea mays

<400> SEQUENCE: 50

```
acttgacaag atcttcatat gggaacaata ccttgttcct cctttaaaca ttgatcaatc    60
ccacaaggct ggttttgaga aattttgaag gcttctttaa aacttcaacc ttggatgctc   120
caaacttttg tagattgctg cttgttgatt gacttgattc acatttgggg gtagatcttt   180
ggtcattttt gttgcaagga ttcttctcat ggccatcatt ttgatatgat gtagacaccc   240
tatcctgtgg cttttgtgct gaaaccacct tacttgatgg gtatggaggc ctcttattca   300
ccgcgtttgc tttcccaata gttcttccag atgacaagct cctttgcagt ggctcactgg   360
cagaagcata tgacccctca caagaactga ccatgtcaga agttaaatag acacctatgt   420
caggctgata aactgtgatg cttgcttttg gctgttttct catgtcagga gcacagctgc   480
taggctgctg tgcattactt ttggcaggat aaattgcatc cccattacca cttattgcat   540
ctgaaccaaa atagttgttt gacaccttgt ttctagataa attttccggt gagtggattt   600
catcatcagc attataatta ttcttttcaa aagatacacc aacagcacca ttttcgctca   660
tatgaaatac cttgatttga tttattcatg ttgcttctgt ctgccaaaaa atggatccac   720
tatctagatt ataaccttca attgtgggaa agaa                                754
```

```
<210> SEQ ID NO 51
<211> LENGTH: 755
<212> TYPE: DNA
<213> ORGANISM: Zea mays

<400> SEQUENCE: 51
agttcatttt ggtgcaagga ttcttctcat ggccatcatt ttgaaatgat gtagacaccc      60
tatcctgtgg tttttgtgct gaaaccacct tacttgatgg gtatggaggc ctcttattca     120
ccgcgtttgc tttcccaata gttcttccag atgacaagct cctttgcagt ggctcactgg     180
cagaagcata tgacccctca caagaactga ccatgtcaga agttaaatag acacctatgt     240
caggctgata aactgtgatg cttgcttttg gctgttttct catgtcagga gcacagctgc     300
taggctgctg tgcattactt ttggcaggat aaattgcatc cccattacca cttattgcat     360
ctgaaccaaa atagttgttt gacaccttgt ttctagataa attttccggt gagtggattt     420
catcatcagc attataatta ttcttttcaa aagatacacc aacagcacca ttttcgctca     480
tatgaatacc ttgatttgat ttattcatgt tgcttctgtc tgccaaaaat ggatcagtat     540
ctagattata accatcagtt gtgggaaagg atggttctga taaagtatcg aagttcaagt     600
cacgcaagtg aatgtcacca cccggaagag gtgaatttaa gttagtcaag aacggcatct     660
gttcagtagc ctcagtgcta gatccaccaa agctgctaga accacttttta agcgactttt     720
ggcatgtttc cttatgtcct tgcctccagt agtac                                755

<210> SEQ ID NO 52
<211> LENGTH: 538
<212> TYPE: DNA
<213> ORGANISM: Cauliflower mosaic virus

<400> SEQUENCE: 52
catggagtca aagattcaaa tagaggacct aacagaactc gccgtaaaga ctggcgaaca      60
gttcatacag agtctcttac gactcaatga caagaagaaa atcttcgtca acatggtgga     120
gcacgacaca cttgtctact ccaaaaatat caaagataca gtctcagaag accaaagggc     180
aattgagact tttcaacaaa gggtaatatc cggaaacctc ctcggattcc attgcccagc     240
tatctgtcac tttattgtga agatagtgga aaggaaggt ggctcctaca atgccatca      300
ttgcgataaa ggaaaggcca tcgttgaaga tgcctctgcc gacagtggtc ccaaagatgg     360
acccccaccc acgaggagca tcgtggaaaa agaagacgtt ccaaccacgt cttcaaagca     420
agtggattga tgtgatatct ccactgacgt aagggatgac gcacaatccc actatccttc     480
gcaagaccct tcctctatat aaggaagttc atttcatttg gagagaacac gggggact       538
```

PLANTS HAVING ALTERED GROWTH AND/OR DEVELOPMENT RESULTED FROM MODULATED EXPRESSION OF UBIQUITIN-SPECIFIC PROTEASES AND A METHOD FOR MAKING THE SAME

RELATED APPLICATIONS

This application is a national stage application (under 35 U.S.C. §371) of PCT/IB2009/050372, filed Jan. 30, 2009, is a continuation-in-part of PCT application PCT/CN2008/000245, filed Jan. 31, 2008.

SUBMISSION OF SEQUENCE LISTING

The sequence Listing with this application is filed in electronic format via EFS-Web and hereby incorporated by reference into the specification in its entirety. The name of the text file containing the Sequence Listing is Sequence$_{13}$List$_{13}$12810$_{13}$01048$_{13}$US. The size of the text file is 127 KB, and the text file was created on Jul. 23, 2010.

The present invention relates generally to the field of molecular biology and concerns a method for altering various aspects of plant growth and/or development by modulating expression in a plant of a nucleic acid encoding an UBiquitin-Specific Protease (UBP) of the UBP15 subfamily or a homologue thereof. The present invention also concerns plants having modulated expression of a nucleic acid encoding such a UBP15 polypeptide or a homologue thereof, which plants have altered growth and/or development relative to corresponding wild type plants or other control plants. The invention also provides constructs useful in the methods of the invention.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

It has now been found that plant growth and/or development may be altered by modulating expression in a plant of a nucleic acid encoding a UBP15 polypeptide or a homologue thereof.

BACKGROUND

Ubiquitin-Specific Proteases (UBPs) are a conserved family of proteins in eukaryotes that play critical roles in protein de-ubiquitination. The covalent modification of proteins by ubiquitin play a central role in diverse cellular pathways such as cell cycle progression, signal transduction, transcriptional regulation, DNA repair, stress responses, endocytosis and apoptosis (Hochstrasser, 1996; Varshaysky, 1997; Hershko and Ciechanover, 1998; Weissman, 2001; Pickart, 2004). Protein ubiquitination is catalyzed by a cascade of three enzymes. Ubiquitn is first activated by ubiquitin-activating enzyme (E1), which forms a thiolester bond with the ubiquitin C-terminus. Ubiquitin is then transferred to ubiquitin-conjugating enzyme (E2). Although some E2s can catalyze ligation of the ubiquitin C-terminus to the lysine residue of target proteins with the aid of ubiquitin ligases (E3s), other E2s transfer their conjugated ubiquitin to E3s before targetting to substrates. Target substrate proteins can be mono-ubiquitinated or multi-ubiquitinated by successive conjugation of the ubiquitin C-terminus to the lysine residue of the prior one through several possible linkages. The fate of ubiquitinated substrate proteins depends in part on the number of conjugated ubiquitin(s) and on the mode of linkage in the ubiquitin chain. The most common ubiquitination is multi-ubiquitin chain (ubiquitin number>=4) linked by Lys48, acting as a signal for protein degradation by 26S proteasome.

Cleavage of ubiquitin from proteins by de-ubiquitination enzymes (DUBs) can also affect the ubiquitinated substrate protein's activity and fate (Wilkinson, 1997; Amerik and Hochstrasser, 2004; Crosas et al., 2006; Hanna et al., 2006). Those DUBs are proteases that specifically cleave the peptide bond between ubiquitins or between the C-terminus of ubiquitin and covalently attached polypeptides. The currently known DUBs together carry out four types of essential biochemical functions: first, they generate mature ubiquitins from ubiquitin precursors (fused to ribosomal protein) and polyubiquitin gene products; secondly, they rescue proteins that are inappropriately ubiquitinated; thirdly, they cleave ubiquitin (chains) from attached substrate proteins; and fourth, release free ubiquitin monomers from multi-ubiquitin chains. The last three roles are accompanied by cleavage of the isopeptide bonds between the ubiquitin C-terminus Gly and Lys ε-amino residue of a target protein.

Cysteine proteases and metalloproteases are the two major groups of the DUB superfamily, with cysteine proteases being most numerous in eukaryotes (Nijman et al., 2005). All known metalloproteases have a JAMM domain for catalytic activity (Verma et al., 2002). The cysteine protease DUBs can be further divided into four families based on the organization of ubiquitin-protease catalytic center structure and organization (Wilkinson, 1997; Amerik and Hochstrasser, 2004; Nijman et al., 2005). Ubiquitin-Specific Proteases (UBP, or USPs as defined in mammals) possess catalytic triad residues in highly conserved cysteine box and histidine box (Hu et al., 2002). Ubiquitin C-terminal Hydrolases (UCHs), with similar catalytic triad residues in two conserved cysteine and histidine boxes (Johnston et al., 1997; Johnston et al., 1999), have a smaller overall protein size as well as a structural obstacle over the catalytic surface to restrict their ability to hydrolyze only small amides and esters at the C-terminus of ubiquitin (Amerik and Hochstrasser, 2004). Ovarian Tumor Proteases (OTUs) have a catalytic triad comparable to above two families in Cysteine and Histidine boxes but containing an OTU-related motif and being considered as a part of UBP family (Balakirev et al., 2003; Nanao et al., 2004). Lastly, Machado-Joseph Disease Protein Domain Proteases (MJDs) possess a cysteine and histidine box-like domain but with rather low sequence similarity to the other three groups (Burnett et al., 2003; Scheel et al., 2003). The UBP family makes up the bulk of the cysteine proteases. All four types of the above mentioned DUB biochemical functions are found in UBPs family, while UCHs only perform their functions on small proteins and ubiquitin precursor.

In the model plant *Arabidopsis thaliana*, an in silico analysis of the completely sequenced genome revealed a total of 27 UBPs based on the presence of the conserved Cys and His boxes; those 27 UBPs were further divided into 14 subfamilies (Yan et al., 2000). Previous reports showed that UBP3 and UBP4 constitute one subfamily, possess UBP activity in vitro and are present in the nucleus (Chandler et al., 1997; Rao-Naik et al., 2000). Another member, UBP5, was shown also to have de-ubiquitination activity in vitro (Rao-Naik et al., 2000). A genetic analysis of UBP1 and UBP2, members of another subfamily, were reported to be required for resistance to the amino acid analog canavanine (Yan et al., 2000). Furthermore, a loss-of-function mutation in UBP14 was shown to be lethal in early embryo development (Doelling et al., 2001).

SUMMARY

Surprisingly, it has now been found that modulating expression of a nucleic acid encoding a UBP15 polypeptide or a homologue thereof gives plants altered growth and/or development relative to control plants.

According one embodiment, there is provided a method for altering plant growth and/or development relative to control plants, comprising modulating expression in a plant of a nucleic acid encoding a UBP15 polypeptide or a homologue thereof.

DEFINITIONS

Polypeptide(s)/Protein(s)

The terms "polypeptide" and "protein" are used interchangeably herein and refer to amino acids in a polymeric form of any length, linked together by peptide bonds.

Polynucleotide(s)/Nucleic Acid(s)/Nucleic Acid Sequence(s)/Nucleotide Sequence(s)

The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

Control Plant(s)

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

Homoloque(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag·100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table A below).

TABLE A

Examples of conserved amino acid substitutions

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

Ortholoque(s)/Paraloque(s)

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

Domain

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

Motif/Consensus Sequence/Signature

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Hybridisation

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore medium stringency hybridisation conditions may sometimes be needed to identify such nucleic acid molecules.

The Tm is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

1) DNA-DNA hybrids (Meinkoth and Wahl, Anal. Biochem., 138: 267-284, 1984):
$T_m=81.5°$ C.$+16.6×\log_{10}[Na^+]^a+0.41×\%[G/C^b]-500x[L^c]^{-1}-0.61×\%$ formamide 2) DNA-RNA or RNA-RNA hybrids:
Tm$=79.8+18.5$ $(\log_{10}[Na^+]^a)+0.58$ (% G/C$^b$)$+11.8$ (% G/C$^b$)$^2-820/L^c$ 3) oligo-DNA or oligo-RNA$^d$ hybrids:
For <20 nucleotides: $T_m=2 (I_n)$
For 20-35 nucleotides: $T_m=22+1.46 (I_n)$ $^a$ or for other monovalent cation, but only accurate in the 0.01-0.4 M range.
$^b$ only accurate for % GC in the 30% to 75% range.
$^c$ L=length of duplex in base pairs.
$^d$ oligo, oligonucleotide; $I_n$=effective length of primer=2×(no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5× Denhardt's reagent, 0.5-1.0% SDS, 100 µg/ml denatured, fragmented salmon sperm DNA, 0.5% sodium pyrophosphate.

For the purposes of defining the level of stringency, reference can be made to Sambrook et al. (2001) Molecular Cloning: a laboratory manual, $3^{rd}$ Edition, Cold Spring Harbor Laboratory Press, CSH, New York or to Current Protocols in Molecular Biology, John Wiley & Sons, N.Y. (1989 and yearly updates).

Splice Variant

The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art (see for example Foissac and Schiex (2005) BMC Bioinformatics 6: 25).

Allelic Variant

Alleles or allelic variants are alternative forms of a given gene, located at the same chromosomal position. Allelic variants encompass Single Nucleotide Polymorphisms (SNPs), as well as Small Insertion/Deletion Polymorphisms (IN-DELs). The size of INDELs is usually less than 100 bp. SNPs and INDELs form the largest set of sequence variants in naturally occurring polymorphic strains of most organisms.

Gene Shuffling/Directed Evolution

Gene shuffling or directed evolution consists of iterations of DNA shuffling followed by appropriate screening and/or selection to generate variants of nucleic acids or portions thereof encoding proteins having a modified biological activity (Castle et al., (2004) Science 304(5674): 1151-4; U.S. Pat. Nos. 5,811,238 and 6,395,547).

Regulatory Element/Control Sequence/Promoter

The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ.

A "plant promoter" comprises regulatory elements, which mediate the expression of a coding sequence segment in plant cells. Accordingly, a plant promoter need not be of plant origin, but may originate from viruses or micro-organisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or comprise a suitable promoter which expresses the gene at the right point in time and with the required spatial expression pattern.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about $1/10,000$ transcripts to about $1/100,000$ transcripts, to about $1/500,0000$ transcripts per cell. Conversely, a "strong promoter" drives expression of a coding sequence at high level, or at about $1/10$ transcripts to about $1/100$ transcripts to about $1/1000$ transcripts per cell.

Operably Linked

The term "operably linked" as used herein refers to a functional linkage between the promoter sequence and the gene of interest, such that the promoter sequence is able to initiate transcription of the gene of interest.

Constitutive Promoter

A "constitutive promoter" refers to a promoter that is transcriptionally active during most, but not necessarily all, phases of growth and development and under most environmental conditions, in at least one cell, tissue or organ. Table B below gives examples of constitutive promoters.

TABLE B

Examples of constitutive promoters

| Gene Source | Reference |
|---|---|
| Actin | McElroy et al, Plant Cell, 2: 163-171, 1990 |
| HMGP | WO 2004/070039 |
| CAMV 35S | Odell et al, Nature, 313: 810-812, 1985 |
| CaMV 19S | Nilsson et al., Physiol. Plant. 100: 456-462, 1997 |
| GOS2 | de Pater et al, Plant J Nov; 2(6): 837-44, 1992, WO 2004/065596 |
| Ubiquitin | Christensen et al, Plant Mol. Biol. 18: 675-689, 1992 |
| Rice cyclophilin | Buchholz et al, Plant Mol Biol. 25(5): 837-43, 1994 |
| Maize H3 histone | Lepetit et al, Mol. Gen. Genet. 231: 276-285, 1992 |
| Alfalfa H3 histone | Wu et al. Plant Mol. Biol. 11: 641-649, 1988 |
| Actin 2 | An et al, Plant J. 10(1); 107-121, 1996 |
| 34S FMV | Sanger et al., Plant. Mol. Biol., 14, 1990: 433-443 |
| Rubisco small subunit | U.S. Pat. No. 4,962,028 |
| OCS | Leisner (1988) Proc Natl Acad Sci USA 85(5): 2553 |
| SAD1 | Jain et al., Crop Science, 39 (6), 1999: 1696 |
| SAD2 | Jain et al., Crop Science, 39 (6), 1999: 1696 |
| Nos | Shaw et al. (1984) Nucleic Acids Res. 12(20): 7831-7846 |
| V-ATPase | WO 01/14572 |
| Super promoter | WO 95/14098 |
| G-box proteins | WO 94/12015 |

Ubiquitous Promoter

A ubiquitous promoter is active in substantially all tissues or cells of an organism.

Developmentally-Regulated Promoter

A developmentally-regulated promoter is active during certain developmental stages or in parts of the plant that undergo developmental changes.

Inducible Promoter

An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens.

Organ-Specific/Tissue-Specific Promoter

An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific".

A seed-specific promoter is transcriptionally active predominantly in seed tissue, but not necessarily exclusively in seed tissue (in cases of leaky expression). The seed-specific promoter may be active during seed development and/or during germination. The seed specific promoter may be endosperm and/or aleurone and/or embryo-specific.

Terminator

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Modulation

The term "modulation" means in relation to expression or gene expression, a process in which the expression level is changed by said gene expression in comparison to the control plant, the expression level may be increased or decreased. The original, unmodulated expression may be of any kind of expression of a structural RNA (rRNA, tRNA) or mRNA with subsequent translation.

Expression

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

Increased Expression/Overexpression

The term "increased expression" or "overexpression" as used herein means any form of expression that is additional to the original wild-type expression level.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

Endogenous Gene

Reference herein to an "endogenous" gene not only refers to the gene in question as found in a plant in its natural form (i.e., without there being any human intervention), but also refers to that same gene (or a substantially homologous nucleic acid/gene) in an isolated form subsequently (re)introduced into a plant (a transgene). For example, a transgenic plant containing such a transgene may encounter a substantial reduction of the transgene expression and/or substantial reduction of expression of the endogenous gene. The isolated gene may be isolated from an organism or may be manmade, for example by chemical synthesis.

Decreased Expression

Reference herein to "decrease depression" or "reduction or substantial elimination" of expression is taken to mean a decrease in endogenous gene expression and/or polypeptide levels and/or polypeptide activity relative to control plants. The reduction or substantial elimination is in increasing order of preference at least 10%, 20%, 30%, 40% or 50%, 60%, 70%, 80%, 85%, 90%, or 95%, 96%, 97%, 98%, 99% or more reduced compared to that of control plants.

For the reduction or substantial elimination of expression an endogenous gene in a plant, a sufficient length of substantially contiguous nucleotides of a nucleic acid sequence is required. In order to perform gene silencing, this may be as little as 20, 19, 18, 17, 16, 15, 14, 13, 12, 11, 10 or fewer nucleotides, alternatively this may be as much as the entire gene (including the 5' and/or 3' UTR, either in part or in whole). The stretch of substantially contiguous nucleotides may be derived from the nucleic acid encoding the protein of interest (target gene), or from any nucleic acid capable of encoding an orthologue, paralogue or homologue of the protein of interest. Preferably, the stretch of substantially contiguous nucleotides is capable of forming hydrogen bonds with the target gene (either sense or antisense strand), more preferably, the stretch of substantially contiguous nucleotides has, in increasing order of preference, 50%, 60%, 70%, 80%, 85%, 90%, 95%, 96% 97%, 98%, 99%, 100% sequence identity to the target gene (either sense or antisense strand). A nucleic acid sequence encoding a (functional) polypeptide is not a requirement for the various methods discussed herein for the reduction or substantial elimination of expression of an endogenous gene.

This reduction or substantial elimination of expression may be achieved using routine tools and techniques. A preferred method for the reduction or substantial elimination of endogenous gene expression is by introducing and expressing in a plant a genetic construct into which the nucleic acid (in this case a stretch of substantially contiguous nucleotides derived from the gene of interest, or from any nucleic acid capable of encoding an orthologue, paralogue or homologue of any one of the protein of interest) is cloned as an inverted repeat (in part or completely), separated by a spacer (non-coding DNA).

In such a preferred method, expression of the endogenous gene is reduced or substantially eliminated through RNA-mediated silencing using an inverted repeat of a nucleic acid or a part thereof (in this case a stretch of substantially contiguous nucleotides derived from the gene of interest, or from any nucleic acid capable of encoding an orthologue, paralogue or homologue of the protein of interest), preferably capable of forming a hairpin structure. The inverted repeat is cloned in an expression vector comprising control sequences. A non-coding DNA nucleic acid sequence (a spacer, for example a matrix attachment region fragment (MAR), an intron, a polylinker, etc.) is located between the two inverted nucleic acids forming the inverted repeat. After transcription of the inverted repeat, a chimeric RNA with a self-complementary structure is formed (partial or complete). This double-stranded RNA structure is referred to as the hairpin RNA (hpRNA). The hpRNA is processed by the plant into siRNAs that are incorporated into an RNA-induced silencing complex (RISC). The RISC further cleaves the mRNA transcripts, thereby substantially reducing the number of mRNA transcripts to be translated into polypeptides. For further general details see for example, Grierson et al. (1998) WO 98/53083; Waterhouse et al. (1999) WO 99/53050).

Performance of the methods of the invention does not rely on introducing and expressing in a plant a genetic construct into which the nucleic acid is cloned as an inverted repeat, but any one or more of several well-known "gene silencing" methods may be used to achieve the same effects.

One such method for the reduction of endogenous gene expression is RNA-mediated silencing of gene expression (downregulation). Silencing in this case is triggered in a plant by a double stranded RNA sequence (dsRNA) that is substantially similar to the target endogenous gene. This dsRNA is further processed by the plant into about 20 to about 26 nucleotides called short interfering RNAs (siRNAs). The siRNAs are incorporated into an RNA-induced silencing complex (RISC) that cleaves the mRNA transcript of the endogenous target gene, thereby substantially reducing the number of mRNA transcripts to be translated into a polypeptide. Preferably, the double stranded RNA sequence corresponds to a target gene.

Another example of an RNA silencing method involves the introduction of nucleic acid sequences or parts thereof (in this case a stretch of substantially contiguous nucleotides derived from the gene of interest, or from any nucleic acid capable of encoding an orthologue, paralogue or homologue of the protein of interest) in a sense orientation into a plant. "Sense orientation" refers to a DNA sequence that is homologous to an mRNA transcript thereof. Introduced into a plant would therefore be at least one copy of the nucleic acid sequence. The additional nucleic acid sequence will reduce expression of the endogenous gene, giving rise to a phenomenon known as co-suppression. The reduction of gene expression will be more pronounced if several additional copies of a nucleic acid sequence are introduced into the plant, as there is a positive correlation between high transcript levels and the triggering of co-suppression.

Another example of an RNA silencing method involves the use of antisense nucleic acid sequences. An "antisense" nucleic acid sequence comprises a nucleotide sequence that is complementary to a "sense" nucleic acid sequence encoding a protein, i.e. complementary to the coding strand of a double-stranded cDNA molecule or complementary to an mRNA transcript sequence. The antisense nucleic acid sequence is preferably complementary to the endogenous gene to be silenced. The complementarity may be located in the "coding region" and/or in the "non-coding region" of a gene. The term "coding region" refers to a region of the nucleotide sequence comprising codons that are translated into amino acid residues. The term "non-coding region" refers to 5' and 3' sequences that flank the coding region that are transcribed but not translated into amino acids (also referred to as 5' and 3' untranslated regions).

Antisense nucleic acid sequences can be designed according to the rules of Watson and Crick base pairing. The antisense nucleic acid sequence may be complementary to the entire nucleic acid sequence (in this case a stretch of substantially contiguous nucleotides derived from the gene of interest, or from any nucleic acid capable of encoding an orthologue, paralogue or homologue of the protein of interest), but may also be an oligonucleotide that is antisense to only a part of the nucleic acid sequence (including the mRNA 5' and 3' UTR). For example, the antisense oligonucleotide sequence may be complementary to the region surrounding the translation start site of an mRNA transcript encoding a polypeptide. The length of a suitable antisense oligonucleotide sequence is known in the art and may start from about 50, 45, 40, 35, 30, 25, 20, 15 or 10 nucleotides in length or less. An antisense nucleic acid sequence according to the invention may be constructed using chemical synthesis and enzymatic ligation reactions using methods known in the art. For example, an antisense nucleic acid sequence (e.g., an antisense oligonucleotide sequence) may be chemically synthesized using naturally occurring nucleotides or variously modified nucleotides designed to increase the biological stability of the molecules or to increase the physical stability of the duplex formed between the antisense and sense nucleic acid sequences, e.g., phosphorothioate derivatives and acridine substituted nucleotides may be used. Examples of modified nucleotides that may be used to generate the antisense nucleic acid sequences are well known in the art. Known nucleotide modifications include methylation, cyclization and 'caps' and substitution of one or more of the naturally occurring nucleotides with an analogue such as inosine. Other modifications of nucleotides are well known in the art.

The antisense nucleic acid sequence can be produced biologically using an expression vector into which a nucleic acid sequence has been subcloned in an antisense orientation (i.e., RNA transcribed from the inserted nucleic acid will be of an antisense orientation to a target nucleic acid of interest). Preferably, production of antisense nucleic acid sequences in plants occurs by means of a stably integrated nucleic acid construct comprising a promoter, an operably linked antisense oligonucleotide, and a terminator.

The nucleic acid molecules used for silencing in the methods of the invention (whether introduced into a plant or generated in situ) hybridize with or bind to mRNA transcripts and/or genomic DNA encoding a polypeptide to thereby inhibit expression of the protein, e.g., by inhibiting transcription and/or translation. The hybridization can be by conventional nucleotide complementarity to form a stable duplex, or, for example, in the case of an antisense nucleic acid sequence which binds to DNA duplexes, through specific interactions in the major groove of the double helix. Antisense nucleic acid sequences may be introduced into a plant by transformation or direct injection at a specific tissue site. Alternatively, antisense nucleic acid sequences can be modified to target selected cells and then administered systemically. For example, for systemic administration, antisense nucleic acid sequences can be modified such that they specifically bind to receptors or antigens expressed on a selected cell surface, e.g., by linking the antisense nucleic acid sequence to peptides or antibodies which bind to cell surface receptors or antigens. The antisense nucleic acid sequences can also be delivered to cells using the vectors described herein.

According to a further aspect, the antisense nucleic acid sequence is an a-anomeric nucleic acid sequence. An a-anomeric nucleic acid sequence forms specific double-stranded hybrids with complementary RNA in which, contrary to the usual b-units, the strands run parallel to each other (Gaultier et al. (1987) Nucl Ac Res 15: 6625-6641). The antisense nucleic acid sequence may also comprise a 2'-o-methylribonucleotide (Inoue et al. (1987) Nucl Ac Res 15, 6131-6148) or a chimeric RNA-DNA analogue (Inoue et al. (1987) FEBS Lett. 215, 327-330).

The reduction or substantial elimination of endogenous gene expression may also be performed using ribozymes. Ribozymes are catalytic RNA molecules with ribonuclease activity that are capable of cleaving a single-stranded nucleic acid sequence, such as an mRNA, to which they have a complementary region. Thus, ribozymes (e.g., hammerhead ribozymes (described in Haselhoff and Gerlach (1988) Nature 334, 585-591) can be used to catalytically cleave mRNA transcripts encoding a polypeptide, thereby substantially reducing the number of mRNA transcripts to be translated into a polypeptide. A ribozyme having specificity for a nucleic acid sequence can be designed (see for example: Cech et al. U.S. Pat. No. 4,987,071; and Cech et al. U.S. Pat. No. 5,116,742). Alternatively, mRNA transcripts corresponding to a nucleic acid sequence can be used to select a catalytic RNA having a specific ribonuclease activity from a pool of RNA molecules (Bartel and Szostak (1993) Science 261, 1411-1418). The use of ribozymes for gene silencing in plants is known in the art (e.g., Atkins et al. (1994) WO 94/00012; Lenne et al. (1995) WO 95/03404; Lutziger et al. (2000) WO 00/00619; Prinsen et al. (1997) WO 97/13865 and Scott et al. (1997) WO 97/38116).

Gene silencing may also be achieved by insertion mutagenesis (for example, T-DNA insertion or transposon insertion) or by strategies as described by, among others, Angell and Baulcombe ((1999) Plant J 20(3): 357-62), (Amplicon VIGS WO 98/36083), or Baulcombe (WO 99/15682).

Gene silencing may also occur if there is a mutation on an endogenous gene and/or a mutation on an isolated gene/nucleic acid subsequently introduced into a plant. The reduction or substantial elimination may be caused by a non-functional polypeptide. For example, the polypeptide may bind to various interacting proteins; one or more mutation(s) and/or truncation(s) may therefore provide for a polypeptide that is still able to bind interacting proteins (such as receptor proteins) but that cannot exhibit its normal function (such as signalling ligand).

A further approach to gene silencing is by targeting nucleic acid sequences complementary to the regulatory region of the gene (e.g., the promoter and/or enhancers) to form triple helical structures that prevent transcription of the gene in target cells. See Helene, C., Anticancer Drug Res. 6, 569-84, 1991; Helene et al., Ann. N.Y. Acad. Sci. 660, 27-36 1992; and Maher, L.J. Bioassays 14, 807-15, 1992.

Other methods, such as the use of antibodies directed to an endogenous polypeptide for inhibiting its function in planta, or interference in the signalling pathway in which a polypeptide is involved, will be well known to the skilled man. In particular, it can be envisaged that manmade molecules may be useful for inhibiting the biological function of a target polypeptide, or for interfering with the signalling pathway in which the target polypeptide is involved.

Alternatively, a screening program may be set up to identify in a plant population natural variants of a gene, which variants encode polypeptides with reduced activity. Such natural variants may also be used for example, to perform homologous recombination.

Artificial and/or natural microRNAs (miRNAs) may be used to knock out gene expression and/or mRNA translation. Endogenous miRNAs are single stranded small RNAs of typically 19-24 nucleotides long. They function primarily to regulate gene expression and/or mRNA translation. Most plant microRNAs (miRNAs) have perfect or near-perfect complementarity with their target sequences. However, there are natural targets with up to five mismatches. They are processed from longer non-coding RNAs with characteristic fold-back structures by double-strand specific RNases of the Dicer family. Upon processing, they are incorporated in the RNA-induced silencing complex (RISC) by binding to its main component, an Argonaute protein. MiRNAs serve as the specificity components of RISC, since they base-pair to target nucleic acids, mostly mRNAs, in the cytoplasm. Subsequent regulatory events include target mRNA cleavage and destruction and/or translational inhibition. Effects of miRNA overexpression are thus often reflected in decreased mRNA levels of target genes.

Artificial microRNAs (amiRNAs), which are typically 21 nucleotides in length, can be genetically engineered specifically to negatively regulate gene expression of single or multiple genes of interest. Determinants of plant microRNA target selection are well known in the art. Empirical parameters for target recognition have been defined and can be used to aid in the design of specific amiRNAs, (Schwab et al., Dev. Cell 8, 517-527, 2005). Convenient tools for design and generation of amiRNAs and their precursors are also available to the public (Schwab et al., Plant Cell 18, 1121-1133, 2006).

For optimal performance, the gene silencing techniques used for reducing expression in a plant of an endogenous gene requires the use of nucleic acid sequences from monocotyledonous plants for transformation of monocotyledonous plants, and from dicotyledonous plants for transformation of dicotyledonous plants. Preferably, a nucleic acid sequence from any given plant species is introduced into that same species. For example, a nucleic acid sequence from rice is transformed into a rice plant. However, it is not an absolute requirement that the nucleic acid sequence to be introduced originates from the same plant species as the plant in which it will be introduced. It is sufficient that there is substantial homology between the endogenous target gene and the nucleic acid to be introduced.

Described above are examples of various methods for the reduction or substantial elimination of expression in a plant of an endogenous gene. A person skilled in the art would readily be able to adapt the aforementioned methods for silencing so as to achieve reduction of expression of an endogenous gene in a whole plant or in parts thereof through the use of an appropriate promoter, for example.

Selectable Marker (Gene)/Reporter Gene

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with *Agrobacteria*, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

Transgenic/Transgene/Recombinant

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein.

Transformation

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with Agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

T-DNA Activation Tagging

T-DNA activation tagging (Hayashi et al. Science (1992) 1350-1353), involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to modified expression of genes near the inserted T-DNA. The resulting transgenic plants show dominant phenotypes due to modified expression of genes close to the introduced promoter.

TILLING

The term "TILLING" is an abbreviation of "Targeted Induced Local Lesions In Genomes" and refers to a mutagenesis technology useful to generate and/or identify nucleic acids encoding proteins with modified expression and/or activity. TILLING also allows selection of plants carrying such mutant variants. These mutant variants may exhibit modified expression, either in strength or in location or in timing (if the mutations affect the promoter for example). These mutant variants may exhibit higher activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Homologous Recombination

Homologous recombination allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offringa et al. (1990) EMBO J 9(10): 3077-84) but also for crop plants, for example rice (Terada et al. (2002) Nat Biotech 20(10): 1030-4; Iida and Terada (2004) Curr Opin Biotech 15(2): 132-8), and approaches exist that are generally applicable regardless of the target organism (Miller et al, Nature Biotechnol. 25, 778-785, 2007).

Increase/Improve/Enhance

The terms "increase", "improve" or "enhance" are interchangeable and shall mean in the sense of the application at least a 3%, 4%, 5%, 6%, 7%, 8%, 9% or 10%, preferably at least 15% or 20%, more preferably 25%, 30%, 35% or 40% more of the factor in question in comparison to any control.

Plant

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida), Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera), Eleusine coracana, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max), Gossypium hirsutum, Helianthus* spp. (e.g. *Helianthus annuus), Hemerocallis fulva, Hibiscus* spp., *Hordeum* spp. (e.g. *Hordeum vulgare), Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme), Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia), Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum), Sorghum bicolor, Spinacia* spp., *Syzygium* spp., *Tagetes* spp., *Tamarindus indica, Theobroma cacao, Trifolium* spp., *Triticosecale rimpaui, Triticum* spp. (e.g. *Triticum aestivum, Triticum durum, Triticum turgidum, Triticum hybernum, Triticum macha, Triticum sativum* or *Triticum vulgare), Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

DETAILED DESCRIPTION OF THE INVENTION

Surprisingly, it has now been found that modulating expression in a plant of a nucleic acid encoding a UBP15 polypeptide or a homologue thereof gives plants having altered growth and/or development relative to control plants. According to a first embodiment, the present invention provides a method for altering plant growth and/or development relative to control plants, comprising modulating expression in a plant of a nucleic acid encoding a UBP15 polypeptide or a homologue thereof.

A preferred method for modulating (preferably, increasing) expression of a nucleic acid encoding a UBP15 polypeptide or a homologue thereof is by introducing and expressing in a plant a nucleic acid encoding a UBP15 polypeptide or a homologue thereof.

Any reference hereinafter to a "protein useful in the methods of the invention" is taken to mean a UBP polypeptide of the UBP15 subfamily or a homologue thereof as defined herein. Any reference hereinafter to a "nucleic acid useful in the methods of the invention" is taken to mean a nucleic acid capable of encoding such a UBP polypeptide. The nucleic acid to be introduced into a plant (and therefore useful in performing the methods of the invention) is any nucleic acid encoding the type of protein which will now be described, hereinafter also referred to as "UBP15 nucleic acid" or "UBP15 gene".

A "UBP15 polypeptide" as defined herein refers to any polypeptide comprising each of the following:
  (i) a Cysteine box (Cys box); and
  (ii) a Histidine box (His box); and
  (iii) a ZnMYND zinc finger domain.

The Cys and His box are two well conserved motifs found in a conserved catalytic domain called the UBP domain (see FIG. 1). The Cys box and the His box comprise the catalytic triad residues (Cys in Cys box, His and Asp/Asn in His box) (Amerik and Hochstrasser, 2004). The length of UBP domains vary from 300 to 900 amino acids in length, and despite sometimes having low overall sequence conservation, they typically display a conserved three dimensional structure. Within the UBP domains, the Cysteine in Cys box plays an essential role in catalytic activity and specific mutation in the Cysteine can abolish the de-ubiquitination activity of UBPs (Papa and Hochstrasser, 1993; Chandler et al., 1997; Rao-Naik et al., 2000; Yan et al., 2000; Baek et al., 2001; Doelling et al., 2001; Hanna et al., 2006).

The UBP15 subfamily includes UBP15, UBP16, UBP17, UBP18 and UBP19. Members of this subfamily and homologues thereof comprise a signature MYND type Zinc finger domain, which was reported to be a protein-protein interaction domain in mammals (Gross and McGinnis, 1996; Lutterbach et al., 1998a; Lutterbach et al., 1998b; Masselink and Bernards, 2000).

A genetic interaction analysis among members of the UBP15 subfamily revealed that UBP15 and UBP16, but not UBP17, have functional redundancy, even though UBP16 and UBP17 are equally related to UBP15. Mutation of another subfamily member, UBP19, leads to embryo lethality, while loss-of-function of its closest related member, UBP18, exhibits no visible defect.

UBP sequences useful in performing the methods of the invention may also be identified by including a query sequence in a UBP phylogenetic tree, such as the one depicted in FIG. 1. UBP15 polypeptides or homologues thereof will cluster with the UPB15 subfamily rather than with any other subfamily.

Furthermore, UBP15 polypeptides and homologues thereof typically have UBP activity In vitro.

UBP15 polypeptides or homologues thereof useful in the methods of the invention typically have in increasing order of preference at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to any one of UBP15 (SEQ ID NO: 2), UBP16 (SEQ ID NO: 4), UBP17 (SEQ ID NO: 6), UBP18 (SEQ ID NO: 8) or UBP19 (SEQ ID NO: 10) from *Arabidopsis thaliana*. The overall sequence identity may be determined using a global alignment algorithm, such as the Needleman Wunsch algorithm in the program GAP (GCG Wisconsin Package, Accelrys), preferably with default parameters. Compared to overall sequence identity, the sequence identity will generally be higher when only conserved domains or motifs are considered.

The term "domain" and "motif" is defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10;4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

Examples of nucleic acids encoding members of the UBP15 subfamily are represented by SEQ ID NOs 1, 3, 5, 7, 9, 11, 13, 15, 17, 19, 39 and 44. Such nucleic acids are useful in performing the methods of the invention. The nucleotide sequence represented by SEQ ID NO: 11 encodes the polypeptide sequence represented by SEQ ID NO: 12, a UBP from rice (Nipponbare strain) that is closely related to AtUBP15, and has 53% identity to AtUBP15 on a nucleotide level, 40% identity on a protein level and 54% similarity on a protein level. The nucleotide sequence represented by SEQ ID NO: 13 encodes the polypeptide sequence represented by SEQ ID NO: 14, a UBP from rice (Nipponbare strain) that is closely related to AtUBP16, and has 44% identity to AtUBP16 on a nucleotide level, 30% identity on a protein level and 44% similarity on a protein level to AtUBP16. The nucleotide sequence represented by SEQ ID NO: 15 encodes the polypeptide sequence represented by SEQ ID NO: 16, a UBP from rice (Nipponbare strain) that is closely related to AtUBP17, and has 40% identity to AtUBP17 on a nucleotide level, 33% identity on a protein level and 45% similarity on a protein level to AtUBP17. The nucleotide sequence represented by SEQ ID NO: 17 encodes the polypeptide sequence represented by SEQ ID NO: 18, a UBP from rice (Nipponbare strain) that is closely related to AtUBP18, and has 34% identity to AtUBP17 on a nucleotide level, 30% identity on a protein level and 39% similarity on a protein level to AtUBP18. SEQ ID NO: 19 is a nucleotide sequence from maize (*Zea mays*) showing some similarity to SEQ ID NO: 11. SEQ ID NO: 19 is the longest cDNA sequence of maize obtained by assembling the ESTs of SEQ ID NOs 20, 21, 22, 23, 24, 25, 26, 27, 28, 29, 30, 31, 32, 33, 34, 35, 36, 37 and 38. SEQ ID NO: 39 is another nucleotide sequence from maize showing some similarity to SEQ ID NO: 11. SEQ ID NO: 39 was assembled from the ESTs of SEQ ID NOs 40, 41, 42 and 43. SEQ ID NO: 44 is another nucleotide sequence from maize showing some similarity to SEQ ID NO: 11. SEQ ID NO: 44 was assembled from the ESTs of SEQ ID NOs 45, 46, 47, 48, 49, 50 and 51.

SEQ ID NOs 12, 14, 16 and 18 are examples of orthologues of the UBP polypeptides represented by SEQ ID NOs: 2, 4, 6 and 8, respectively. The terms "orthologues" and "paralogues" are as defined herein. Further orthologues and paralogues may readily be identified by performing a so-called reciprocal blast search. Typically, this involves a first BLAST involving BLASTing a query sequence (for example using any of sequences SEQ ID NOs 2, 4, 6, 8 or 10) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1 to SEQ ID NO: 10, the second BLAST would therefore be against *Arabidopsis* sequences). The results of the first and second BLASTs are then compared. A paralogue is identified if a high-ranking hit from the first blast is from the same species as from which the query sequence is derived, a BLAST back then ideally results in the query sequence being amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Nucleic acid variants may also be useful in practising the methods of the invention. Examples of such variants include nucleic acids encoding homologues and derivatives of any one of the amino acid sequences represented by SEQ ID NOs 2, 4, 6, 8 or 10, the terms "homologue" and "derivative" being as defined herein. Also useful in the methods of the invention are nucleic acids encoding homologues and derivatives of orthologues or paralogues of any one of the amino acid sequences represented by SEQ ID NOs 2, 4, 6, 8 or 10. Homologues and derivatives useful in the methods of the present invention have substantially the same biological and functional activity as the unmodified protein from which they are derived.

Further nucleic acid variants useful in practising the methods of the invention include portions of nucleic acids encoding UBP15 polypeptides or homologues thereof, nucleic acids hybridising to nucleic acids encoding UBP15 polypeptides or homologues thereof, splice variants of nucleic acids encoding UBP15 polypeptides or homologues thereof, allelic variants of nucleic acids encoding UBP15 polypeptides or homologues thereof and variants of nucleic acids encoding UBP15 polypeptides obtained by gene shuffling. The terms hybridising sequence, splice variant, allelic variant and gene shuffling are as described herein.

Nucleic acids encoding UBP15 polypeptides or homologues thereof need not be full-length nucleic acids, since performance of the methods of the invention does not rely on the use of full-length nucleic acid sequences. According to the present invention, there is provided a method for altering plant growth and development, comprising introducing and expressing in a plant a portion of any one of the nucleic acid sequences represented by SEQ ID NOs 1, 3, 5, 7, 9, 11, 13, 15, 17, 19, 39 or 44, or a portion of a nucleic acid encoding an orthologue, paralogue or homologue of any of the amino acid sequences represented by SEQ ID NOs 2, 4, 6, 8, 10, 12, 14, 16 or 18.

A portion of a nucleic acid may be prepared, for example, by making one or more deletions to the nucleic acid. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Portions useful in the methods of the invention, encode a UBP15 polypeptide or a homologue thereof as defined herein, and have substantially the same biological activity as the amino acid sequences represented by any of SEQ ID NOs 2, 4, 6, 8, 10, 12, 14, 16 or 18. Preferably, the portion is a portion of any one of the nucleic acids given in represented by SEQ ID NOs 1, 3, 5, 7, 9, 11, 13, 15, 17, 19, 39 or 44, or is a portion of a nucleic acid encoding an orthologue or paralogue of any one of the amino acid sequences represented by SEQ ID NOs 2, 4, 6, 8, 10, 12, 14, 16 or 18. Preferably the portion is at least 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 1200, 2250, 2300, 2350, 2400, 2450, 2500, 2550, 2600, 2650, 2700, 2750, 2800, 2850, 2900, 2950, 3000, 3050, 3100, 3150 or more consecutive nucleotides in length, the consecutive nucleotides being of any one of the nucleic acid sequences represented by SEQ ID NOs 1, 3, 5, 7, 9, 11, 13, 15, 17, 19, 39 or 44, or of a nucleic acid encoding an orthologue or paralogue of any one of the amino acid sequences represented by SEQ ID NOs 2, 4, 6, 8, 10, 12, 14, 16 or 18. Most preferably the portion is a portion of the nucleic acid of any one of SEQ ID NOs 1, 3, 5, 7 or 9. Preferably, the portion encodes a fragment of an amino acid sequence which, when used in the construction of a UBP phylogenetic tree, such as the one depicted in FIG. 1, clusters with the UBP15 subfamily of proteins rather than with any other subfamily of UBPs.

Another nucleic acid variant useful in the methods of the invention is a nucleic acid capable of hybridising, under reduced stringency conditions, preferably under stringent conditions, with a nucleic acid encoding a UBP15 polypeptide or a homologue thereof as defined herein, or with a portion as defined herein.

According to the present invention, there is provided a method for altering plant growth and/or development, comprising introducing and expressing in a plant a nucleic acid capable of hybridizing to any one of the nucleic acids represented by SEQ ID NOs 1, 3, 5, 7, 9, 11, 13, 15, 17, 19, 39 or 44, or comprising introducing and expressing in a plant a nucleic acid capable of hybridising to a nucleic acid encoding an orthologue, paralogue or homologue of any of the nucleic acid sequences represented by SEQ ID NOs 2, 4, 6, 8, 10, 12, 14, 16 or, 18.

Hybridising sequences useful in the methods of the invention encode a UBP15 polypeptide as defined herein, having substantially the same biological activity as the amino acid sequences represented by any one of SEQ ID NOs 2, 4, 6, 8, 10, 12, 14, 16 or 18. Preferably, the hybridising sequence is capable of hybridising to any one of the nucleic acids represented by SEQ ID NOs 1, 3, 5, 7, 9, 11, 13, 15, 17, 19, 39 or 44, or to a portion of any of these sequences, a portion being as defined above, or the hybridising sequence is capable of hybridising to a nucleic acid encoding an orthologue or paralogue of any one of the amino acid sequences represented by SEQ ID NOs 2, 4, 6, 8, 10, 12, 14, 16 or 18. Most preferably, the hybridising sequence is capable of hybridising to a nucleic acid as represented by SEQ ID NOs 1, 3, 5, 7, 9, 11, 13, 15 or 17 or to a portion thereof.

Preferably, the hybridising sequence encodes a polypeptide with an amino acid sequence which, when full-length and used in the construction of a UBP phylogenetic tree, such as the one depicted in FIG. 1, clusters with the subfamily of UBP15 polypeptides rather than with any other UBP subfamily.

Another nucleic acid variant useful in the methods of the invention is a splice variant encoding a UBP15 polypeptide or a homologue thereof as defined hereinabove, a splice variant being as defined herein.

According to the present invention, there is provided a method for altering plant growth and/or development, comprising introducing and expressing in a plant a splice variant of any one of the nucleic acid sequences represented by SEQ ID NOs 1, 3, 5, 7, 9, 11, 13, 15, 17, 19, 39 or 44, or a splice variant of a nucleic acid encoding an orthologue, paralogue or homologue of any of the amino acid sequences represented by SEQ ID NOs 2, 4, 6, 8, 10, 12, 14, 16 or 18.

Preferred splice variants are splice variants of a nucleic acid represented by any one of SEQ ID NOs 1, 3, 5, 7, 9, 11, 13, 15 or 17, or a splice variant of a nucleic acid encoding an orthologue or paralogue of SEQ ID NO: 2, 4, 6, 8, 10, 12, 14, 16 or 18. Preferably, the amino acid sequence encoded by the splice variant, when used in the construction of a UBP phylogenetic tree, such as the one depicted in FIG. 1, clusters with the subfamily of UBP15 polypeptides rather than with any other UBP subfamily.

Another nucleic acid variant useful in performing the methods of the invention is an allelic variant of a nucleic acid encoding a UBP15 polypeptide or a homologue thereof as defined hereinabove, an allelic variant being as defined herein.

According to the present invention, there is provided a method for altering plant growth and/or development, comprising introducing and expressing in a plant an allelic variant of any one of the nucleic acids represented by SEQ ID NOs 1, 3, 5, 7, 9, 11, 13, 15, 17, 19, 39 or 44, or comprising introducing and expressing in a plant an allelic variant of a nucleic acid encoding an orthologue, paralogue or homologue of any of the amino acid sequences represented by SEQ ID NOs 2, 4, 6, 8, 10, 12, 14, 16 or 18.

The allelic variants useful in the methods of the present invention have substantially the same biological activity as any one of the UBP15 subfamily polypeptides represented by SEQ ID NO: 2, 4, 6, 8, 10, 12, 14, 16 or 18. Allelic variants exist in nature, and encompassed within the methods of the present invention is the use of these natural alleles. Preferably, the allelic variant is an allelic variant of any one of SEQ ID NOs 1, 3, 5, 7, 9, 11, 13, 15, 17, 19, 39 or 44, or an allelic variant of a nucleic acid encoding an orthologue or paralogue of SEQ ID NO: 2, 4, 6, 8, 10, 12, 14, 16 or 18. Preferably, the amino acid sequence encoded by the allelic variant, when used in the construction of a UBP phylogenetic tree, such as the one depicted in FIG. 1, clusters with the UBP15 subfamily rather than with any other UBP subfamily.

Gene shuffling or directed evolution may also be used to generate variants of nucleic acids encoding UBP15 polypeptides or homologues thereof as defined above; the term "gene shuffling" being as defined herein.

According to the present invention, there is provided a method for altering plant growth and/or development in plants, comprising introducing and expressing in a plant a variant of any one of the nucleic acid sequences represented by any one of SEQ ID NOs 1, 3, 5, 7, 9, 11, 13, 15, 17, 19, 39 or 44, or comprising introducing and expressing in a plant a variant of a nucleic acid encoding an orthologue, paralogue or homologue of any of the amino acid sequences represented by any one of SEQ ID NOs 2, 4, 6, 8, 10, 12, 14, 16 or 18, which variant nucleic acid is obtained by gene shuffling.

Preferably, the amino acid sequence encoded by the variant nucleic acid obtained by gene shuffling, when used in the construction of a UBP phylogenetic tree such as the one depicted in FIG. 1, clusters with the subfamily of UBP15 polypeptides rather than with any other UBP subfamily.

Furthermore, nucleic acid variants may also be obtained by site-directed mutagenesis. Several methods are available to achieve site-directed mutagenesis, the most common being PCR based methods (Current Protocols in Molecular Biology. Wiley Eds.).

Nucleic acids encoding UBP15 polypeptides may be derived from any natural or artificial source. The nucleic acid may be modified from its native form in composition and/or genomic environment through deliberate human manipulation. Preferably the UBP polypeptide-encoding nucleic acid is from a plant, further preferably from a dicotyledonous plant, more preferably from the family Brassicaceae, most preferably the nucleic acid is from *Arabidopsis thaliana*.

Performance of the methods of the invention gives plants having altered plant growth and/or development.

The altered development may be in any part of a plant, in any cell, tissue or organ, particularly in the leaves. The altered development may be altered reproductive development. The altered development may cause altered plant phenotypes, such as altered leaf shape (particularly narrower and/or serrated and/or flat leaves); and altered phenotypes (such as altered flowering and/or changes in apical dominance and/or altered fertility). The altered development or phenotype may be caused by a change in cell proliferation.

The present invention encompasses plants or parts thereof (including seeds) obtainable by the methods according to the present invention. The plants or parts thereof comprise a nucleic acid transgene encoding a UBP15 polypeptide or a homologue thereof as defined above.

The invention also provides genetic constructs and vectors to facilitate introduction and/or expression in plants of nucleic acids encoding UBP15 polypeptides or homologues thereof. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising:

(a) a nucleic acid encoding a polypeptide that is a member of the UBP15 subfamily or a homologue thereof as defined above;
(b) one or more control sequences capable of driving expression of the nucleic acid sequence of (a); and optionally
(c) a transcription termination sequence.

Preferably, the nucleic acid encoding the UBP15 polypeptide or a homologue thereof is as defined above. The term "control sequence" and "termination sequence" are as defined herein.

Plants are transformed with a vector comprising any of the nucleic acids described above. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter, whether natural or synthetic, may be used to drive expression of the nucleic acid sequence. A constitutive promoter is particularly useful in the methods. Preferably the constitutive promoter is also a ubiquitous promoter. See the "Definitions" section herein for definitions of the various promoter types.

The constitutive promoter is preferably a CaMV35S promoter. Further preferably, the constitutive promoter is represented by a nucleic acid sequence substantially similar to SEQ ID NO: 52, most preferably the constitutive promoter is as represented by SEQ ID NO: 52. See Table B in the "Definitions" section herein for further examples of constitutive promoters.

Optionally, one or more terminator sequences may be used in the construct introduced into a plant. Additional regulatory elements may include transcriptional as well as translational enhancers. Those skilled in the art will be aware of terminator and enhancer sequences that may be suitable for use in performing the invention. An intron sequence may also be added to the 5' untranslated region (UTR) or in the coding sequence to increase the amount of the mature message that accumulates in the cytosol, as described in the definitions section. Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. Selectable markers are described in more detail in the "definitions" section herein. The marker genes may be removed or excised from the transgenic cell once they are no longer needed. Techniques for marker removal are known in the art, useful techniques are described above in the definitions section.

The invention also provides a method for the production of transgenic plants having altered growth and/or development relative to control plants, comprising introduction and expression in a plant of any nucleic acid encoding a UBP15 polypeptide or a homologue thereof as defined hereinabove.

More specifically, the present invention provides a method for the production of transgenic plants having altered growth and/or development, which method comprises:
(i) introducing and expressing in a plant or plant cell a UBP15 polypeptide-encoding nucleic acid; and
(ii) cultivating the plant cell under conditions promoting plant growth and development.

The nucleic acid of (i) may be any of the nucleic acids capable of encoding a UBP15 polypeptide or a homologue thereof as defined herein.

The nucleic acid may be introduced directly into a plant cell or into the plant itself (including introduction into a tissue, organ or any other part of a plant). According to a preferred feature of the present invention, the nucleic acid is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S. D. Kung and R. Wu, Potrykus or Hofgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding a UBP15 polypeptide or a homologue thereof as defined hereinabove. Preferred host cells according to the invention are plant cells. Host plants for the nucleic acids or the vector used in the method according to the invention, the expression cassette or construct or vector are, in principle, advantageously all plants, which are capable of synthesizing the polypeptides used in the inventive method.

The methods of the invention are advantageously applicable to any plant. Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

The invention also extends to harvestable parts of a plant such as, but not limited to seeds, leaves, fruits, flowers, stems, roots, rhizomes, tubers and bulbs. The invention furthermore relates to products derived, preferably directly derived, from a harvestable part of such a plant, such as dry pellets or powders, oil, fat and fatty acids, starch or proteins.

According to a preferred feature of the invention, the modulated expression is increased expression. Methods for increasing expression of nucleic acids or genes, or gene products, are well documented in the art and examples are provided in the definitions section.

As mentioned above, a preferred method for modulating expression of a nucleic acid encoding a UBP15 polypeptide or a homologue thereof is by introducing and expressing in a plant a nucleic acid encoding a UBP15 polypeptide or a homologue thereof; however the effects of performing the method, i.e. altered plant growth and/or development may also be achieved using other well known techniques, including but not limited to T-DNA activation tagging, TILLING, homologous recombination. A description of these techniques is provided in the definitions section.

The present invention also encompasses use of nucleic acids encoding UBP15 polypeptides or homologues thereof as described herein and use of these UBP15 polypeptides in altering growth and/or development in plants.

Nucleic acids encoding UBP15 polypeptide described herein, or the UBP15 polypeptides themselves, may find use in breeding programmes in which a DNA marker is identified which may be genetically linked to a UBP15 polypeptide-encoding gene. The nucleic acids/genes, or the UBP15 polypeptides themselves may be used to define a molecular marker. This DNA or protein marker may then be used in breeding programmes to select plants having altered growth and/or development as defined hereinabove in the methods of the invention.

Allelic variants of a UBP15 polypeptide-encoding nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give altered growth and/or development. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acids encoding UBP15 polypeptides or homologues thereof may also be used as probes for genetically and physically mapping the genes that they are a part of, and as markers for traits linked to those genes. Such information may be useful in plant breeding in order to develop lines with desired phenotypes. Such use of UBP15 polypeptide-encoding nucleic acids requires only a nucleic acid sequence of at least 15 nucleotides in length. The UBP15 polypeptide-encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the UBP15-encoding nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the UBP15 polypeptide-encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having altered growth and/or development, as described hereinbefore. These traits may also be combined with other economically advantageous traits, such as yield-enhancing traits, tolerance to other abiotic and biotic stresses, traits modifying various architectural features and/or biochemical and/or physiological features.

EXAMPLES

The present invention will now be described with reference to the following examples, which are by way of illustration alone. The following examples are not intended to completely define or to otherwise limit the scope of the invention.

1. Plant Material and Growth Conditions

The wild-type *Arabidopsis thaliana* plants used in this study were of the Columbia-0 ecotype. The 38 T-DNA insertion lines (including ubp15-1, ubp15-2 and ubp19-1 those three lines with observed phenotypes) listed in Table 1 were obtained from the SALK collection. UBP15 (or UBP15C447A/S)-overexpressing transgenic plants were obtained by transforming $P_{UBP15}$:UBP15 (or $P_{UBP15}$:UBP15C447A/S) into wild type background. UBP15 complemented (or UBP15C447A/S) transgenic plants were obtained by transforming $P_{UBP15}$:UBP15 (or $P_{UBP15}$: UBP15C447A/S) into ubp15-1 background. $P_{UBP19}$:GUS transgenic plants were obtained by transforming the $P_{UBP19}$: GUS construct into the wild type background. ubp15 ubp16, ubp15 ubp17 and ubp16 ubp17 double mutants were obtained by crossing ubp15-1 (or ubp15-2) with ubp16-1 or ubp17-1, or by crossing ubp16-1 with ubp17-1; homozygotes of F2 generation were confirmed by PCR analysis. Triple mutants ubp15 ubp16 ubp17 were obtained by crossing ubp15 with double mutants ubp16 ubp17; homozygotes of F2 generation were confirmed by PCR analysis.

Seeds were surface sterilized with 15% (v/v) NaOCl. After 48 h at 4° C. for vernalization, seeds were placed onto 1× Murashige and Skoog (MS) plates (containing 1% sucrose, and 0.3% Phytagel) and placed in a chamber at 22° C. under continuous light for 7 days before transferring to soil. Plants were then grown in standard long day (16 h light/8 h dark) growth rooms. Seeds grown in short day (8 h light/16 h dark) conditions were sown directly onto soil and were grown in a short day condition room.

2. Sequence Alignment and Phylogenetic Analysis

The search for the common domains shared among the 27 UBP proteins was performed by TAIR and NCBI CDART. The conserved domains within each protein were joined by eliminating variant regions and by alignment of the fragments using ClustalW (Thompson et al., 1994), followed by manual alignment.

A phylogenetic tree was constructed using MAGA version 3.1 (Kumar et al., 2004) on conserved positions of the alignment, using the neighbour-joining algorithm with 1000 bootstrap replicates.

3. Measurement of the Length of Seedlings, Root, Silique and Width and Length of Rosette Leaf To obtain the root length of seedlings, wild type, ubp15-1 and ubp15-2 were grown vertically on plates. The root length of 20 randomly selected seedlings of either wild type or mutants was determined. 20 randomly selected mature siliques (older than 8 d after pollination) of wild type or mutants were measured. Mature rosette leaves from the first true leaf to the last one was dissected from wild type or ubp15-1, and the width and length of the leaves was measured.

4. Measurement of the Flowering Time and Rosette Leaf Number

The flowering time of wild type, ubp15-1, UBP15-overexpressing line was measured as the number of days from seed germination to the opening of the first flower. Rosette leaf numbers were counted at bolting.

5. RNA Isolation and RT-PCR

RNA was isolated using Trizol (Invitrogen). Before performing RT-PCR, 4 µgs RNA was treated with RNase-Free DNase (Premega) to avoid contamination of DNA, followed by chloroform: phenol (1:1) extraction to avoid the affect of the ions. A portion of RNA was then used for PCR by At3g04120/GAPDH primers to confirm elimination of the DNA. The remaining sample was subjected to the RT reaction using a Superscript™ II RNase H⁻ Reverse Transcriptase kit (Invitrogen) and random primers. The reaction mixture was diluted 10 times and 1 µL was subjected to the PCR using rTaq DNA polymerase (TaKaRa). At3g04120/GAPDH was used as an internal control. Linearity of the PCR reaction was monitored by comparing relative amounts of PCR products after 22, 30, and 35 cycles. Forward and reverse primer sequences, used for detection of gene transcripts, were as follows At3g04120/GAPDH, 5'-CACTTGAAGGGTGGT-GCCAAG-3' and 5'-CCTGTTGTCGCCAACGAAGTC-3'; UBP15, 5'-TCGAGAGGCAACAGTTATGCTG-3' and 5'-CTCAGGCCTCCAGTAACTGTAAGTTCTATCCTG-3'.

6. RNA Gel Blot Analysis

RNA blot was performed as previously described (Yang et al., 2005). The total RNA from different regions of leaves was extracted and 20 µgs of total RNA for each lane was separated on an agarose gel, transferred to a Hybond-N⁺ membrane (Amersham Biosciences), and hybridized with a UBP15-specific probe. 18S rRNA served as the loading control. Primers were as follows: UBP15, 5'-TCGAGAGGCAACAGTTAT-GCTG-3' and 5'-CTCAGGCCTCCAGTAACTGTAAGT-TCTATCCTG-3'.

7. Transient Expression in Onion Epidermal Cells

The procedure for transient expression in living onion (Allium cepa) epidermal cells using particle bombardment was performed as previously described (Ang et al., 1998). After bombardment, onion cell layers were incubated for 24 h at 22° C. in the light. The cell layers were then examined by confocal microscopy.

8. Constructs of Transgenic Lines

To obtain UBP15-overexpressing and UBP15 complemented plants, a HindIII/XbaI-digested UBP15 promoter (1.8 kb upstream of ATG) fragment and an XbaI/StuI UBP15 CDS fragment (2.8 kb) was inserted into pCAMBIA1300 binary vector. The resulting construct was then transformed into wild type and ubp15-1 by means of Agrobacterium-mediated transformation. Constructs mutated in Cys site $P_{UBP15}$: UBP15C447A and $P_{UBP15}$:UBP15C447S were also made in the same way and transformed into wild type and ubp15-1. Transgenic plants were selected with hygromycin (20 µg/mL; Roche) on MS plates.

To make 35S:GFP-UBP15 (or 35S:UBP15-GFP) constructs, 35S as well as GFP-fused full-length UBP15 CDS (or full-length UBP15 CDS fused GFP) was subcloned into the XbaI/SphI site of pCAMBIA1300.

To detect tissue expression pattern of UBP19 using GUS staining, a BamHI/KpnI fragment of UBP19 promoter (1.2 kb) was inserted into pCAMBIA1381Z and transformed into a wild type background using Agrobacterium-mediated transformation. Transgenic lines were selected using hygromycin (20 µg/mL; Roche).

9. In Vitro DUB Activity Assay

The ability of UBP15 to cleave ubiquitin linked via a-amino linkages was performed in E. coli. using his-tagged substrates polyubiquitin UBQ10 and ubiquitin-extension protein UBQ1. Each of the two α-amino substrates (UBQ1 in pET28a and UBQ10 in pACYCDuet-1) were co-expressed with either GST or GST-UBP15 or GST-UBP15C447A/S in pGEX4T-3 in E. coli. strain NovaBlue (DE3) under standard conditions (22° C. induce) (Novagen). Lysates were analyzed on a Western blot with anti-ubiquitin antibody (Sigma) or anti-his antibody (Sigma). ECL chemiluminescences system (Amersham) was used for detection.

10. Tissue Fixation and Embedding for Histological Sections

To observe the transverse structure of leaves, samples were fixed for more than 24 h in FAA (50% ethanol, 5% acetic acid, and 5% formaldehyde) at room temperature, dehydrated in a graded series of mixture of $H_2O$: 95% alcohol: tert-butyl alcohol (4:5:1, 3:5:2, 1.5:5:3.5, 0:5:5, 0:2.5:7.5, 100% tert-butyl alcohol twice) with a 2 h incubation in each solution and then infiltrated by adding paraffin gradually (tert-butyl alcohol: paraffin as 3:1, 2:2, 1:3, 0:4, 0:4). Embedded tissues were cut into 8 µm sections with a microtome (Leica RM2255). Sections were placed onto poly-L lysine coated slides, deparaffinized and rehydrated using an ethanol series (ethanol: $H_2O$ as 1:0, 1:0, 9.5:0.5, 9:1, 8:2, 7:3, and 1:1) with a 5 min incubation in each solution. Sections were then stained with 1% safranin O and 0.02% fast green. The cover glasses were adhibited on slides by resin. The numbers of adaxial epidermal and palisade cells were counted under a microscope.

11. Microarray Analysis and Quantitative RT-PCR

The procedures used in the microarray experiments and data analysis were described previously (Ma et al., 2002). Early emerged 9th rosette leaves of wild type and ubp15-1 were used as samples. Total RNA was isolated using RNAwiz reagent (Ambion) and purified by the RNeasy kit (Qiagen). For each sample, 50 µg of total RNA was labeled with aminoallyl-dUTP (aa-dUTP, Sigma-Aldrich) by reverse transcription. The aminoallyl-dUTP-labeled cDNAs were purified using a Microcon YM-30 filter (Millipore) and resuspended in 0.1 M NaHCO$_3$. The purified cDNAs were further fluorescently labeled by conjugating monofunctional Cy3 or Cy5 dye (Amersham) to the aminoallyl functional groups. Pair-wise combinations of two selected samples were used to simultaneously probe one slide, and four independent biological replicates were performed (two replicates with dyes exchange). Hybridized slides were scanned with a GenePix 4000B scanner (Axon), and independent TIFF images for Cy3 and Cy5 channels were used for subsequent analysis by GenePix Pro5.0 software package.

To confirm the microarray result, real-time PCR was performed using the ABI SYBR Green PCR master mix in a volume of 20 µL on an ABI 7900 system. The PCR mixture consisted of 0.3 µL of cDNA, 0.6 µM primers, and 1× master mix. In every real-time PCR run, At1 g42970/GAPDH was used as an internal control to normalize for variation in the amount of cDNA template. The results of a t test confirmed it to be a constitutively expressed gene. The primer sequences used were: At1 g42970/GAPDH, 5'-TCTTTCCCTGCT-CAATGCTCCTC-3' and 5'-TTTCGCCACTGTCTCTC-CTCTAAC-3'. 7 genes down regulated and 2 genes up regulated were picked for quantitative RT-PCR test. Primers used to quantify those genes were At1g71030/MYB, 5'-CATTTGCCTGACCTAAACATTG-3' and 5'-AAGCGTTTCTTGACCTGTTGA-3'; At5g57660/TRANSCR/PT FACTOR, 5'-GGCTCATCCACCACCGTT-3' and 5'-GGGAGAGGCTCTGTTTTCGTC-3'; At5g67030/ABA 1, 5'-GGGCTTGGTCCTCTGTCTT-3' and 5'-GTGAGTCTGCAACTAGGTGGC3'; At5g35970/HELI-CASE-LIKE, 5'-CCACAGGGCTCGGAGGTAT-3' and 5'-TCGTAAGTAAGGGCATCGGC-3'; At3g49160/PYRU-VATE KINASE FAMILY PROTEIN, 5'-TCCAGCAGGTCT-CACATAAACAA-3' and 5'-CTGCTGCTAAGAGATGT-GACCG-3'; At1g73480/HYDROLASE, 5'-AATGGCGGTGGAAACAATG-3' and 5'-ACGACGC-GAAACGGAAGGAG-3'; At5g24470/APRR5, 5-TAC-CCTACGCCAACCCCTAT-3' and 5'-ATGTGATTGCCTAT-TGCACTATGT-3'; At3g20810/TRANSCRIPTION FACTOR, 5'-CCTCAATGCTGTTGCTGGTAA-3' and 5'-TGGGCAAGATAAGTAGGCTCC-3'; At4g21990/APR3, 5'-CTGTCAACACGCTTCACGC-3' and 5'-TCTTTCCG-GTTCTCTAACTTCATC-3'. To determine the specificity of those primers, the amplified products were subjected to melt curve analysis using the machine's standard method. Cycling conditions were as follows: 50° C. for 2 min, 95° C. for 10 min, 40 cycles of 95° C. for 15 s, 60° C. for 30 s, and 72° C. for 1 min. The reported values were averages of six independent trials (two biological replicates and three technical replicates). Relative expression levels were calculated as follows. Transcript levels of those genes were normalized relative to a standard (GAPDH) using the formula $\Delta C_T = C_{T(gene\,X)\,mean\,of\,technical\,repeat} - C_{T(GAPDH)\,mean\,of\,technical\,repeat}$ either in wild type or ubp15-1. Then, the $\Delta Ct_{(wild\,type)}$ and $\Delta Ct_{(ubp15-1)}$ of each gene was obtained. Wild type was used as the standard for the comparison of expression levels. Relative expression levels were then calculated using the equation $2^{-[\Delta CT\,(ubp15-1) - \Delta CT\,(wild\,type)]}$. Next, the $C_T$ average of 2 biological repeats was calculated.

12. Detection of GUS Activity

P$_{UBP19}$:GUS transgenic lines were grown on MS plates. Seedlings were washed gently with 100 mM sodium phosphate buffer, pH 7.0, and then stained for 4 h at 37° C. in 2 mM X-glucuronide dissolved in 0.1 mM potassium ferricyanide, 0.1 mM potassium ferrocyanide, 10% Triton X-100, 100 µg/ml chloramphenicol, and 500 mM sodium phosphate buffer, pH 7.0 (Weigel and Glazebrook, 2002; Byrne et al., 2003). The tissue was then washed in 100 mM sodium phosphate buffer followed by 95% and 70% ethanol at room temperature. Microscopy was performed by a dissection microscope (Leica MZFLIII) with a 10× objective, and images were captured by Canon digital camera (Power Shot S70).

13. Accession Numbers

*Arabidopsis* Genome Initiative locus identifiers for the genes mentioned in this article are listed in Table 1.

14. The UBP Genes Exhibited Non-Identical Expression Profiles

To obtain expression patterns of the UBP genes, a previously described microarray data set was examined covering 18 different *Arabidopsis* organs, including cauline leaves, rosette leaves, pistil one day before pollination, pistil one day after pollination, silique 3 day after pollination, silique 8 day after pollination, stem, sepal, stamen, petal, seed, cultured cell, root dark, root white light, hypocotyl dark, hypocotyl white light, cotyledon dark and cotyledon white light (Ma et al., 2005; Supplemental Table 1). In that described study, 24 of 27 UBP genes were covered by the microarray used and expression for all 24 genes was detected in one or more tissues. Among those 24 genes, UBP9 and UBP10 were found to be essentially identical and their oligo probes were cross-hybridized to each other, thus not enabling definitive definition of the expression of both genes. The expression of the three genes not covered by this microarray, UBP13, UBP14 and UBP20, were reported in a prior study (Yan et al., 2000). As a sample case, the tissue-specific expression profiles for the 5 genes in UBP15 subfamily were present in FIG. 13. The 5 genes appear to have distinct expression profiles.

15. Genome Wide Isolation and Analysis of T-DNA Insertional Mutants of the UBP Genes As a first step in the functional analysis of the UBP gene family, the North America *Arabidopsis* Resource Center database was searched for all available T-DNA insertion lines for the UBP gene family members. A total of 38 T-DNA insertion lines corresponding to 25 UBP genes were obtained and verified, as summarized in Table 1 with the locations of the T-DNA insertion sites for each line. Following PCR-based genotyping, forward and reverse primers (Supplemental Table 2) were designed. Examination of possible phenotypes of those individual mutant homozygous lines revealed that only 5 loss-of-function mutant lines in 3 genes of 2 subfamilies exhibited visible phenotypes (Table 1). Two independent T-DNA alleles for UBP14 exhibited recessive embryo lethality, similar to a previous report (Doelling et al., 2001). Another three mutant lines belonging to the UBP15 subfamily, with two alleles for UBP15, exhibited a leaf morphology phenotype, and one allele for UBP19 exhibited embryo lethality. The 5 genes in this subfamily had not previously been characterised and so were selected for in-depth analysis.

A search for homologous genes of AtUBP15 subfamily in Rice (*Oriza Sativa*) to find out whether they have similar functions was carried out. Four genes were found with high similarity, and were aligned with the 5 AtUBP15 subfamily genes. The resultant phylogenetic tree is shown in FIG. 14. One of the rice genes was even more similar to AtUBP15 than other *Arabidopsis* genes.

16. The Two ubp15 Mutant Alleles Exhibited Similar Leaf Development Defects

The two T-DNA insertion lines for UBP15, Salk_018601 and Salk_015611, designated ubp15-1 and ubp15-2, were identified from the Salk collection and have T-DNA insertions in the 12th and 8th exon of the UBP15 gene respectively (FIG. 2A). Semi-quantitative RP-PCR showed the mRNA expression level could not be detected in either of the two mutants (FIG. 2B), suggesting both are null alleles. Both lines segregated a single, recessive Mendelian trait (described below) similar to each other co-segregating with the T-DNA, indicating the trait was caused by a single insertion in UBP15. Compared to wild type adult plants, both mutants give smaller plants and narrow, serrated leaves, with the leaf phenotype becoming more severe in the later rosette leaves (FIG. 2C). The mutants also exhibited shorter roots in seedling stage (FIG. 2D), smaller flowers (FIG. 2E), shorter siliques (FIG. 2F) as well as short and slim stems. Those morphopmetric changes (silique length, root length, primary stem length and primary stem diameter) are summarized in Table 2.

The morphology of rosette leaves using ubp15-1 were further analysed. The rosette leaves of wild type *Arabidopsis* grown in long day condition (16 h light/8 h dark) gradually change their overall patterns, starting with true leaves round and flat, slowing become more ovule shaped and a little downward-curled, eventually become long and narrow shape, with severe downward-curled margin. While the rosette leaves of ubp15-1 mutants are more flat even at a later stage and consistently produce fewer rosette leaves (10.8 versus 12.6 of wild type) before bolting (FIG. 2C). The ratio of length and width of ubp15-1 and wild type was plotted and defined as a leaf index value (Tsukaya, 2006), and revealed a much stronger reduction in width than in length of the rosette leaf blade in the mutant (FIG. 2G). On the contrary, cauline leaves of ubp15-1 did not show any obvious difference compared to the wild type.

Consistent with the reduced number of vegetative leaves, ubp15-1 also exhibited an early flowering phenotype, with average flowering time of 39.1 (±2.02) days versus the 41.5 (±3.79) days for wild type (Table 2). Even in short day condition (8 h light/16 h dark), ubp15-1 was also slight early flowering (Table 2). Also noted was that ubp15-1 rosette leaves had less weight (Table 2) and were thinner, implying alteration of the cell structure.

17. UBP15 Expressed Highly in Rosette Leaves and Reproductive Tissues, and Localized to Both Cytosol and Nucleus The presence of defects in ubp15-1 rosette leaves and flowers suggested involvement of UBP15 in regulation of vegetative and reproductive development. To support this, and to verify the prior microarray analysis, a semi quantitative RT-PCR was employed to examine tissue specific expression of UBP15. As shown in FIG. 3A, the mRNA level of UBP15 was highly accumulated in the rosette leaves and inflorescences, while low in roots, siliques and cotyledons, intermediate level in stems and cauline leaves. This expression pattern is largely consistent with microarray data (Supplemental Table 1 and FIG. 13).

The spatial expression pattern of UBP15 within a rosette leaf was further examined. As in FIG. 3B, rosette leaves at early, middle, and late stages were selected and dissected into center and margin regions for separate RNA preparations (FIG. 3B upper part, shown by the black lines) and RNA blot analysis (FIG. 3B, bottom). UBP15 mRNA level increased from early leaf to late leaf, together with a more evident higher expression in margin of leaf in late stage. These leaf expression patterns during development were consistent with a role of UBP15 in defining the leaf pattern and shapes of leaves margin, such as serrating and curling.

To assess the subcellular distribution of UBP15, constructs containing either 35S:GFP-UBP15 or 35S:UBP15-GFP were transformed into onion epidermal cell. Transient expression showed the fusion proteins ubiquitously present in both cytosol and nucleus, and the result for 35S:GFP-UBP15 is shown in FIG. 3C.

18. UBP15 Possess De-Ubiquitinatination Activity in Vitro and this Biochemical Activity is Essential for Function in Vivo To verify UBP15 is a bona fide de-ubiquitinating enzyme, UBP15 as well as two mutated forms (changed the conserved catalytic center Cysteine$^{447}$ residue to Alanine or Serine) were co-expressed as GST fusion proteins in *E. coli*. The his tagged UBQ1 or UBQ10 poly-ubiquitin proteins were used as substrates for in vitro DUB activity assay with recombinant GST-UBP15 wild type or mutant form proteins. Immunoblot analysis with anti-ubiquitin antibody showed UBP15 was capable of cleaving the two substrates and that Cysteine$^{447}$ is essential for this DUB activity (FIGS. 4A and 4B respectively).

To test the essential role of DUB activity of UBP15 in plant development, we introduced wild type UBP15 and its two Cysteine$^{447}$ mutant forms under the control of the UBP15 native promoter into wild type *Arabidopsis* and ubp15-1 background by means of *Agrobacterium*-mediated transformation. For the transgenic lines with wild type background, we obtained in total 36 independent $T_0$ generation plants for the wild type UBP15 transgene. Half of the lines (18 out of 36) exhibited no phenotypic changes, whereas the other half displayed interesting differences from wild type, opposite to the ubp15 mutant phenotypes (FIG. 4C, middle left). For those lines with wild type transgenes in ubp15-1 background, 5 independent lines showed wild type phenotype (FIG. 4C, middle right), thus functionally rescued the mutant defect. RNA gel blot analysis with two representative lines from each groups (FIG. 4D) revealed that high level expression of the transgene in wild type background was responsible for the abnormal phenotype opposite to ubp15-1 mutant, while expression level similar to endogenous gene confer phenotype rescue in ubp15-1 mutant and no phenotype effect in wild type background. Where the wild type transgene failed to rescue the ubp15-1 phenotype, those transgenic lines only expressed truncated ubp15 mRNA and failed to express wild type mRNA.

Introduction of UBP15C447A or UBP15C447S mutant transgenes under the control of the UBP15 native promoter into wild type, and ubp15-1, failed to cause overexpression phenotype in wild type background and complementation of mutant phenotype in ubp15-1 background, as the RNA gel blot analysis showed normal or even higher level expression of mutant genes (FIGS. 4C and 4E). In contrast, some lines with UBP15C447A in wild type exhibited phenotype similar to ubp15-1 mutant (FIG. 4C, bottom left, and 4E), which was opposite to the UBP15-overexpression in wild type background, as did transgenic lines of wild type overexpressing UBP15C447S (data not shown). Those lines tended to express the mutant transgene at higher levels, likely caused a dominant negative interference with endogenous protein function. These results imply that DUB activity is essential for UBP15 function in vivo.

19. Over-Expression of UBP15 Displaying Phenotypes Opposite to ubp15-1 Mutants

We further examined the phenotypes of UBP15-overexpressing lines (wild type transgenes in wild type background) above. One obvious phenotype was the larger overall status of the plants as well as each rosette leaf. The rosette leaves of those over-expressing lines were rounder than of wild types starting at very early stage and were severely downwardly-curled in the middle to later stages (FIG. 4C, middle left). Later developed rosette leaves, such as the ninth rosette leaf, were not only downwardly-curled, but also sometimes displayed a knot in the leaf tip region (arrow in FIG. 5B, compare 5A and 5B), possibly caused by the uneven proliferation of the cells in different positions within a leaf. In addition, the UBP15-overexpressing line was also late flowering, with the greater number of rosette leaves (16.2) before bolting than that of wild type, and the delay in flowering time under long day conditions (Table 2). The fresh weight of the rosette leaves of UBP15-overexpressing lines per area was also increased compared to wild type (Table 2).

There was also an evident flower phenotype in UBP15-overexpressing lines. Compared to the wild type, UBP15-overexpressing lines exhibited larger flowers (compare FIGS. 5I and 5J) with a high rate of abnormality in petal or stamen number (by 91.3%, 40 out of 46 in one plant) in the early flowers (FIGS. 5C and 5D, 5E, 5K). However this flower pattern abnormality was less frequent in late flowers. The overexpression lines also has siliques larger than wild type (FIG. 5L), opposite to the ubp15-1 mutants. Flower and silique abnormalities do not affect fertility, unless in extreme cases where damaged sexual organs prevented fertilization (FIG. 5H and 5M). An increased apical dominance in overexpressing lines was seen compared to the reduce apical dominance in ubp15 mutants (Table 2 and FIG. 15). In some extreme cases of UBP15 over-expression plants, positions for expected secondary bolts in the only main bolt degenerated into a flower then silique (FIG. 5G) contrasting to wild type (FIG. 5F).

20. The Ubp15 Loss-of-Function Mutants and UBP15-Overexpressing Plants Display Opposite Abnormality in Leaf Cell Proliferation To further characterize the role of UBP15 in *Arabidopsis* leaf development, the morphogenetic patterns of all leaves, from cotyledons, true leaves, to cauline leaves from loss-of-function mutants, over-expressing plants, and wild type were compared. As shown in FIG. 6A, wild type plants had about 11 rosette leaves, while both two ubp15 mutants had about 9 rosette leaves. In contrast, UBP15-overexpressing line produced about 14 rosette leaves. Rosette leaves in the two mutants were narrow, serrated and flat, but were more round in early leaves and downwardly-curled in later leaves in UBP15-overexpressing plants. The cauline leaves did not exhibit obvious differences amongst those lines examined, except two mutants had slightly narrower leaves.

To examine the cellular basis for their small plant size and narrow leaf lamina of the ubp15 mutants, transverse sections of leaves from mutants as well as UBP15-overexpressing line were compared with wild type leaves. The cartoon in the right of FIG. 6B illustrates the positions of representative sections routinely obtained and analyzed, which was in the middle region of the leaf. The left cartoon in FIG. 5B was the section model of the middle region of wild type. Six leaves (leaves with odd numbers in FIG. 6A) were selected for measurement, from the first cotyledon to the first, the third, the fifth, the ninth true leaf and the first grown cauline leaf. Those true leaves later than the ninth were not included for uniformity, because two mutants produced only 9~10 true leaves. Adaxial epidermal cell number and palisade cell numbers in each line were counted in serial sections (3~4) under microscope.

For adaxial epidermal cells, the cell number of each position in each line is shown in FIG. 6C. At the beginning of leaf development, the adaxial epidermal cell numbers across the lamina among those lines was similar, which was ~30 cells in the cotyledon of each line, but the difference increased with the development of the leaves, and severely differed in the ninth rosette leaf, cell numbers across the lamina of which were ~290 in wild type, ~180 in two mutants (decreased by ~40%) and ~400 in UBP15-overexpressing line (increased by ~40%). It was consistent with the phenotype observed, for distinction became noticeable in late development phases. Adaxial epidermal cell number of cauline leaf was higher than that of any rosette leaves. This may possibly be caused by more density in the adaxial epidermal cell number across the cauline leaf. Similar results were observed in the measuring of palisade cell number (FIG. 16). Mutation of UBP15 gave a decrease in adaxial epidermal and palisade cell number in a lateral direction, while overexpression of UBP15 led to the opposite.

21. *Arabidopsis* UBP15 is Involved in Leaf Cell Layer Organization

To extend the findings of cell number alteration, the cellular structure of the leaves of those lines was examined. Based on the result that late developed rosette leaves exhibited severe phenotype, the fully expanded ninth rosette leaf was chosen for comparison of the transverse sections of cellular structure in the middle region of the lines (FIG. 6B). As FIG. 7A left first wild type shown, leaf had an organized internal anatomy containing a layer of vertically packed palisade cells beneath the adaxial surface, and ~4 layers spongy parenchyma cells, interspersed with air spaces, were loosely arranged below the palisade layer. ubp15-1 and ubp15-2 also exhibited similar structure but the number of spongy cell layers in mutants was less than that of wild type, whereas that of UBP15-overexpressing line was more (FIG. 7A, from left, the second to the fourth). The spongy cell layers in wild type was generally ~4, but in two mutants the spongy cell layers were ~3, while in UBP15-overexpressing line the spongy cell layers reached ~5. The defects in cell layer structure in ubp15-1 was rescued by expression of its corresponding wild-type UBP15, confirming that these ubp15-1 phenotype was caused directly by disruption of the UBP15 gene (data not shown). These results were consistent with the fresh weight results for less weight corresponding to the less cell layers (Table 2), greater weight resulting from more cell layers (see above). A slight increase in the cell size of mutants was detected, implying partial compensation of the loss of cell number.

The mid-vein and peripheral structure of those lines was also compared. The vascular bundle of wild type was composed of several layers of xylem and phloem surrounded by layers of parenchyma cell (FIG. 7B, left first). In contrast, two mutants showed decreased thickness. The vascular bundles of the two mutants were slimmer than of the wild type due to decreased cell number in xylem and phloem. In addition, the numbers of parenchyma cells surrounding the vascular bundles of two mutants was also reduced. In UBP15-overexpressing line, opposite results were obtained, showing advanced vascular bundle, strong both in xylem and phloem (FIG. 7B, from left, the second to the fourth).

22. Transcriptome Analysis Shows UBP15 Influences Expression Level of 804 Genes (Adjusted P<0.15)

To examine the cell cycle effects in ubp15-1 and to explore the possible role of UBP15 in regulating the transcription of other genes, we performed microarray assay to conduct a genome wide expression analysis on the ninth rosette leaf immediately emerged. Microarray analysis also confirmed no expression of UBP15 mRNA in ubp15-1 (Supplemental Table 3). Statistical analysis showed a total of 804 out of 20,000 genes were differentially expressed in ubp15-1 compared with wild type at adjusted P<0.15 (4% of the expressed genes), among which 406 (50.5%) were up regulated and 398 (49.5%) were down regulated with fold change expression ranging from 1.72 to 8.35 and 0.09 to 0.56, respectively (Supplemental Table 3). To confirm the trends observed in the transcriptome analysis, we randomly picked 9 genes with 7 down regulated and 2 up regulated and performed real-time PCR. Expression levels of those genes was consistent with that of microarray result at 100% (FIG. 8), suggesting microarray assay was reliable. At1g42970/GAPDH served as an internal control.

To characterize the biological processes involved, representatives of those genes influenced by the ubp15-1 mutant were analyzed for gene ontology (GO) (Maere et al., 2005) (Table 3). Two genes related to cell cycle were differentially expressed in ubp15-1 (Table 3). Because the flowering time was also influenced in ubp15-1, genes controlling flowering were the focus. Floral homeotic gene CAL, positively regulating flower development, was up regulated 1.98 fold in ubp15-1 background, while another one, MAF5, negatively regulated flower development was down regulated 0.31 fold (Table 3).

Other categories influenced by ubp15-1 comprised genes involved in biosynthetic metabolism, chlorophyll biosynthesis, photosynthesis, signal transduction and also included a large number of transcription factors (Table 3). Thus, besides effects on some phenotype-related genes such as cell cycle and flowering control, the ubp15-1 mutant was in general defective in numerous plant metabolism pathways at the transcriptional level, suggesting secondary and not only primary effects on the observed growth defects.

23. UBP15 and UBP16 are Partially Redundant but not with UBP17

UBP16 and UBP17 are two closely related proteins (FIG. 1), suggesting they may have functional redundancy. Knockout lines of the two genes (ubp16-1, ubp17-1 and ubp17-2) (FIG. 9A) did not show any observable phenotype. ubp16-1 was crossed with ubp17-1 or ubp17-2 to examine whether there was any defect in double mutants. Homozygote F2 generation of crossed lines did not show noticeable phenotype, indicating there may be other proteins for redundancy. Subsequently crossed were ubp15 mutants with the double mutant ubp16 ubp17. In the F2 generation, three gene types of double mutants ubp15 ubp16, ubp15 ubp17 and ubp16 ubp17 were obtained, as well as a triple mutant ubp15 ubp16 ubp17 (FIGS. 9B and 9C, ubp16 ubp17 not shown). Double mutant ubp15 ubp16 showed a similar but more severe phenotype to the ubp15 mutant, indicating there may be functional redundancy of the two genes. ubp15 ubp16 exhibited dwarf plants and aborted siliques, rosette leaves, which were narrower than that of ubp15 mutants (FIG. 9C). The alteration in cellular level was also conspicuous, only 2 spongy cell layers (FIG. 7A, right first) and strikingly degenerated vascular bundle (FIG. 7B, right first). In the case of the ninth leaf, the adaxial epidermal cell number cross the leaf lamina decreased by 60% over that of wild type (FIG. 17), as did the palisade cell number (data not shown). In contrast, ubp15 ubp17 did not further the defect of ubp15 mutants, implying those two gene may work in two different pathways to regulate cellular function. The triple mutant ubp15 ubp16 ubp17 was similar to the double mutant ubp15 ubp16, further confirming UBP17 involves in another regulating pathway from UBP15 and UBP16, although it had higher sequence homology to UBP16.

The data suggest that the UBP15 mutation disrupted rosette leaf development, and its effect was more prominent when combined with UBP16. The effect of UBP16 was only detectable in the presence of UBP15. There was no detectable effect of the UBP17 mutation on this process. These results indicate that UBP15 is a major regulator of the shape of rosette leaves and development of the whole plants. UBP16 is also involved in these processes, although its contribution was less prominent than that of UBP15.

24. UBP19 May be Involved in Embryo Development While the Function of UBP18 is Unknown FIG. 9A shows UBP18 and UBP19 gene structure with two T-DNA mutants each. ubp19-1, with T-DNA inserted in the 5'UTR region 195 bp upstream of ATG, exhibited recessive embryo lethality, with ~1/4 (13/47) aborted embryos in one heterozygote silique (FIG. 9B, arrow indicated yellow embryos). Further statistical analysis of an average of 10 siliques in each heterozygote line showed the ratio of the normal:abnormal was ~3:1 (372/136), confirming it was a recessive embryo lethal line. The embryo development in a specific heterozygote silique, from mature stage tracing back to globular stage was examined. It was found that ubp19-1 stopped developing at globular stage (FIG. 10C).

It is therefore proposed that UBP19 is involved in early stage embryo development. A GUS construct driven by a 1.2 kb UBP19 promoter was made to transform wild types and to examine tissue expression pattern. It was found that UBP19 was ubiquitously expressed, including in the whole young seedling, except the root meristemetic region (FIG. 11A) (Enlarged in FIG. 11A was the detailed demonstration of root tip region), in the vascular tissues and stomas of mature rosette leaves (FIG. 11B) as well as in inflorescence. Detailed examination found GUS expressed in the sepal and petal vascular tissues, also in anthers and styles (FIG. 11C). GUS was detected in the tip and basal regions of siliques but hardly within the embryos (FIG. 11D).

Another ubp19 mutant, 205 bp upstream of ATG, did not show any obvious phenotype, indicating the region between 195 bp to 205 bp upstream of ATG was essential for the function of UBP19.

Neither of the two mutants inserted in UBP18 exon and intron exhibited any observable phenotype, implying potential functional redundancy between UBP18 and other proteins in this family.

25. UBP15 is Involved in Rosette Leaf Development

Phenotype of ubp15 mutants and UBP15-overexpressing lines provided a basis for further analysis of this gene in plant leaf development. Both ubp15 mutants showed rosette leaves that were narrow, serrated and flat, whereas UBP15-overexpressing lines produced an opposite phenotype with rosette leaves that were round (early developed) and downwardly-curled (late developed) (FIG. 2A and FIG. 5B). The cell number of transverse sections (both palisade and adaxial epidermal cells across the leaf lamina) of ubp15 mutants decreased whereas that of UBP15-overexpressing line dramatically increased compared to wild types. This indicates that UBP15 alters leaves shape by cell proliferation, possibly by regulating cell cycle proteins. Recently, hub1 was found to exhibit narrower rosette leaves, caused by cell number decrease and a microarray assay discovered that the amount of genes related to cell cycle and cytokinesis were changed (Fleury et al., 2007). In this study, although microarray data showed there were only two genes related to cell cycle altered (ICK1 and Cycle-like F box domain containing protein), their expression level was consistent with the cell number decrease. The rosette leaves in mutants became flat while they were downwardly-curled in UBP15-overexpressing lines. The expression level of UBP15 in rosette leaves increased in the leaf margin with the development of plants (FIG. 3B), suggesting that UBP15 specifically (at least partly) determines the margin of rosette leaves. This was similar to iamt1-D, which displayed dramatic hyponastic leaf phenotypes caused by increased expression levels of the IAMT1 gene, and which was found to be specifically expressed in the margin of rosette leaves by GUS expression assay (Qin et al., 2005).

The leaf index increased in ubp15-1 mutants because of narrower rosette leaves (although leaf length was shorter but less altered and lead to a large leaf index value). Polarized growth of leaf blades in the leaf-width direction is governed by polar elongation of leaf cells or polar cell proliferation (Tsukaya, 2006). Genes altered cell proliferation in leaf-width direction reported until now are GIF1 (also named AN3) (Kim and Kende, 2004), GRF5 (Horiguchi et al., 2005), and HUB1 (Kim and Kende, 2004; Horiguchi et al., 2005; Fleury et al., 2007). They all are important in positive control of cell number in leaf width direction. ubp15 mutants altered adaxial epidermal and palisade cell numbers in leaf width direction, but microarray data did not show there was any change of the expression level of GIF1 (AN3), GRF5 or HUB1 in ubp15-1 background. This may because of distinct pathways involved by UBP15 and those genes.

26. The Cysteine Amino Acid of UBP15 is Critical for its Function in Vitro and in Vivo In vitro co-expression assay showed UBP15 is a bona fide ubiquitin specific protease and $Cys^{447}$ is critical for this activity. It was found that UBP15 can only cleave a-linked peptide (polyubiquitin and ubiquitin-extension gene) (FIG. 5A), not c-linked isopeptide (multiubiquitin chain linked by iso-peptide) (data not shown), suggesting it may only function on a-linked peptide or can only recognize the site of substrate-proximal end of the chain. UBP3, 4 and 5 proteins were reported to contain nuclear localization signal and were deduced to only function on isopeptide-linked substrates (Chandler et al., 1997; Rao-Naik et al., 2000). The subcellular localization of UBP15, ubiquitous expression throughout the cell, suggests that this enzyme may recognize more than one substrate to execute its diverse functions; or it has other function addition of de-ubiquitination.

In this study, we first proved in vivo function of $Cys^{447}$ of UBP15 in leaf development. While expressing UBP15 wild type construct in ubp15-1 can rescue the mutant phenotype, neither overexpressing UBP15C447A or UBP15C447S showed complementation of mutant deficiency. This implied $Cysteine^{447}$ was the functional residue of UBP15. On the other hand, transgenic lines of wild type with constructs containing wild type UBP15 exhibited downwardly-curled mature rosette leaves while those with constructs containing mutation in Cys447Ala or Cys447Ser showed ubp15-1 mutant phenotype. This result confirmed the phenotype of rosette leaves was caused by overexpression of UBP15 and that the $Cys^{447}$ is critical for this function. It also implies that it is the de-ubiquitination activity but not other domains (such as Zinc finger MYND) that cause the abnormality. Recently found gene HUB1 (Fleury et al., 2007), an E3 ligase mono-ubiquitinating H2B, with similar phenotype as ubp15 mutants, possibly shares the same pathway as UBP15.

There is also another result that transgenic lines with construct containing UBP15 driven by 35S promoter in wild type background did not show any phenotype, nor did the mutant can be rescued (data not shown). This suggested the native promoter may provide a favorable spatial structure for better executing the function of exogenous proteins.

27. UBP15 Regulates Transcription of Many Genes

A microarray assay was performed to analyze the possible role of UBP15 in regulating other genes at a transcriptional level. Two genes related to cell cycle were found to be altered and may directly cause the cell number changes in ubp15-1, although not like HUB1, which altered cell cycle proteins across the genome (24 genes).

We also found two genes controlling flowering were altered and this alteration caused the phenotype we observed. MAF5 and Floral homeotic gene CAL, regulate flowering in opposition, both showed altered ubp15-1 and caused the early flower phenotype.

Although numerous other genes were up- or down-regulated in ubp15-1, they seem to be the secondary effectors instead of proximal downstream targets.

28. Functional Redundancy Among the UBP15 Subfamily Members

UBP15 subfamily members encode proteins containing zinc finger MYND domains. They can be further divided into 3 groups based on the sequence similarity. UBP16 and UBP17 have 50% amino acid identity in their two conserved domains, while UBP18 and UBP19 have 68% identity in the full length. But UBP15 is less similar to other four (UBP15 to UBP16 is 37% identity in the UBP domain and to UBP18 is 45% identity in the full length), and this explains the ubp15 mutant phenotype. To see if UBP16 and UBP17 have functional redundancy, the two mutants of the two genes were crossed to give double mutants. Homozygotes of double mutants did not show any phenotype suggesting they may work in different pathways. Subsequently, the double mutant was crossed with ubp15 mutants to examine whether there is any alteration. In the F2 generation, only ubp15 ubp16 but no others intensified the phenotype of ubp15 mutants. This indicated that UBP15 and UBP16 may have functional redundancy. Triple mutant ubp15 ubp16 ubp17 exhibited similar phenotypes as ubp15 ubp16 further suggesting UBP17 did not involve in the function shared by the other two. On the other hand, ubp16 mutant did not display any visible phenotype, but it intensified the phenotype of ubp15 mutants, suggesting that in *Arabidopsis*, UBP15 is a master regulator in this pathway. Functional redundancy was also observed in another subfamily UBP1 and UBP2, whose double mutants but not each mutant were sensitive to Canavanine (Yan et al., 2000).

The sequence homology of UBP18 and UBP19 also imply functional redundancy. However, only one mutant (ubp19-1) out of four showed recessive embryo lethality. Furthermore, insertion in the 195 bp upstream of UBP19 5'UTR caused a phenotype, whereas inserting 205 bp upstream of UBP19 5'UTR did not show any phenotype. This implies the region from 195 bp tracing to 205 bp upstream of UBP19 5'UTR is critical for the function of UBP19.

On the other hand, although UBP16 and UBP17 are more related to each other than to UBP15 in protein sequences, the exhibited phenotype of ubp15 ubp16 similar to ubp15 mutant suggested UBP16 was more related to UBP15 instead of UBP17 in function. This also applies to the group of UBP18 and UBP19, since the phenotype can only be detected in the ubp19 mutant but not in ubp18 mutants. This shows that proteins closely related at a sequence level are not always functionally redundant.

DESCRIPTION OF FIGURES

The present invention will now be described with reference to the following figures in which.

The Phylogenetic tree of 27 UBPs. The branch lengths of the tree are proportional to divergence. The 0.1 scale represents 10% change. Bootstrap values are shown in percentages at nodes. 27 proteins can be subdivided into 14 subfamilies differing in distinct colors based on the domain similarity. Multiple alignments used for this analysis are shown in FIG. 12.

Proteins with conserved domains are plotted on a schematically scale. Each colored box represents a domain. Black lines represent the length of UBP proteins, while the length of the domains can be estimated by the binding black lines. aa, amino acids; UBP, ubiquitin specific protease; ZnF, zinc finger; MYND, myeloid, Nervy, and DEAF-1; DUSP, domain in ubiquitin-specific proteases; UBQ, ubiquitin homologues; MATH, meprin and TRAF homology; UBA, ubiquitin-associated.

Figure 1:
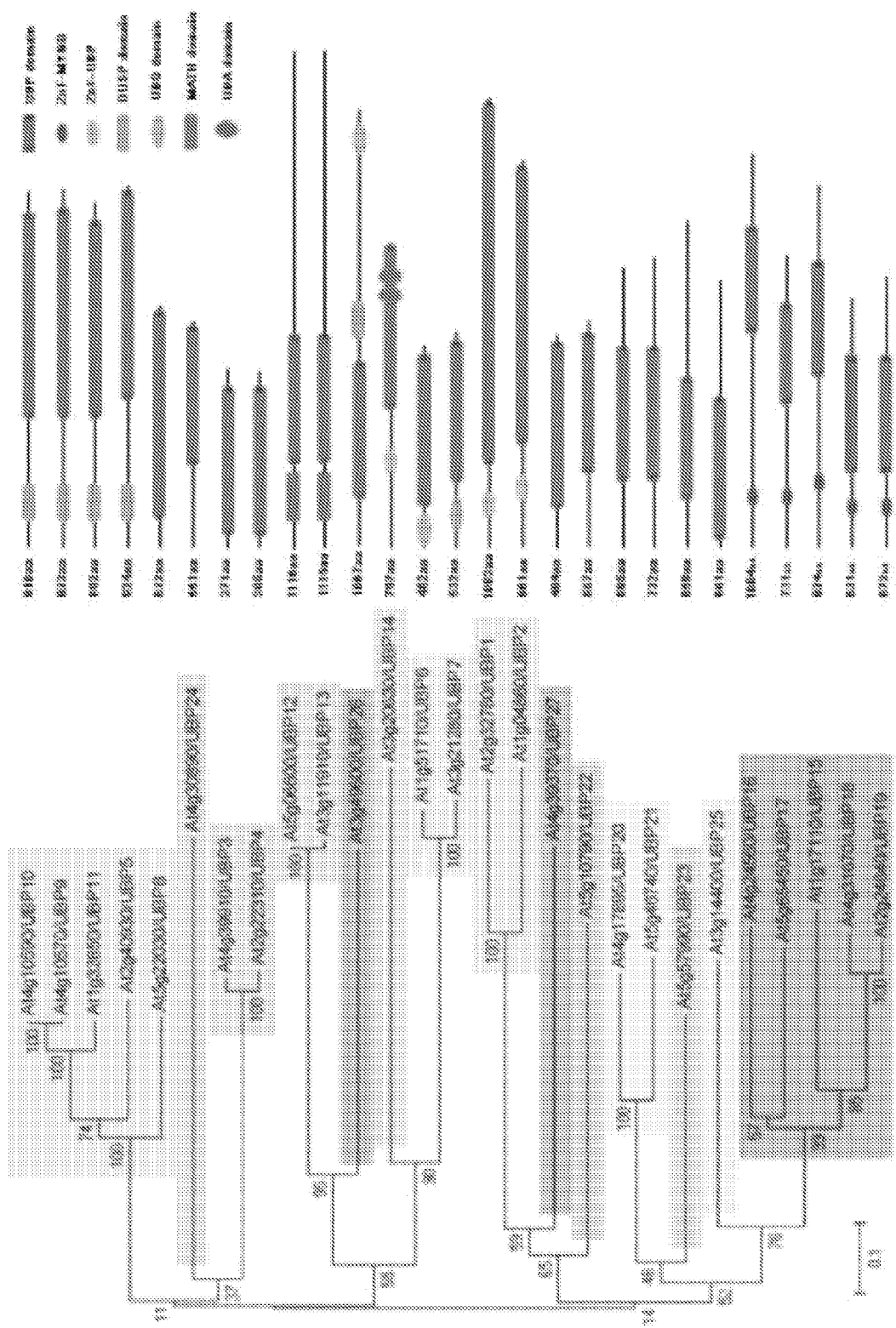
FIG. 1. Phylogenetic Analysis of 27 UBPs family of *Arabidopsis*.
Figure 2:
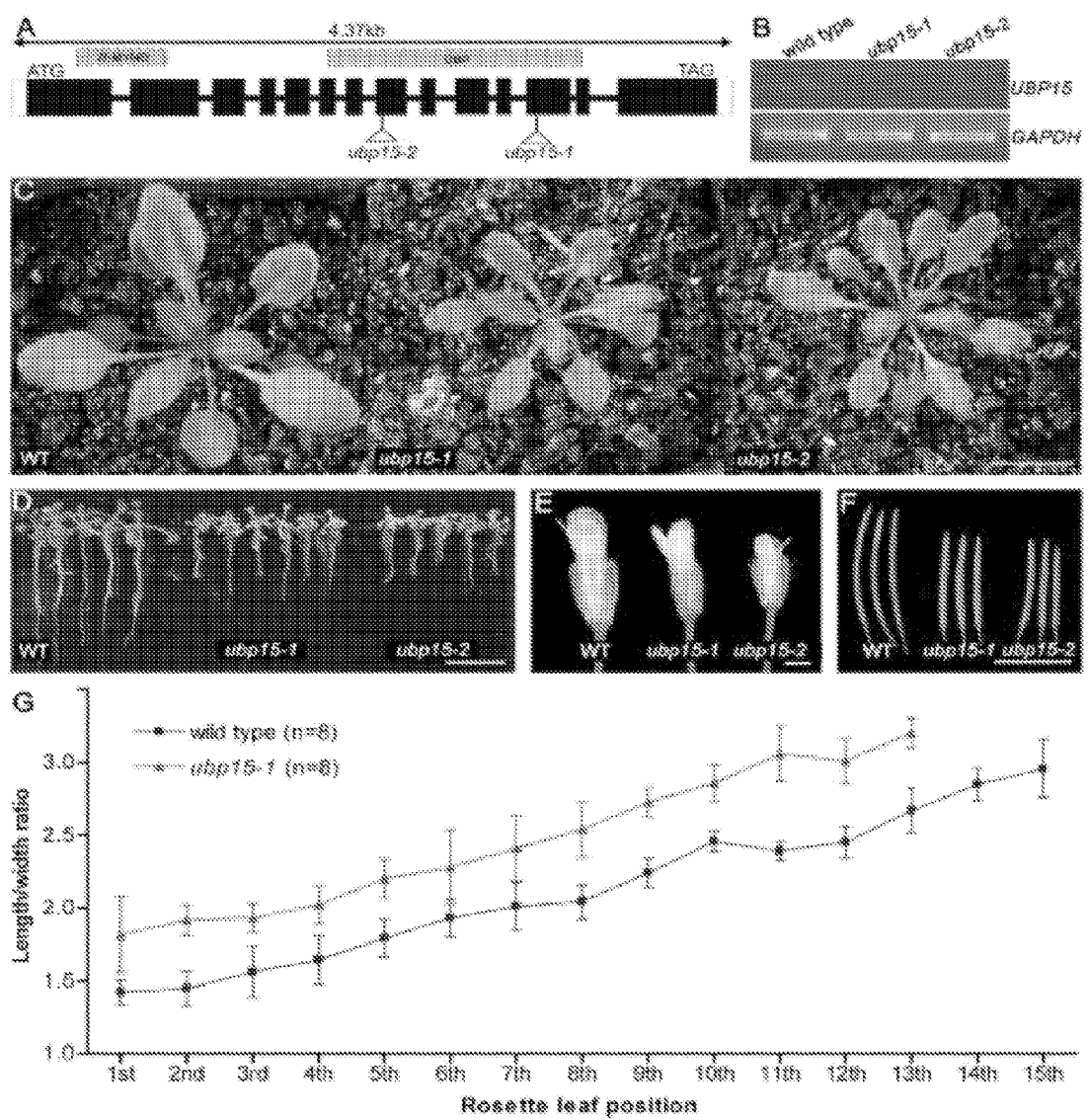

FIG. 2. Characterization of the Ubiquitin-Specific Protease gene UBP15.
(A) Gene structure of UBP15. There are 14 exons dispersed within the 4.37 kb genomic region. Black boxes represent the exons while lines between those exons are introns. White boxes in the two ends stand for 5' and 3' UTRs. Two T-DNA knockout lines inserted in the 8th and 12th exon respectively, each resulting in destroyed UBP domain.
(B) Expression of UBP15 in the wild type and the homozygous ubp15-1 and ubp15-2 by RT-PCR with the primer of UBP15FP and UBP15RP. At3g04120/GAPDH served as an internal control.
(C) One-month-old plants of wild type, homozygous ubp15-1 and homozygous ubp15-2. Bar=1 cm.
(D) 12-d-old seedlings of wild type, homozygous ubp15-1 and homozygous ubp15-2. Bar=1 cm.
(E) Flowers of wild type, homozygous ubp15-1 and homozygous ubp15-2. Bar=1 mm.
(F) Siliques of wild type, homozygous ubp15-1 and homozygous ubp15-2. Bar=1 cm. Plants above all grow in 16 light/8 dark condition.
(G) Length and width ratio of the rosette leaves of wild type and ubp15-1 in short day condition (8 h light/16 h dark). Error bars represent the standard deviation of the 7 repeats.

Figure 3:
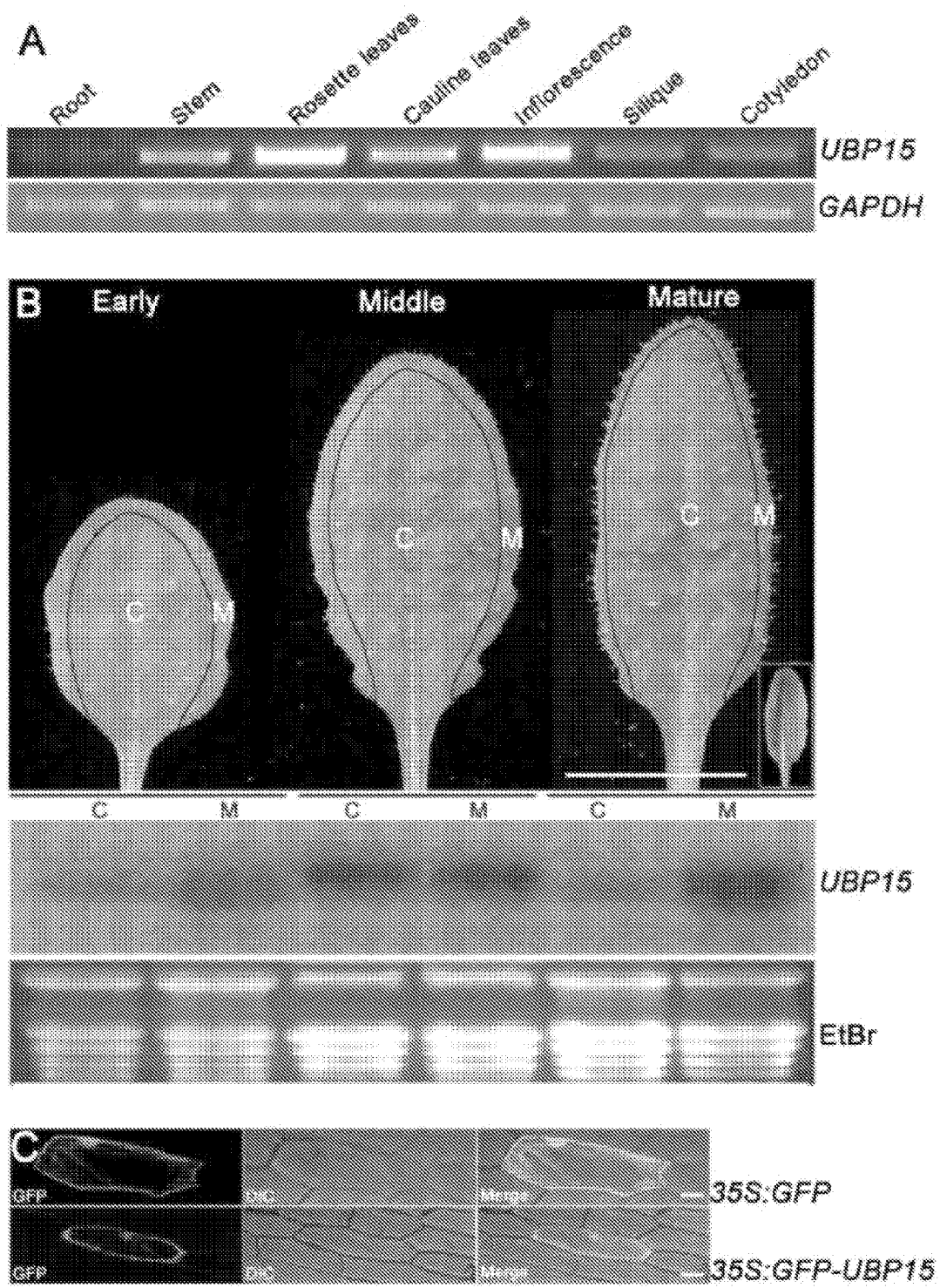

FIG. 3. Tissue and developmental expression patterns of UBP15, and subcellular localization of UBP15 in onion epidermal cells.
(A) RT-PCR analysis of tissue expression pattern of UBP15. At3g04120/GAPDH as an internal control.
(B) Northern blot analysis of UBP15 expression pattern in leaf center and margin regions in three developmental stages, P1, P2 and P3. Leaves were dissected in two parts: center and margin as the lines shown in the figure. Equal amounts of total RNA from the different samples were used, and gel blot was hybridized and labeled with UBP15 gene-specific probes. The rRNA band pattern was used to show equal loading. C, center region; M, margin region. Bar=1 cm.
(C) Subcellular localization of UBP15 in onion epidermal cells. Bar=100 μm.

Figure 4:
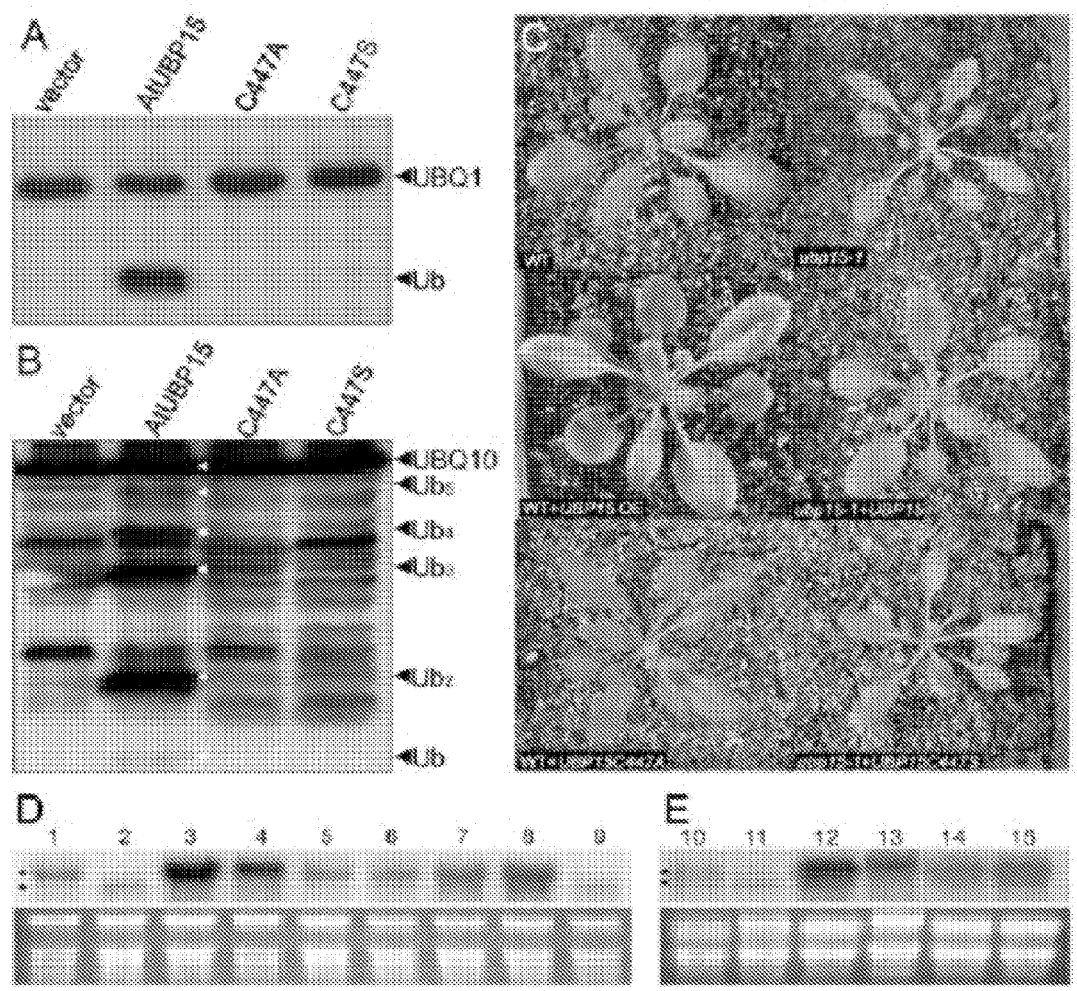

FIG. 4. UBP15 encodes a functional deubiquitinating enzyme capable of cleaving the polypeptides, and its Cys$^{447}$ is essential for the function in vitro and in vivo.
(A) UBP15 can cleave substrate UBQ1 (ubiquitin-extension protein). Co-expressed plasmids in *E. coli*. Novablue (DE3) strain (Novagen) was UBQ1 with GST vector (lane 1), GST-UBP15 (lane 2), GST-UBP15C447A (lane 3) and GST-UBP15C447S (lane 4). The cleaved products were detected by immunoblot analysis with anti-ubiquitin antibody.
(B) UBP15 can cleave substrate UBQ10 (hexameric polyubiquitin). Co-expressed plasmids in *E. coli*. Novablue (DE3) strain (Novagen) was UBQ10 with GST vector (lane 1), GST-UBP15 (lane 2), GST-UBP15C447A (lane 3) and GST-UBP15C447S (lane 4). The cleaved products were detected by immunoblot analysis with anti-ubiquitin antibody. Cleaved products are shown as white arrows.
(C) Expression of UBP15 in ubp15-1 recapitulates its wild type function, while overexpression of UBP15, but not UBP15C447A or UBP15C447S, causes phenotype with round (early developed) and curled down (mature) rosette leaves opposite to the ubp15-1 mutants. Samples one-month-old from left to right and up to bottom are: wild type, ubp15-1, UBP15-overexpressing line, UBP15-complemented line, UBP15C447A-overexpressing line and UBP15C447A-overexpressing in ubp15-1 line. Bar=1 cm.
(D) RNA gel blot analysis of the UBP15 gene expression in transgenic lines. RNA levels from wild type (1), ubp15-1 (2), wild type with UBP15 transgene (3-6) and ubp15-1 with UBP15 transgene (7-9) plants were analyzed. Total RNA was isolated from rosette leaves grown for 4 weeks. Equal amounts of total RNA from the different plant samples were used, and gel blot was hybridized and labeled with UBP15 gene-specific probes. The rRNA band pattern was used to show equal loading. The upper band (upper arrow) was the full length of the UBP15 mRNA, while the lower band (lower arrow) represented the truncated mRNA. Lane 3, 4 were the samples with UBP15-overexpressing phenotype while lane 5, 6 were similar to wild type without obviously UBP15-overexpressing phenotype. Lane 7, 8 but not 9 were rescued samples for they did not exhibit mutants phenotype but as normal as wild type. Line 9 sample showed ubp15-1 mutant phenotype.
(E) RNA gel blot analysis of the UBP15C447A gene expression in transgenic lines.

Figure 5:
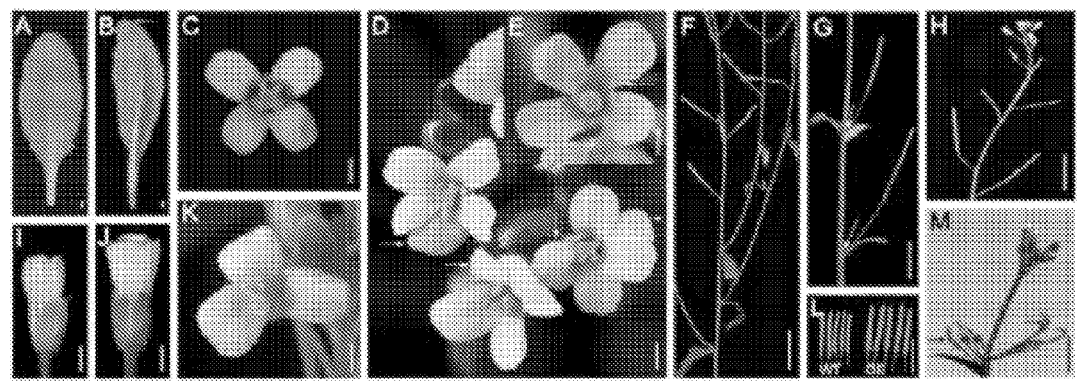

FIG. 5. Comparison of wild type and UBP15-overexpressing line.
(A) Ninth rosette leaf of wild type. Bar=1 mm.
(B) Ninth rosette leaf of UBP15-overexpressing line. Bar=1 mm.
(C) Top view of wild type flower. Bar=1 mm.
(D) (E) (K) Ectopic flowers of UBP15-overexpressing line. Bar=1 mm.
(I) Side view of the flower of wild type. Bar=1 mm.
(J) Side view of the flower of UBP15-overexpressing line. Bar=1 mm.
(F) Secondary stems of wild type. Bar=1 cm.
(G) Degenerated secondary stems of UBP15-overexpressing line. Bar=1 cm.
(H) Siliques of wild type. Bar=1 cm.
(M) Abnormal siliques of UBP15-overexpressing line. Bar=1 cm.
(L) Comparison the normal siliques of wild type (left) and UBP15-overexpressing line (right). Bar=1 cm.

Figure 6:
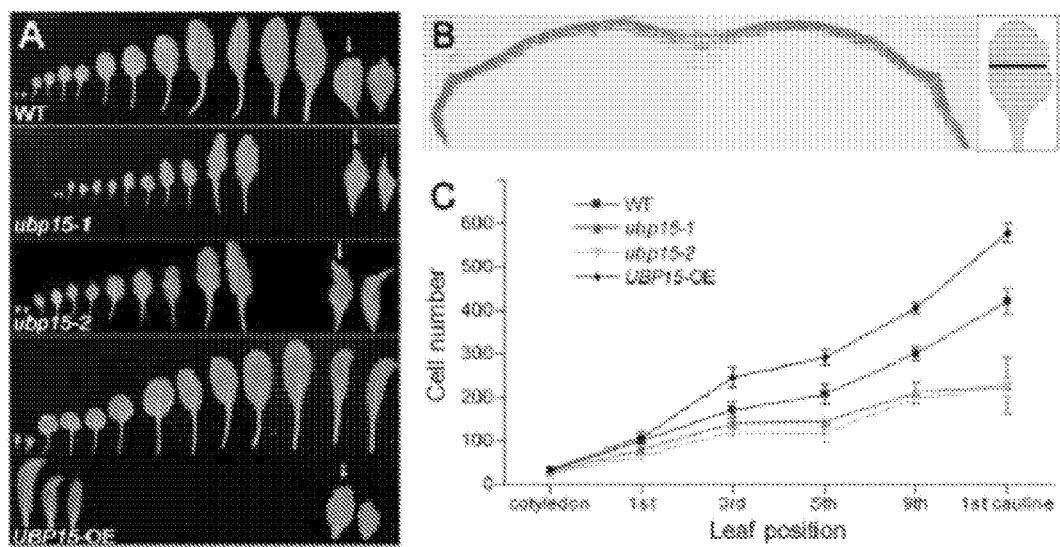

FIG. 6. Comparison of the transverse sections of rosette leaves across the lamina in four lines.
(A) From top to the bottom: wild type, ubp15-1, ubp15-2 and UBP15-overexpressing line. In each panel, two cotyledons and rosette leaves from the first to the last as well as two first cauline leaves are placed from left to the right. Arrows indicate positions of cauline leaves. Bar=1 cm.
(B) Models demonstrate the position of transverse sections.

(C) Comparison of adaxial epidermal cell number in transverse sections across the rosette leaves lamina. Error bars represent standard deviation of three biological repeats.

Figure 7:
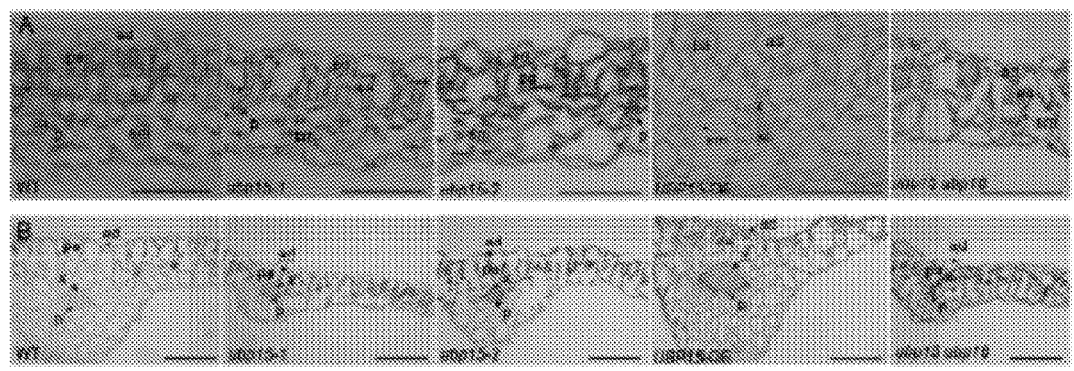

FIG. 7. Histological comparison of the transverse sections of the ninth rosette leaf middle region.
(A) Comparison of the cell layer in transverse sections of wild type, ubp15-1, ubp15-2, UBP15-overexpressing line and ubp15 ubp16. ad, adaxial; pa, palisade; sm, spongy mesophyll; ab, abaxial; x, xylem; p, phloem. Bar=0.1 mm.
(B) Comparison of the mid vein structure in transversal sections of wild type, ubp15-1, ubp15-2, UBP15-overexpressing line and ubp15 ubp16. Bar=0.1 mm.

Figure 8:
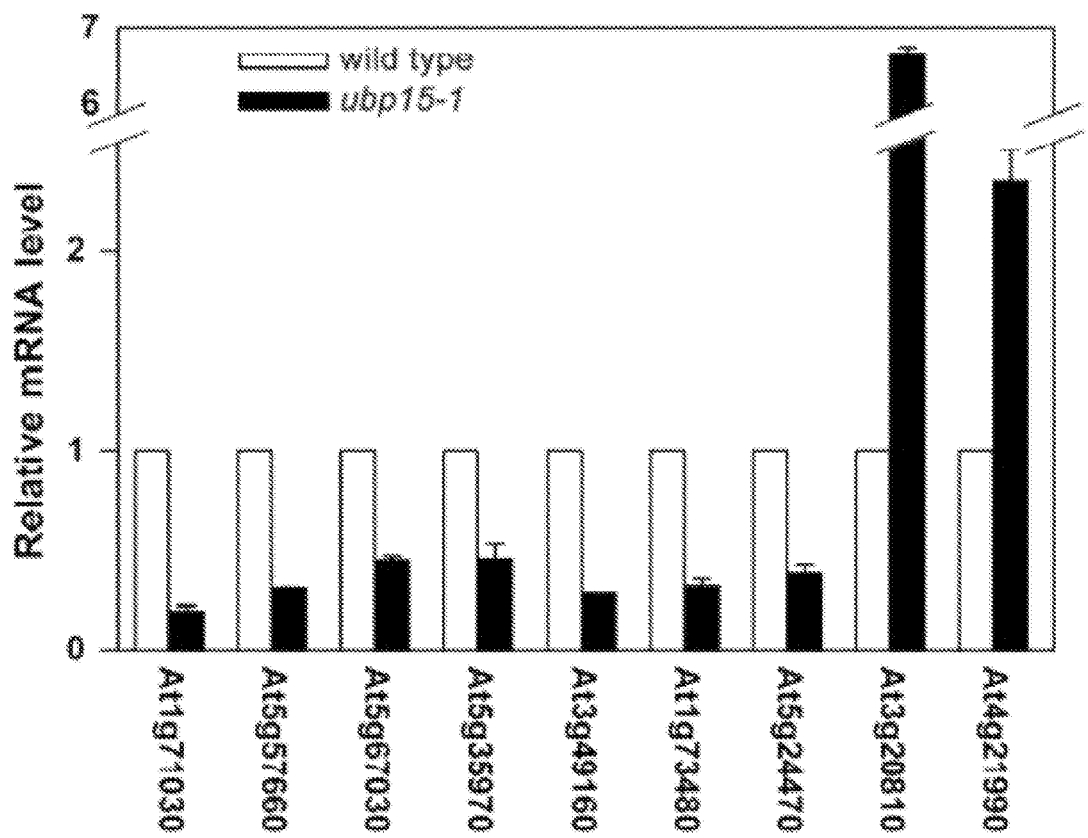

FIG. 8. Real-time PCR confirm the microarray results.
7 down regulated genes and 2 up regulated genes are randomly picked for real-time PCR analysis which confirms microarray result.

Figure 9:
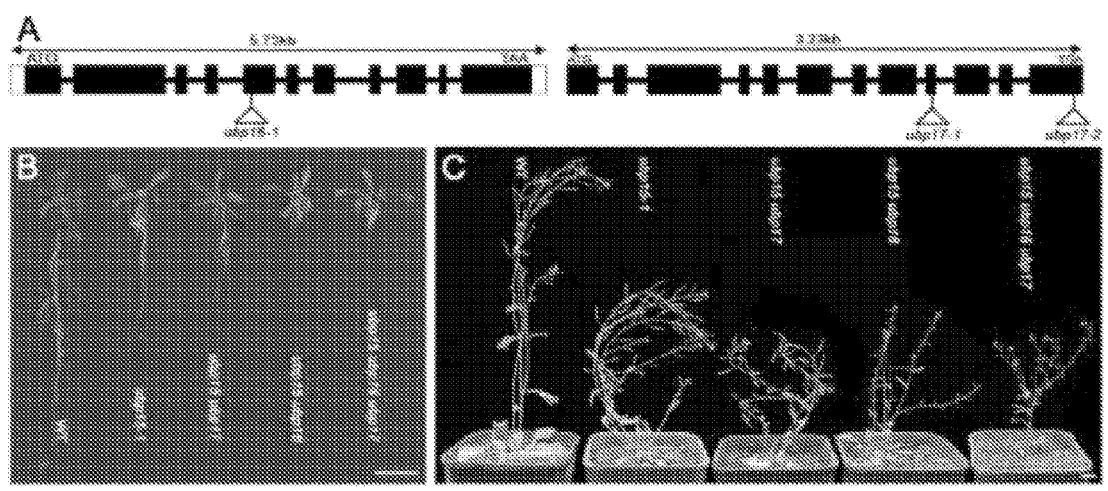

FIG. 9. Characterization of the UBP16 and UBP17.
(A) Gene structure of UBP16 (left) and UBP17 (right).
(B) 12-d-old seedlings of wild type, ubp15-1, ubp15 ubp17, ubp15 ubp16 and ubp15 ubp16 ubp17. Bar=1 cm.
(C) 2-month-old plants of wild type, ubp15-1, ubp15 ubp17, ubp15 ubp16 and ubp15 ubp16 ubp17. Bar=1 cm.

Figure 10:
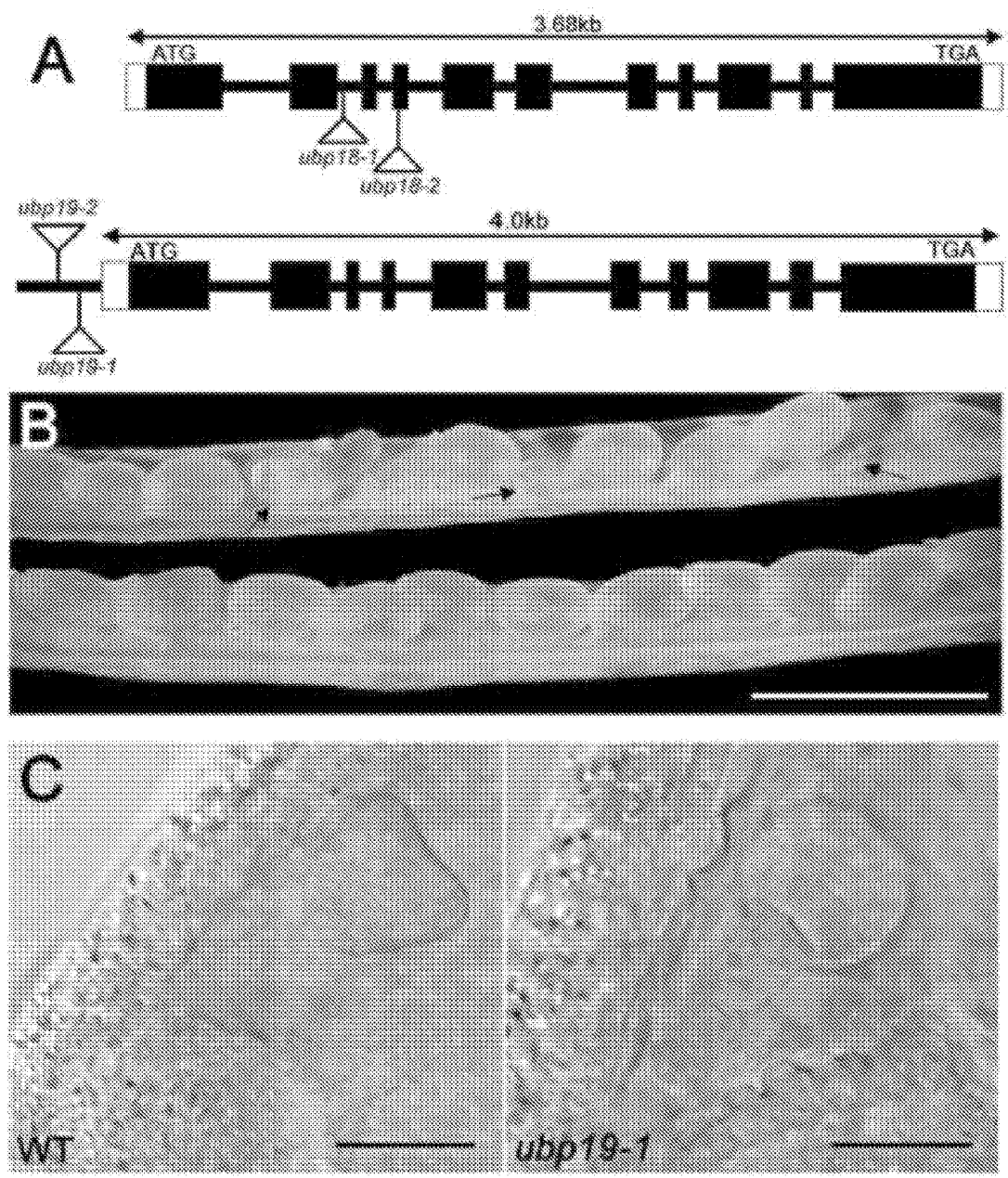

FIG. 10. Characterization of the UBP18 and UBP19.
(A) Gene structure of UBP18 (up panel) and UBP19 (bottom panel).
(B) ubp19 exhibits recessive embryo lethality. The upper silique is ubp19 Heterzygote and the lower is wild type. Arrows refer to those abnormal homozygote embryos. Bar=1 mm.
(C) Microscopic examination of embryos of wild type (left) and ubp19 homozygote (right). ubp19 homozygote stagnates developing at global stage. Bar=20 μm.

Figure 11:
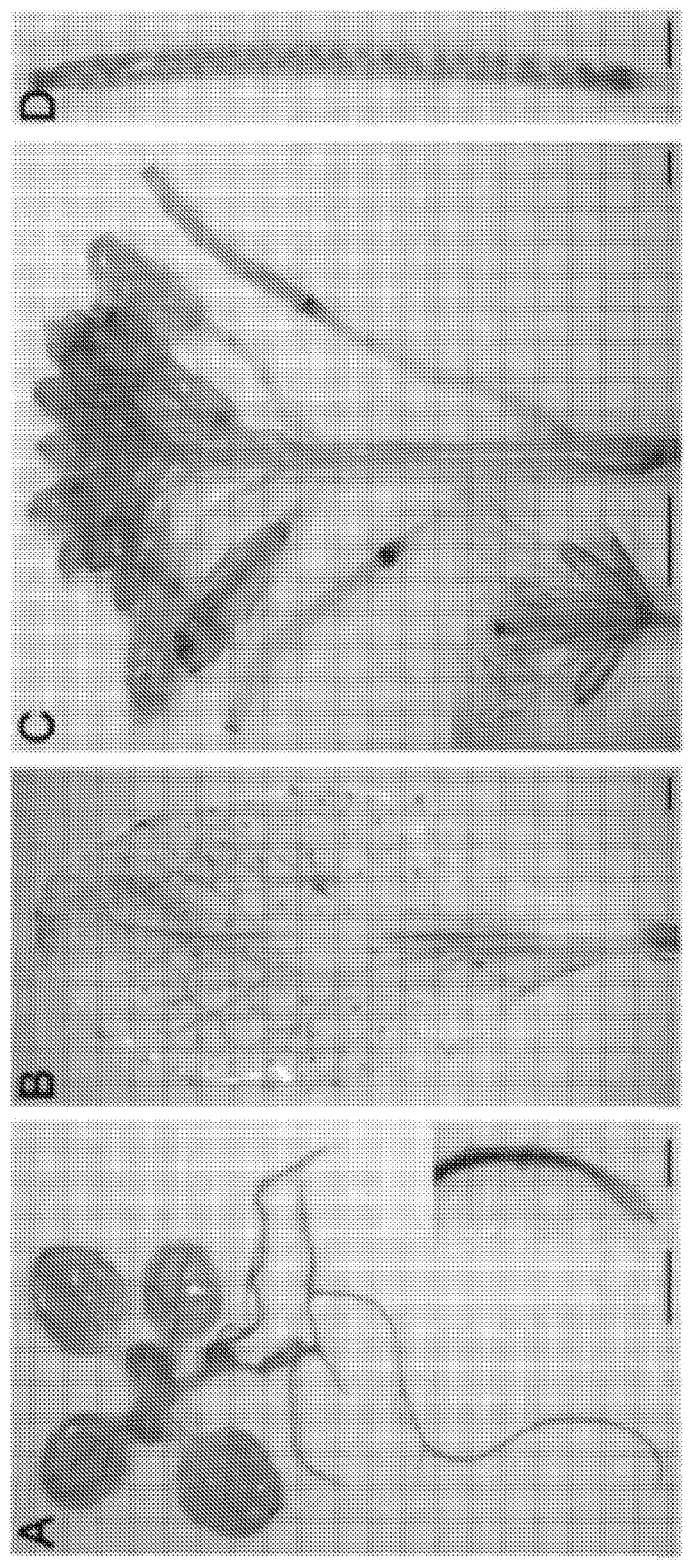

FIG. 11. Tissue expression pattern of UBP19. The expression pattern of UBP19 was determined using $P_{UBP19}$:GUS transgenic lines.
(A) 12-d-old seedling of the $P_{UBP19}$:GUS line. Bar=1 mm. Figure in the right bottom is 6 fold enlarged of the root tip region.
(B) Mature rosette leaf of the $P_{UBP19}$:GUS line. Bar=1 mm.
(C) Inflorescence of the $P_{UBP19}$:GUS line. Figure in the left bottom is 2 fold of a flower. Bar=1 mm.
(D) Silique of the $P_{UBP19}$:GUS line. Bar=1 mm.

TABLE 1

Analysis of T-DNA insertion lines for UBP genes.

| Arabidopsis Genome ID | Protein | Mutant allele | T-DNA line | Insertion site | Phenotype |
|---|---|---|---|---|---|
| At2g32780 | UBP1 | ubp1-2 | SALK_086190 | Promoter | ND |
| At1g04860 | UBP2 | ubp2-2 | SALK_064103 | $1^{st}$ exon | ND |
|  |  | ubp2-3 | SALK_059858 | $1^{st}$ exon | ND |
| At4g39910 | UBP3 | ubp3-1 | SALK_112950 | $3^{rd}$ exon | ND |
| At2g22310 | UBP4 | ubp4-1 | SALK_043210 | $4^{th}$ exon | ND |
| At2g40930 | UBP5 | ubp5-1 | SALK_08839 | 5'UTR | ND |
| At1g51710 | UBP6 | ubp6-1 | SALK_108832 | $14^{th}$ intron | ND |
| At3g21280 | UBP7 | ubp7-1 | SALK_014223 | ND | ND |
| At5g22030 | UBP8 | ubp8-1 | SALK_034744 | $5^{th}$ intron | ND |
|  |  | ubp8-2 | SALK_149329 | $6^{th}$ intron | ND |
|  |  | ubp8-3 | SALK_088692 | $7^{th}$ exon | ND |
| At4g10570 | UBP9 | ubp9-1 | SALK_141485 | 5'UTR | ND |
| At4g10590 | UBP10 | ubp10-1 | SALK_093503 | $9^{th}$ exon | ND |
| At1g32850 | UBP11 | ubp11-1 | SALK_043515 | $8^{th}$ intron | ND |
| At5g06600 | UBP12 |  | NONE |  |  |
| At3g11910 | UBP13 | ubp13-1 | SALK_128312 | $5^{th}$ exon | ND |
|  |  | ubp13-2 | SALK_024054 | $6^{th}$ exon | ND |
|  |  | ubp13-3 | SALK_130784 | $17^{th}$ exon | ND |
|  |  | ubp13-4 | SALK_132368 | $21^{th}$ intron | ND |
| At3g20630 | UBP14 | ubp14-3 | SALK_050151 | $9^{th}$ exon | Recessive embryo lethal |
|  |  | ubp14-4 | SALK_012863 | $19^{th}$ exon | Recessive embryo lethal |
| At1g17110 | UBP15 | ubp15-1 | SALK_018601 | $12^{th}$ exon | Recessive rosette leaves narrow and serrated |
|  |  | ubp15-2 | SALK_015611 | $8^{th}$ exon | Recessive rosette leaves narrow and serrated |
| At4g24560 | UBP16 | ubp16-1 | SALK_023552 | $5^{th}$ exon | ND |
| At5g65450 | UBP17 | ubp17-1 | SALK_087726 | $9^{th}$ exon | ND |
|  |  | ubp17-2 | SALK_113300 | $12^{th}$ exon | ND |
|  |  | ubp17-3 | SALK_009641 | $8^{th}$ intron | ND |
| At4g31670 | UBP18 | ubp18-1 | SALK_101685 | $2^{nd}$ intron | ND |
|  |  | ubp18-2 | SALK_126252 | $4^{th}$ exon | ND |
| At2g24640 | UBP19 | ubp19-1 | SALK_084566 | 5'UTR | Recessive embryo lethal |
|  |  | ubp19-2 | SALK_117787 | 5'UTR | ND |
| At4g17890 | UBP20 |  | NONE |  |  |
| At5g46740 | UBP21 | ubp21-1 | SALK_079015 | $1^{st}$ exon | ND |
| At5g10790 | UBP22 |  | NONE |  |  |
| At5g57990 | UBP23 | ubp23-1 | SALK_121772 | $10^{th}$ exon | ND |
| At4g30890 | UBP24 | ubp24-1 | SALK_001531 | $3^{rd}$ exon | ND |
| At3g14400 | UBP25 | ubp25-1 | SALK_088458 | 5'UTR | ND |
|  |  | ubp25-2 | SALK_111336 | $2^{nd}$ exon | ND |
| At3g49600 | UBP26 | ubp26-1 | SALK_024392 | $4^{th}$ intron | ND |
| At4g39370 | UBP27 | ubp27-1 | SALK_067020 | 5'UTR | ND |
|  |  | ubp27-2 | SALK_027968 | $1^{st}$ exon | ND |

38 T-DNA knockout lines corresponding to the 24 out of 27 UBP genes are screened for their phenotype. Only 5 lines belong to 3 genes exhibit observable phenotype.

TABLE 2

Morphometric analysis of wild type, ubp15-1 mutant, and UBP15 over-expressing plants.

| Body parameters | Wild type | ubp15-1 | UBP15 over-expressing plants |
|---|---|---|---|
| Number of rosette leaves (LD)[a] | 12.58 ± 0.95 (n = 26) | 10.82 ± 1.36 (n = 18) | 16.21 ± 1.63 (n = 26) |
| Flowering time (LD) (day)[a] | 41.54 ± 3.79 (n = 26) | 39.13 ± 2.02 (n = 46) | 46.07 ± 2.37 (n = 26) |
| Number of rosette leaves (SD)[b] | 15.92 ± 2.11 (n = 7) | 13.08 ± 1.77 (n = 7) | 20.22 ± 2.66 (n = 7) |
| Flowering time (SD) (day)[b] | 69.04 ± 1.41 (n = 8) | 65.69 ± 4.66 (n = 21) | 75.45 ± 4.87 (n = 8) |
| Fresh weight of the rosette leaves (mg/cm$^2$)[b] | 13.24 ± 0.48 (n = 24) | 10.74 ± 0.29 (n = 40) | 15.6 ± 0.46 (n = 24) |
| Silique length (cm)[c] | 1.36 ± 0.08 (n = 50) | 1.09 ± 0.08 (n = 50) | 1.42 ± 0.07 (n = 40) |
| Root length (cm)[d] | 5.87 ± 0.75 (n = 22) | 4.64 ± 0.74 (n = 22) | 6.84 ± 0.69 (n = 26) |
| Primary stem length (cm)[c] | 26.09 ± 2.68 (n = 11) | 23.77 ± 2.98 (n = 15) | 29.25 ± 4.44 (n = 6) |
| Primary stem diameter (mm)[c] | 0.80 ± 0.08 (n = 14) | 0.65 ± 0.09 (n = 18) | 0.98 ± 0.07 (n = 8) |

[a]Measurements were taken from bolting plants. Plants grow in 16 h light/8 h dark.
[b]Measurements were taken from bolting plants. Plants grow in 8 h light/16 h dark.
[c]Measurements were taken from plants 60 d after sowing. Plants grow in 16 h light/8 h dark.
[d]Measurements were taken from plant 14 d after sowing. Plants grow in 16 h light/8 h dark.

TABLE 3

Microarray Data for Selected Genes with Various Functions

| AGI Code | Fold Change | Gene Description and Putative Function | GO Category |
|---|---|---|---|
| | | Proteins related to cell cycle | |
| At2g23430 | 1.72 | ICK1 | Negative regulation of cell division and promoter of endoreduplication. |
| At1g77880 | 0.3 | Cyclin-like F box domain containing protein | |
| | | Proteins regulating flowering | |
| At1g26310 | 1.98 | Floral homeotic gene CAL | Positive regulation of flower development |
| At5g65080 | 0.31 | MAF5 | Negative regulation of flower development, vernalization response |
| | | Transcription factors | |
| At1g74080 | 4.26 | MYB122 | Encodes a putative transcription factor |
| At3g07650 | 2.39 | CONSTANS gene family | Negative regulation of long-day photoperiodism, flowering |
| At4g17980 | 2.32 | No apical meristem (NAM) family protein | Transcription factor activity |
| At3g20810 | 2.05 | jmjC domain-containing transcription factor | Transcription factor activity |
| At3g23250 | 2.03 | MYB15 | Transcription factor activity, response to kinds of hormone |
| At1g21910 | 1.92 | ERF/AP2 transcription factor | Transcription factor activity, TINY-like protein |
| At2g31220 | 1.86 | Basic helix-loop-helix (bHLH) family protein | Transcription factor activity |
| At2g19810 | 0.56 | Zinc finger (CCCH-type) family protein | Transcription factor activity |
| At5g57660 | 0.51 | B-box type zinc finger family protein | Transcription factor activity |
| At1g71030 | 0.42 | MYB family transcription factor | Transcription factor activity, response to kinds of hormone, mainly in leaves. |
| At4g16780 | 0.42 | Homeobox-leucine zipper protein 4 | Transcription factor activity, response to cytokinin stimulus |
| At3g04070 | 0.45 | No apical meristem (NAM) family protein | Transcription factor activity |
| | | Biosynthetic metabolism | |
| At5g38710 | 4.81 | Proline oxidase | Glutamate biosynthesis, proline catabolic process, located in MT |
| At4g21990 | 3.31 | APS REDUCTASE 3 | Sulfate assimilation, located in chloroplast |
| At3g12430 | 3.24 | 3'-5' exonuclease | Nucleic binding, 3'-5' exonuclease activity |
| At5g06290 | 2.53 | 2-cys peroxiredoxin | Located in chloroplast, antioxidant activity |
| At3g24420 | 2.48 | Hydrolase, alpha/beta fold family protein | Located in endomembrane system |
| At5g61440 | 2.04 | Thioredoxin family protein | Thiol-disulfide exchange intermediate activity, located in chloroplast |

TABLE 3-continued

Microarray Data for Selected Genes with Various Functions

| AGI Code | Fold Change | Gene Description and Putative Function | GO Category |
|---|---|---|---|
| At1g51760 | 1.96 | IAA-amino acid hydrolase 3 | IAA-Ala conjugate hydrolase activity |
| At1g76130 | 1.92 | Alpha-amylase | Carbohydrate metabolic process, located in extracellular region |
| At4g19170 | 0.54 | Putative nine-cis-epoxycarotenoid dioxygenase | Located in plastoglobule |
| At5g35970 | 0.48 | DNA helicase-like | DNA-binding protein, located in chloroplast |
| At1g73480 | 0.47 | Alpha/beta fold family hydrolase | Aromatic compound metabolism, located in chloroplast |
| At1g77760 | 0.47 | Nitrate reductase 1 (NR1) | |
| At3g49160 | 0.43 | Pyruvate kinase-like protein | Pyruvate kinase activity, involved in glycolysis |
| At1g77760 | 0.43 | Nitrate reductase | Response to light stimulus, nitric oxide biosynthetic process |
| At5g24470 | 0.42 | APRR5 | Circadian rhythm, photomorphogenesis |
| At5g11330 | 0.41 | Monooxygenase family protein | Electron transport, metabolic process, Located in endomembrane system |
| At1g32900 | 0.39 | Starch synthase | Transferase activity, transferring glycosyl groups, located in chloroplast |
| At5g48490 | 0.28 | Lipid transfer protein (LTP) family protein | Lipid binding and transport, located in endomembrane system |
| Polysaccharide metabolism | | | |
| At5g25980 | 4.53 | Glycosyl hydrolase family 1 | Hydrolase activity, hydrolyzing O-glycosyl compounds |
| At1g55850 | 3.57 | Cellulose synthase family protein | Polysaccharide biosynthetic process, cell wall biosynthetic process |
| At3g44990 | 2.52 | Xyloglucan: xyloglucosyl transferase | Hydrolase activity, acting on glycosyl bonds, located in chloroplast |
| At2g32290 | 2.3 | Putative 1,4-alpha-D-glucan maltohydrolase | Polysaccharide catabolic process |
| At3g21750 | 2.17 | UDP-glucosyl transferase family protein | Transferring glycosyl groups |
| Signal transduction | | | |
| At5g39670 | 3.03 | Calcium-binding EF hand family protein | |
| At1g14320 | 2.52 | Wilm's tumor suppressor protein-related | Involved in translation |
| At5g35735 | 2.04 | Auxin-responsive family protein | Dopamine beta-monooxygenase activity, located in membrane |
| At1g61370 | 2.1 | S-locus lectin protein kinase family protein | Protein amino acid phosphorylation, located in endomembrane system |
| At1g51760 | 1.96 | IAA amino acid hydrolase (IAR3) | Proteolysis, located in endomembrane system |
| At5g67030 | 0.55 | Zeaxanthin epoxidase | Abscisic acid biosynthetic process |
| At5g45830 | 0.52 | Tumor-related protein like | |
| At4g12980 | 0.51 | Auxin-responsive family protein, putative | Dopamine beta-monooxygenase activity, located in membrane |
| At4g28950 | 0.47 | ROP GTPase gene family protein | Protein transport, small GTPase mediated signal transduction |
| At5g45820 | 0.26 | CBL-interacting protein kinase 20 (CIPK20) | Kinase activity |
| Photosynthesis | | | |
| At3g17040 | 0.5 | Tetratricopeptide repeat (TPR)-containing protein | Chloroplast precursor |
| At3g59400 | 0.37 | GUN4 | Chlorophyll biosynthetic process, located in chloroplast |
| At1g44446 | 0.34 | Chlorophyll a oxygenase/chlorophyll b synthase | Chlorophyll biosynthetic process |

FIG. 12. Alignment of 27 UBP proteins.

Highly conserved amino acids are shaded in black while less conserved ones are shaded in gray. Numbers above the alignment indicate the amino acid position in the consensus.

Figure 13:
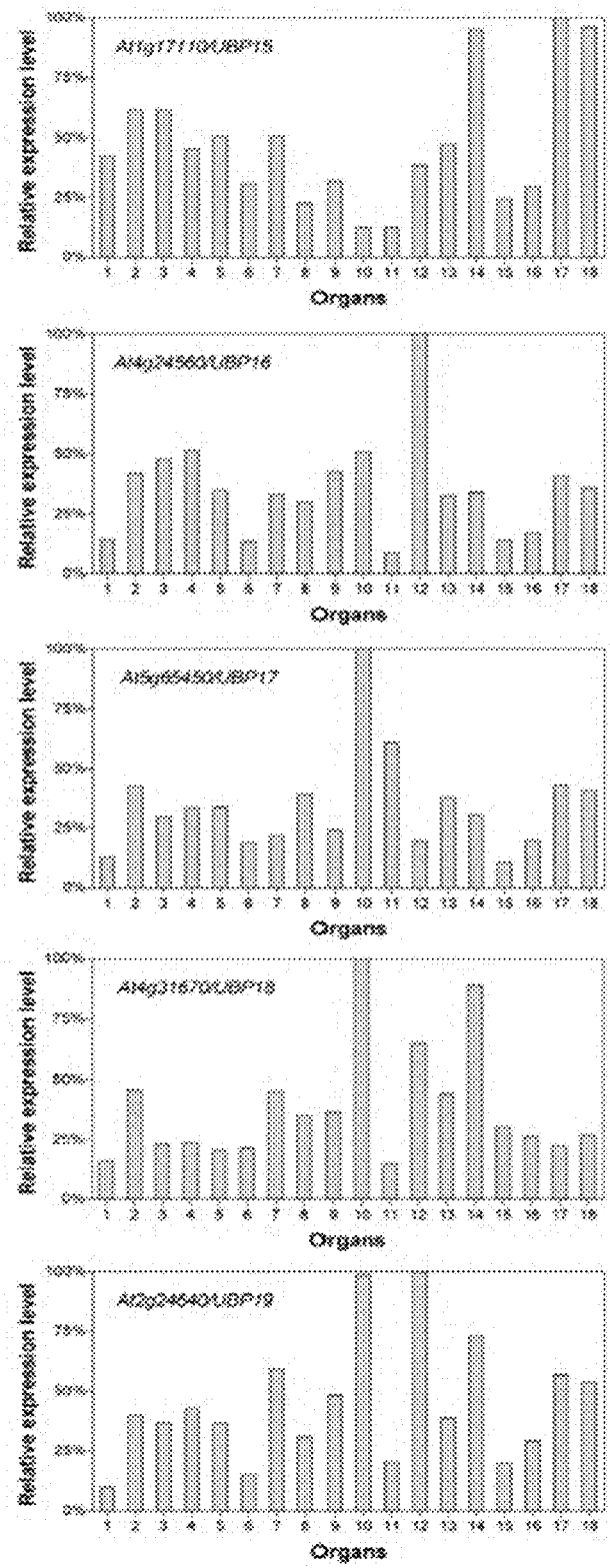

FIG. 13. Gene expression pattern of UBP15 subfamily.

Organs from 1 to 18 are cauline leaves, rosette leaves, pistil one day before pollination, pistil one day after pollination, silique 3 day after pollination, silique 8 day after pollination, stem, sepal, stamen, petal, seed, cultured cell, root dark, root white light, hypocotyl dark, hypocotyl white light, cotyledon dark and cotyledon white light.

Figure 14:
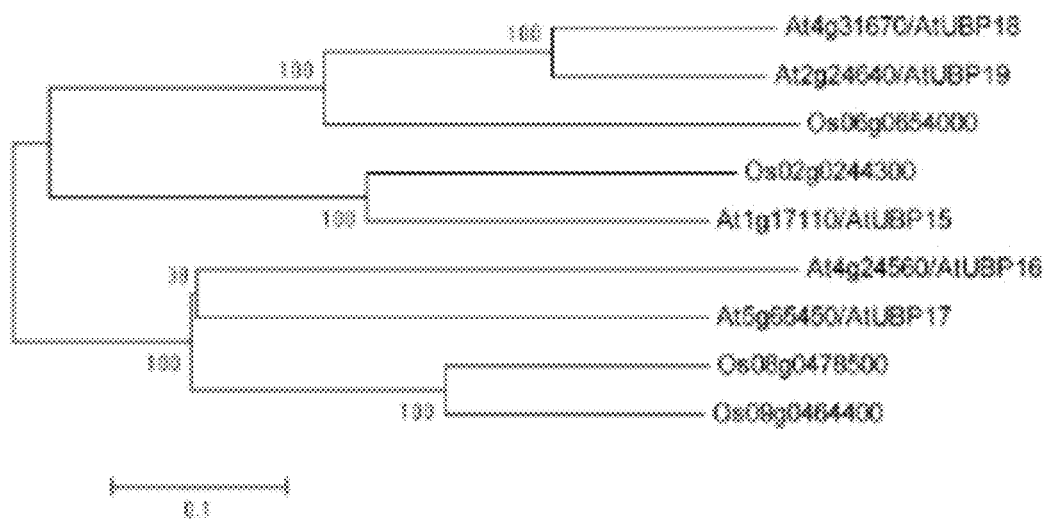

FIG. 14. Phylogenetic Analysis of AtUBP15 subfamily and its homologues in Rice.

The Phylogenetic tree of 9 UBPs in *Arabidopsis* or Rice. Bootstrap values are shown in percentages at nodes.

Figure 15:
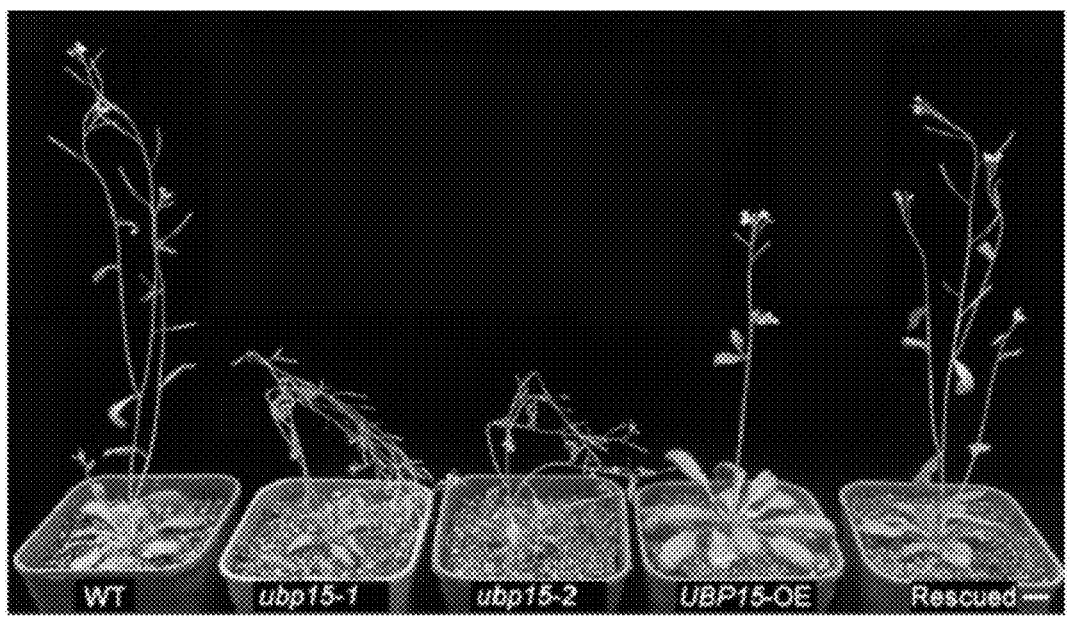

FIG. 15. Two month old lines of wild type, two ubp15 mutants and UBP15-overexpressing line.

Two-month-old wild type, ubp15-1, ubp15-2, UBP15-overexpressing line and rescued line. Mutants are weak, with early flowering time and more secondary stems while UBP15-overexpressing line showed opposite phenotype with late flower and strong apical dominance. Bar=1 cm.

Figure 16:
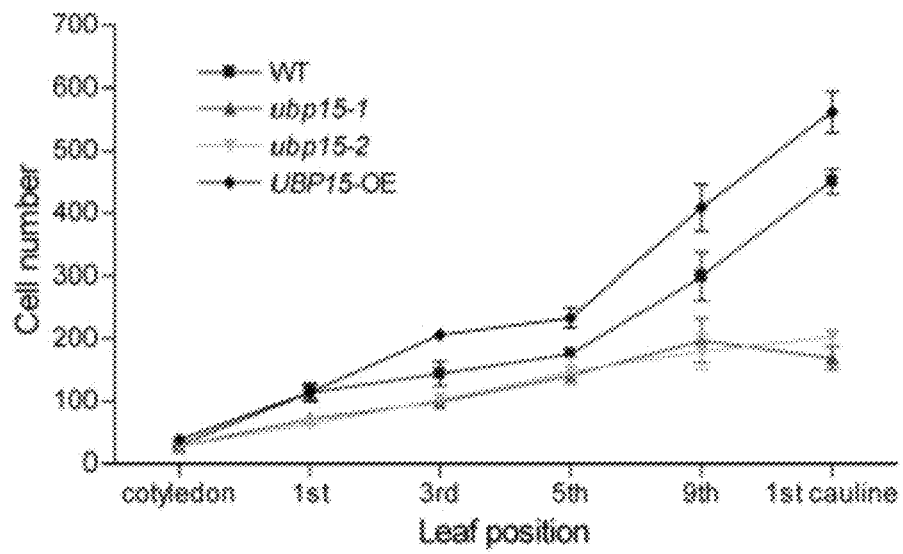

FIG. 16. Comparison of palisade cell number in transverse sections across the lamina of rosette leaf. Error bars represent standard deviation of three biological repeats.

Figure 17:
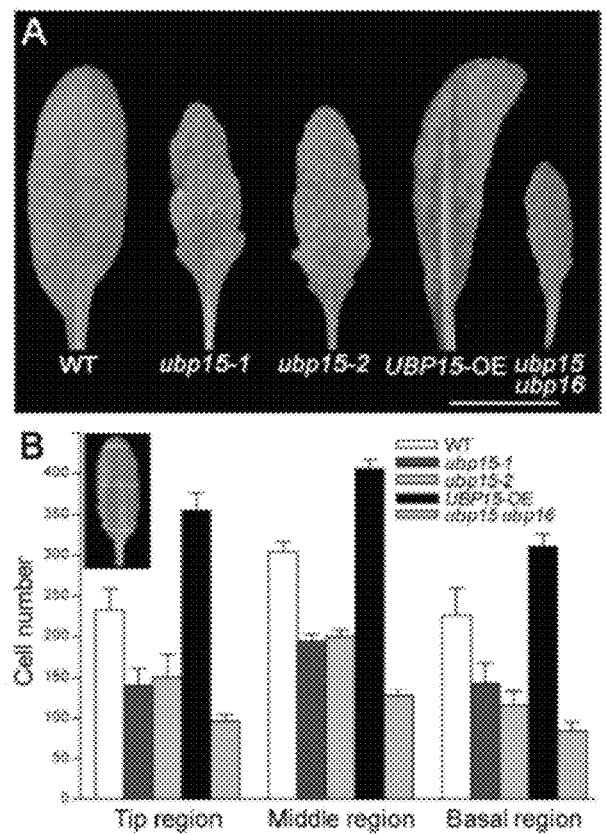

FIG. 17. Comparison of the ninth rosette leaf of wild type and mutants as well as transgenic lines.

(A) Mature ninth rosette leaf of wild type, ubp15-1, ubp15-2, UBP15-overexpressing line and ubp15 ubp16. Bar=1 cm.

(B) Comparison of adaxial epidermal cell numbers of transverse sections in three regions of the ninth rosette leaf.

SUPPLEMENTAL TABLES

SUPPLEMENTAL TABLE 1

Microarray data of 27 UBP genes expression in various organs.

| Gene code | gene name | Cauline leaf | Rosette leaf | Pistil one day after pollenation | Pistil one day before pollenation | Silique 3 day after pollenation | Silique 8 day after pollenation |
|---|---|---|---|---|---|---|---|
| At4g10590 | UBP10 | 253.2371134 | 538 | 318.9969539 | 178.5757576 | 209.7058824 | 69 |
| At4g10570 | UBP9 | 253.2371134 | 538 | 318.9969539 | 178.5757576 | 209.7058824 | 69 |
| At1g32850 | UBP11 | 14.17808219 | 19 | 10.58646617 | 12.07272727 | 38.05147059 | 14.80555556 |
| At2g40930 | UBP5 | 114.5257732 | 497.5804196 | 350.327381 | 404.625 | 337.3897059 | 70 |
| At5g22030 | UBP8 | 123.0618557 | 309.4912281 | 218.0594178 | 315.5220588 | 311 | 89.97222222 |
| At4g30890 | UBP24 | 248 | 584.2237762 | 655.5600733 | 568 | 736.5073529 | 168.5555556 |
| At4g39910 | UBP3 | 172.9726027 | 350.6993007 | 302.4974359 | 372.8897059 | 208.8602941 | 130.9722222 |
| At2g22310 | UBP4 | 38.41237113 | 66.24561404 | 63.11683054 | 48 | 28 | 22 |
| At5g06600 | UBP12 | 1141 | 1519.146853 | 1139.097744 | 599.6121212 | 1186.024096 | 247.1388889 |
| At3g49600 | UBP26 | 190 | 480.2807018 | 330.575188 | 343.5955882 | 313.1325301 | 219 |
| At1g51710 | UBP6 | 621 | 1231.754386 | 891.3714671 | 781.1764706 | 754.2647059 | 574 |
| At3g21280 | UBP7 | 71 | 292.9370629 | 145.1863505 | 160.5073529 | 136.1397059 | 107 |
| At2g32780 | UBP1 | 7 | 8.251748252 | 51.91666667 | 29.67878788 | 15.22058824 | 35 |
| At1g04860 | UBP2 | 211.2680412 | 381.2307692 | 367.7518797 | 222.8424242 | 306.9485294 | 149 |
| At4g39370 | UBP27 | 46.94845361 | 74.52631579 | 127.5 | 61.02941176 | 57 | 77.9 |
| At5g10790 | UBP22 | 379.1443299 | 600.3508772 | 273.7743975 | 238.0147059 | 289.1911765 | 91 |
| At5g46740 | UBP21 | 120.9278351 | 158.4335664 | 383.9718913 | 241.4545455 | 222.3897059 | 124.1388889 |
| At5g57990 | UBP23 | 491 | 1614.736842 | 1162.335897 | 1227.911765 | 1056 | 726.6111111 |
| At3g14400 | UBP25 | 407.5979381 | 719.3859649 | 611.4935415 | 376.2666667 | 496.0240964 | 315.4722222 |
| At4g24560 | UBP16 | 152.2268041 | 443.9440559 | 509.277381 | 546.8235294 | 367.1686747 | 142.3611111 |
| At5g65450 | UBP17 | 59.04123711 | 193.0909091 | 134.8794872 | 150.9090909 | 152.2058824 | 85 |
| At1g17110 | UBP15 | 711.3402062 | 1031.982456 | 1031.665293 | 758.0666667 | 845 | 514.7777778 |
| At4g31670 | UBP18 | 142 | 404.3356643 | 203.3615577 | 209.3308824 | 181.8014706 | 188 |
| At2g24640 | UBP19 | 56 | 222 | 205.9252747 | 238.0147059 | 203 | 84.27777778 |

| Gene code | gene name | Stem | Sepal | Stamen | Petal | Seed | Cultured cell |
|---|---|---|---|---|---|---|---|
| At4g10590 | UBP10 | 266 | 504.8139535 | 661.641791 | 290 | 95.75543478 | 963.8555417 |
| At4g10570 | UBP9 | 266 | 504.8139535 | 661.641791 | 290 | 95.75543478 | 963.8555417 |
| At1g32850 | UBP11 | 52 | 91.84883721 | 64.74129353 | 134 | -3.02173913 | 34.26132223 |
| At2g40930 | UBP5 | 315.9270073 | 246.3023256 | 270 | 798 | 67.02173913 | 1217.020979 |
| At5g22030 | UBP8 | 444 | 29.51162791 | 451.2704918 | 886.7755102 | 116.8865489 | 417.7322314 |
| At4g30890 | UBP24 | 646.8076923 | 562.5348837 | 707 | 1767.030612 | 191.9293478 | 1559.865613 |
| At4g39910 | UBP3 | 524.2627737 | 458.3953488 | 750.5721393 | 1617 | 68.875 | 1084.045697 |
| At2g22310 | UBP4 | 143.0192308 | 90.53488372 | 101 | 160 | -10.30366848 | 65.2861244 |
| At5g06600 | UBP12 | 1903.386861 | 204.5813953 | 1246 | 2006 | 401.0923913 | 2426.601399 |
| At3g49600 | UBP26 | 551.4615385 | 195.755814 | 215.6721311 | 465.122449 | 213.3043478 | 560.5384615 |
| At1g51710 | UBP6 | 1669.846154 | 406.5465116 | 901 | 1469 | 394.9476902 | 6227.830303 |
| At3g21280 | UBP7 | 263.1094891 | 138.7674419 | 125 | 294.505102 | 71.46195652 | 274.6139657 |
| At2g32780 | UBP1 | 21 | 67.65116279 | 39.12935323 | 118 | 30.04415761 | 28.70312881 |
| At1g04860 | UBP2 | 324 | 590.1046512 | 639.5870647 | 256.4693878 | 261.9293478 | 819.7538462 |
| At4g39370 | UBP27 | 43 | 114.4302326 | 122.3681592 | 116 | 248.3913043 | 64.60289855 |
| At5g10790 | UBP22 | 289 | 409.6046512 | 407 | 834 | 139.798913 | 371.109589 |
| At5g46740 | UBP21 | 243.5192308 | 135.1860465 | 118.0995025 | 146.7091837 | 72.24456522 | 93.65178979 |
| At5g57990 | UBP23 | 2079.445255 | 431.5581395 | 346 | 929.1581633 | 534.28125 | 3446.150487 |
| At3g14400 | UBP25 | 697.0576923 | 277.3837209 | 758 | 214.0867347 | 207.9673913 | 1548.92372 |
| At4g24560 | UBP16 | 351.75 | 318.744186 | 454 | 542 | 93.54076087 | 1062.276923 |
| At5g65450 | UBP17 | 98.78832117 | 178.4767442 | 108.8507463 | 455 | 276.5108696 | 88.66155158 |
| At1g17110 | UBP15 | 851.6730769 | 379.5930233 | 534.2935323 | 207.5663265 | 210.125 | 641.6596737 |
| At4g31670 | UBP18 | 398.0875912 | 309.0348837 | 322 | 880 | 130.9728261 | 574.4164103 |
| At2g24640 | UBP19 | 331 | 172.5348837 | 269.6368159 | 547.7142857 | 112.7391304 | 556.7737557 |

| Gene code | gene name | Root dark | Root white light | Hypocotyl dark | Hypocotyl white light | Cotyledon dark | Cotyledon white light |
|---|---|---|---|---|---|---|---|
| At4g10590 | UBP10 | 424.8228346 | 438.28125 | 173.40625 | 131.5095238 | 393.2027027 | 370.7176157 |
| At4g10570 | UBP9 | 424.8228346 | 438.28125 | 173.40625 | 131.5095238 | 393.2027027 | 370.7176157 |
| At1g32850 | UBP11 | 51.77382175 | 85.8125 | 17.91666667 | 36.67142857 | 44.11560694 | 39.55357143 |
| At2g40930 | UBP5 | 325.4406923 | 344.65625 | 97.63541667 | 123.1904762 | 353.9322034 | 313.0154762 |
| At5g22030 | UBP8 | 279.9637111 | 408.21875 | 129.2604167 | 143.8857143 | 419.0860927 | 422.2265816 |
| At4g30890 | UBP24 | 414.0984252 | 531.8125 | 188.71875 | 313.3857143 | 467.1186441 | 429.1309524 |
| At4g39910 | UBP3 | 462.4347826 | 666.46875 | 311.2708333 | 294.1071429 | 540.1788079 | 598.1203056 |
| At2g22310 | UBP4 | 128.5507246 | 111.09375 | 20.54166667 | 46.95714286 | 62.12582781 | 101.2047619 |
| At5g06600 | UBP12 | 1517.831793 | 2085.65625 | 416.6458333 | 406.9738095 | 1479 | 1652.075033 |
| At3g49600 | UBP26 | 425.0354331 | 616.53125 | 202.71875 | 183.6095238 | 397.9595376 | 378.8214286 |

SUPPLEMENTAL TABLE 1-continued

Microarray data of 27 UBP genes expression in various organs.

| | | | | | | | |
|---|---|---|---|---|---|---|---|
| At1g51710 | UBP6 | 1981.102362 | 3926.3125 | 569.9583333 | 668.4071429 | 889 | 1159.790698 |
| At3g21280 | UBP7 | 105.6540784 | 209.125 | 42.21875 | 91.56428571 | 131.4277457 | 177.4428571 |
| At2g32780 | UBP1 | 62.84468789 | 34.8125 | 20.13541667 | 28.72619048 | 26.65317919 | 26.14784053 |
| At1g04860 | UBP2 | 502.2960018 | 594.59375 | 183.71875 | 200.4095238 | 438.0397351 | 410.7517483 |
| At4g39370 | UBP27 | 92.94123017 | 106.28125 | 28.96875 | 47.19047619 | 109 | 73.32009044 |
| At5g10790 | UBP22 | 410.9566929 | 420.59375 | 106.6354167 | 127.0714286 | 470.7118644 | 562.8515873 |
| At5g46740 | UBP21 | 146.8093119 | 215.71875 | 63.33333333 | 84.58809524 | 145.2138728 | 122.7753913 |
| At5g57990 | UBP23 | 832.6963369 | 1380.65625 | 540.7708333 | 948.9547619 | 817.1125828 | 1300.761526 |
| At3g14400 | UBP25 | 730.0184868 | 1210.8125 | 323.5520833 | 322.2595238 | 837.2774566 | 704.6364653 |
| At4g24560 | UBP16 | 345.6990291 | 359.90625 | 148.8854167 | 179.4928571 | 431.9653179 | 379.5714286 |
| At5g65450 | UBP17 | 171.0468619 | 137.28125 | 48.69791667 | 90.40714286 | 195.8543046 | 184.5927003 |
| At1g17110 | UBP15 | 787.4924113 | 1596.84375 | 409.7291667 | 498.3833333 | 1680.243243 | 1613.125 |
| At4g31670 | UBP18 | 388.7701246 | 783.5625 | 268.8229167 | 230.0404762 | 196.7288136 | 236.5464286 |
| At2g24640 | UBP19 | 216.5870136 | 405.65625 | 110.78125 | 162.3714286 | 315.8513514 | 298.2021164 |

SUPPLEMENTAL TABLE 2

Primers designed to identify the genotype of T-DNA insertion lines.

| T-DNA insertion lines | Forward (FP) and reverse (RP) primers |
|---|---|
| SALK_086190 | FP: 5'-TGCGTGAAGGAATTCAGATCCA-3'<br>RP: 5'-TTCAGCGTTATATCTAAAAGAATTG-3' |
| SALK_064103 | FP: 5'-GCTTCGCTTACGTTATACCACGC-3'<br>RP: 5'-CTGAAGCCTCGGGAGTTGGTT-3' |
| SALK_059858 | FP: 5'-CGGGTCTTCTCCGCTACACCT-3'<br>RP: 5'-CCTTTGGTGGTTGCAGATTCG-3' |
| SALK_112950 | FP: 5'-TGTGCACAACACCATTTGCCT-3'<br>RP: 5'-TCTCTCCCTTGTGCAGGCTCTT-3' |
| SALK_043210 | FP: 5'-TGTGATTGGGTTTGGTTTGGG-3'<br>RP: 5'-TCTCTTGACCTGCTTGGCTGA-3' |
| SALK_088398 | FP: 5'-GTGCTGCTACTGCTGCTTCCC-3'<br>RP: 5'-CAACAGCAGCTAAATCAAAAGG-3' |
| SALK_108832 | FP: 5'-AAAATGTGGTCCAAGTGGATGG-3'<br>RP: 5'-TGAGAAGGAAACTCACATGACTGGA-3' |
| SALK_014223 | FP: 5'-CCAATTACAGTGCGTTCCAAGC-3'<br>RP: 5'-TGGCCAACTTTGTTAGATGTTTCA-3' |
| SALK_034744 | FP: 5'-GACCAAGGGGATTCCAAATGC-3'<br>RP: 5'-TTTCTGGTTGCAGGGCCAATA-3' |
| SALK_149329 | FP: 5'-AGCGGGAAATCCACATATGCC-3'<br>RP: 5'-CCTTTCCAATGGTTTTCAGGC-3' |
| SALK_088692 | FP: 5'-CGTAAGCAGCCGAGGTCTTGA-3'<br>RP: 5'-TCCAAGCGGTTGAATGTGCTT-3' |
| SALK_141485 | FP: 5'-TGCAATGATGCTAATTGGATCAAGA-3'<br>RP: 5'-TTTTATTATGCTTCTGTTCCTTTTT-3' |
| SALK_093503 | FP: 5'-AGCATCAGGAAGGTGGCCATT-3'<br>RP: 5'-TCGGTTACCATTTCCTTCCATTG-3' |
| SALK_043515 | FP: 5'-CACTAGGAAACCAGTGCCTTCG-3'<br>RP: 5'-ACACTTTGGGCCCCTGTCACT-3' |
| SALK_128312 | FP: 5'-CCCTCCACAACAGTTCCCTTG-3'<br>RP: 5'-TTGGAATGGAGTCAAGTTACCGC-3' |
| SALK_024054 | FP: 5'-CGCACTATGAACCCCAACACC-3'<br>RP: 5'-GAAAGGTTGGATGCTTGTTTTG-3' |
| SALK_130784 | FP: 5'-GCTTTTGTTGGAACAGATGTCAA-3'<br>RP: 5'-TCCTCATGTAGGAAGAGGTAGCCA-3' |
| SALK_132368 | FP: 5'-CCAAGCTTCTCAGCCACCCTT-3'<br>RP: 5'-TGTTGGCAGGCTAATGGTGAAA-3' |
| SALK_050151 | FP: 5'-GCCGAAAAGGAGTATCGTTCCA-3'<br>RP: 5'-CAAGGTAGATGCCATTGCCCA-3' |
| SALK_012863 | FP: 5'-GGAGGCAAATTAAAAGACAGCGA-3'<br>RP: 5'-ATGCACCAATCTCCCACCAGA-3' |
| SALK_018601 | FP: 5'-ATGGTGAACCGGAGCTTTTCC-3'<br>RP: 5'-CCAGGTTAAATGCCTGAGGTGTG-3' |
| SALK_015611 | FP: 5'-TCACACCTCAGGCATTTAACC-3'<br>RP: 5'-TTGTGGAAACAGGTATTGTCTC-3' |
| SALK_023552 | FP: 5'-TACGCAAATGAAAGACCATGA-3'<br>RP: 5'-TGGGTTTGAGAAGCTGGTCGT-3' |
| SALK_087726 | FP: 5'-GGTGAATCATATGGGTTTTGCTTT-3'<br>RP: 5'-TTTGAACCAATCTCCATCAAGGG-3' |
| SALK_113300 | FP: 5'-TGCTTCTTTATGCAAGGTGAATGA-3'<br>RP: 5'-CATACTCCCTCCGTTTTCACAA-3' |
| SALK_009641 | FP: 5'-AAAGGCAAGGGGAGGAGAATC-3'<br>RP: 5'-GAAGCTCGGGAAAATGGATGG-3' |
| SALK_101685 | FP: 5'-TGAGCATCCTCCTGTCTTCCA-3'<br>RP: 5'-TTTTTCACATTGTTACCCAAAAA-3' |
| SALK_126252 | FP: 5'-TGAGCATCCTCCTGTCTTCCA-3'<br>RP: 5'-TTTTTCACATTGTTACCCAAAAA-3' |
| SALK_084566 | FP: 5'-TCGGCGATGGTCTCTATCGAA-3'<br>RP: 5'-GGTTGATAACAATTTACCAAAGTCG-3' |
| SALK_117787 | FP: 5'-TGCGTGAAGGAATTCAGATCCA-3'<br>RP: 5'-TTCAGCGTTATATCTAAAAGAATTG-3' |
| SALK_079015 | FP: 5'-TTTAAGTTTTCTAGACACTATTTTT-3'<br>RP: 5'-GGGAGAAAGCCGAGAGTCTGTG-3' |
| SALK_121772 | FP: 5'-TGTAACCTCGATCCCTCAGCATC-3'<br>RP: 5'-TTGCCAAATGGGATGAGGAAA-3' |
| SALK_001531 | FP: 5'-CCTTCCCAGTAACCGAGGCTCT-3'<br>RP: 5'-CCTTTTGTGCAGCTCCTCCAG-3' |
| SALK_088458 | FP: 5'-CGGAGAAAACCAACCAAGCAA-3'<br>RP: 5'-ACAGCTATTGCCGGTGTAGCG-3' |

SUPPLEMENTAL TABLE 2-continued

Primers designed to identify the genotype of T-DNA insertion lines.

| T-DNA insertion lines | Forward (FP) and reverse (RP) primers |
|---|---|
| SALK_111336 | FP: 5'-TGAACGTTGCAAATTCATTCGAT-3'<br>RP: 5'-CCGATGCGCCTAACAAGATTTC-3' |
| SALK_024392 | FP: 5'-TTGTGGAAACACCCCACAAAA-3'<br>RP: 5'-TTGGCTTCGTCTATGGGCTGA-3' |
| SALK_067020 | FP: 5'-TTCTCAAAACATTCGCAGTGGC-3'<br>RP: 5'-AATAGACCGTGCTGTTGGGCA-3' |
| SALK_027968 | FP: 5'-TTTCAAATCAAATAAGCTAAAAAG-3'<br>RP: 5'-TGGCTTGTCAAATTGAAATTTTG-3' |

SUPPLEMENTAL TABLE 3

Transcriptome analysis of ubp15-1.

| Gene Code | ID | M | W | M/W |
|---|---|---|---|---|
| At1g17110 | AF302665 | 110 | 1959 | 0.06 |
| At1g28375 | AC010155 | 21 | 221 | 0.09 |
| At4g01525 | AC069551 | 25 | 236 | 0.11 |
| At1g14550 | AC010657 | 32 | 204 | 0.16 |
| At3g59970 | AF181966 | 39 | 239 | 0.16 |
| At5g05820.a | F15569 | 45 | 270 | 0.17 |
| At3g29000 | AB025615 | 37 | 209 | 0.18 |
| At4g12900 | AL079349 | 47 | 247 | 0.19 |
| At1g38450 | AC006918 | 50 | 233 | 0.22 |
| At1g41720 | AC006918 | 50 | 233 | 0.22 |
| At2g06330 | AC006918 | 50 | 233 | 0.22 |
| At1g42360 | AC006918 | 50 | 233 | 0.22 |
| At1g42370 | AC006918 | 50 | 233 | 0.22 |
| At1g37160 | AC006918 | 50 | 233 | 0.22 |
| At5g39890 | AB010077 | 57 | 256 | 0.22 |
| At1g63530 | AC008047 | 56 | 253 | 0.22 |
| At1g71150 | AC016972 | 55 | 244 | 0.22 |
| At1g32060 | AC074309 | 517 | 2159 | 0.24 |
| At5g66990 | AB026640 | 73 | 302 | 0.24 |
| At1g35690 | AC007887 | 81 | 322 | 0.25 |
| At5g41315 | AB006707 | 60 | 230 | 0.26 |
| At3g02120 | AC011664 | 76 | 290 | 0.26 |
| At4g02240 | AL096882 | 64 | 244 | 0.26 |
| At5g65330 | AL096882 | 64 | 244 | 0.26 |
| At5g45820 | AB016870 | 495 | 1874 | 0.26 |
| At2g06410 | AC006918 | 69 | 244 | 0.28 |
| At5g48490 | AB020745 | 2248 | 7953 | 0.28 |
| At4g28440 | AV557403 | 62 | 217 | 0.29 |
| At1g62710 | AF367254 | 85 | 281 | 0.3 |
| At1g77880 | AC009243 | 83 | 276 | 0.3 |
| At1g48980 | AC016041 | 61 | 203 | 0.3 |
| At3g60500 | AL138646 | 62 | 206 | 0.3 |
| At3g01650 | AC009325 | 71 | 241 | 0.3 |
| At5g01600 | AF326869 | 5374 | 17383 | 0.31 |
| At5g16580 | AB008270 | 72 | 231 | 0.31 |
| At1g14500 | AC012188 | 71 | 228 | 0.31 |
| At5g65080 | AF214485 | 114 | 363 | 0.31 |
| At4g07938 | AC006423 | 63 | 200 | 0.31 |
| At5g02720 | AL162973 | 66 | 212 | 0.31 |
| At5g58830 | AB016885 | 120 | 386 | 0.31 |
| At1g43830 | AC006423 | 63 | 200 | 0.31 |
| At2g38690 | AC005499 | 90 | 287 | 0.31 |
| At2g02690 | AC002521 | 64 | 201 | 0.32 |
| At1g51960 | AC006216 | 160 | 502 | 0.32 |
| At1g48660 | AC073555 | 116 | 364 | 0.32 |
| At5g19840 | AB024038 | 71 | 218 | 0.33 |
| At1g65920 | AC009513 | 123 | 376 | 0.33 |
| At4g24080 | AC002343 | 94 | 282 | 0.33 |
| At3g55240 | AL132954 | 508 | 1545 | 0.33 |
| At1g44446 | AB021316 | 3029 | 8868 | 0.34 |
| At4g39090 | AL035679 | 2180 | 6320 | 0.34 |
| At4g38590 | AL035540 | 74 | 220 | 0.34 |
| At4g12440 | AL049730 | 80 | 231 | 0.34 |
| At4g20450 | AL080253 | 104 | 308 | 0.34 |
| At2g29670 | AF375460 | 6906 | 19504 | 0.35 |
| At4g31360 | AL021633 | 190 | 547 | 0.35 |
| At1g53930 | AC006577 | 112 | 318 | 0.35 |
| At3g63160 | BE039458 | 1963 | 5579 | 0.35 |
| At2g34940 | AC004238 | 113 | 320 | 0.35 |
| At3g26210 | AB024038 | 515 | 1421 | 0.36 |
| At5g44510 | AB017065 | 73 | 202 | 0.36 |
| At1g32810 | AC006424 | 153 | 421 | 0.36 |
| At4g13490.a | AA404812 | 4980 | 13728 | 0.36 |
| At3g58650 | AL137082 | 87 | 244 | 0.36 |
| At5g62080 | AB016880 | 81 | 217 | 0.37 |
| At4g09930 | AL049481 | 110 | 297 | 0.37 |
| At1g47730 | AC007519 | 110 | 296 | 0.37 |
| At2g22240 | U30250 | 235 | 626 | 0.37 |
| At3g59400 | AL356014 | 6379 | 17232 | 0.37 |
| At3g01080 | AC008261 | 102 | 276 | 0.37 |
| At2g46590 | AC006418 | 145 | 386 | 0.38 |
| At4g20970 | AL080282 | 95 | 248 | 0.39 |
| At3g27500 | AB025626 | 78 | 200 | 0.39 |
| At1g17740 | AB010407 | 105 | 267 | 0.39 |
| At4g26460 | AL022223 | 100 | 256 | 0.39 |
| At5g54190 | U29699 | 880 | 2255 | 0.39 |
| At3g56790 | AL390921 | 111 | 287 | 0.39 |
| At3g46760 | AL096859 | 80 | 207 | 0.39 |
| At1g32900 | AC006424 | 158 | 406 | 0.39 |
| At5g49140 | AB023028 | 107 | 268 | 0.4 |
| At4g36195 | AL022141 | 97 | 242 | 0.4 |
| At4g35960 | AL022373 | 96 | 242 | 0.4 |
| At3g30130 | AY046045 | 221 | 555 | 0.4 |
| At1g74980 | AY045856 | 476 | 1195 | 0.4 |
| At1g77410 | AC078898 | 85 | 214 | 0.4 |
| At1g49800 | AC079674 | 112 | 280 | 0.4 |
| At1g28470 | AV567286 | 152 | 381 | 0.4 |
| At1g56350 | AY046045 | 221 | 555 | 0.4 |
| At2g18150 | AC007212 | 152 | 383 | 0.4 |
| At1g05700 | AC007153 | 108 | 273 | 0.4 |
| At4g29230 | AL161574 | 126 | 313 | 0.4 |
| At3g52040 | AL049711 | 94 | 236 | 0.4 |
| At1g63570 | AC008047 | 151 | 378 | 0.4 |
| At5g11330 | AL360314 | 1143 | 2805 | 0.41 |
| At3g13760 | AP001307 | 151 | 368 | 0.41 |
| At1g27220 | AC004557 | 85 | 207 | 0.41 |
| At1g04710 | AC002376 | 144 | 356 | 0.41 |
| At5g51670 | AB025607 | 198 | 477 | 0.41 |
| At1g63840 | H77052 | 242 | 585 | 0.41 |
| At2g31670 | AV540982 | 214 | 519 | 0.41 |
| At4g20380 | U87834 | 101 | 247 | 0.41 |
| At3g18780 | U41998 | 687 | 1650 | 0.42 |
| At3g03590 | AC009327 | 190 | 450 | 0.42 |
| At3g27160 | AY039901 | 6880 | 16566 | 0.42 |
| At4g16780 | X68146 | 1165 | 2800 | 0.42 |
| At1g56080 | AC009894 | 115 | 272 | 0.42 |
| At3g25080 | AB026647 | 163 | 389 | 0.42 |
| At3g10440 | AC011560 | 231 | 555 | 0.42 |
| At2g11010 | AB028615 | 133 | 315 | 0.42 |
| At2g46570 | AC006418 | 84 | 200 | 0.42 |
| At1g71030 | Z68157 | 3598 | 8496 | 0.42 |
| At1g41630 | AC006250 | 238 | 572 | 0.42 |
| At1g41600 | AC006250 | 238 | 572 | 0.42 |
| At1g41660 | AC006250 | 238 | 572 | 0.42 |
| At4g23700 | AL035394 | 142 | 336 | 0.42 |
| At4g10220 | AF096373 | 89 | 211 | 0.42 |
| At5g37230 | AB017069 | 104 | 245 | 0.42 |
| At5g37250 | AB017069 | 104 | 245 | 0.42 |
| At5g37270 | AB017069 | 104 | 245 | 0.42 |
| At5g03350 | AL162751 | 2212 | 5268 | 0.42 |
| At5g24470 | AF027408 | 407 | 972 | 0.42 |
| At1g79910 | AC011717 | 104 | 247 | 0.42 |
| At1g62690 | AC007190 | 137 | 317 | 0.43 |
| At5g06980 | AY042849 | 657 | 1544 | 0.43 |
| At1g75100 | AC013258 | 117 | 271 | 0.43 |
| At1g30080 | AC022455 | 108 | 251 | 0.43 |
| At2g35310 | AC004667 | 171 | 397 | 0.43 |
| At1g44542 | AC084807 | 133 | 312 | 0.43 |
| At1g50720 | AC079027 | 120 | 276 | 0.43 |

SUPPLEMENTAL TABLE 3-continued

Transcriptome analysis of ubp15-1.

| Gene Code | ID | M | W | M/W |
|---|---|---|---|---|
| At2g47150 | AC004411 | 103 | 238 | 0.43 |
| At2g46140 | AC005397 | 112 | 259 | 0.43 |
| At3g51150 | AL132980 | 93 | 218 | 0.43 |
| At3g42230 | AL138645 | 168 | 390 | 0.43 |
| At3g49160 | AL132956 | 485 | 1128 | 0.43 |
| At4g36470 | AL161589 | 146 | 340 | 0.43 |
| At1g36960 | AC051631 | 86 | 202 | 0.43 |
| At1g66100 | AF380652 | 6908 | 15905 | 0.43 |
| At2g47860 | AC005309 | 117 | 275 | 0.43 |
| At3g60570 | AL138646 | 116 | 260 | 0.44 |
| At1g08630 | AC003981 | 93 | 213 | 0.44 |
| At3g04360 | AC016829 | 89 | 201 | 0.44 |
| At5g26700 | AF058914 | 111 | 255 | 0.44 |
| At1g04570 | AC002376 | 117 | 263 | 0.44 |
| At2g19070 | AC002392 | 92 | 206 | 0.44 |
| At2g04440 | AC006951 | 113 | 256 | 0.44 |
| At2g41300 | AC005662 | 107 | 245 | 0.44 |
| At4g23970 | AL078468 | 114 | 254 | 0.45 |
| At1g43880 | AC006423 | 147 | 331 | 0.45 |
| At1g27490 | AC004557 | 116 | 260 | 0.45 |
| At1g65300 | AC004512 | 106 | 236 | 0.45 |
| At3g04070 | AC011698 | 152 | 335 | 0.45 |
| At1g38196 | AC006423 | 147 | 331 | 0.45 |
| At3g58350 | AL137081 | 180 | 401 | 0.45 |
| At1g80640 | AC018849 | 96 | 214 | 0.45 |
| At3g45390 | AL132953 | 115 | 254 | 0.45 |
| At1g14390 | AC012188 | 188 | 407 | 0.46 |
| At1g37130 | AF367272 | 4767 | 10361 | 0.46 |
| At5g51760 | AB010074 | 132 | 289 | 0.46 |
| At2g11760 | AC074109 | 217 | 468 | 0.46 |
| At2g12010 | AC074109 | 217 | 468 | 0.46 |
| At2g34980 | AC004238 | 100 | 215 | 0.46 |
| At5g39330 | AB009054 | 171 | 370 | 0.46 |
| At4g12210 | AL080318 | 103 | 224 | 0.46 |
| At4g12220 | AL080318 | 103 | 224 | 0.46 |
| At3g45650 | AL138657 | 239 | 519 | 0.46 |
| At5g62130 | AB016880 | 343 | 745 | 0.46 |
| At3g59060 | AL163527 | 2960 | 6497 | 0.46 |
| At1g38340 | AC074109 | 217 | 468 | 0.46 |
| At5g27700 | AV534288 | 124 | 271 | 0.46 |
| At1g38149 | AC074109 | 217 | 468 | 0.46 |
| At4g07733 | AC074109 | 217 | 468 | 0.46 |
| At3g16320 | AC001645 | 119 | 260 | 0.46 |
| At1g09150 | AC003114 | 104 | 227 | 0.46 |
| At1g20030 | AC022472 | 330 | 699 | 0.47 |
| At1g19010 | AF360209 | 217 | 458 | 0.47 |
| At2g36050 | AY044326 | 179 | 381 | 0.47 |
| At3g48800 | AL132963 | 186 | 397 | 0.47 |
| At4g00320 | AL161471 | 202 | 429 | 0.47 |
| At3g19050 | AP000735 | 149 | 315 | 0.47 |
| At5g46330 | AB010698 | 101 | 216 | 0.47 |
| At1g73480 | AY045929 | 1324 | 2806 | 0.47 |
| At1g77760 | AC012193 | 1190 | 2545 | 0.47 |
| At5g08480 | AB006697 | 120 | 255 | 0.47 |
| At3g51830 | U72504 | 886 | 1904 | 0.47 |
| At4g28950 | AF079484 | 112 | 237 | 0.47 |
| At4g18250 | AL021713 | 116 | 249 | 0.47 |
| At3g19700 | AP000417 | 186 | 400 | 0.47 |
| At3g48940 | AL132954 | 98 | 207 | 0.47 |
| At5g42250 | AB023032 | 935 | 1961 | 0.48 |
| At5g35970 | AB026643 | 2449 | 5056 | 0.48 |
| At1g06210 | AC025290 | 265 | 546 | 0.48 |
| At4g17460 | U09332 | 2470 | 5158 | 0.48 |
| At1g44860 | AC007264 | 125 | 259 | 0.48 |
| At2g10370 | AC007264 | 125 | 259 | 0.48 |
| At1g43740 | AC009526 | 126 | 262 | 0.48 |
| At1g43750 | AC009526 | 126 | 262 | 0.48 |
| At5g41040 | AY034954 | 221 | 456 | 0.48 |
| At5g04950 | AB005245 | 161 | 338 | 0.48 |
| At4g35820 | AL031986 | 162 | 338 | 0.48 |
| At5g02810 | AY039943 | 2587 | 5372 | 0.48 |
| At1g42400 | AC007264 | 125 | 259 | 0.48 |
| At2g31900 | AC006533 | 127 | 261 | 0.48 |
| At3g02380 | AF370149 | 221 | 459 | 0.48 |
| At4g27310 | AL030978 | 621 | 1281 | 0.49 |
| At1g76310 | AC012394 | 245 | 504 | 0.49 |
| At4g23520 | AL031326 | 121 | 245 | 0.49 |
| At3g50900 | AL049862 | 116 | 238 | 0.49 |
| At3g15353 | AF013959 | 11215 | 22738 | 0.49 |
| At1g12490 | AC025416 | 138 | 282 | 0.49 |
| At4g17000 | AL161545 | 195 | 396 | 0.49 |
| At2g15730 | AC006248 | 139 | 283 | 0.49 |
| At5g16190 | AL391148 | 141 | 287 | 0.49 |
| At3g59580 | AL138659 | 145 | 298 | 0.49 |
| At3g61190 | AL137898 | 119 | 243 | 0.49 |
| At5g53040 | AB018116 | 108 | 221 | 0.49 |
| At5g64170 | AB008266 | 736 | 1512 | 0.49 |
| At1g13650 | AC027656 | 1432 | 2937 | 0.49 |
| At5g10660 | AL392144 | 125 | 255 | 0.49 |
| At1g52300 | AF370216 | 3677 | 7323 | 0.5 |
| At4g29650 | AL079344 | 247 | 497 | 0.5 |
| At1g31300 | AI995950 | 108 | 214 | 0.5 |
| At4g29960 | AL050352 | 120 | 238 | 0.5 |
| At1g63420 | AF372939 | 221 | 441 | 0.5 |
| At1g61220 | AV565744 | 174 | 352 | 0.5 |
| At3g26610 | X98130 | 167 | 337 | 0.5 |
| At4g38970 | AV440437 | 123 | 249 | 0.5 |
| At5g42160 | AB017067 | 129 | 257 | 0.5 |
| At3g60380 | AL138646 | 115 | 230 | 0.5 |
| At4g36050 | AL022373 | 127 | 251 | 0.5 |
| At5g65380 | AB011479 | 545 | 1080 | 0.5 |
| At5g03090 | AL163002 | 472 | 950 | 0.5 |
| At1g80310 | AC018848 | 740 | 1489 | 0.5 |
| At3g17040 | AB026636 | 1749 | 3490 | 0.5 |
| At3g44530 | AL353818 | 170 | 339 | 0.5 |
| At1g17990 | AF344314 | 1752 | 3437 | 0.51 |
| At5g64840 | AB019236 | 3117 | 6109 | 0.51 |
| At1g64740 | M21414 | 1506 | 2968 | 0.51 |
| At2g43040 | AC006224 | 188 | 371 | 0.51 |
| At5g57660 | AB018118 | 6011 | 11797 | 0.51 |
| At3g20540 | AP000410 | 219 | 432 | 0.51 |
| At5g39865 | AB010077 | 136 | 268 | 0.51 |
| At5g17300 | AB005238 | 211 | 412 | 0.51 |
| At1g18020 | AF344314 | 1752 | 3437 | 0.51 |
| At1g50910 | AC079284 | 261 | 513 | 0.51 |
| At5g51440 | AB025621 | 184 | 363 | 0.51 |
| At2g06880.a | AF147259 | 117 | 230 | 0.51 |
| At3g32020.b | AF147259 | 117 | 230 | 0.51 |
| At4g07730.a | AF147259 | 117 | 230 | 0.51 |
| At2g03200 | AC005313 | 159 | 312 | 0.51 |
| At3g60870 | AL162295 | 234 | 458 | 0.51 |
| At3g50800 | AL049862 | 131 | 259 | 0.51 |
| At5g41830 | AB016871 | 339 | 668 | 0.51 |
| At5g53310 | AF361603 | 583 | 1145 | 0.51 |
| At4g12980 | AL079349 | 2345 | 4580 | 0.51 |
| At2g30730 | AC002340 | 178 | 350 | 0.51 |
| At3g52270 | AL132972 | 135 | 265 | 0.51 |
| At3g21080 | AP000604 | 172 | 336 | 0.51 |
| At2g30510 | AF181683 | 3085 | 6075 | 0.51 |
| NoAnno | AA585895 | 189 | 364 | 0.52 |
| At2g34480 | AY042803 | 2958 | 5666 | 0.52 |
| At1g06450 | AC007592 | 229 | 437 | 0.52 |
| At5g52020 | AB015478 | 104 | 200 | 0.52 |
| At1g62060 | X91954 | 145 | 279 | 0.52 |
| At2g13690 | AC006436 | 107 | 205 | 0.52 |
| At1g20780 | AC069251 | 379 | 729 | 0.52 |
| At3g17930 | AY039550 | 1550 | 2953 | 0.52 |
| At3g54590 | AP002543 | 190 | 364 | 0.52 |
| At4g08410 | AP002543 | 190 | 364 | 0.52 |
| At5g06640 | AP002543 | 190 | 364 | 0.52 |
| At2g44470 | AC004521 | 114 | 219 | 0.52 |
| At1g34740 | AC007894 | 113 | 219 | 0.52 |
| At1g52020 | AC007894 | 113 | 219 | 0.52 |
| At2g14770 | AC007894 | 113 | 219 | 0.52 |
| At3g24390 | AC007894 | 113 | 219 | 0.52 |
| At3g42730 | AC007894 | 113 | 219 | 0.52 |
| At4g05280 | AC007894 | 113 | 219 | 0.52 |
| At5g36860 | AC007894 | 113 | 219 | 0.52 |
| At1g21940 | AC013482 | 128 | 248 | 0.52 |
| At1g34290 | AC007454 | 110 | 213 | 0.52 |
| At1g62000 | X91954 | 145 | 279 | 0.52 |
| At1g62080 | X91954 | 145 | 279 | 0.52 |

SUPPLEMENTAL TABLE 3-continued

Transcriptome analysis of ubp15-1.

| Gene Code | ID | M | W | M/W |
|---|---|---|---|---|
| At3g06020 | AC013454 | 171 | 328 | 0.52 |
| At1g17390 | AC007843 | 254 | 492 | 0.52 |
| At2g05560 | AC007894 | 113 | 219 | 0.52 |
| At1g68850 | AC011914 | 144 | 276 | 0.52 |
| At1g73600 | AC079676 | 6072 | 11568 | 0.52 |
| At2g05130 | AB015477 | 113 | 217 | 0.52 |
| At1g04380 | AC000104 | 119 | 227 | 0.52 |
| At4g04710 | AB015477 | 113 | 217 | 0.52 |
| At1g25886 | AC007894 | 113 | 219 | 0.52 |
| At4g03300 | AC007894 | 113 | 219 | 0.52 |
| At4g08880 | AC007894 | 113 | 219 | 0.52 |
| At4g08400 | AP002543 | 190 | 364 | 0.52 |
| At4g10710 | AF080119 | 208 | 402 | 0.52 |
| At3g43990 | AB015477 | 113 | 217 | 0.52 |
| At5g34940 | AA586196 | 211 | 403 | 0.52 |
| At3g54500 | AL138656 | 183 | 350 | 0.52 |
| At3g27560 | X92728 | 167 | 323 | 0.52 |
| At5g16030 | AL391145 | 7145 | 13777 | 0.52 |
| At3g25960 | AB023041 | 434 | 835 | 0.52 |
| At2g16980 | AC002354 | 204 | 389 | 0.52 |
| At4g10670 | AF080119 | 208 | 402 | 0.52 |
| At1g61500 | AC005850 | 247 | 475 | 0.52 |
| At5g45830 | AB016870 | 306 | 590 | 0.52 |
| At5g35520 | AB015477 | 113 | 217 | 0.52 |
| At3g54860 | AL049655 | 130 | 247 | 0.52 |
| At1g31710 | AC074360 | 240 | 449 | 0.53 |
| At2g21110 | AC006264 | 117 | 219 | 0.53 |
| At5g60390 | AF360167 | 7372 | 13840 | 0.53 |
| At5g44220 | AB005239 | 225 | 423 | 0.53 |
| At3g57160 | AL138655 | 194 | 362 | 0.53 |
| At1g11620 | AC007296 | 128 | 239 | 0.53 |
| At4g14450 | AF067468 | 114 | 213 | 0.53 |
| At2g42340 | AC005956 | 162 | 304 | 0.53 |
| At3g21670 | AF372959 | 748 | 1399 | 0.53 |
| At1g54300.a | AC005287 | 174 | 327 | 0.53 |
| At2g02850 | AC004138 | 129 | 246 | 0.53 |
| At2g26690 | AC003105 | 2529 | 4731 | 0.53 |
| At4g17910 | AP002057 | 118 | 222 | 0.53 |
| At3g58340 | AL137081 | 131 | 248 | 0.53 |
| At4g24480 | AL078637 | 191 | 362 | 0.53 |
| At2g29000 | AC005315 | 124 | 236 | 0.53 |
| At5g45810 | AB016870 | 272 | 514 | 0.53 |
| At2g18000 | AC006201 | 123 | 233 | 0.53 |
| At2g25260 | AC007070 | 232 | 437 | 0.53 |
| NoAnno | AI099709 | 159 | 295 | 0.54 |
| At4g19170 | AL021687 | 1362 | 2532 | 0.54 |
| At1g10610 | AC007067 | 221 | 412 | 0.54 |
| At5g05690 | X87368 | 2014 | 3720 | 0.54 |
| At1g51480 | AB026651 | 186 | 343 | 0.54 |
| At5g43730 | AB026651 | 186 | 343 | 0.54 |
| At1g37040 | AC020646 | 158 | 292 | 0.54 |
| At2g04770 | AC020646 | 158 | 292 | 0.54 |
| At2g38320 | AF370310 | 200 | 371 | 0.54 |
| At4g37550 | AY045895 | 1113 | 2075 | 0.54 |
| At1g49090 | AC020646 | 158 | 292 | 0.54 |
| At5g03415 | AJ294532 | 249 | 458 | 0.54 |
| At5g16700 | AL391147 | 182 | 337 | 0.54 |
| At1g20390 | AC027665 | 185 | 340 | 0.54 |
| At1g77150 | AV544954 | 127 | 236 | 0.54 |
| At1g77170 | AV544954 | 127 | 236 | 0.54 |
| At1g68870 | AC011914 | 438 | 804 | 0.54 |
| At3g43210 | AL353871 | 174 | 326 | 0.54 |
| At3g05880 | AC012393 | 7580 | 14042 | 0.54 |
| At5g20410 | AJ000331 | 111 | 205 | 0.54 |
| At2g24430 | AC006403 | 157 | 292 | 0.54 |
| At1g26800.a | AC006535 | 155 | 288 | 0.54 |
| At1g73660.a | BE037745 | 371 | 684 | 0.54 |
| At1g64860 | AB004821 | 2996 | 5515 | 0.54 |
| At5g34810 | AL161499 | 222 | 411 | 0.54 |
| At5g30480 | AC020646 | 158 | 292 | 0.54 |
| At3g01120 | AF039206 | 227 | 417 | 0.54 |
| At5g53260 | AB013388 | 128 | 236 | 0.54 |
| At4g04130 | AL161499 | 222 | 411 | 0.54 |
| At5g62780 | AB009053 | 150 | 278 | 0.54 |
| At3g22060 | AY034900 | 1041 | 1922 | 0.54 |
| At1g62070 | AC000375 | 336 | 620 | 0.54 |
| At1g06570 | AF000228 | 713 | 1301 | 0.55 |
| At4g01740 | AL161492 | 182 | 333 | 0.55 |
| At5g18620 | U95990 | 188 | 344 | 0.55 |
| At3g26190 | AB024038 | 218 | 394 | 0.55 |
| At3g61580 | AJ224161 | 139 | 250 | 0.55 |
| At4g12010 | AL049638 | 199 | 360 | 0.55 |
| At2g37640 | AC004684 | 134 | 245 | 0.55 |
| At1g26390 | AC013427 | 174 | 317 | 0.55 |
| At1g26400 | AC013427 | 174 | 317 | 0.55 |
| At1g26420 | AC013427 | 174 | 317 | 0.55 |
| At2g28440 | AC006283 | 190 | 345 | 0.55 |
| At4g18110 | AL110123 | 143 | 262 | 0.55 |
| At1g70260 | AC002062 | 176 | 319 | 0.55 |
| At1g58310 | AC008051 | 117 | 212 | 0.55 |
| At3g13229 | AB024034 | 190 | 345 | 0.55 |
| At3g12440 | AC069474 | 145 | 263 | 0.55 |
| At3g31930 | AP001301 | 217 | 394 | 0.55 |
| At2g20740 | AC006234 | 150 | 272 | 0.55 |
| At1g26810 | AC006535 | 166 | 302 | 0.55 |
| At1g47790 | AC012463 | 302 | 545 | 0.55 |
| At1g47560 | AC007519 | 149 | 273 | 0.55 |
| At4g14790.a | AJ132843 | 250 | 453 | 0.55 |
| At3g62260 | AL138651 | 180 | 327 | 0.55 |
| At3g32091 | BE521910 | 134 | 244 | 0.55 |
| At4g34720 | AC002534 | 126 | 227 | 0.55 |
| At2g34320 | AC004481 | 156 | 284 | 0.55 |
| At4g34840 | AL079347 | 109 | 201 | 0.55 |
| At3g61750 | AL132959 | 176 | 318 | 0.55 |
| At5g39530 | AA395409 | 5835 | 10560 | 0.55 |
| At5g26840 | AL132976 | 5258 | 9555 | 0.55 |
| At2g23330 | AC002391 | 284 | 519 | 0.55 |
| At2g11680 | AC007187 | 165 | 298 | 0.55 |
| At3g54210 | AL132957 | 5028 | 9190 | 0.55 |
| At5g49050 | AB017061 | 151 | 273 | 0.55 |
| At5g67030 | AB030296 | 3968 | 7179 | 0.55 |
| At1g28300 | AC021044 | 127 | 229 | 0.56 |
| At1g07180 | AC067971 | 774 | 1388 | 0.56 |
| At2g28580 | AC007171 | 178 | 319 | 0.56 |
| At5g16440 | AF188067 | 218 | 390 | 0.56 |
| At2g19810 | AC005169 | 516 | 927 | 0.56 |
| At5g44690 | AB016874 | 140 | 251 | 0.56 |
| At4g17720 | AL161547 | 639 | 1148 | 0.56 |
| At5g10220 | AY014798 | 487 | 272 | 1.79 |
| At4g20990 | AL080282 | 306 | 171 | 1.79 |
| At4g12290 | AL080318 | 1516 | 845 | 1.79 |
| At3g04640 | AC011437 | 1081 | 604 | 1.79 |
| At3g19280 | AP000419 | 835 | 465 | 1.79 |
| At1g11170 | AC007259 | 370 | 207 | 1.79 |
| At1g55550 | AC005223 | 319 | 178 | 1.79 |
| At2g30400 | U93215 | 311 | 174 | 1.79 |
| At3g56400 | AY039933 | 14429 | 8054 | 1.79 |
| At1g76960 | AF370567 | 591 | 328 | 1.8 |
| At2g22790 | AC005617 | 228 | 127 | 1.8 |
| At1g52620 | AC008016 | 678 | 377 | 1.8 |
| At1g68570 | AC008075 | 857 | 475 | 1.8 |
| At3g43250 | AL353871 | 211 | 117 | 1.8 |
| At4g27900 | AL035524 | 1215 | 676 | 1.8 |
| At2g17190 | AF360159 | 250 | 139 | 1.8 |
| At4g23240 | AL022347 | 415 | 231 | 1.8 |
| At4g23320 | AL022347 | 415 | 231 | 1.8 |
| At4g23290 | AL022347 | 415 | 231 | 1.8 |
| At3g13010 | AC024128 | 230 | 127 | 1.81 |
| At4g10340 | AF134129 | 6930 | 3820 | 1.81 |
| At4g31630 | AL031004 | 213 | 118 | 1.81 |
| At5g56840 | AB013392 | 502 | 278 | 1.81 |
| At1g55490 | AF386945 | 22830 | 12641 | 1.81 |
| At3g02470 | AY042824 | 24562 | 13607 | 1.81 |
| At1g74310 | U13949 | 663 | 365 | 1.82 |
| At2g36980 | AC006922 | 398 | 219 | 1.82 |
| At3g17360 | AB022216 | 296 | 163 | 1.82 |
| At1g17150 | AC007651 | 210 | 115 | 1.82 |
| At4g30500 | AL161577 | 708 | 388 | 1.82 |
| At5g62690 | M84701 | 554 | 304 | 1.82 |
| At5g62700 | M84701 | 554 | 304 | 1.82 |
| At3g17790 | AJ133747 | 537 | 294 | 1.83 |
| At3g23690 | AP000377 | 17759 | 9687 | 1.83 |

SUPPLEMENTAL TABLE 3-continued

Transcriptome analysis of ubp15-1.

| Gene Code | ID | M | W | M/W |
|---|---|---|---|---|
| At3g12500 | AC069474 | 264 | 144 | 1.83 |
| At4g38970 | AL035679 | 11816 | 6462 | 1.83 |
| At1g71250 | AC016162 | 263 | 144 | 1.83 |
| At5g53420 | AB020754 | 563 | 307 | 1.83 |
| At1g70760 | AC011663 | 236 | 129 | 1.83 |
| At1g29600 | AC068667 | 226 | 123 | 1.83 |
| At5g37770 | AB016873 | 7766 | 4226 | 1.84 |
| At1g75950 | AF059294 | 514 | 280 | 1.84 |
| At1g78980 | AC002986 | 231 | 126 | 1.84 |
| At2g28040 | AC005851 | 292 | 158 | 1.84 |
| At3g01350 | AC010676 | 345 | 187 | 1.84 |
| At3g59630 | AL138659 | 309 | 168 | 1.84 |
| At1g09340 | AY035050 | 18319 | 9954 | 1.84 |
| At4g18100 | AL110123 | 25024 | 13606 | 1.84 |
| At4g23310 | AL022347 | 225 | 123 | 1.84 |
| At2g26840 | AC005168 | 678 | 369 | 1.84 |
| NoAnno | F15338 | 312 | 169 | 1.85 |
| At1g02400 | AC064879 | 297 | 161 | 1.85 |
| At2g48090 | AC006072 | 258 | 140 | 1.85 |
| At5g39610 | AB012243 | 263 | 142 | 1.85 |
| At2g31220 | AC006593 | 477 | 257 | 1.86 |
| At2g24300 | AC006403 | 205 | 110 | 1.86 |
| At5g42500 | AB016888 | 256 | 137 | 1.86 |
| At3g01570 | AC009325 | 426 | 229 | 1.86 |
| At3g05710 | AJ245408 | 257 | 139 | 1.86 |
| At1g07470 | X98861 | 13725 | 7392 | 1.86 |
| At1g07480 | X98861 | 13725 | 7392 | 1.86 |
| At3g14620 | AB023038 | 519 | 277 | 1.87 |
| At1g67920 | AC012563 | 291 | 156 | 1.87 |
| At1g68590 | AC008075 | 19955 | 10683 | 1.87 |
| At5g45850 | AB016870 | 8826 | 4711 | 1.87 |
| At3g62550 | AY035146 | 23437 | 12503 | 1.87 |
| At5g67250 | AF263378 | 17304 | 9265 | 1.87 |
| At2g43670 | AC002333 | 203 | 108 | 1.88 |
| At1g56040 | AC009894 | 492 | 261 | 1.88 |
| At4g05180 | AF372897 | 5948 | 3170 | 1.88 |
| At3g08940 | AF134127 | 17812 | 9497 | 1.88 |
| At5g35340 | AF058826 | 232 | 123 | 1.88 |
| At4g20370 | AB027506 | 233 | 124 | 1.88 |
| NoAnno | M63234 | 207 | 110 | 1.89 |
| At4g20950 | AL080282 | 277 | 147 | 1.89 |
| At1g31630 | AC074360 | 573 | 302 | 1.89 |
| At1g33070 | AC074360 | 573 | 302 | 1.89 |
| At4g12800 | AJ245867 | 5393 | 2859 | 1.89 |
| At5g14840 | AL080282 | 277 | 147 | 1.89 |
| At5g15240 | AL353993 | 474 | 251 | 1.89 |
| At4g34190 | AF133716 | 18097 | 9574 | 1.89 |
| At4g32260 | AY042873 | 15062 | 7907 | 1.9 |
| At2g43790 | AV558477 | 440 | 232 | 1.9 |
| At3g01440 | AC010870 | 5091 | 2683 | 1.9 |
| At1g02200 | U40489 | 5410 | 2841 | 1.9 |
| At3g22120 | AF104328 | 22876 | 12056 | 1.9 |
| At2g20880 | AC006234 | 332 | 174 | 1.91 |
| At1g31940 | AC079041 | 207 | 108 | 1.91 |
| At1g32470 | AF385740 | 18411 | 9658 | 1.91 |
| At4g08730 | AL161512 | 403 | 211 | 1.91 |
| At3g44320 | X63445 | 22225 | 11646 | 1.91 |
| At3g44300 | X63445 | 22225 | 11646 | 1.91 |
| At3g44310 | X63445 | 22225 | 11646 | 1.91 |
| At5g24210 | AB006701 | 2109 | 1105 | 1.91 |
| At3g16640 | AY045802 | 1511 | 792 | 1.91 |
| At1g76130 | AC009978 | 868 | 451 | 1.92 |
| At1g51140 | AY034941 | 891 | 463 | 1.92 |
| At1g74980 | AY045856 | 17627 | 9200 | 1.92 |
| At1g27270 | AC004557 | 224 | 117 | 1.92 |
| At1g05880 | AC009999 | 279 | 146 | 1.92 |
| At4g02770 | AF389290 | 8820 | 4595 | 1.92 |
| At1g27980 | AF360166 | 961 | 499 | 1.92 |
| At1g21910 | AC013482 | 2917 | 1523 | 1.92 |
| At5g58570 | AY045817 | 656 | 339 | 1.93 |
| At4g36510 | AL161589 | 207 | 107 | 1.93 |
| At3g58380 | AL137081 | 266 | 138 | 1.93 |
| At3g12810 | AB024033 | 207 | 107 | 1.93 |
| At2g28340 | AC006283 | 417 | 215 | 1.94 |
| At4g03890 | AL161498 | 298 | 153 | 1.94 |
| At4g02250 | AL161494 | 201 | 104 | 1.94 |
| NoAnno | F15136 | 271 | 139 | 1.95 |
| At5g02260 | AL162874 | 306 | 157 | 1.95 |
| At1g30060 | AC022455 | 303 | 156 | 1.95 |
| At2g38140 | AC003028 | 12398 | 6316 | 1.96 |
| At1g25988 | AC084221 | 235 | 120 | 1.96 |
| At1g51760 | Y13577 | 208 | 106 | 1.96 |
| At2g14990 | AL161509 | 252 | 129 | 1.96 |
| At2g46870 | AC004411 | 19086 | 9748 | 1.96 |
| At2g14970 | AF262043 | 16604 | 8412 | 1.97 |
| At1g58290 | AC008051 | 15587 | 7898 | 1.97 |
| At4g16080 | AL161543 | 703 | 357 | 1.97 |
| At5g02520 | AL162971 | 202 | 103 | 1.97 |
| At4g08060 | AF262043 | 16604 | 8412 | 1.97 |
| At3g27860 | AP000371 | 270 | 137 | 1.97 |
| At1g64670 | AC009519 | 239 | 121 | 1.98 |
| At1g26310 | AF061410 | 275 | 139 | 1.98 |
| At5g38730 | AB011478 | 307 | 155 | 1.98 |
| At1g23205 | AC002311 | 2171 | 1098 | 1.98 |
| At4g04640 | M61741 | 8213 | 4124 | 1.99 |
| At1g52220 | AC022354 | 21605 | 10842 | 1.99 |
| At4g02870 | AL161495 | 273 | 137 | 1.99 |
| At1g34740 | AF104920 | 212 | 107 | 1.99 |
| At2g05560 | AF104920 | 212 | 107 | 1.99 |
| At2g14770 | AF104920 | 212 | 107 | 1.99 |
| At3g24390 | AF104920 | 212 | 107 | 1.99 |
| At3g42730 | AF104920 | 212 | 107 | 1.99 |
| At4g08880 | AF104920 | 212 | 107 | 1.99 |
| At5g36860 | AF104920 | 212 | 107 | 1.99 |
| At4g24570 | AY042859 | 3564 | 1794 | 1.99 |
| At1g52020 | AF104920 | 212 | 107 | 1.99 |
| At3g15720 | AB017071 | 423 | 212 | 1.99 |
| At1g25886 | AF104920 | 212 | 107 | 1.99 |
| At3g43390 | AF104920 | 212 | 107 | 1.99 |
| At4g03300 | AF104920 | 212 | 107 | 1.99 |
| At4g05280 | AF104920 | 212 | 107 | 1.99 |
| At3g28610 | AP000420 | 205 | 103 | 1.99 |
| At3g09440 | Y17053 | 3577 | 1784 | 2 |
| At1g30250 | AC073506 | 6659 | 3331 | 2 |
| At5g36960 | AB016877 | 271 | 135 | 2.01 |
| At2g37220 | AY048251 | 14320 | 7098 | 2.02 |
| At1g71691 | AC012654 | 288 | 142 | 2.02 |
| At2g31980 | AC006223 | 211 | 105 | 2.02 |
| At2g27400 | AC006233 | 313 | 154 | 2.03 |
| At1g11260 | X55350 | 17446 | 8597 | 2.03 |
| At3g23250 | Y14207 | 215 | 106 | 2.03 |
| At5g53490 | AF370552 | 19631 | 9694 | 2.03 |
| At2g33830 | AB050786 | 14290 | 7021 | 2.04 |
| At4g14950 | AV537413 | 254 | 124 | 2.04 |
| At1g22270 | AC068562 | 290 | 142 | 2.04 |
| At5g35735 | AF372955 | 4539 | 2220 | 2.04 |
| At2g15960 | AC006438 | 23165 | 11339 | 2.04 |
| At2g36800 | AC006282 | 584 | 287 | 2.04 |
| At5g61440 | AF144389 | 6829 | 3348 | 2.04 |
| At1g10040 | AC004122 | 352 | 173 | 2.04 |
| At3g20810 | AB025629 | 4866 | 2370 | 2.05 |
| At2g42730 | AC006931 | 248 | 121 | 2.05 |
| At3g47960 | AF370202 | 5950 | 2905 | 2.05 |
| At2g01600 | AV541295 | 265 | 129 | 2.06 |
| At3g07480 | AF386949 | 267 | 130 | 2.06 |
| At1g56070 | AC009894 | 26599 | 12925 | 2.06 |
| At2g43940 | AC004005 | 607 | 294 | 2.06 |
| At4g04610 | U53864 | 1154 | 559 | 2.07 |
| At3g13340 | AY048298 | 1955 | 945 | 2.07 |
| At5g59220 | AB016890 | 282 | 137 | 2.07 |
| At2g28960 | AC005315 | 231 | 112 | 2.07 |
| At2g19350 | AC003058 | 210 | 101 | 2.08 |
| At1g21960 | AC013482 | 298 | 144 | 2.08 |
| At2g30860 | AF372905 | 25890 | 12409 | 2.09 |
| At2g45350 | AC002387 | 585 | 280 | 2.09 |
| At5g37640 | L05363 | 11449 | 5488 | 2.09 |
| At4g05320 | L05363 | 11449 | 5488 | 2.09 |
| At4g05050 | L05363 | 11449 | 5488 | 2.09 |
| At5g20620 | L05363 | 11449 | 5488 | 2.09 |
| At5g03240 | L05363 | 11449 | 5488 | 2.09 |
| At3g09790 | L05363 | 11449 | 5488 | 2.09 |
| At1g65350 | L05363 | 11449 | 5488 | 2.09 |

SUPPLEMENTAL TABLE 3-continued

Transcriptome analysis of ubp15-1.

| Gene Code | ID | M | W | M/W |
|---|---|---|---|---|
| At1g55060 | L05363 | 11449 | 5488 | 2.09 |
| At3g62250 | L05363 | 11449 | 5488 | 2.09 |
| At4g02890 | L05363 | 11449 | 5488 | 2.09 |
| At4g16690 | AL161544 | 1258 | 601 | 2.1 |
| At1g08640 | AF370182 | 372 | 178 | 2.1 |
| At2g02815 | AF175994 | 283 | 134 | 2.1 |
| At3g62150 | AL138651 | 293 | 140 | 2.1 |
| At1g56430 | AC058785 | 641 | 306 | 2.1 |
| At1g61370 | AC004255 | 444 | 211 | 2.1 |
| At3g24100 | AF370331 | 463 | 220 | 2.1 |
| At4g02140 | AL161493 | 252 | 119 | 2.11 |
| At3g46190 | AL355775 | 210 | 100 | 2.11 |
| At3g56260 | AL163763 | 349 | 166 | 2.11 |
| At2g21170 | AF247559 | 20479 | 9650 | 2.12 |
| At1g80280 | AV547254 | 221 | 104 | 2.12 |
| At3g21760 | AF372973 | 1223 | 575 | 2.13 |
| At1g14600 | AC010657 | 413 | 193 | 2.14 |
| At3g15650 | AB017071 | 416 | 194 | 2.14 |
| At2g25510 | AC006300 | 14882 | 6928 | 2.15 |
| At4g11440 | AL050399 | 402 | 187 | 2.15 |
| At5g03000 | AL163002 | 249 | 116 | 2.15 |
| At1g50560 | AC012561 | 241 | 111 | 2.16 |
| At3g04120 | AC016829 | 19007 | 8803 | 2.16 |
| At5g26000 | AY045681 | 4323 | 1999 | 2.16 |
| At1g15620 | AC013453 | 277 | 128 | 2.16 |
| At1g65400 | AF325110 | 2725 | 1260 | 2.16 |
| At1g55290 | AC027034 | 243 | 112 | 2.16 |
| At1g50540 | AC012561 | 241 | 111 | 2.16 |
| At3g46890 | AL096859 | 16966 | 7863 | 2.16 |
| At1g61400 | AC004255 | 248 | 115 | 2.16 |
| At1g61430 | AC004255 | 248 | 115 | 2.16 |
| At1g61440 | AC004255 | 248 | 115 | 2.16 |
| NoAnno | AF003102 | 550 | 254 | 2.17 |
| At3g47470 | M63931 | 5758 | 2649 | 2.17 |
| At4g01530 | AL161492 | 212 | 98 | 2.17 |
| At3g21750 | AB025634 | 825 | 381 | 2.17 |
| At2g18120 | AC007212 | 258 | 119 | 2.17 |
| At4g22020 | AJ002892 | 3194 | 1468 | 2.18 |
| At1g21310 | AB031821 | 278 | 128 | 2.18 |
| At1g49490 | AJ002892 | 3194 | 1468 | 2.18 |
| At4g27440 | AY042883 | 279 | 128 | 2.18 |
| At3g46250 | AL355775 | 207 | 95 | 2.18 |
| At2g40200 | AF085279 | 212 | 97 | 2.19 |
| At4g01310 | AL161491 | 15461 | 7075 | 2.19 |
| At5g65980 | AB011474 | 204 | 93 | 2.19 |
| At3g63290 | AV543251 | 247 | 113 | 2.19 |
| At5g27280 | AF007271 | 303 | 139 | 2.19 |
| At4g35100 | AY049238 | 16586 | 7554 | 2.2 |
| At2g22760 | AC005617 | 203 | 92 | 2.2 |
| At2g45960 | AY049238 | 16586 | 7554 | 2.2 |
| At2g16850 | AY049238 | 16586 | 7554 | 2.2 |
| At2g39310 | AC004697 | 205 | 93 | 2.2 |
| At3g61430 | AY049238 | 16586 | 7554 | 2.2 |
| At4g19700 | AL024486 | 975 | 443 | 2.2 |
| At2g14800 | AC004705 | 483 | 219 | 2.21 |
| At2g03020 | AC004138 | 362 | 164 | 2.21 |
| At3g60810 | AL162295 | 261 | 118 | 2.21 |
| At3g52145 | AI995315 | 206 | 93 | 2.22 |
| At2g16600 | U40399 | 24863 | 11149 | 2.23 |
| At2g30570 | U93215 | 8840 | 3958 | 2.23 |
| At3g53420 | AY039579 | 20978 | 9407 | 2.23 |
| At5g13510 | AL391710 | 21808 | 9770 | 2.23 |
| At4g35450 | U70425 | 19189 | 8562 | 2.24 |
| At3g61700 | AV557897 | 238 | 106 | 2.24 |
| At5g66570 | AF372898 | 8498 | 3775 | 2.25 |
| At2g46330 | AC006526 | 18763 | 8298 | 2.26 |
| At5g06540 | AP002543 | 307 | 136 | 2.26 |
| At3g15530 | AC024081 | 1342 | 592 | 2.27 |
| At1g20300 | AC026234 | 653 | 286 | 2.28 |
| At2g27385 | AV531683 | 327 | 144 | 2.28 |
| NoAnno | AF360265 | 27827 | 12129 | 2.29 |
| At1g75350 | AF370226 | 16420 | 7163 | 2.29 |
| At1g30260 | AC073506 | 4248 | 1858 | 2.29 |
| At2g32290 | AC005700 | 434 | 189 | 2.3 |
| At3g46430 | AL133298 | 19794 | 8588 | 2.3 |
| At4g16370 | AL161543 | 3197 | 1382 | 2.31 |
| At1g44810 | AY042861 | 277 | 120 | 2.32 |
| At4g17980 | AL021889 | 357 | 154 | 2.32 |
| At5g52050 | AB015478 | 478 | 205 | 2.33 |
| At3g50820 | AJ145957 | 16012 | 6873 | 2.33 |
| At5g42900 | AB008264 | 7894 | 3370 | 2.34 |
| At4g30750 | AY037251 | 209 | 89 | 2.36 |
| At2g31920 | AC006533 | 210 | 89 | 2.36 |
| At2g01300 | AC006200 | 1094 | 461 | 2.37 |
| At5g08280 | X73535 | 25523 | 10707 | 2.38 |
| At5g62300 | AF370460 | 27616 | 11598 | 2.38 |
| At5g50610 | AB025619 | 222 | 93 | 2.38 |
| At5g50710 | AB025619 | 222 | 93 | 2.38 |
| At3g07650 | AC009176 | 4686 | 1965 | 2.39 |
| At5g11780 | AL163814 | 274 | 114 | 2.39 |
| At4g32430 | AL034567 | 394 | 164 | 2.4 |
| At5g02500 | X74604 | 20275 | 8429 | 2.41 |
| At3g54890 | AF326866 | 9157 | 3789 | 2.42 |
| At3g59340 | AF370505 | 692 | 284 | 2.43 |
| At1g79850 | Z11151 | 830 | 339 | 2.45 |
| At2g21660 | AY042826 | 613 | 250 | 2.45 |
| At2g39320 | AC004697 | 773 | 316 | 2.45 |
| At2g21420 | AC006841 | 260 | 106 | 2.45 |
| At4g36010 | AF360165 | 958 | 388 | 2.47 |
| At4g13940 | AF325037 | 26706 | 10790 | 2.48 |
| At1g32080 | AC084165 | 20969 | 8468 | 2.48 |
| At4g01260 | AL161491 | 227 | 91 | 2.48 |
| At4g31830 | AL049607 | 292 | 118 | 2.48 |
| At3g24420 | AP000382 | 8999 | 3623 | 2.48 |
| At2g28900 | AY045593 | 21483 | 8645 | 2.49 |
| At1g63820 | AC010852 | 214 | 86 | 2.5 |
| At5g16400 | AF144386 | 19378 | 7696 | 2.52 |
| At1g14320 | AY045866 | 22985 | 9128 | 2.52 |
| At1g27710 | AC012375 | 213 | 85 | 2.52 |
| At1g75690 | AC006434 | 24943 | 9882 | 2.52 |
| At3g44990 | X92975 | 865 | 343 | 2.52 |
| At5g06290 | AF326871 | 22183 | 8782 | 2.53 |
| At3g15630 | AB017071 | 22541 | 8902 | 2.53 |
| At5g01100 | AL137189 | 595 | 235 | 2.53 |
| At1g73810 | AC012679 | 279 | 110 | 2.54 |
| At5g14610 | AL163792 | 30717 | 12004 | 2.56 |
| At5g42530 | AB016888 | 7812 | 3054 | 2.56 |
| At2g28800 | U89272 | 22626 | 8809 | 2.57 |
| At2g36970 | AC006922 | 308 | 120 | 2.57 |
| At1g77110 | AC002291 | 255 | 99 | 2.58 |
| At1g28410 | AC010155 | 257 | 99 | 2.6 |
| At1g32990 | AF325023 | 20190 | 7763 | 2.6 |
| At5g63580 | AB005234 | 209 | 80 | 2.62 |
| At2g21800 | AC007019 | 204 | 78 | 2.63 |
| At2g33450 | AC002332 | 25052 | 9518 | 2.63 |
| At2g43910 | AC005170 | 699 | 266 | 2.63 |
| At2g19150 | AC002392 | 206 | 78 | 2.64 |
| At5g23660 | AF095641 | 2931 | 1106 | 2.65 |
| At3g21470 | AB019232 | 401 | 151 | 2.66 |
| At5g13630 | Z68495 | 21783 | 8155 | 2.67 |
| At2g42220 | AY045616 | 20113 | 7535 | 2.67 |
| At2g03190 | AC005313 | 206 | 77 | 2.68 |
| At1g44880 | AC020576 | 245 | 91 | 2.68 |
| At2g10350 | AC020576 | 245 | 91 | 2.68 |
| At4g03970 | AC020576 | 245 | 91 | 2.68 |
| At3g42530 | AC020576 | 245 | 91 | 2.68 |
| At3g01310 | AC010676 | 212 | 79 | 2.68 |
| At3g45680 | AL157735 | 258 | 95 | 2.72 |
| At3g45690 | AL157735 | 258 | 95 | 2.72 |
| At2g10940 | AC006429 | 8529 | 3119 | 2.73 |
| At5g46110 | AY037211 | 7130 | 2614 | 2.73 |
| At2g41430 | AC004625 | 8374 | 3041 | 2.75 |
| At1g48300 | AC007932 | 2604 | 935 | 2.78 |
| At1g28760 | AC007508 | 310 | 111 | 2.8 |
| At1g44040 | AC022314 | 360 | 129 | 2.8 |
| At1g08790 | AC003981 | 277 | 99 | 2.81 |
| At5g63900 | AB008265 | 223 | 80 | 2.81 |
| At3g49910 | AF370158 | 22291 | 7877 | 2.83 |
| At3g12840 | AB024033 | 220 | 77 | 2.84 |
| At2g29280 | AC004561 | 496 | 175 | 2.84 |
| At1g12610 | AC025417 | 293 | 103 | 2.85 |
| At2g28460 | AC006587 | 256 | 89 | 2.86 |

SUPPLEMENTAL TABLE 3-continued

Transcriptome analysis of ubp15-1.

| Gene Code | ID | M | W | M/W |
|---|---|---|---|---|
| At2g38240 | AC003028 | 282 | 98 | 2.87 |
| At2g05070 | AY045787 | 20173 | 6958 | 2.9 |
| At2g05100 | AY045787 | 20173 | 6958 | 2.9 |
| At4g25050 | T45818 | 15045 | 5121 | 2.94 |
| At4g10260 | AL049488 | 309 | 105 | 2.94 |
| At1g49500 | AF370563 | 22168 | 7513 | 2.95 |
| At5g58310 | AB019228 | 1438 | 487 | 2.95 |
| At3g45520 | AL161500 | 215 | 72 | 2.97 |
| At4g04380 | AL161500 | 215 | 72 | 2.97 |
| At3g25290 | AB026647 | 307 | 103 | 2.99 |
| At3g01500 | AC009325 | 616 | 205 | 3 |
| At4g24420 | AL078637 | 202 | 67 | 3 |
| At3g43600 | AB005805 | 19762 | 6576 | 3.01 |
| At5g11370 | AL360314 | 236 | 78 | 3.01 |
| At2g28000 | AC006929 | 27972 | 9297 | 3.01 |
| At5g39670 | AB012243 | 291 | 96 | 3.03 |
| At5g24780 | AF386930 | 375 | 123 | 3.05 |
| At1g23310 | AF360195 | 31336 | 10247 | 3.06 |
| At2g34420 | X64460 | 7379 | 2403 | 3.07 |
| At3g21640 | AJ224640 | 20590 | 6686 | 3.08 |
| At5g15960 | X55053 | 22316 | 7183 | 3.11 |
| At5g15970 | X55053 | 22316 | 7183 | 3.11 |
| At3g01600 | AC009325 | 233 | 75 | 3.11 |
| At4g32540 | AL050398 | 303 | 97 | 3.12 |
| At2g11820 | AB047398 | 207 | 66 | 3.12 |
| At4g17350 | AL161546 | 215 | 69 | 3.13 |
| At1g04270 | AY048221 | 22066 | 7025 | 3.14 |
| At2g17180 | AC007127 | 345 | 109 | 3.15 |
| At4g21280 | AL021960 | 7348 | 2313 | 3.18 |
| At3g53290 | AL132958 | 228 | 71 | 3.2 |
| At5g44980 | AB010693 | 210 | 65 | 3.22 |
| At2g30950 | AF135189 | 29571 | 9161 | 3.23 |
| At3g12430 | AC069474 | 270 | 83 | 3.24 |
| At4g32490 | AL034567 | 261 | 81 | 3.25 |
| At1g69990 | AC002062 | 249 | 76 | 3.26 |
| At5g05250 | AB010692 | 1176 | 358 | 3.28 |
| At3g56360 | AL163972 | 1291 | 391 | 3.3 |
| At1g72150 | AY045913 | 24133 | 7291 | 3.31 |
| At4g21990 | U53865 | 1684 | 509 | 3.31 |
| At2g30840 | AC004669 | 308 | 93 | 3.32 |
| At1g41810 | AC022456 | 240 | 71 | 3.37 |
| At5g29090 | AC022456 | 240 | 71 | 3.37 |
| At5g32610 | AC022456 | 240 | 71 | 3.37 |
| At3g59170 | AL356014 | 217 | 64 | 3.41 |
| At5g37470 | AP000607 | 223 | 65 | 3.45 |
| At2g25040.a | AV558611 | 287 | 83 | 3.46 |
| At3g32370.a | AV558611 | 287 | 83 | 3.46 |
| At5g37300 | AB017069 | 753 | 217 | 3.48 |
| At4g22214 | AL021712 | 256 | 73 | 3.51 |
| At1g48700 | AC073555 | 275 | 78 | 3.52 |
| At1g55850 | AC002304 | 267 | 75 | 3.57 |
| At1g04920 | AC004809 | 362 | 99 | 3.64 |
| At4g03280 | AJ243702 | 1486 | 400 | 3.71 |
| At1g35660.a | AC007887 | 203 | 55 | 3.73 |
| At4g27110 | AL035680 | 201 | 51 | 3.9 |
| At2g04820 | AC006955 | 341 | 85 | 4.01 |
| At1g75910 | AC007396 | 205 | 51 | 4.04 |
| At3g21980 | AB028622 | 215 | 52 | 4.15 |
| At3g27830 | AP000371 | 25310 | 6009 | 4.21 |
| At1g74080 | AC016662 | 352 | 83 | 4.26 |
| At2g17850 | AC003952 | 277 | 65 | 4.29 |
| At2g45570 | AC003680 | 251 | 58 | 4.33 |
| At3g56040 | AV548493 | 280 | 62 | 4.49 |
| At5g25980 | AF360348 | 28538 | 6306 | 4.53 |
| At3g43580 | AL391734 | 222 | 48 | 4.61 |
| At5g38710 | AB011478 | 376 | 78 | 4.81 |
| At3g12760 | AB024033 | 271 | 50 | 5.41 |
| At1g32920.a | BE522104 | 235 | 28 | 8.35 |

W, wild type;
M, mutant.

References

Amerik, A. Y., and Hochstrasser, M. (2004). Mechanism and function of deubiquitinating enzymes. BBA 1695, 189-207.

Ang, L. H., Chattopadhyay, S., Wei, N., Oyama, T., Okada, K., Batschauer, A., and Deng, X. W. (1998). Molecular interaction between COP1 and HY5 defines a regulatory switch for light control of *Arabidopsis* development. Mol Cell 1, 213-222.

Baek, K. H., Mondoux, M. A., Jaster, R., Fire-Levin, E., and D'Andrea, A.D. (2001). DUB-2A, a new member of the DUB subfamily of hematopoietic deubiquitinating enzymes. Blood 98, 636-642.z767

Balakirev, M. Y., Tcherniuk, S. O., Jaquinod, M., and Chroboczek, J. (2003). Otubains: a new family of cysteine proteases in the ubiquitin pathway. EMBO Rep 4, 517-522.

Burnett, B., Li, F., and Pittman, R. N. (2003). The polyglutamine neurodegenerative protein ataxin-3 binds polyubiquitylated proteins and has ubiquitin protease activity. Hum Mol Genet 12, 3195-3205.

Byrne, M. E., Groover, A. T., Fontana, J. R., and Martienssen, R. A. (2003). Phyllotactic pattern and stem cell fate are determined by the *Arabidopsis* homeobox gene BELL-RINGER. Development 130, 3941-3950.

Chandler, J. S., McArdle, B., and Callis, J. (1997). AtUBP3 and AtUBP4 are two closely related *Arabidopsis* thaliana ubiquitin-specific proteases present in the nucleus. Mol Gen Genet 255, 302-310.

Crosas, B., Hanna, J., Kirkpatrick, D. S., Zhang, D. P., Tone, Y., Hathaway, N. A., Buecker, C., Leggett, D. S., Schmidt, M., King, R. W., Gygi, S. P., and Finley, D. (2006). Ubiquitin chains are remodeled at the proteasome by opposing ubiquitin ligase and deubiquitinating activities. Cell 127, 1401-1413.

Doelling, J. H., Yan, N., Kurepa, J., Walker, J., and Vierstra, R. D. (2001). The ubiquitin-specific protease UBP14 is essential for early embryo development in *Arabidopsis* thaliana. Plant J 27, 393-405.

Fleury, D., Himanen, K., Cnops, G., Nelissen, H., Boccardi, T. M., Maere, S., Beemster, G. T., Neyt, P., Anami, S., Robles, P., Micol, J. L., Inze, D., and Van Lijsebettens, M. (2007). The *Arabidopsis* thaliana Homolog of Yeast BRE1 Has a Function in Cell Cycle Regulation during Early Leaf and Root Growth. Plant Cell.

Gross, C. T., and McGinnis, W. (1996). DEAF-1, a novel protein that binds an essential region in a Deformed response element. EMBO J. 15, 1961-1970.

Hanna, J., Hathaway, N. A., Tone, Y., Crosas, B., Elsasser, S., Kirkpatrick, D. S., Leggett, D. S., Gygi, S. P., King, R. W., and Finley, D. (2006). Deubiquitinating enzyme Ubp6 functions noncatalytically to delay proteasomal degradation. Cell 127, 99-111.

Hershko, A., and Ciechanover, A. (1998). The ubiquitin system. Annu. Rev. Biochem. 67, 425-479.

Hochstrasser, M. (1996). Ubiquitin-dependent protein degradation. Annu. Rev. Genet. 30, 405-439.

Hofmann, K., and Bucher, P. (1996). The UBA domain: a sequence motif present in multiple enzyme classes of the ubiquitination pathway. Trends Biochem Sci 21, 172-173.

Horiguchi, G., Kim, G. T., and Tsukaya, H. (2005). The transcription factor AtGRF5 and the transcription coactivator AN3 regulate cell proliferation in leaf primordia of *Arabidopsis* thaliana. Plant J 43, 68-78.

Hu, M., Li, P., Li, M., Li, W., Yao, T., Wu, J. W., Gu, W., Cohen, R. E., and Shi, Y. (2002). Crystal structure of a UBP-family deubiquitinating enzyme in isolation and in complex with ubiquitin aldehyde. Cell 111, 1041-1054.

Johnston, S. C., Riddle, S. M., Cohen, R. E., and Hill, C. P. (1999). Structural basis for the specificity of ubiquitin C-terminal hydrolases. Embo J 18, 3877-3887.

Johnston, S. C., Larsen, C. N., Cook, W. J., Wilkinson, K. D., and Hill, C. P. (1997). Crystal structure of a deubiquitinating enzyme (human UCH-L3) at 1.8 A resolution. Embo J 16, 3787-3796.

Kim, J. H., and Kende, H. (2004). A transcriptional coactivator, AtGIF1, is involved in regulating leaf growth and morphology in *Arabidopsis*. Proc Natl Acad Sci USA 101, 13374-13379.

Kumar, S., Tamura, K., and Nei, M. (2004). MEGA3: Integrated software for Molecular Evolutionary Genetics Analysis and sequence alignment. Brief Bioinform 5, 150-163.

Lutterbach, B., Sun, D., Schuetz, J., and Hiebert, S. W. (1998a). The MYND motif is required for repression of basal transcription from the multidrug resistance 1 promoter by the t(8;21) fusion protein. Mol. Cell. Biol. 18, 3604-3611.

Lutterbach, B., Westendorf, J. J., Linggi, B., Patten, A., Moniwa, M., Davie, J. R., Huynh, K. D., Bardwell, V. J., Lavinsky, R. M., Rosenfeld, M. G., Glass, C., Seto, E., and Hiebert, S. W. (1998b). ETO, a target of t(8;21) in acute leukemia, interacts with the N-CoR and mSin3 corepressors. Mol. Cell Biol. 18, 7176-7184.

Ma, L., Sun, N., Liu, X., Jiao, Y., Zhao, H., and Deng, X. W. (2005). Organ-specific expression of *Arabidopsis* genome during development. Plant Physiol 138, 80-91.

Ma, L., Gao, Y., Qu, L., Chen, Z., Li, J., Zhao, H., and Deng, X. W. (2002). Genomic evidence for COP1 as a repressor of light-regulated gene expression and development in *Arabidopsis*. Plant Cell 14, 2383-2398.

Maere, S., Heymans, K., and Kuiper, M. (2005). BiNGO: a Cytoscape plugin to assess overrepresentation of gene ontology categories in biological networks. Bioinformatics 21, 3448-3449.

Masselink, H., and Bernards, R. (2000). The adenovirus E1A binding protein BS69 is a corepressor of transcription through recruitment of N-CoR. Oncogene 19, 1538-1546.

Mueller, T. D., and Feigon, J. (2002). Solution structures of UBA domains reveal a conserved hydrophobic surface for protein-protein interactions. J Mol Biol 319, 1243-1255.

Nanao, M. H., Tcherniuk, S. O., Chroboczek, J., Dideberg, O., Dessen, A., and Balakirev, M. Y. (2004). Crystal structure of human otubain 2. EMBO Rep 5, 783-788.

Nijman, S. M., Luna-Vargas, M. P., Velds, A., Brummelkamp, T. R., Dirac, A. M., Sixma, T. K., and Bernards, R. (2005). A genomic and functional inventory of deubiquitinating enzymes. Cell 123, 773-786.

Papa, F. R., and Hochstrasser, M. (1993). The yeast DOA4 gene encodes a deubiquitinating enzyme related to a product of the human tre-2 oncogene. Nature 366, 313-319.

Park, Y. C., Burkitt, V., Villa, A. R., Tong, L., and Wu, H. (1999). Structural basis for self-association and receptor recognition of human TRAF2. Nature 398, 533-538.

Pickart, C. M. (2004). Back to the future with ubiquitin. Cell 116, 181-190.

Qin, G., Gu, H., Zhao, Y., Ma, Z., Shi, G., Yang, Y., Pichersky, E., Chen, H., Liu, M., Chen, Z., and Qu, L. J. (2005). An indole-3-acetic acid carboxyl methyltransferase regulates *Arabidopsis* leaf development. Plant Cell 17, 2693-2704.

Rao-Naik, C., Chandler, J. S., McArdle, B., and Callis, J. (2000). Ubiquitin-specific proteases from *Arabidopsis thaliana*: cloning of AtUBP5 and analysis of substrate specificity of AtUBP3, AtUBP4, and AtUBP5 using *Escherichia coli* in vivo and in vitro assays. Arch Biochem Biophys 379, 198-208.

Scheel, H., Tomiuk, S., and Hofmann, K. (2003). Elucidation of ataxin-3 and ataxin-7 function by integrative bioinformatics. Hum Mol Genet 12, 2845-2852.

Sunnerhagen, M., Pursglove, S., and Fladvad, M. (2002). The new MATH: homology suggests shared binding surfaces in meprin tetramers and TRAF trimers. FEBS Lett 530, 1-3.

Thompson, J. D., Higgins, D. G., and Gibson, T. J. (1994). CLUSTAL W: improving the sensitivity of progressive multiple sequence alignment through sequence weighting, position-specific gap penalties and weight matrix choice. Nucleic Acids Res 22, 4673-4680.

Tsukaya, H. (2006). Mechanism of leaf-shape determination. Annu. Rev. Plant Biol. 57, 477-496.

Varshaysky, A. (1997). The ubiquitin system. TIBS 22, 383-387.

Verma, R., Aravind, L., Oania, R., McDonald, W. H., Yates, J. R., 3rd, Koonin, E. V., and Deshaies, R. J. (2002). Role of Rpn11 metalloprotease in deubiquitination and degradation by the 26S proteasome. Science 298, 611-615.

Weigel, D., and Glazebrook, J. (2002). *Arabidopsis* A laboratory Manual. (New York: Cold Spring Harbor Laboratory Press).

Weissman, A. M. (2001). Themes and variations on ubiquitylation. Nat. Rev. Mol. Cell Biol. 2, 169-177.

Wilkinson, K. D. (1997). Regulation of ubiquitin-dependent processes by deubiquitinating enzymes. FASEB J. 11, 1245-1256.

Wilkinson, K. D. (1999). Ubiquitin-dependent signaling: the role of ubiquitination in the response of cells to their environment. J Nutr 129, 1933-1936.

Yan, N., Doelling, J. H., Falbel, T. G., Durski, A. M., and Vierstra, R. D. (2000). The ubiquitin-specific protease family from *Arabidopsis*. AtUBP1 and 2 are required for the resistance to the amino acid analog canavanine. Plant Physiol 124, 1828-1843.

Yang, J., Lin, R., Sullivan, J., Hoecker, U., Liu, B., Xu, L., Deng, X. W., and Wang, H. (2005). Light regulates COP1-mediated degradation of HFR1, a transcription factor essential for light signaling in *Arabidopsis*. Plant Cell 17, 804-821.

Ye, H., Park, Y. C., Kreishman, M., Kieff, E., and Wu, H. (1999). The structural basis for the recognition of diverse receptor sequences by TRAF2. Mol Cell 4, 321-330.

The invention claimed is:

1. A method for altering plant growth, comprising introducing and expressing in a plant a nucleic acid encoding a plant UBiquitin-Specific Protease 15 (UBP15) polypeptide comprising the following motifs:
   (i) a Cysteine box (Cys box);
   (ii) a Histidine box (His box); and
   (iii) a ZnMYND zinc finger domain,
   wherein said nucleic acid is selected from the group consisting of:
   (a) a nucleic acid comprising the nucleotide sequence of SEQ ID NO: 1;
   (b) a nucleic acid encoding a polypeptide comprising the amino acid sequence of SEQ ID NO: 2; and
   (c) a nucleic acid encoding a polypeptide having at least 95% sequence identity to the amino acid sequence of SEQ ID NO: 2, wherein said polypeptide has de-ubiquitination activity in vitro,
   and wherein said plant has one or more of the following: increased number of rosette leaves, increased flowering time, increased fresh weight of rosette leaves, increased silique length, increased root length, increased primary stem length, and/or increased primary stem diameter relative to a control plant.

2. The method of claim 1, wherein said nucleic acid is operably linked to a constitutive promoter.

3. A plant having increased number of rosette leaves, increased flowering time, increased fresh weight of rosette leaves, increased silique length, increased root length, increased primary stem length, and/or increased primary stem diameter relative to a control plant, wherein the increased number of rosette leaves, increased flowering time, increased fresh weight of rosette leaves, increased silique length, increased root length, increased primary stem length, and/or increased primary stem diameter is obtained by the method of claim 1.

4. A construct comprising:
(i) a nucleic acid encoding a plant UBiquitin-Specific Protease 15 (UBP15) polypeptide comprising the following motifs:
a) a Cysteine box (Cys box);
b) a Histidine box (His box); and
c) a ZnMYND zinc finger domain,
wherein said nucleic acid is selected from the group consisting of:
(a) a nucleic acid comprising the nucleotide sequence of SEQ ID NO: 1;
(b) a nucleic acid encoding a polypeptide comprising the amino acid sequence of SEQ ID NO: 2; and
(c) a nucleic acid encoding a polypeptide having at least 95% sequence identity to the amino acid sequence of SEQ ID NO: 2, wherein said polypeptide has de-ubiquitination activity in vitro;
(ii) one or more heterologous control sequences capable of driving expression of the nucleic acid of (i); and optionally
(iii) a transcription termination sequence,
wherein expression of said nucleic acid in a plant confers one or more of the following: increased number of rosette leaves, increased flowering time, increased fresh weight of rosette leaves, increased silique length, increased root length, increased primary stem length, and/or increased primary stem diameter relative to a control plant.

5. The construct of claim 4, wherein one of said heterologous control sequences is a constitutive promoter.

6. A method for making a plant having altered growth relative to a control plant, comprising transforming a plant cell with the construct of claim 4 and regenerating a plant from the plant cell, wherein said plant has increased expression of said nucleic acid and has one or more of the following: increased number of rosette leaves, increased flowering time, increased fresh weight of rosette leaves, increased silique length, increased root length, increased primary stem length, and/or increased primary stem diameter relative to a control plant.

7. A method for the production of a transgenic plant having altered growth relative to a control plant, comprising:
(i) introducing and expressing in a plant or plant cell a nucleic acid encoding a plant UBiquitin-Specific Protease 15 (UBP15) comprising the following motifs:
(a) a Cysteine box (Cys box);
(b) a Histidine box (His box); and
(c) a ZnMYND zinc finger domain;
and
(ii) cultivating the plant or plant cell under conditions promoting plant growth and development,
wherein said nucleic acid is selected from the group consisting of:
(a) a nucleic acid comprising the nucleotide sequence of SEQ ID NO: 1;
(b) a nucleic acid encoding a polypeptide comprising the amino acid sequence of SEQ ID NO: 2; and
(c) a nucleic acid encoding a polypeptide having at least 95% sequence identity to the amino acid sequence of SEQ ID NO: 2, wherein said polypeptide has de-ubiquitination activity in vitro,
wherein said plant or plant cell has increased expression of said nucleic acid,
and wherein said plant has one or more of the following: increased number of rosette leaves, increased flowering time, increased fresh weight of rosette leaves, increased silique length, increased root length, increased primary stem length, and/or increased primary stem diameter relative to a control plant.

8. A transgenic plant having an increase in one or more of rosette leaves, flowering time, fresh weight of rosette leaves, silique length, root length, primary stem length, and/or primary stem diameter relative to a control plant, wherein said increase results from introducing and expressing in said plant a nucleic acid encoding a plant UBP15 polypeptide comprising:
(a) a Cysteine box (Cys box);
(b) a Histidine box (His box); and
(c) a ZnMYND zinc finger domain,
wherein said nucleic acid is selected from the group consisting of:
(a) a nucleic acid comprising the nucleotide sequence of SEQ ID NO: 1;
(b) a nucleic acid encoding a polypeptide comprising the amino acid sequence of SEQ ID NO: 2; and
(c) a nucleic acid encoding a polypeptide having at least 95% sequence identity to the amino acid sequence of SEQ ID NO: 2, wherein said polypeptide has de-ubiquitination activity in vitro.

9. The plant of claim 3, wherein said plant is a crop plant.

10. Harvestable parts of the plant of claim 9, wherein said harvestable parts comprise the nucleic acid encoding the UBP15 polypeptide, and wherein said harvestable parts comprise shoot biomass and/or seeds.

11. The method of claim 1, wherein said nucleic acid encoding a plant UBP15 polypeptide is from a dicotyledonous plant.

12. The plant of claim 3, wherein said plant is rice, maize, wheat, barley, millet, rye, triticale, sorghum, or oats.

13. A plant, plant part, plant cell, or progeny thereof comprising the construct of claim 4, wherein the plant, a plant generated from the plant part or plant cell, or the progeny has one or more of the following: increased number of rosette leaves, increased flowering time, increased fresh weight of rosette leaves, increased silique length, increased root length, increased primary stem length, and/or increased primary stem diameter relative to a control plant.

14. The plant of claim 3, wherein said plant is a monocot.

15. The plant of claim 3, wherein said plant is a cereal.

16. The method of claim 1, wherein said nucleic acid comprises the nucleotide sequence of SEQ ID NO: 1 or encodes a polypeptide comprising the amino acid sequence of SEQ ID NO: 2.

17. The construct of claim 4, wherein said nucleic acid comprises the nucleotide sequence of SEQ ID NO: 1 or encodes a polypeptide comprising the amino acid sequence of SEQ ID NO: 2.

18. The method of claim 7, wherein said nucleic acid comprises the nucleotide sequence of SEQ ID NO: 1 or encodes a polypeptide comprising the amino acid sequence of SEQ ID NO: 2.

19. The transgenic plant of claim 8, wherein said nucleic acid comprises the nucleotide sequence of SEQ ID NO: 1 or encodes a polypeptide comprising the amino acid sequence of SEQ ID NO: 2.

20. A plant part or seed of the plant of claim 3, wherein said plant part or seed comprises the nucleic acid encoding the UBP15 polypeptide.

* * * * *